(12) United States Patent
Bongiorni et al.

(10) Patent No.: US 8,476,042 B2
(45) Date of Patent: *Jul. 2, 2013

(54) BACILLUS STRAIN FOR INCREASED PROTEIN PRODUCTION

(71) Applicant: Danisco US Inc., Palo Alto, CA (US)

(72) Inventors: Cristina Bongiorni, Fremont, CA (US); Eugenio Ferrari, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/622,968

(22) Filed: Sep. 19, 2012

(65) Prior Publication Data

US 2013/0029402 A1 Jan. 31, 2013

Related U.S. Application Data

(63) Continuation of application No. 13/377,529, filed as application No. PCT/US2010/037040 on Jun. 2, 2010, now Pat. No. 8,293,499.

(60) Provisional application No. 61/186,321, filed on Jun. 11, 2009.

(51) Int. Cl.
*C12Q 1/70* (2006.01)
*C12N 1/20* (2006.01)
*C12P 21/06* (2006.01)

(52) U.S. Cl.
USPC ...... 435/69.1; 435/252.3; 435/6.11; 435/6.12

(58) Field of Classification Search
USPC .......................................... 435/252.3, 69.1, 6
See application file for complete search history.

(56) References Cited

U.S. PATENT DOCUMENTS

| | | | |
|---|---|---|---|
| 5,387,521 | A | 2/1995 | Ferrari |
| 6,911,322 | B2 | 6/2005 | Valle et al. |
| 7,413,877 | B2 | 8/2008 | Collier et al. |
| 2003/0148461 | A1 | 8/2003 | Valle et al. |
| 2005/0202535 | A1 | 9/2005 | Collier et al. |

FOREIGN PATENT DOCUMENTS

| | | |
|---|---|---|
| JP | 2006-325586 A | 12/2006 |
| JP | 2009-072154 A | 4/2009 |
| WO | WO-03/070963 A2 | 8/2003 |
| WO | WO-2006/033668 A2 | 3/2006 |
| WO | WO-2008/126929 A1 | 10/2008 |
| WO | WO-2009/094084 A1 | 7/2009 |

OTHER PUBLICATIONS

Ferrari et al., "Transcription of *Bacillus subtilis* Subtilisin and Expression of Subtilisin in Sporulation Mutants," *J. Bacteriol.* 170:289-295, Jan. 1988.

Gabala et al. "The *Bacillus subtilis* Iron-sparing Response is Mediated by a Fur-regulated Small RNA and Three Small, Basic Proteins," *PNAS US* 105:11927-11932, Aug. 2008.

Grossman, "Genetic Networks Controlling the Initiation of Sporulation and the Development of Genetic Competence in *Bacillus subtilis*," *Annual Reviews Genetics* 29: 477-508 (1995).

International Search Report mailed Sep. 22, 2010 for PCT/US2010/037040, 5 pages.

Kunst et al., "The DegS/DegU and ComP/ComA Two-component Systems are Part of a Network Controlling Degradative Enzyme Synthesis and Competence in *Bacillus subtilis*," *Research in Microbiology* 145:393-402, 1994.

Marahiel et al., "Regulation of Peptide Antibiotic Production in *Bacillus*," *Molecular Microbiology* 7:631-636, Mar. 1993.

McQuade et al. "Control of a Family of Phosphatase Regulatory Genes (phr) by the Alternate Sigma Factor Sigma-H of *Bacillus subtilis*," *J. Bacteriology* 183(16):4905-4909, Aug. 2001.

Perego et al., "Pentapeptide Regulation of Aspartyl-phosphate Phosphatases," *Peptides* 22:1541-1547, Oct. 2001.

Perego et al., "Multiple Protein-Aspartate Phosphatases Provide a Mechanism for the Integration of Diverse Signals in the Control of Development in *B. subtilis*," *Cell* 79: 1047-1055, Dec. 1994.

Pottathil et al., "The Extracellular Phr Peptide-Rap Phosphatase Signaling Circuit of *Bacillus subtilis*," *Front. Biosci.* 8:d32-45, Jan. 2003.

Sauter et al., "Sm-like Proteins in Eubacteria: The Crystal Structure of the Hfq Protein from *Escherichia coli*," *Nucleic Acid Res* 31:4091-4098, Jul. 2003.

Slivaggi et al., "Small Untranslated RNA Antitoxin in *Bacillus subtilis*," *J Bacteriol.* 187:6641-6650, Oct. 2005.

Tjalsma et al., "Signal Peptide-dependent Protein Transport in *Bacillus subtilis*: A Genome-based Survey of the Secretome," *Microbiol Mol Biol Rev* 64:515-547, Sep. 2000.

Westers et al. "Genome Engineering Reveals Large Dispensable Regions in *Bacillus subtilus*," *Molecular Biology and Evolution* 20:2076-2090, Dec. 2003.

Wu et al., "Engineering a *Bacillus subtilis* Expression-secretion System with a Strain Deficient in Six Extracellular Proteases," *J. Bacteriol.* 173:4952-4958, Aug. 1991.

Ye et al., "Construction of Protease Deficient *Bacillus subtilis* Strains for Expression Studies: Inactivation of Seven Extracellular Proteases and the Intracellular Lona Protease," *Proc. Internatl. Symp. Rec. Adv. Bioindustry*, Seoul, Korea: The Korean Society for Applied Microbiology, pp. 160-169, Apr. 1996.

*Primary Examiner* — Maryam Monshipouri
(74) *Attorney, Agent, or Firm* — Danisco US Inc.

(57) ABSTRACT

The present invention provides host cells that have been genetically manipulated to have an enhanced capacity to produce proteins of interest. In particular, the invention relates to modified *Bacillus* sp. Host cells that have at least one inactivated phr gene. The enhanced production of proteins of interest by the modified *Bacillus* sp. Host cells is further increased in modified *Bacillus* sp. Host cells that overexpress YmaH. Methods for producing proteins of interest in the modified host cells are also provided.

30 Claims, 16 Drawing Sheets

TCATACCCTGAAAGGAAAGACAAGGGAAATTGTCGGCAATGAGCCGCTCGGCAGGTAGAAGGATGTTTACCGATGCAAAAAA

GGGCAAAATGGATAGGTGGTTGTCCATGTTGAATGCTATAATGGGGAGATTTATAAAGAGAGTGATACATATTGAATAATAC
                                                                      misA coding →

GAAGCAGCCCGTTGTCATTTAGTCGGACCGACGGCAGTGGGCAGTGGGAGAAACCAATTTAAGTATTCAGCTAGCCAAATCCTTAAACGC

GGAAATTATCAGCGGAGATTCGATGCAGATTTATAAAGGGATGGATATTGGAACAGCTAAAATTACCGAACAGGAGATGGAGGG

AGTGCCCCATCATCTGATTGACATTTAGATCCCCAAGACTCTTTCTCTACTGCCGATTATCAAAGCTTAGTAAGAAATAAATCA

GCCGAGATTGCAAATAGAGGAAAGCTTCCGATGATTGACGGCCGTACAGGGCTTTATATACAATCTGAGCTTTACGATTATACATT

TACGGAAGAGGCAAATGCCCGTGTTTCGAGAGAGCATGCAAATGCTGCTGAGCGGGAAGCGCTGACTTTCTTCATGCCA

AACTTGCTGCACAGATCCCGAGGCAGCAGCTGCGATTCATCCGAATAATACAAGAAGAGAACTTCTGTACAATGCAGTGTTAATTGGCCTGACAAT

ATACGTCCGGAAAAACGATGTCCCAGCATTGAAGGAACAAAAACGAGAACTTCTGTACAATGCAGTGTTAATTGGCCTGACAAT

GGATAGAGACACGCTTTACGAAAGAATTAATCACGCGGGTCGATTTGAYGATGCAGTCAGGCCTTCTCCGAAGTGAAACGCTT

ATACGACAAGAACGTGAGAGACTGTCAATCAATACAGGCGATAGGCTATAAAGAGCTGTATGCATATTTTGACGGTTTGTGACA

CTTTCCGATGCGTCGAACAGCTAAAAGCAGAACTCGAGGGCGTATGCGAAACGCCAGCTGACGTGGTTTCGCAACAAAATGCA

GGTCACATGGTTCGATATGACACCGCCCTGTTGATATGGAGCTGAAAAAAGGAAATTTCACACATATAGCAGGAAAACTCGA

ACTTTAATCGAAACTGTATGATATAGAAATCAAGGAGGACGAAACATGAAACCGATTAATATTCAGGATCAGTTTTGAATCA
                                                      ymsH coding →

AATCCCGGAAAAGAAAATACGTATGTCACTCGTTTTTTCCTGAACGGCTTTCAGTTGCCGGGCCAGGTGAAAGGCTTTGATAACT

TTACCGTATTGTTGGAATCGGAAGGTAAGCAGCAGCTTATATATAAACATGCGATCTCAACGTTTGCGCCGCAAAAAACGT

CCAGCTTGAACTCGAATAGATCAAAAAATGCCATGTCAAGACATGAGGAAAGGCTGTCGGGGGTTCCCGGCCGCAAAAAACGT

CATGAATCCACTTTTGCTCCAAGCTTTTGCTCCAAGCTTTTTGTGTAAGCTGACCATGCCAAGGCACGGTCTCTTTTTTATGAG (SEQ ID NO: 101)

Figure 8

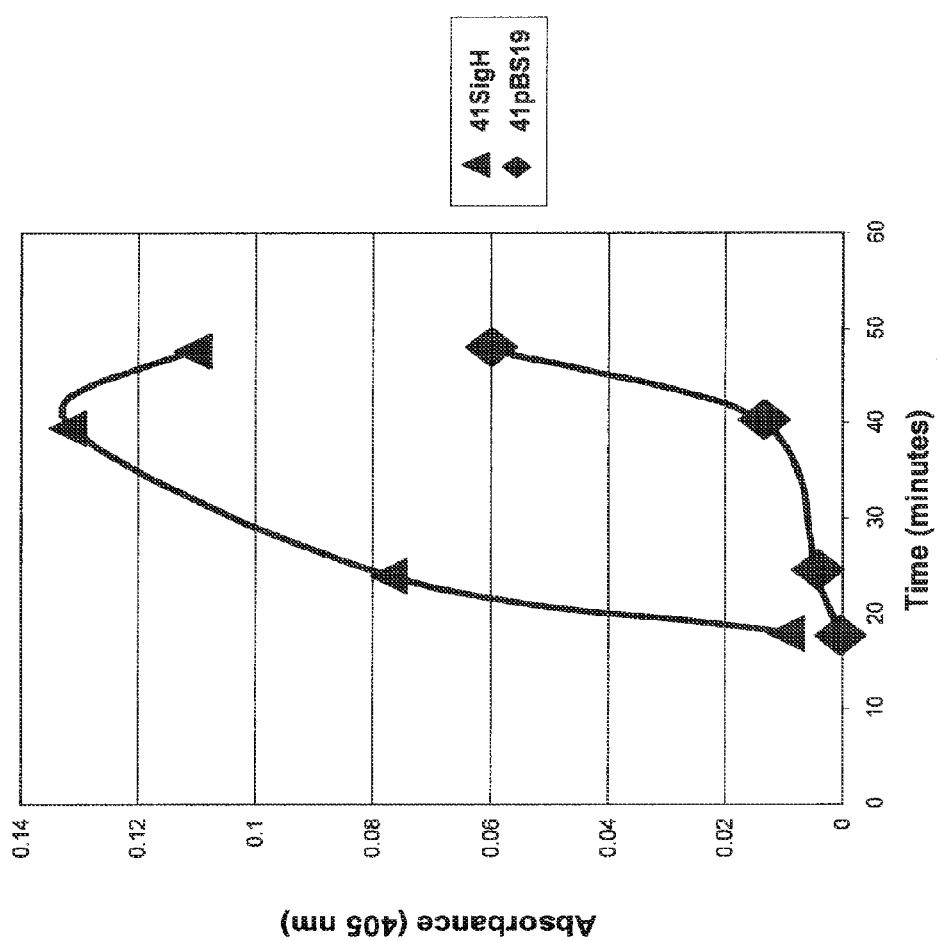

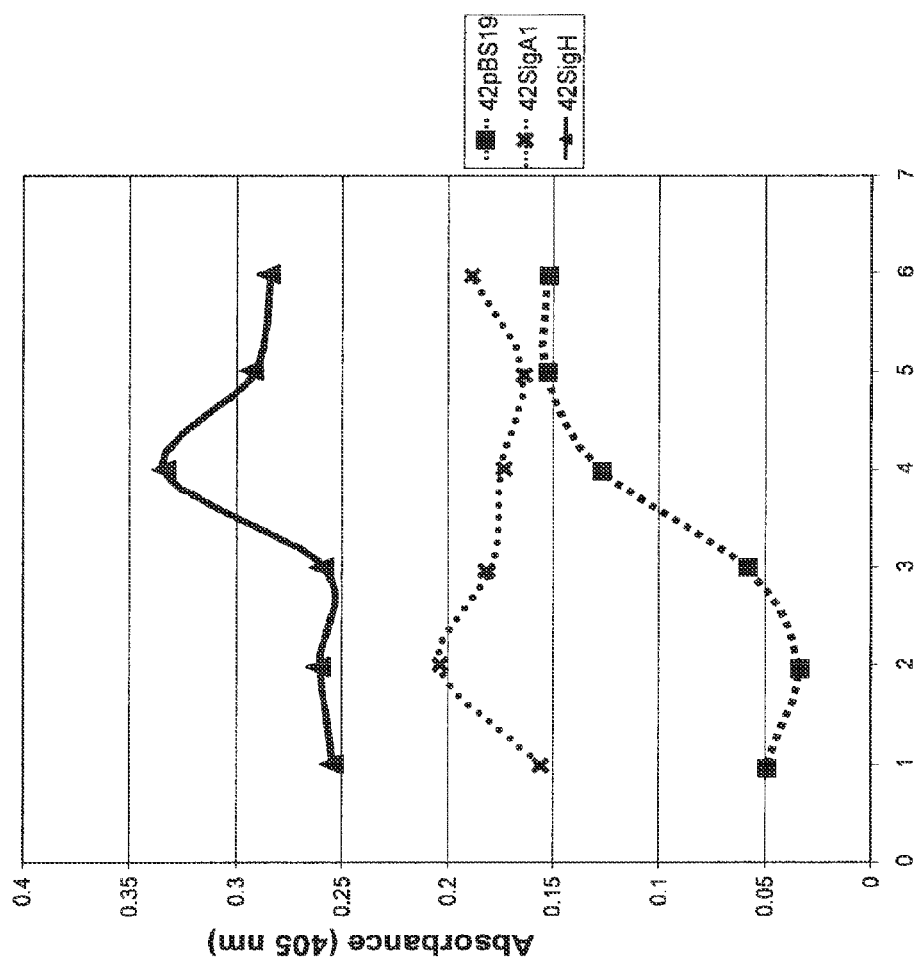

US 8,476,042 B2

BACILLUS STRAIN FOR INCREASED PROTEIN PRODUCTION

CROSS REFERENCE TO RELATED APPLICATION

This application is a Continuation of U.S. application Ser. No. 13/377,529, now U.S. Pat. No. 8,293,499, which is a National Stage under 35 U.S.C. §371 of International Application No. PCT/US2010/037040, filed on Jun. 2, 2010, which claims the benefit of U.S. Provisional Application No. 61/186,321, filed on Jun. 11, 2009, each of which is hereby incorporated by reference in their entirety.

The present invention provides host cells that have been genetically manipulated to have an enhanced capacity to produce proteins of interest. In particular, the invention relates to modified *Bacillus* sp. host cells that have at least one inactivated phr and/or rap gene. The enhanced production of proteins of interest by the modified *Bacillus* sp. host cells is further increased in modified *Bacillus* sp. host cells that over-express YmaH. Methods for producing proteins of interest in the modified host cells are also provided.

BACKGROUND

Expression and recombinant production of exogenous polypeptides is a widely used technique. It is well known that cells can be transformed with nucleic acids encoding exogenous polypeptides of interest for expression and production of large quantities of the desired polypeptides. In some applications, the methods are used to produce amounts of polypeptide over what would be produced naturally by the originating organism. Indeed, expression of exogenous nucleic acid sequences, as well as over-expression of endogenous sequences have been extensively used in modern biotechnology.

In spite of the implementation of various approaches for increasing protease yield, including screening for hyper-producing strains, cloning and over-expressing proteases, improving fed-batch and chemostat fermentations, and optimizing fermentation technologies, there remains a need for additional means for enhancing the production of proteases.

SUMMARY OF THE INVENTION

The present invention provides host cells that have been genetically manipulated to have an enhanced capacity to produce proteins of interest. In particular, the invention relates to modified *Bacillus* sp. host cells that have at least one inactivated phr and/or rap gene. The enhanced production of proteins of interest by the modified *Bacillus* sp. host cells is further increased in modified *Bacillus* sp. host cells that over-express YmaH. Methods for producing proteins of interest in the modified host cells are also provided.

In one embodiment, the invention provides a modified *Bacillus* sp. host cell that comprises a genome comprising a rap operon that has at least one inactivated phr gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and an inactivated rap gene, and a recombinant nucleic acid for producing a protein of interest at a level that is greater than that produced by the unmodified precursor host cell. Preferably, the inactivated rap gene is the rapA gene. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and an inactivated rap gene, (e.g., rapA gene), and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably, the promoter is the wild-type or mutant aprE promoter. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and a recombinant nucleic acid for producing a protein of interest at a level that is greater than that produced by the unmodified precursor host cell. The at least one inactivated phr gene is chosen from phrA, phrE, phrC, phrF, phrG, phrI, and phrK. In some embodiments, the inactivated phr gene is the inactivated phrA gene, while, other embodiments the inactivated phr gene is the phrE gene. The protein of interest is an enzyme, and preferably, a protease (e.g., a subtilisin)

In another embodiment, the invention provides a modified *Bacillus* sp. host cell that comprises a genome comprising a rap operon that has at least one inactivated phr gene, and a recombinant nucleic acid for producing a protein of interest at a level that is greater than that produced by the unmodified precursor host cell. The at least one inactivated phr gene is chosen from phrA, phrE, phrC, phrF, phrG, phrI and phrK. In some embodiments, the inactivated phr gene is the inactivated phrA gene, while, other embodiments the inactivated phr gene is the phrE gene. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and an inactivated rap gene, and a recombinant nucleic acid for producing a protein of interest at a level that is greater than that produced by the unmodified precursor host cell. Preferably, the inactivated rap gene is the rapA gene, and the at least one inactivated phr gene is chosen from phrA, phrE, phrC, phrF, phrG, phrI and phrK. In some embodiments, the inactivated phr gene is the inactivated phrA gene, while, other embodiments the inactivated phr gene is the phrE gene. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and an inactivated rap gene (e.g., rapA gene), and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably, the promoter is the wild-type or mutant aprE promoter. The at least one inactivated phr gene is chosen from phrA, phrE, phrC, phrF, phrG, phrI and phrK. Preferably, the inactivated phr gene is the inactivated phrA or phrE gene. The protein of interest is an enzyme, and preferably, a protease (e.g., a subtilisin).

In another embodiment, the invention provides a modified *Bacillus* sp. host cell that comprises a genome comprising a rap operon that has an inactivated phrA gene and an inactivated phrE gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that comprises a genome comprising a rap operon that has an inactivated phrA gene and an inactivated phrE gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that comprises a genome comprising a rap operon that has an inactivated phrA gene, an inactivated phrE gene, an inactivated rapA gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that comprises a genome comprising a rap operon that has an inactivated phrA gene, an inactivated phrE gene, an inactivated rapA gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that over expresses YmaH and that comprises a genome comprising a rap operon that has at least one inactivated phr gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and an inactivated rap gene, and a recombinant nucleic acid for producing a protein of interest at a level that is greater than that produced by the unmodified precursor host cell. Preferably, the inactivated rap gene is the rapA gene. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and an inactivated rap gene (e.g., rapA gene), and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably, the promoter is the wild-type or mutant aprE promoter. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and a recombinant nucleic acid for producing a protein of interest at a level that is greater than that produced by the unmodified precursor host cell. The at least one inactivated phr gene is chosen from phrA, phrE, phrC, phrF, phrG, phrI, and phrK. In some embodiments, the inactivated phr gene is the inactivated phrA gene, while, other embodiments the inactivated phr gene is the phrE gene. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and a recombinant nucleic acid for producing a protein of interest at a level that is greater than that produced by the unmodified precursor host cell. The at least one inactivated phr gene is chosen from phrA, phrE, phrC, phrF, phrG, phrI, and phrK. In some embodiments, the inactivated phr gene is the inactivated phrA gene, while, other embodiments the inactivated phr gene is the phrE gene. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and an inactivated rap gene, and a recombinant nucleic acid for producing a protein of interest at a level that is greater than that produced by the unmodified precursor host cell. Preferably, the inactivated rap gene is the rapA gene, and the at least one inactivated phr gene is chosen from phrA, phrE, phrC, phrF, phrG, phrI, and phrK. In some embodiments, the inactivated phr gene is the inactivated phrA gene, while, other embodiments the inactivated phr gene is the phrE gene. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and an inactivated rap gene (e.g., rapA gene), and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably, the promoter is the wild-type or mutant aprE promoter. The at least one inactivated phr gene is chosen from phrA, phrE, phrC, phrF, phrG, phrI, and phrK. Preferably, the inactivated phr gene is the inactivated phrA or phrE gene. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has an inactivated phrA gene and an inactivated phrE gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has an inactivated phrA gene and an inactivated phrE gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has an inactivated phrA gene, an inactivated phrE gene, an inactivated rapA gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has an inactivated phrA gene, an inactivated phrE gene, an inactivated rapA gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a method for producing a protein of interest in a host cell that comprises introducing into a precursor *Bacillus* sp. host cell an inactivating DNA construct comprising an inactivating polynucleotide that results in the inactivation of at least one indigenous phr and/or rap gene to generate a modified *Bacillus* sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation.

In another embodiment, the invention provides a method for producing a protein of interest in a host cell that comprises introducing into a precursor *Bacillus* sp. host cell an inactivating DNA construct comprising an inactivating polynucleotide that results in the inactivation of at least one indigenous phr and/or rap gene to generate a modified *Bacillus* sp. host cell; and growing said modified host cell under suitable conditions, wherein production of a protein of interest is greater in said modified host cell when compared to the production of said protein of interest in said precursor host cell. The at least one indigenous phr gene that is inactivated is chosen from phrA, phrE, phrC, phrF, phrG, phrI, and phrK. In some embodiments, the inactivated phr gene is the inactivated phrA gene, while, other embodiments the inactivated phr gene is the phrE gene. The protein of interest is an enzyme, and preferably, a protease (e.g., a subtilisin). In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation.

In another embodiment, the invention provides a method for producing a protein of interest in a host cell that comprises introducing into a precursor *Bacillus* sp. host cell an inactivating DNA construct comprising an inactivating polynucleotide that results in the inactivation of the indigenous phrA and phrE genes and/or rap gene to generate a modified *Bacillus* sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation.

In another embodiment, the invention provides a method for producing a protein of interest in a host cell that comprises introducing into a precursor *Bacillus* sp. host cell an inactivating DNA construct comprising an inactivating polynucleotide that results in the inactivation of the indigenous phrA and rap genes to generate a modified *Bacillus* sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation.

In another embodiment, the invention provides a method for producing a protein of interest in a host cell that comprises introducing into a precursor *Bacillus* sp. host cell that overexpresses YmaH, an inactivating DNA construct comprising an inactivating polynucleotide that results in the inactivation of at least one indigenous phr and/or rap gene to generate a modified *Bacillus* sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation. Overexpression of YmaH is achieved by introducing into either the precursor or the modified host cell a SigH construct (e.g., SEQ ID NO:23), comprising a SigH promoter operably linked to a polynucleotide encoding a YmaH protein. Alternatively, overexpression of YmaH is achieved by introducing into either the precursor or the modified host cell a SigA construct (e.g., SEQ ID NOS:26 and 31), comprising a SigA promoter operably linked to a polynucleotide encoding YmaH.

In another embodiment, the invention provides a method for producing a protein of interest in a host cell that comprises introducing into a precursor Bacillus sp. host cell that overexpresses YmaH, an inactivating DNA construct comprising an inactivating polynucleotide that results in the inactivation of at least one indigenous phr and/or rap gene to generate a modified Bacillus sp. host cell; and growing said modified host cell under suitable conditions, wherein production of a protein of interest is greater in said modified host cell when compared to the production of said protein of interest in said precursor host cell. The at least one indigenous phr gene that is inactivated is chosen from phrA, phrE, phrC, phrF, phrG, phrI, and phrK. In some embodiments, the inactivated phr gene is the inactivated phrA gene, while, other embodiments the inactivated phr gene is the phrE gene. The protein of interest is an enzyme, and preferably, a protease (e.g., a subtilisin). In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation. Overexpression of YmaH is achieved by introducing into either the precursor or the modified host cell a SigH construct (e.g., SEQ ID NO:23), comprising a SigH promoter operably linked to a polynucleotide encoding a YmaH protein. Alternatively, overexpression of YmaH is achieved by introducing into either the precursor or the modified host cell a SigA construct (e.g., SEQ ID NOS:26 and 31), comprising a SigA promoter operably linked to a polynucleotide encoding YmaH.

In another embodiment, the invention provides a method for producing a protein of interest in a host cell that comprises introducing into a precursor Bacillus sp. host cell that overexpresses YmaH, an inactivating DNA construct comprising an inactivating polynucleotide that results in the inactivation of the indigenous phrA and phrE genes and/or rap gene to generate a modified Bacillus sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation. Overexpression of YmaH is achieved by introducing into either the precursor or the modified host cell a SigH construct (e.g., SEQ ID NO:23), comprising a SigH promoter operably linked to a polynucleotide encoding a YmaH protein. Alternatively, overexpression of YmaH is achieved by introducing into either the precursor or the modified host cell a SigA construct (e.g., SEQ ID NOS:26 and 31), comprising a SigA promoter operably linked to a polynucleotide encoding YmaH.

In another embodiment, the invention provides a method for producing a protein of interest in a host cell that comprises introducing into a precursor Bacillus sp. host cell that overexpresses YmaH, an inactivating DNA construct comprising an inactivating polynucleotide that results in the inactivation of the indigenous phrA and rap genes to generate a modified Bacillus sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation. Overexpression of YmaH is achieved by introducing into either the precursor or the modified host cell a SigH construct (e.g., SEQ ID NO:23), comprising a SigH promoter operably linked to a polynucleotide encoding a YmaH protein. Alternatively, overexpression of YmaH is achieved by introducing into either the precursor or the modified host cell a SigA construct (e.g., SEQ ID NOS:26 and 31), comprising a SigA promoter operably linked to a polynucleotide encoding YmaH. protein.

The Bacillus sp. host cell of the embodiments described is a Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, or Bacillus thuringiensis cell. Preferably, the Bacillus sp. host cell of the embodiments described is a Bacillus subtilis host cell. In each of the present embodiments provided herein, the present invention provides isolated host cells, as well as cells in culture.

The present invention provides a host cell comprising a rap operon comprising at least one inactivated phr and/or at least one inactivated rap gene. In some embodiments, the host cell overexpresses YmaH. In some further embodiments, the host cell further comprises a recombinant nucleic acid. In still some further embodiments, the host cell further comprises a polynucleotide sequence encoding a protein of interest. In some additional embodiments, the recombinant nucleic acid comprises a promoter that is operably linked to the polynucleotide sequence encoding a protein of interest. In some further embodiments, the promoter is the wild-type or a mutant aprE promoter. In some additional embodiments, the host cell is a Bacillus sp. host cell. In still some further embodiments, the Bacillus sp. host cell is Bacillus subtilis. In some additional embodiments, the host cell produces the protein of interest at a level that is greater than that produced by a host cell that does not comprise at least one inactivated phr and/or rap gene. In some further embodiments, the protein of interest is an enzyme. In some additional embodiments, the enzyme is a protease. In still some additional embodiments, the at least one inactivated rap gene is the rapA gene. In some further embodiments, the at least one inactivated phr gene is selected from phrA, phrE, phrC, phrF, phrG, phrI, and phrK. In some embodiments, the at least one inactivated phr gene is phrA, while in some alternative embodiments, the at least one inactivated phr gene is phrE. In still some further embodiments, the host cell comprises at least one inactivated phr gene and at least one inactivated rap gene. In some further embodiments, the inactivated rap gene is the rapA gene. In still some further embodiments, there is at least one inactivated rap gene (e.g., rapA) and at least one inactivated phr gene selected from phrA, phrE, phrC, phrF, phrG, phrI, and phrK. In some embodiments, the at least one inactivated phr gene is phrA, while in some alternative embodiments, the at least one inactivated phr gene is phrE. In still some further embodiments, the host cell comprises an inactivated phrA gene, an inactivated phrE gene, an inactivated rapA gene, and a recombinant nucleic acid encoding a protein of interest. In some embodiments, the protein of interest is an enzyme. In still some further embodiments, the enzyme is a protease. In some embodiments, the host cell is a *Bacillus* sp. host cell. In some further embodiments, the *Bacillus* sp. host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* cell. In some additional embodiments, the *Bacillus* sp. host cell is a *Bacillus subtilis* host cell.

The present invention also provides methods for producing at least one protein of interest comprising providing a precursor host cell and an inactivating nucleotide construct comprising an inactivating polynucleotide that inactivates at least one indigenous phr and/or rap gene; introducing said inactivating nucleotide construct into said precursor host cell to generate a modified host cell; and growing the modified host cell under suitable conditions for producing of the at least one protein of interest. In some embodiments of the present methods, the protein of interest is encoded by a recombinant nucleic acid present in the precursor host cell. In some embodiments of the present methods, the protein of interest is encoded by a recombinant nucleic acid present in the modified host cell. In some embodiments of the present methods, the protein of interest is encoded by a recombinant nucleic acid present in the precursor host cell and/or the modified host cell. In some embodiments of the present methods, the recombinant nucleic acid comprises a promoter that is operably linked to the polynucleotide sequence encoding the protein of interest. In some additional embodiments of the present methods, the protein of interest is a wild-type protein of interest. In still some additional embodiments of the present methods, the precursor host cell naturally produces the protein of interest. In some further embodiments of the present methods, the production of the protein of interest by the modified host cell is greater than the production of the protein of interest by the precursor host cell. In some embodiments of the present methods, the methods further comprise the step of recovering the protein of interest. In some embodiments of the present methods, the protein of interest is an enzyme. In some further embodiments of the present methods, the enzyme is a protease. In still some further embodiments of the present methods, the modified host cell comprises a mutation in at least one gene chosen from degU, degQ, degS, sco4, spoIIE, degQ and degR. In some embodiments of the present methods, the host cell comprises a deg (Hy)32 mutation. In some further embodiments of the present methods, the at least one indigenous phr gene that is inactivated is chosen from phrA, phrE, phrC, phrF, phrG, phrI, and phrK. In still some further embodiments of the present methods, the inactivating polynucleotide inactivates the indigenous phrA and phrE genes and/or rap gene. In some embodiments of the present methods, the at least one indigenous phr gene is phrA, while in some alternative embodiments, the at least one indigenous phr gene is phrE. In still some additional embodiments of the present methods, the indigenous rap gene is inactivated. In some further embodiments of the present methods, the indigenous rap gene is rapA. In some additional embodiments of the present methods, the precursor or modified host cell overexpresses YmaH. In some embodiments of the present methods, the overexpression of YmaH is achieved by introducing a SigH construct into the precursor or the modified host cell. In some further embodiments of the present methods, the SigH construct comprises SEQ ID NO:23, comprising a SigH promoter operably linked to a polynucleotide encoding YmaH protein. In some additional embodiments of the present methods, the overexpression of YmaH is achieved by introducing a SigA construct into the precursor or said modified host cell. In still some further embodiments of the present methods, the SigA construct comprises SEQ ID NO:26 and/or 31, comprising a SigA promoter operably linked to a polynucleotide encoding YmaH. In some embodiments of the present methods, the host cell is a *Bacillus* sp. host cell. In some further embodiments of the present methods, the *Bacillus* sp. host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* cell. In some additional embodiments of the present methods, the *Bacillus* sp. host cell is a *Bacillus subtilis* cell.

BRIEF DESCRIPTION OF THE DRAWINGS

Certain aspects of the following detailed description are best understood when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 8 shows the polynucleotide sequence of a portion of the *Bacillus subtilis* genome that comprises the sequence defining a sigA promoter to the end of the sequence encoding the YmaH protein (SEQ ID NO:101). This sequence is diagrammed in FIG. 7, panel A. The beginning of the sequence encoding the miaA protein is indicated and the entire miaA coding sequence shown in bold letters; the beginning of sequence encoding the YmaH protein is indicated and the entire ymaH coding sequence shown in underlined bold letters.

FIG. 11 shows the level of production of subtilisin by *Bacillus subtilis* control host cells 42pBS19 and by *Bacillus* host cells 42SigH and 42SigA1, which overexpress ymaH.

DESCRIPTION OF THE INVENTION

Figure 1:
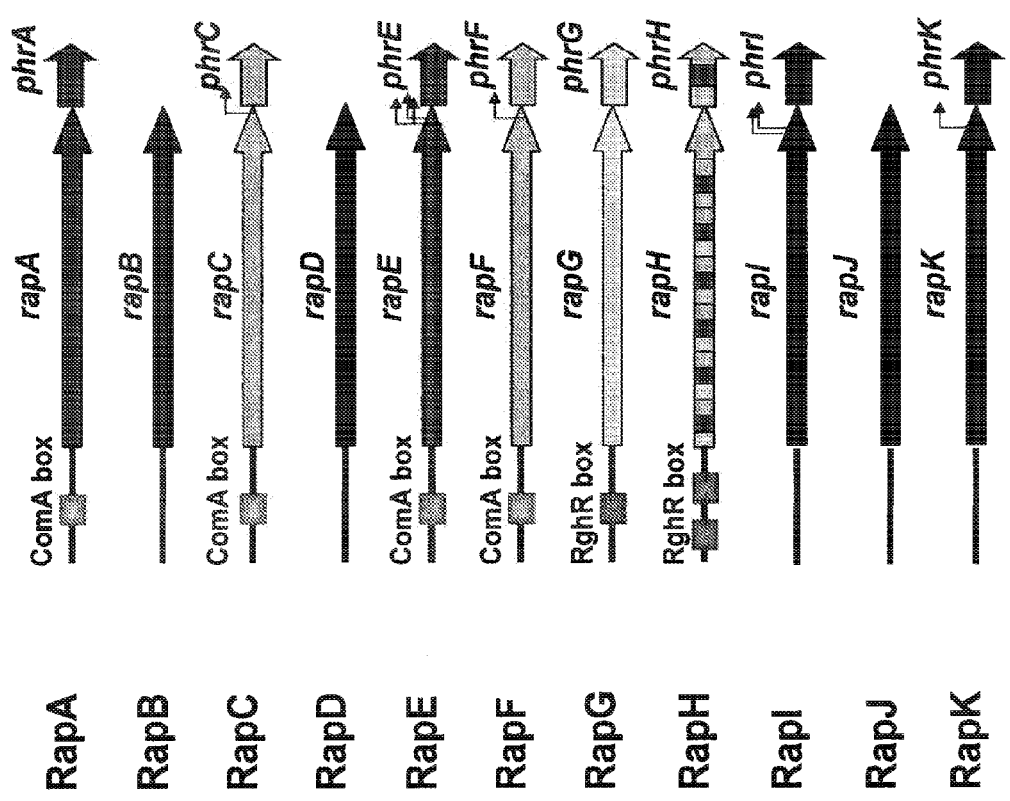
FIG. 1 illustrates the arrangement of phr and rap genes in the *Bacillus subtilis* rap operons.

The present invention provides host cells that have been genetically manipulated to have an enhanced capacity to produce proteins of interest. In particular, the invention relates to modified *Bacillus* sp. host cells that have at least one inactivated phr and/or rap gene. The enhanced production of proteins of interest by the modified *Bacillus* sp. host cells is further increased in modified *Bacillus* sp. host cells that overexpress YmaH. Methods for producing proteins of interest in the modified host cells are also provided.

Although described herein in regard to exemplary serine proteases (e.g., FNA and AprE), the compositions and methods of the present invention are not limited to serine proteases. Indeed, the present invention finds use in improving the production of various classes of enzymes as well as proteases (e.g., amylases, cellulases, oxidases, oxidoreductases, cutinases, mannanases, pectinases, amylases, lipases. etc). Indeed, it is not intended that the present invention be limited to any particular enzyme nor class of enzyme.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and
reagents described, as these may vary, depending upon the context they are used by those of skill in the art.

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

All patents, patent applications, and other publications, including all sequences disclosed within these references, referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

Definitions

As used herein, a "modified host cell" is a recombinant host cell that contains at least one inactivated phr and/or a rap gene. A modified host cell is derived from a precursor host cell, which can be a wild-type or a recombinant precursor host cell comprising a phr gene that is not inactivated.

As used herein, "recombinant host cell" refers to a cell that has been modified by the introduction of at least one recombinant/heterologous nucleic acid. Thus, for example, recombinant host cells express genes that are not found in identical form within the parent form of the cell or express native genes that are otherwise abnormally expressed, under expressed or not expressed at all as a result of deliberate human intervention.

As used herein "precursor host cell" is used interchangeably with "parent host cell" to refer to a host cell that is genetically altered to generate a modified host cell.

As used herein, the term "recombinant polynucleotide" and "recombinant polypeptide" respectively refer to a polynucleotide and a polypeptide that do not naturally occur in a host cell. A recombinant polynucleotide or polypeptide molecule may contain two or more naturally-occurring sequences that are linked together in a way that does not occur naturally. "Recombination, "recombining," or generating a "recombined" or "recombinant" nucleic acid is generally the assembly of two or more nucleic acid fragments wherein the assembly gives rise to a chimeric gene.

As used herein, the term "recombinant" when used in reference to a cell means a cell that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, an "analogous sequence" is a primary biological sequence, such as the amino-acid sequence or the nucleotides of DNA sequences wherein the function of the protein or encoded protein is essentially the same as that designated for Phr, Rap and YmaH proteins recited herein. Additionally, analogous proteins have at least about 60%, at least about 65%, at least about 70%, at least about 75%, at least about 80%, at least about 85%, at least about 90%, at least about 95%, at least about 97%, at least about 98%, at least about 99% or about 100% sequence identity to the sequence of variants of Phr, Rap and YmaH proteins recited herein. Analogous sequences are determined by known methods of sequence alignment. A commonly used alignment method is BLAST, although as indicated above and below, there are other methods that also find use in aligning sequences. One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). A preferred method utilizes the BLASTN module of WU-BLAST-2 set to the default parameters, with overlap span and overlap fraction set to 1 and 0.125, respectively.

As used herein, "percent (%) sequence identity" or "percent homology" when used in reference to a polynucleotide or to a polypeptide sequence is defined as the percentage of nucleotide or amino acid residues in a candidate sequence that are identical with the nucleotide or amino acid residues of a starting sequence (i.e., the sequence of interest). The percent identity shared by polynucleotide or polypeptide sequences is determined by direct comparison of the sequence information between the molecules by aligning the sequences and determining the identity by methods known in the art. In some embodiments, the alignment includes the introduction of gaps in the sequences to be aligned. In addition, for sequences which contain either more or fewer nucleotides or amino acids than those of the candidate polynucleotide or polypeptide sequences, it is understood that the percentage of homology will be determined based on the number of homologous nucleotides or amino acids in relation to the total number of nucleotides or amino acids. As used herein "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, the term "heterologous" refers to elements that are not normally associated with each other. For example, if a host cell produces a heterologous protein, that protein is a protein that is not normally produced by that host cell. Likewise, a promoter that is operably linked to a heterologous coding sequence is a promoter that is operably linked to a coding sequence that it is not a wild-type sequence.

As used herein, a "protein of interest," or "polypeptide of interest," refers to a protein that is expressed/produced by a host cell. Generally, proteins of interest are desirable proteins that have commercial significance. The protein of interest may be either homologous or heterologous to the host. In some embodiments, the protein of interest is a secreted polypeptide, particularly an enzyme, including but not limited to amylolytic enzymes, proteolytic enzymes, cellulytic enzymes, oxidoreductase enzymes and plant wall degrading enzymes. In further embodiments, these enzyme include, but are not limited to amylases, proteases, xylanases, lipases, laccases, phenol oxidases, oxidases, cutinases, cellulases, hemicellulases, esterases, peroxidases, catalases, glucose oxidases, phytases, pectinases, glucosidases, isomerases, transferases, galactosidases and chitinases. In still further embodiments, the expressed polypeptide is a hormone, cytokine, growth factor, receptor, vaccine, antibody, or the like. While it is not intended that the present invention be limited to any particular protein/polypeptide, in some most preferred embodiments, the expressed protein of interest is a protease.

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology*, [1988]). For example, proteolytic activity may be ascertained by comparative assays which analyze the respective protease's ability to hydrolyze a commercial substrate. Exemplary substrates useful in the analysis of protease or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference). The pNA assay (See e.g., Del Mar et al., Anal. Biochem., 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In addition, absorbance measurements at 280 nm can be used to determine the total protein concentration. The active enzyme/total-protein ratio gives the enzyme purity.

As used herein, the term "subtilisin" refers to a protease belonging to the group of serine proteases which initiate the nucleophilic attack on the peptide bond through a serine residue at the active site (serine endopeptidase). Subtilisins are secreted in large amounts from many *Bacillus* species. For example, FNA, which is subtilisin BPN' containing the Y217L substitution, is a subtilisin obtained from *Bacillus amyloliquefaciens*, and AprE is the subtilisin obtained from *Bacillus subtilis*.

As used herein, "deletion" of a gene refers to deletion of the entire coding sequence, deletion of part of the coding sequence, or deletion of the coding sequence including flanking regions. The deletion may be partial as long as the sequences left in the chromosome provides the desired loss of the biological activity of the gene. The flanking regions of the coding sequence may include from about 1 bp to about 500 bp at the 5' and 3' ends. The flanking region may be larger than 500 bp but will preferably not include other genes in the region which may be inactivated or deleted according to the invention. The end result is that the deleted gene is effectively non-functional. In simple terms, a "deletion" is defined as a change in either nucleotide or amino acid sequence in which one or more nucleotides or amino acid residues, respectively, have been removed (i.e., are absent). Thus, a "deletion mutant" has fewer nucleotides or amino acids than the respective parent host cell. In some embodiments, deletion of a phr gene provides enhanced expression of a protein of interest (e.g., a protease).

In some embodiments, deletion of one or more of genes selected from the group consisting of phrA, phrC, phrE, phrF, phrI, and phrK, provides an improved strain for the enhanced production of a protease.

As used herein, a "corresponding unmodified *Bacillus* strain" or "parent" or "precursor" *Bacillus* sp. host cell is the originating host strain from which the indigenous chromosomal region (e.g., phrA and/or phrE gene), is inactivated and from which the altered/recombinant strain is derived.

A polypeptide is "overexpressed" in a recombinant host cell if the polypeptide is expressed in the recombinant cell at a higher level that the level at which it is expressed in the precursor cell.

As used herein, the term "homologous," when used in reference to a polynucleotide or protein, refers to a polynucleotide or protein that occurs naturally in a host cell.

The term "polypeptide," as used herein, refers to a compound made up of amino acid residues linked by peptide bonds. The term "protein" as used herein, may be synonymous with the term "polypeptide" or may refer, in addition, to a complex of two or more polypeptides. Thus, the terms "protein," "peptide," and "polypeptide" are used interchangeably.

As used herein, the terms "chimeric polypeptide" and "fusion polypeptide" are used interchangeably to refer to a protein that comprises at least two separate and distinct regions that may or may not originate from the same protein. For example, a signal peptide linked to the protein of interest wherein the signal peptide is not normally associated with the protein of interest would be termed a chimeric polypeptide or chimeric protein.

As used herein, a "signal sequence" is a sequence of amino acids present at the N-terminal portion of a protein which facilitates the secretion of the mature form of the protein outside the cell. The definition of a signal sequence is a functional one. The mature form of the extracellular protein lacks the signal sequence which is cleaved off during the secretion process.

A "prosequence" is an amino acid sequence between the signal sequence and mature protease that is necessary for the secretion of the protease. Cleavage of the pro sequence results in a mature active protease.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., protease), or may be from a gene encoding another secreted protein. One exemplary exogenous signal sequence comprises the first seven amino acid residues of the signal sequence from *Bacillus subtilis* subtilisin fused to the remainder of the signal sequence of the subtilisin from *Bacillus lentus* (ATCC 21536).

The term "aprE promoter" herein refers to the polynucleotide promoter sequence that naturally drives the expression of subtilisin in *B. subtilis* (Ferrari et al., J Bacteriol. 170:289-295 [1988]). In the context of aprE promoter, "an aprE promoter" herein refers to a wild-type aprE promoter and mutants thereof. In some embodiments, the aprE promoter includes the nucleotide sequences necessary for the transcriptional regulation exerted by DegU, ScoC, AbrB and any other regulator of such promoter, and/or the aprE transcriptional leader (Hambraeus et al., Microbiology 148:1795-1803 [2002]). In some alternative embodiments, the aprE promoter does not include all of the nucleotide sequences necessary for the transcriptional regulation exerted by DegU, ScoC, AbrB and other regulators, and/or does not include the aprE transcriptional leader sequence.

As used herein, an "inactivated gene" is a locus of a genome that, prior to its inactivation, was capable of producing a protein (i.e., capable of being transcribed into an RNA that could be translated to produce a full length polypeptide). A gene encoding a polypeptide is inactivated when it not transcribed and translated into a full length protein that has biological activity (e.g., catalytic activity, in the case of an enzyme). A gene may be inactivated by altering a sequence required for its transcription, for example by altering a sequence required for RNA processing (e.g., poly-A tail addition), by altering a sequence required for translation, or by altering the amino acid sequence of the encoded polypeptide (e.g., by a nucleotide substitution, etc). Examples of inactivated genes include but are not limited to a deleted gene, a gene containing a deleted region, a gene containing a rearranged region, a gene having an inactivating point mutation or frameshift, and a gene containing an insertion. A gene may also be inactivated by altering or deleting the sequence of the adjacent gene in an operon. In addition, a gene may also be inactivated using antisense or any other method that abolishes expression of that gene.

As used herein, the term "nucleic acid" encompasses DNA, RNA, whether single stranded or double stranded, and encompasses chemically modified DNA or RNA. The terms "nucleic acid" and "polynucleotide" are used interchangeably herein.

The term "inactivation" includes any method that prevents the functional expression of one or more of the phr genes (phrA, phrC, phrE, phrF, phrI, and phrK), wherein the gene or gene product (i.e., the encoded Phr protein), is unable to exert its known function. Inactivation occurs via any suitable means, including deletions, substitutions (e.g., mutations), interruptions, and/or insertions in the nucleic acid gene sequence. In some embodiments, an altered/recombinant Bacillus strain comprises inactivation of one or more genes that results preferably in stable and non-reverting inactivation. In some embodiments, inactivation is achieved by deletion. In some preferred embodiments, the gene is deleted by homologous recombination. For example, in some embodiments when phrA is the gene to be deleted, an inactivating DNA construct comprising an incoming sequence having a selective marker flanked on each side by a homology box is used. The homology box comprises nucleotide sequences homologous to nucleic acids flanking regions of the chromosomal phrA gene. The inactivating DNA construct aligns with the homologous sequences of the Bacillus host chromosome and in a double crossover event the phrA gene is excised out of the host chromosome.

In certain embodiments, the altered/recombinant cell is a Bacillus sp. host cell that comprises two inactivated genes (e.g., phrA and phrE). In other embodiments, the Bacillus sp. host cell comprises three inactivated genes, four inactivated genes, five inactivated genes, six inactivated genes, or more. Thus, it is not intended that the number of inactivated genes be limited to any particular number of genes. In some embodiments, the inactivated genes are contiguous to each another, while in other embodiments, they are located in separate regions of the Bacillus chromosome. In some embodiments, an inactivated chromosomal gene has a necessary function under certain conditions, but the gene is not necessary for Bacillus strain viability under laboratory conditions. Preferred laboratory conditions include but are not limited to conditions such as growth in a fermenter, in a shake flask, plated media, etc., suitable for the growth of the microorganism.

As used herein, the terms "inactivating DNA construct", "inactivating polynucleotide" and "deletion cassette" are used interchangeably to refer to a DNA construct comprising a non-functional sequence that may be inserted into a gene to disrupt the function of the gene. In some embodiments, the inactivating DNA construct comprises a sequence encoding a selective marker. The inactivating DNA construct may also include two homology boxes.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In preferred embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the terms "DNA construct" and "transforming DNA" are used interchangeably to refer to DNA used to introduce sequences into a host cell or organism. The DNA may be generated in vitro by PCR or any other suitable technique(s) known to those in the art. In particularly preferred embodiments, the DNA construct comprises a sequence of interest (e.g., as an incoming sequence). In some embodiments, the sequence is operably linked to additional elements such as control elements (e.g., promoters, etc.). The DNA construct may further comprise a selectable marker. It may further comprise an incoming sequence flanked by homology boxes. In a further embodiment, the transforming DNA comprises other non-homologous sequences, added to the ends (e.g., stuffer sequences or flanks). In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell, and/or 2) mutagenize a region of the host cell chromosome (i.e., replace an endogenous sequence with a heterologous sequence), 3) delete target genes; and/or introduce a replicating plasmid into the host.

As used herein, the term "heterologous DNA sequence" refers to a DNA sequence that does not naturally occur in a host cell. In some embodiments, a heterologous DNA sequence is a chimeric DNA sequence that is comprised of parts of different genes, including regulatory elements.

As used herein, the term "heterologous protein" refers to a protein or polypeptide that does not naturally occur in the host cell (i.e., it is encoded by a heterologous sequence).

As used herein, "homologous protein" refers to a protein or polypeptide native or naturally occurring in a cell.

The term "YmaH protein" is interchangeably used with "Hfq protein" and refers to a protein that enhances the expression of a protein of interest. In the context of YmaH, "a YmaH protein" herein refers to a wild-type YmaH protein and variants thereof, including orthologs.

As used herein, the term "vector" refers to a polynucleotide designed to introduce nucleic acids into one or more host cells. In preferred embodiments, vectors autonomously replicate in different host cells. The term is intended to encompass, but is not limited to cloning vectors, expression vectors, shuttle vectors, plasmids, phage particles, cassettes, and the like.

An "expression vector" as used herein refers to a DNA construct comprising a protein-coding region that is operably linked to a suitable control sequence capable of effecting expression of the protein in a suitable host cell. In some embodiments, such control sequences include a promoter to effect transcription, an optional operator sequence to control transcription to produce mRNA, a sequence encoding suitable ribosome binding sites on the mRNA, and enhancers and sequences which control termination of transcription and translation.

As used herein, the term "promoter" refers to a regulatory sequence that initiates transcription of a downstream nucleic acid.

As used herein, the term "operably linked" refers to an arrangement of elements that allows them to be functionally related. For example, a promoter is operably linked to a coding sequence if it controls the transcription of the sequence.

As used herein, the term "derived" encompasses the terms "originated from," "obtained," or "obtainable from," and "isolated from".

As used herein, a "non-pathogenic" organism is an organism that is not pathogenic to humans and/or other animals.

The terms "recovered," "isolated," and "separated," as used herein refer to a protein, cell, nucleic acid or amino acid that is removed from at least one component with which it is naturally associated.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "Genetics," in Hardwood et al, (eds.), *Bacillus*, Plenum Publishing Corp., pages 57-72, [1989]).

As used herein, the terms "transformed" and "stably transformed" refers to a cell that has a non-native (heterologous) polynucleotide sequence integrated into its genome or as an episomal plasmid that is maintained for at least two generations.

As used herein, the term "expression" refers to the process by which a polypeptide is produced based on the nucleic acid sequence of a gene. The process includes both transcription and translation.

As used herein, the term "selectable marker-encoding nucleotide sequence" refers to a nucleotide sequence, which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell, which allows for ease of selection of those hosts containing the vector. Examples of such selectable markers include but are not limited to antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, preferably the marker is an antimicrobial resistant marker (e.g., $amp^R$; $phleo^R$; $spec^R$; $kan^R$; $ery^R$; $tet^R$; $cmp^R$; and $neo^R$ (See e.g., Guerot-Fleury, Gene, 167:335-337, 1995; Palmeros et al., Gene 247:255-264, 2000; and Trieu-Cuot et al., Gene, 23:331-341, 1983). Other markers useful in accordance with the invention include, but are not limited to auxotrophic markers, such as tryptophan; and detection markers, such as β-galactosidase.

As used herein, "culturing" refers to growing a population of microbial cells under suitable conditions in a liquid or solid medium. In some embodiments, culturing refers to fermentative recombinant production of an exogenous protein of interest or other desired end products (typically in a vessel or reactor).

As used herein, the term "production" when used in reference to a protein of interest encompasses the processes of transcription, and translation, and when needed, the processes of secretion and maturation, which creates the active from of the protein. For proteins that are secreted into the extracellular medium (e.g., proteases), the level of protein production is assessed as the amount of active protein secreted into the extracellular medium.

As used herein, "*Bacillus* sp." refers to all of the species within the genus "*Bacillus*," which are Gram-positive bacteria classified as members of the Family Bacillaceae, Order Bacillales, Class Bacilli. The genus "*Bacillus*" includes all species within the genus "*Bacillus*," as known to those of skill in the art, including but not limited to *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

Other definitions of terms may appear throughout the Specification.

Before the exemplary embodiments are described in more detail, it is to be understood that the present invention is not limited to particular embodiments described, as such may, of course, vary. It is also to be understood that the terminology used herein is for the purpose of describing particular embodiments only, and is not intended to be limiting.

Before the exemplary embodiments are described in more detail, it is to be understood that the present invention is not limited to particular embodiments described, as such may, of course, vary. It is also to be understood that the terminology used herein is for the purpose of describing particular embodiments only, and is not intended to be limiting.

Modified Host Cells

*Bacillus* sp. cells make use of two-component signal transduction systems, each containing a sensor kinase and a response regulator, to sense and respond to a wide variety of extracellular stimuli. Known two-component systems are involved in various processes, such as competence development (Dubnau, Microbiological Reviews 1991 55, 395-424), protein secretion (Kunst, Research in Microbiology 1994 145, 393-402; Darmon, Journal of Bacteriology 2002 184, 5661-5671), synthesis of peptide antibiotics and bacteriocins (Marahiel Molecular Microbiology 1993 7, 631-636; Stein, Molecular Microbiology 2002 44, 403-416) and sporulation (Grossman, Annual Reviews Genetics 1995 29, 477-508). These regulatory systems are governed by intracellular response regulators aspartyl phosphatases (Raps), and their antagonistic phosphatase regulators (Phrs). The Raps dephosphorylate response regulators, which alter gene expression thereby produce cellular responses. The Phr peptides serve as cell density-signaling molecules and inhibit the Rap phosphatases (Perego, Proceedings of the National Academy of Science USA 1997 94, 8612-8617; Perego, M. Trends in Microbiology 1998 6, 366-370; Perego, Cell 1994 79, 1047-1055).

While the Rap phosphatases remain in the cytoplasm, Phr peptides contain an amino-terminal signal peptide and are exported as pro-peptides, most likely via the Sec pathway (Perego, Molecular Microbiology 1996 19, 1151-1170; Tjalsma. Microbiological and Molecular Biology Reviews 2000 64, 515-547). Further, extracellular processing results in active Phr pentapeptides. After re-import by cells in the culture via the oligopeptide permease (Opp) system, Phr peptides specifically inhibit the activity of their cognate Rap phosphatase (Solomon, Genes and Development 1996 10, 2014-2024; Perego, Proceedings of the National Academy of Science USA 1997 94, 8612-8617; Perego, Trends in Microbiology 1998 6, 366-370). The Phr peptides act as quorum sensors in that they initiate cellular responses in response to changes in cell density. A Rap protein and the Phr peptide that inhibits the Rap protein are encoded on a single operon. There are eight rap operons transcribed with their cognate phr genes, and three other rap coding genes in the *B. subtilis* genome (Kunst, Nature 1997 390, 249-256). The rap/phr signaling systems of *Bacillus subtilis* are reviewed in Pottathil (Front Biosci. 2003 8:d32-45) and Perego (Peptides 2001 22:1541-7).

The present invention provides modified *Bacillus* sp. host cells that are genetically manipulated to have an enhanced capacity to produce proteins of interest. In particular, the present invention relates to modified *Bacillus* sp. cells that contain a genome comprising at least one rap operon that comprises an inactivated phr gene. In some embodiments, the modified *Bacillus* sp. cells contain a genome comprising at least one rap operon that comprises an inactivated phr gene and an inactivated rap gene. Inactivation of the phr and/or rap gene enhances the production of a protein of interest by the modified *Bacillus* sp. cell when compared to the production of the same protein by the unmodified precursor *Bacillus* sp. cell. Thus, the modified *Bacillus* sp. cell comprises at least one inactivated phr and/or rap gene and a polynucleotide that encodes a protein of interest. In some embodiments, the polynucleotide that encodes the protein of interest is a wild-type polynucleotide. In other embodiments, the polynucleotide that encodes the protein of interest is a recombinant polynucleotide.

The DNA sequences of several *Bacillus* sp. rap operons and the Rap and Phr proteins encoded by the operons have been determined and deposited into NCBI's Genbank database. In certain embodiments, a *Bacillus* sp. rap operon modified in the subject cell: a) may have at least about 70%, at least about 80%, at least about 90%, at least about 95%, at least about 97% or at least about 98% sequence identity to the sequence of a rap operon sequence deposited in NCBI's Genbank database; b) may hybridize under stringent conditions to a rap operon sequence deposited in NCBI's Genbank database; or c) may encode a polypeptide that has at least about 70% sequence identity (e.g., at least about 80%, at least about 90%, at least about 93%, at least about 95%, at least about 97% or at least about 98% sequence identity) to a Rap or Phr sequence deposited in NCBI's Genbank database. Exemplary phr protein and nucleotide sequences deposited in NCBI's Genbank database include those annotated in Genbank accession no. NC_000964.2; GID: 50812173 (*B. subtilis*), Genbank accession no. NC_009848.1; GID: 157690798 (*Bacillus pumilus*), Genbank accession no. NC_006270.3; GID: 163119169 (*Bacillus licheniformis*) and Genbank accession no. NC_005957.1; GID 49476684 (*Bacillus thuringiensis*) among others. Rap proteins may be identified as containing a so-called tetratricopeptide repeat domain, a pfam domain that typically contains 34 amino acids and contains the following amino acid sequence [WLF]-X(2)-[LIM]-[GAS]-X(2)-[YLF]-X(8)-[ASE]-X(3)-[FYL]-X(2)-[ASL]-X(4)-[PKE]. The above Genbank accessions are incorporated by reference in their entirety, including the nucleic acid and protein sequences therein and the annotation of those sequences, as of the earliest filing date of this patent application.

In some embodiments, the well-known *Bacillus subtilis* strain 168 finds use in the present invention. Indeed, the genome of this strain has been well-characterized (See, Kunst et al., Nature 390:249-256 [1997]; and Henner et al., Microbiol. Rev., 44:57-82 [1980]). The genome is comprised of one 4215 kb chromosome. While the coordinates used herein refer to the 168 strain, the invention encompasses analogous sequences from *Bacillus* strains other than *Bacillus subtilis* 168.

In one embodiment, a modified *Bacillus* sp. cell comprises a single inactivated phr gene (e.g., a rapA operon containing an inactive phrA gene, a rapC operon containing an inactive phrC gene; a rapE operon containing an inactive phrE gene, a rapF operon containing an inactive phrF gene, a rapI operon containing an inactive phrI gene, or a rapK operon containing an inactive phrK gene).

In one embodiment, the modified *Bacillus* sp. cell comprises an inactivated phrA gene (e.g., a rapA operon containing an inactive phrA gene). In some embodiments, inactivation results from the deletion of the entire endogenous DNA sequence that encodes the PhrA protein. In some embodiments, the entire endogenous DNA sequence of the *Bacillus subtilis* phrA gene is deleted using the inactivating DNA deletion construct of SEQ ID NO:17. In *Bacillus subtilis* 168, the DNA sequence that encodes the phrA protein MKSKWMSGLL LVAVGFSFTQ VMVHAGETAN TEGK-TFHIAA RNQT; SEQ ID NO:42 (Swiss-Prot:Q00829) is atgaaatctaaatggatgtcaggtttgttgctcgttgcggtcgggttcagctttac-tcaggtgatggttcatgcaggtgaaacagcaaacacagaagggaaaacatttcat-attgcggcacgcaatcaaaca; SEQ ID NO:41 (NP_389126).

Alternatively, inactivation of the phrA gene results from the deletion of a fragment of the phrA gene that prevents the functional expression of the PhrA protein. The phrA gene is located at about 1316305-1316439 bp of the *B. subtilis* 168 chromosome (Accession no. NC_000964). According to one embodiment, inactivation of the phrA gene is by insertion of a selectable marker that interrupts the phrA gene.

In another embodiment, the modified *Bacillus* sp. cell comprises an inactivated phrE gene (e.g., a rapE operon containing an inactive phrE gene). In some embodiments, inactivation results from the deletion of the entire endogenous DNA sequence that encodes the PhrE protein.

In some embodiments, the entire endogenous DNA sequence of the *Bacillus subtilis* phrE gene is deleted using the inactivating DNA deletion construct of SEQ ID NO:18. In *Bacillus subtilis* 168, the DNA sequence that encodes the phrE protein MKSKLFISLS AVLIGLAFFG SMYN-GEMKEA SRNVTLAPTH EFLV; SEQ ID NO:44 (Swiss-Prot:032025) is atgaaatctaaattgtttatcagtttatccgccgttttaattgg-acttgccttttcggatctatgtataatggcgaaatgaaggaagcatcccggaatgt-aactctcgcacctactcatgaattccttgtt; SEQ ID NO:43 (NP_390461). Alternatively, inactivation of the phrE gene results from the deletion of a fragment of the phrE gene that prevents the functional expression of the PhrE protein. The phrE gene is located at about 2659557-2659691 bp of the *B. subtilis* 168 chromosome (Accession no. NC_000964). According to one embodiment, inactivation of the phrE gene is by insertion of a selectable marker that interrupts the phrE gene.

In yet other embodiments, the phrA and the phrE genes are deleted from the *Bacillus subtilis* chromosome using the phrA and the phrE deletion constructs set forth in SEQ ID NOS:17 and 18, respectively.

In some other embodiments, the modified *Bacillus* sp. cell comprises at least two inactivated phr genes (e.g., two rap operons each containing an inactivated phr gene), at least three inactivated phr genes (e.g., three rap operons each containing an inactivated phr gene) at least four inactivated phr genes (e.g., four rap operons each containing an inactivated phr gene), at least five inactivated phr genes (e.g., five rap operons each containing an inactivated phr gene), at least six inactivated phr genes (e.g., six rap operons each containing an inactivated phr gene), at least seven inactivated phr genes, (e.g., seven rap operons each containing an inactivated phr gene), or at least eight inactivated phr genes (e.g., eight rap operons each containing an inactivated phr gene). In one exemplary embodiment, a subject host cell may contain both a) a rapA operon containing an inactive phrA gene and b) a rapE operon containing an inactive phrE gene. In some embodiments, inactivation results from the deletion of the entire endogenous DNA sequences that encode the PhrA and the PhrE proteins, respectively. Alternatively, inactivation of the phrA and phrE gene results from the deletion of a fragment of the phrA and the phrE gene that prevents the functional expression of the PhrA and the PhrE proteins, respectively. Thus, in some embodiments, a segment of the phrA gene is deleted, and a segment of the phrE gene is deleted from the chromosome. Similarly, the inactivation of the phrA and the phrE genes results from the deletion of the entire endogenous DNA sequence that encodes the PhrA and the deletion of a DNA sequence that encodes a fragment of the PhrE protein. Alternatively, the inactivation of the phrA and the phrE genes results from the deletion of the entire endogenous DNA sequence that encodes the PhrE and the deletion of a DNA sequence that encodes a fragment of the PhrA protein. Fragments of phr genes (e.g. phrA and/or phrE), include a range of about 1% to about 99% of the indigenous chromosomal region encoding the phrA and/or phrE proteins.

In other embodiments, fragments include a range of about 5% to 95% of the indigenous chromosomal region. In yet additional embodiments, fragments comprise at least about 99%, about 98%, about 97%, about 96%, about 95%, about 94%, about 93%, about 92%, about 90%, about 88%, about 85%, about 80%, about 75%, about 70%, about 65%, about 50%, about 40%, about 30%, about 25%, about 20% and about 10% of the indigenous chromosomal region.

In some embodiments, inactivation of the phrA and/or phrE genes is achieved by deletion resulting from homologous recombination. For example, in some embodiments when phr is the gene to be deleted, an inactivating DNA construct comprising a selectable marker flanked on each side by a homology box is used. The homology box comprises nucleotide sequences homologous to nucleic acids flanking regions of the chromosomal phr gene. The DNA construct aligns with the homologous sequences of the *Bacillus* host chromosome and in a double crossover event the phr gene is excised out of the host chromosome. The inactivating DNA construct is assembled in vitro, followed by direct cloning of the construct into a competent *Bacillus* host, such that the DNA construct becomes integrated into the *Bacillus* chromosome. For example, PCR fusion and/or ligation can be employed to assemble a DNA construct in vitro. In some embodiments, the DNA construct is a non-plasmid construct, while in other embodiments it is incorporated into a vector (e.g., a plasmid).

In other embodiments, the inactivating DNA construct comprises a selectable marker flanked on the 5' and 3' ends with a fragment of the gene sequence. In some embodiments, when the DNA construct comprising the selectable marker and gene, gene fragment or homologous sequence thereto is transformed into a host cell, the location of the selectable marker renders the gene non-functional for its intended purpose. In some embodiments, the inactivating DNA construct comprises the selectable marker located in the promoter region of the gene. In other embodiments, the inactivating DNA construct comprises the selectable marker located 3' to the promoter region of gene. In yet other embodiments, the inactivating DNA construct comprises the selectable marker located in the coding region of the gene. In further embodiments, the inactivating DNA construct comprises a selectable marker flanked by a homology box on both ends. In still further embodiments, the inactivating DNA construct includes a sequence that interrupts the transcription and/or translation of the coding sequence. In yet additional embodiments, the DNA construct includes restriction sites engineered at the upstream and downstream ends of the construct.

In another embodiment, inactivation of the phrA and/or phrE gene is by insertion of a selectable marker that interrupts the phrA and/or phrE gene in a single crossover event. In some embodiments, the selectable marker is located within the gene coding sequence or on a part of the plasmid separate from the gene. The vector is integrated into the *Bacillus* chromosome, and the gene is inactivated by the insertion of the vector in the coding sequence.

Other suitable means for inactivating a phr gene include introducing mutations that result in amino acid substitutions, and truncations that accompany a corresponding loss in the biological activity of the phr protein. In some embodiments, a modified *Bacillus* sp. cell comprises inactivation of one or more phr genes that results preferably in stable and non-reverting inactivation. Methods of mutating genes are well known in the art and include but are not limited to site-directed mutation, generation of random mutations, and gapped-duplex approaches (See e.g., U.S. Pat. No. 4,760,025;

Moring et al., Biotech. 2:646 [1984]; and Kramer et al., Nucleic Acids Res., 12:9441 [1984]).

Whether the inactivating DNA construct is incorporated into a vector or used without the presence of plasmid DNA, it is used to transform microorganisms. It is contemplated that any suitable method for transformation will find use with the present invention. In some embodiments, at least one copy of the inactivating DNA construct is integrated into the host *Bacillus* chromosome. In some embodiments, one or more inactivating DNA constructs of the invention are used to transform host cells. For example, one inactivating DNA construct may be used to inactivate a phrA gene and another construct may be used to inactivate a phrE gene. Of course, additional combinations are contemplated and provided by the present invention.

In some embodiments, the phrA and/or phrE gene is deleted in a precursor recombinant *Bacillus subtilis* strain in which one or more genes encoding an endogenous protease have been deleted. In some embodiments, the *Bacillus* sp. host cell comprises two or more inactivated protease genes. In some embodiments, the *Bacillus* host cell contains two inactivated protease genes (See e.g., U.S. Pat. No. 5,387,521) while in other embodiments, the *Bacillus* host cell contains 5 inactivated protease genes: nprE, aprE, epr, ispA, and bpr genes (See e.g., US20050202535). Since the sequence of the entire *B. subtilis* genome is publicly available and annotated (See e.g., Moszer, FEBS Lett., 430:28-36 [1998]), the proteases of *B. subtilis* have been identified and reviewed in detail (See e.g., He et al., Res. Microbiol., 142:797-803 [1991]). In addition, gene disruption methods for *Bacillus* cells are generally well known in the art (See e.g., Lee et al., Appl. Environ. Microbiol., 66: 476-480 [2000]; Ye et al., Proc. Internatl. Symp. Rec. Adv. Bioindustry, Seoul, Korea: The Korean Society for Applied Microbiology, pp. 160-169 [1996]; Wu et al., J. Bacteriol., 173:4952-4958 [1991]; and Sloma et al., J. Bacteriol., 173: 6889-6895 [1991]). Thus, the construction of such strains is well within the ability of one of skill in the art.

As indicated above, in some embodiments, the modified *Bacillus* sp. host cell comprises an inactivated phr gene and an inactivated rap gene. In one embodiment, the modified *Bacillus* sp. cell comprises a single rap operon that contains an inactivated phr gene and an inactivated rap gene (e.g., a rapA operon containing an inactive phrA gene and an inactivated rapA gene, a rapC operon containing an inactive phrC gene and an inactivated rapC gene; a rapE operon containing an inactive phrE gene and an inactivated rapE gene, a rapF operon containing an inactive phrF gene and an inactivated rapF gene, a rapI operon containing an inactive phrI gene and an inactivated rapI gene, or a rapK operon containing an inactive phrK gene and an inactivated rapK gene). In other embodiments, the modified *Bacillus* sp. cell comprises at least two rap operons each containing an inactivated phr gene and an inactivated rap gene. In some embodiments, inactivation results from the deletion of the entire endogenous DNA sequences that encode the Phr and the Rap proteins.

In some embodiments, the entire endogenous DNA sequence of the *Bacillus subtilis* phrA gene is deleted using the inactivating DNA deletion construct of SEQ ID NO:17. In *Bacillus subtilis* 168, the DNA sequence that encodes the PhrA protein MKSKWMSGLL LVAVGFSFTQ VMVHAG-ETAN TEGKTFHIAA RNQT; SEQ ID NO:42 (Swiss-Prot: Q00829) is:

```
                                            SEQ ID NO: 41
atgaaatctaaatggatgtcaggtttgttgctcgttgcggtcgggttc agctttactcaggtgatggttcatgcaggtgaaacagcaaacacagaa gggaaaacatttcatattgcggcacgcaatcaaaca;
(NP_389126).
```

Alternatively, inactivation of the phrA gene results from the deletion of a fragment of the phrA gene that prevents the functional expression of the PhrA protein. The phrA gene is located at about 1316305-1316439 bp of the *B. subtilis* 168 chromosome (Accession no. NC_000964). According to one embodiment, inactivation of the phrA gene is by insertion of a selectable marker that interrupts the phrA gene. Alternatively, inactivation of the phrA gene results from the inactivation of the rapA gene by introducing a selectable marker comprising a terminator sequence in the rapA gene thereby preventing the functional expression of the rapA and phrA protein According to one embodiment, inactivation of the rapA gene is by insertion of a selectable marker that interrupts the rapA gene.

In one embodiment, the endogenous DNA sequence of the *Bacillus subtilis* rapA gene is deleted using the inactivating DNA deletion construct of SEQ ID NO:52. In *Bacillus subtilis* 168, the DNA sequence that encodes the rapA protein:

```
                                                    SEQ ID NO: 54
MRMKQTIPSSYVGLKINEWYTHIRQFHVAEAERVKLEVEREIEDMEEDQDLLLYY

SLMEFRHRVMLDYIKPFGEDTSQLEFSELLEDIEGNQYKLTGLLEYYFNFFRGMYEFKQK

MFVSAMMYYKRAEKNLALVSDDIEKAEFAFKMAEIFYNLKQTYVSMSYAVQALETYQMY

ETYTVRRIQCEFVIAGNYDDMQYPERALPHLELALDLAKKEGNPRLISSALYNLGNCYEK

MGELQKAAEYFGKSVSICKSEKFDNLPHSIYSLTQVLYKQKNDAEAQKKYREGLEIARQY

SDELFVELFQFLHALYGKNIDTESVSHTFQFLEEHMLYPYIEELAHDAAQFYIENGQPEKA

LSFYEKMVHAQKQIQRGDCLYEI;
(Swiss-Prot: O00828) is
```

```
                                                    SEQ ID NO: 53
ttgaggatgaagcagacgattccgtcctcttatgtcgggcttaaaattaatgaatggtatactcatatccggcagttcc acgtcgctgaagccgaacgggtcaagctcgaagtagaaagagaaattgaggatatggaagaagaccaagatttgctgctg tattattctttaatggagttcaggcaccgtgtcatgctggattacattaagccttttggagaggacacgtcgcagctagagttttca
```

```
                                     -continued
gaattgttagaagacatcgaagggaatcagtacaagctgacagggcttctcgaatattactttaattttttcgaggaatgtatga atttaagcagaagatgtttgtcagtgccatgatgtattataaacgggcagaaaagaatcttgccctcgtctcggatgatattgag aaagcagagtttgcttttaaaatggctgagatttttttacaatttaaaacaaacctatgtttcgatgagctacgccgttcaggcatta gaaacataccaaatgtatgaaacgtacaccgtccgcagaatccaatgtgaattcgttattgcaggtaattatgatgatatgcag tatccagaagagcattgccccacttagaactggctttagatcttgcaaagaaagaaggcaatcccgcctg atcagttctgc cctatataatctcggaaactgctatgagaaatgggtgaactgcaaaaggcagccgaatactttgggaaatctgtttctatttgc aagtcggaaaagttcgataatcttccgcattctatctactctttaacacaagttctgtataaacaaaaaaatgacgccgaagcg caaaaaaagtatcgtgaaggattggaaatcgcccgtcaatacagtgatgaattatttgtggagcttttcaattttttacatgcgtta tacggaaaaaacattgacacagaatcagtctcacacacctttcaatttcttgaagaacatatgctgtatccttatattgaagagct ggcgcatgatgctgcccaattctatatagaaaacggacagcccgaaaaagcactttcattttatgagaaaatggtgcacgca caaaacaaatccagagaggagattgtttatatgaaatc;
```

(NP_389125).

In certain embodiments, the modified *Bacillus* sp. cell comprising the rap operon containing the inactive phr gene may contain an active or inactive rap gene. If the rap gene is active, it may have a wild-type sequence (e.g., may be endogenous to the cell) or may be modified such that it is functionally equivalent to the wild type protein of the same species.

In some embodiments, the modified *Bacillus* sp. host cell comprises an inactivated rap gene. In one embodiment, the modified *Bacillus* sp. cell comprises a single rap operon that contains an inactivated rap gene (e.g., a rapA operon containing an inactive an inactivated rapA gene, a rapB operon containing an inactive an inactivated rapB gene, a rapC operon containing an inactivated rapC gene, a rapD operon containing an inactive an inactivated rapD gene, a rapE operon containing an inactivated rapE gene, a rapF operon containing an inactivated rapF gene, a rapG operon containing an inactivated rapG, a rapI operon containing an inactivated rapI gene, a rapD operon containing an inactivated rapJ gene, or a rapK operon containing an inactivated rapK gene). In other embodiments, the modified *Bacillus* sp. cell comprises at least two rap operons each containing an inactivated rap gene. In some embodiments, inactivation results from the deletion of the entire endogenous DNA sequences that encode the Rap proteins.

The modified *Bacillus* sp. cell is derived from a precursor host cell of a *Bacillus* sp. strain including *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* strains. In some embodiments, the modified *Bacillus* sp. cell is derived from an alkalophilic *Bacillus* sp. cell. Numerous alkalophilic *Bacillus* sp. are known (See e.g., U.S. Pat. No. 5,217,878; and Aunstrup et al., Proc IV IFS: Ferment. Technol. Today, 299-305 [1972]). In some particular embodiments, the *Bacillus* sp. precursor host cell is an industrial *Bacillus* sp. host cell. Examples of industrial *Bacillus* sp. host cells include, but are not limited to *Bacillus licheniformis, Bacillus lentus, Bacillus subtilis,* and *Bacillus amyloliquefaciens* host cells. In additional embodiments, the *Bacillus* sp. host cell is selected from the group consisting of *Bacillus lentus, Bacillus brevis, Bacillus stearothermophilus, Bacillus alkalophilus, Bacillus coagulans, Bacillus circulans, Bacillus pumilus, Bacillus thuringiensis, Bacillus clausii,* and *Bacillus megaterium*, as well as other organisms within the genus *Bacillus*, as discussed above. In some particularly preferred embodiments, *Bacillus subtilis* is used. For example, U.S. Pat. Nos. 5,264,366 and 4,760,025 (RE 34,606) describe various *Bacillus* host strains that find use in the present invention, although other suitable strains (e.g., industrial strains) are contemplated for use in the present invention.

An industrial strain may be a non-recombinant strain of a *Bacillus* sp., a mutant of a naturally occurring strain, or a recombinant strain. Preferably, the host strain is a recombinant host strain wherein a recombinant polynucleotide encoding a polypeptide of interest has been introduced into the host. In some embodiments, the polypeptide of interest is an enzyme (e.g., a protease). A further preferred host strain is a *Bacillus subtilis* host strain, and in particular a recombinant *Bacillus subtilis* host strain. Numerous *Bacillus subtilis* strains are known, including but not limited to 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics, 73:215-228 [1973]; U.S. Pat. No. 4,450,235; U.S. Pat. No. 4,302,544; and EP 0134048). The use of *B. subtilis* as an expression host is further described by Palva et al. and others (See, Palva et al., Gene 19:81-87 [1982]; See also, Fahnestock and Fischer, J. Bacteriol., 165:796-804 [1986]; and Wang et al., Gene 69:39-47 [1988]).

Industrial protease producing *Bacillus* sp. host cells provide particularly preferred host cells. In some preferred embodiments, use of these host cells in the present invention enhances protease production. Two general types of proteases are typically secreted by *Bacillus* sp., namely neutral (or "metalloproteases") and alkaline (or "serine") proteases. Serine proteases are enzymes which catalyze the hydrolysis of peptide bonds in which there is an essential serine residue at the active site. Serine proteases have molecular weights in the 25,000 to 30,000 range (See, Priest, Bacteriol. Rev., 41:711-753 [1977]). Subtilisin is a preferred serine protease that is produced by the modified *Bacillus* sp. host cells of the present invention. A wide variety of *Bacillus* subtilisins have been identified and sequenced, for example, GG36, subtilisin 168, subtilisin BPN', subtilisin Carlsberg, subtilisin DY, subtilisin 147 and subtilisin 309 (See e.g., EP 414279 B; WO 89/06279; and Stahl et al., J. Bacteriol., 159:811-818 [1984]). In some embodiments of the present invention, the *Bacillus* host strains produce mutant (e.g., variant) proteases. Numerous references provide examples of variant proteases and reference (See e.g., WO 99/20770; WO 99/20726; WO 99/20769; WO 89/06279; RE 34,606; U.S. Pat. No. 4,914, 031; U.S. Pat. No. 4,980,288; U.S. Pat. No. 5,208,158; U.S. Pat. No. 5,310,675; U.S. Pat. No. 5,336,611; U.S. Pat. No. 5,399,283; U.S. Pat. No. 5,441,882; U.S. Pat. No. 5,482,849; U.S. Pat. No. 5,631,217; U.S. Pat. No. 5,665,587; U.S. Pat. No. 5,700,676; U.S. Pat. No. 5,741,694; U.S. Pat. No. 5,858, 757; U.S. Pat. No. 5,880,080; U.S. Pat. No. 6,197,567; and U.S. Pat. No. 6,218,165).

In another embodiment, a preferred Bacillus sp. host is a Bacillus sp. that includes a mutation or deletion in at least one of the following genes, degU, degS, degR and degQ. Preferably the mutation is in a degU gene, and more preferably the mutation is degU(Hy)32 (See e.g., Msadek et al., J. Bacteriol., 172:824-834 [1990]; and Olmos et al., Mol. Gen. Genet., 253:562-567 [1997]). In one embodiment, the host cell is a Bacillus subtilis host cell that carries a degU32(Hy) mutation. In a further embodiment, the Bacillus sp. host cell comprises a mutation or deletion in scoC4, (See e.g., Caldwell et al., J. Bacteriol., 183:7329-7340 [2001]); spoIIE (See e.g., Arigoni et al., Mol. Microbiol., 31:1407-1415 [1999]); oppA or other genes of the opp operon (See e.g., Perego et al., Mol. Microbiol., 5:173-185 [1991]). Indeed, it is contemplated that any mutation in the opp operon that causes the same phenotype as a mutation in the oppA gene will find use in some embodiments of the modified Bacillus sp. cell of the present invention. In some embodiments, these mutations occur alone, while in other embodiments, combinations of mutations are present. In some embodiments, a modified Bacillus sp. cell of the invention is derived from a Bacillus sp. host cell that already includes a mutation to one or more of the above-mentioned genes. In alternate embodiments, a modified Bacillus sp. cell of the invention is further engineered to include mutation of one or more of the above-mentioned genes.

Proteins of Interest

The invention provides modified Bacillus sp. cells that are used to produce proteins of interest at a level that is greater than that produced by the unmodified precursor host cells. Generally, proteins of interest are desirable proteins that have commercial significance. The protein of interest may be either homologous or heterologous to the host. In some embodiments, the protein of interest is a secreted polypeptide, particularly an enzyme, including but not limited to amylolytic enzymes, proteolytic enzymes, cellulytic enzymes, oxidoreductase enzymes and plant wall degrading enzymes. In further embodiments, these enzyme include, but are not limited to amylases, proteases, xylanases, lipases, laccases, phenol oxidases, oxidases, cutinases, cellulases, hemicellulases, esterases, peroxidases, catalases, glucose oxidases, phytases, pectinases, glucosidases, isomerases, transferases, galactosidases and chitinases. In still further embodiments, the expressed polypeptide is a hormone, cytokine, growth factor, receptor, vaccine, antibody, or the like. While it is not intended that the present invention be limited to any particular protein/polypeptide, in some most preferred embodiments, the expressed protein of interest is a protease.

As noted above, in certain embodiments the host cell contains a recombinant expression cassette that comprises a polynucleotide sequence encoding a protein of interest (i.e., an expression cassette for production of a protein that is not native to the host cell). In some embodiments, the host cell comprises a recombinant nucleic acid comprising an expression cassette (i.e., a promoter, a polynucleotide encoding the protein of interest, and a transcriptional terminator), wherein the expression cassette is sufficient for the production of the protein by the Bacillus sp. host cell. In some embodiments, the recombinant nucleic acid is integrated into the genome of the host cell, while in other embodiments, the recombinant nucleic acid is present in a vector that replicates autonomously from the genome. In some embodiments, the polynucleotide encoding the protein of interest is codon optimized for expression of the protein in the Bacillus sp. host cell. While any promoter may be employed in a subject expression cassette, promoters that are regulated by the rap/phr systems (e.g., the aprE and nprE promoters) may be employed in some embodiments.

In one embodiment, the protein of interest may be, for example, an enzyme (e.g., a so-called "industrial enzyme"), or a protein having therapeutic activity such an antibody. In one particular embodiment, the protein of interest is a subtilisin, where the term "subtilisin" refers to a serine endopeptidase of the S8 family of peptidases. Subtilisin protein has an activity described as EC 3.4.21.62 (previously EC 3.4.4.16), according to IUMBM enzyme nomenclature. The activity of exemplary subtilisin proteins is generally described in Philipp et al, (Mol. Cell. Biochem. 1983 51: 5-32), Siezen (Protein Sci., 1997 6:501-523); Bryan (Biochim. Biophys. Acta, 2000 1543:203-222); Maurer, 2004 Curr. Op, Biotechnol., 2004 15:330-334); and Gupta, Appl. Microbiol. Biotechnol., 2002 59:15-32).

In some embodiments, a subtilisin has an amino acid sequence that is found in a wild-type genome (i.e., the subtilisin is a naturally-occurring subtilisin), while in other embodiments, the subtilisin is a variant of a naturally-occurring subtilisin. In some embodiments, the variant subtilisin comprises an amino acid sequence that is at least about 80%, at least about 90%, at least about 95% or at least about 98% identical to a subtilisin encoded by a wild-type genome. Exemplary subtilisins include, but are not limited to: ALCALASE® (Novozymes), FNA™ (Genencor), SAVINASE® (Novozymes) PURAFECT™ (Genencor), KAP™ (Kao), EVERLASE™ (Novozymes), PURAFECT OxP™ (Genencor), FN4™ (Genencor), BLAP S™ (Henkel), BLAP X™ (Henkel), ESPERASE® (Novozymes), KANNASE™ (Novozymes) and PROPERASE™ (Genencor). In yet additional embodiments, the subtilisin includes, but is not limited to subtilisin BPN', subtilisin Carlsberg, subtilisin DY, subtilisin 147, or subtilisin 309 (See e.g., WO89/06279; and Stahl et al., J. Bacteriol., 159:811-818 [1984]). Additional subtilisins and other proteases that find use in the present invention include but are not limited to those described in WO 99/20770; WO 99/20726; WO 99/20769; WO 89/06279; RE 34,606; U.S. Pat. No. 4,914,031; U.S. Pat. No. 4,980,288; U.S. Pat. No. 5,208,158; U.S. Pat. No. 5,310,675; U.S. Pat. No. 5,336,611; U.S. Pat. No. 5,399,283; U.S. Pat. No. 5,441,882; U.S. Pat. No. 5,482,849; U.S. Pat. No. 5,631,217; U.S. Pat. No. 5,665, 587; U.S. Pat. No. 5,700,676; U.S. Pat. No. 5,741,694; U.S. Pat. No. 5,858,757; U.S. Pat. No. 5,880,080; U.S. Pat. No. 6,197,567; and U.S. Pat. No. 6,218,165.

In some embodiments, the expression of the protein of interest in a host cell is driven by the aprE promoter of the aprE gene from which the B. subtilis subtilisin is naturally transcribed. The aprE gene is transcribed by sigma A ($\sigma^A$) factor and its expression is highly controlled by several regulators, such as: DegU/DegS, AbrB, Hpr and SinR (Valle and Ferrari (1989) In: Smith I, Slepecky R A, Setlow P (eds) Regulation of Procaryotic Development. American Society for Microbiology. Washington, D.C. pp 131-146), and aprE Sigma A promoter has been identified tgggtcttgacaaatattattc-catctattacaataaattcacaga (SEQ ID NO:38; US 20030148461; Helman et al., 1995, Nucleic Acid Research, Vol. 24, pp. 2351-2360). In some embodiments, the host cell comprises an aprE promoter that is the wild-type aprE promoter tgggtc-tactaaaatattattccatctattacaataaattcacaga (SEQ ID NO:39; U.S. Patent Application Publication No. 20030148461).

In other embodiments, the expression of a protein of interest by a host cell is driven by mutant of the *B. subtilis* aprE promoters. In some embodiments, the invention provides for a *Bacillus* host cell that contains a mutant aprE promoter operably linked to a polynucleotide sequence that encodes a protein of interest. Thus, the invention encompasses host cells that express a protein of interest from a mutant aprE promoter. An example of a mutant aprE promoter is the mutant aprE promoter having the sequence:

tgggtc ttgaca aatattattccatctat tacaat aaattcacaga (SEQ ID NO:40), which is described in U.S. Patent Application Publication No. 20030148461. Any one of the proteins of interest recited herein (e.g., *Bacillus* subtilisins) can be transcribed from an aprE promoter. In some embodiments, the invention provides for a modified *Bacillus* host cell that is capable of expressing a protein of interest from an aprE promoter. In some embodiments, the modified host cell is a modified *B. subtilis* host cell capable of expressing a protease driven by an aprE promoter. In some embodiments, the aprE promoter includes the aprE promoter regulatory elements and/or the aprE transcriptional leader, while in other embodiments, the aprE promoter does not include the aprE promoter regulatory elements and/or the aprE transcriptional leader.

In addition to the aprE promoter, the invention also encompasses compositions and methods for expressing a protein of interest by a host cell, wherein the expression is driven by any promoter suitable for driving the transcription of the gene of interest as long as the promoter comprises the transcriptional leader sequence of the aprE gene. Other suitable promoters and terminators for use in *Bacillus* host cells are known and include: the promoters and terminators of npr (neutral protease; i.e., NprE promoter), amy (α-amylase) and α-lactamase genes, as well as the *B. subtilis* levansucrase gene (sacB), *B. licheniformis* alpha-amylase gene (amyL), *B. stearothermophilus* maltogenic amylase gene (amyM), *B. amyloliquefaciens* alpha-amylase gene (amyQ), *B. licheniformis* penicillinase gene (penP), *B. subtilis* xylA and xylB genes, the promoters and terminators described in WO 93/10249, WO 98/07846, and WO 99/43835.

In other embodiments, the modified host cell may produce a protein of interest that is a recombinant carbohydrase, such as a liquefying and saccharifying α-amylase, an alkaline α-amylase, a α-amylase, a cellulase; a dextranase, an α-glucosidase, an α-galactosidase, a glucoamylase, a hemicellulase, a pentosanase, a xylanase, an invertase, a lactase, a naringanase, a pectinase or a pullulanase; a protease such as an acid protease, an alkali protease, bromelain, ficin, a neutral protease, papain, pepsin, a peptidase, rennet, rennin, chymosin, thermolysin, an aspartic proteinase, or trypsin; a lipase or esterase, such as a triglyceridase, a phospholipase, a pregastric esterase, a phosphatase, a phytase, an amidase, an iminoacylase, a glutaminase, a lysozyme, or a penicillin acylase; an isomerase such as glucose isomerase; an oxidoreductases (e.g., an amino acid oxidase), a catalase, a chloroperoxidase, a glucose oxidase, a hydroxysteroid dehydrogenase or a peroxidase; a lyase such as a acetolactate decarboxylase, a aspartic β-decarboxylase, a fumarase or a histadase; a transferase such as cyclodextrin glycosyltransferase; or a ligase, for example. In particular embodiments, the protein may be an aminopeptidase, a carboxypeptidase, a chitinase, a cutinase, a deoxyribonuclease, an α-galactosidase, a β-galactosidase, a β-glucosidase, a laccase, a mannosidase, a mutanase, a pectinolytic enzyme, a polyphenoloxidase, ribonuclease or transglutaminase.

In particular embodiments, the protein may be a therapeutic protein. Examples of suitable target therapeutic proteins which may be produced using a subject cell include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, IgA, interleukins, urokinase, chymase, and urea trypsin resume inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist. Monoclonal antibodies may also be made.

In certain embodiments, the cell may be engineered so that the protein produced by the cell may be secreted from the cell into culture media. As such, the cell may further contain a recombinant nucleic acid encoding a fusion polypeptide containing a signal sequence, a protease cleavage site and the protein. In some embodiments, the signal sequence may be one that is naturally associated with the polypeptide to be expressed. The signal sequence may be any sequence of amino acids that is capable of directing the fusion protein into the secretory pathway of the *Bacillus* host cell. In certain cases, signal sequences that may be employed include the signal sequences of proteins that are secreted from wild-type *Bacillus* cells. Such signal sequences include the signal sequences encoded by α-amylase, protease (e.g., aprE or subtilisin E), or β-lactamase genes. Exemplary signal sequences include, but are not limited to, the signal sequences encoded by an α-amylase gene, a subtilisin gene, a β-lactamase gene, a neutral protease gene (e.g., nprT, nprS, nprM), or a prsA gene from any suitable *Bacillus* species, including, but not limited to *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis*. In one embodiment, the signal sequence is encoded by the aprE gene of *B. subtilis* (as described in Appl. Microbiol. Biotechnol. 2003 62:369-73). Further signal peptides are described by Simonen and Palva (Microbiological Reviews 1993 57: 109-137), and other references.

The invention also provides methods for producing a protein of interest in a modified *Bacillus* sp. host cell, which comprises at least one inactivated phr gene (e.g., an inactivated phrA and/or a phrE gene), or an inactivated phr and an inactivated rap gene by culturing a modified cell that is capable of producing a protein of interest and growing the cell under suitable growth conditions for expressing the protein of interest. The methods provide for the production of any one protein of interest described above. In preferred embodiments, the protein of interest produced by the method of the invention is a protease (e.g., a subtilisin). Production of a protein of interest by a modified *Bacillus* sp. cell is greater than that obtained from a corresponding unmodified precursor host cell. In some embodiments, the improved level of protease production by a modified *Bacillus* sp. cell is further enhanced in the modified cell by overexpressing ymaH, as described below.

Modified *Bacillus* sp. Host Cells that Overexpress YmaH

In the embodiments described above, the modified *Bacillus* sp. cells, which comprise at least one inactivated phr gene and/or an inactivated rap gene, have an enhanced capacity to produce a protein of interest at a level that is greater than that reached by an unmodified precursor cell. In further embodiments described below, the enhanced level of production of a protein of interest by the modified *Bacillus* sp. cells is further increased by altering the modified cell to overexpress the RNA-binding protein ymaH. Thus, in one embodiment, the invention provides for a modified *Bacillus* sp. cell that comprises at least one inactivated phr gene (e.g., an inactivated phrA and/or phrE gene), a polynucleotide that encodes a protein of interest (e.g., a protease), and a heterologous polynucleotide that encodes a YmaH protein. In another embodiment, the modified *Bacillus* sp. cell comprises at least one inactivated phr gene (e.g. an inactivated phrA and/or phrE gene), and/or an inactivated rap gene, a polynucleotide that encodes a protein of interest (e.g., a protease), and a heterologous polynucleotide that encodes a YmaH protein.

In some embodiments, the modified *Bacillus* sp. cell comprises a polynucleotide expression construct comprising a YmaH promoter that is operably linked to a polynucleotide sequence that encodes a YmaH protein. The *Bacillus subtilis* YmaH, also known as HFQ_BACSU is an RNA-binding protein, is a member of the Hfq family of RNA-binding proteins (Sauter et al., Nucleic Acid Res 31:4091-4098, [2003]). The YmaH protein is encoded in *Bacillus subtilis* by the ymaH gene, which is an ortholog of the hfq gene of *E. coli*. (Silvaggi et al., J Bacteriol. 187(19): 6641-6650, [2005]). YmaH is an abundant and ubiquitous RNA-binding protein that functions as a pleiotrophic regulator of RNA metabolism in prokaryotes, and is required for stabilization of some transcripts and degradation of others. YmaH binds preferentially to unstructured A/U-rich RNA sequences and is similar to the eukaryotic Sm proteins in both sequence and structure. YmaH is also known to bind small RNA molecules called riboregulators that modulate the stability or translation efficiency of RNA transcripts.

The naturally-occurring YmaH protein from *Bacillus subtilis* is a 73 amino acid protein:

MKPINIQDQFLNQIRKENTYVTVFLLNGFQLRGQV-KGFDNFTVLLESEGKQQLIYKHAISTFAPQKNVQLE-LE (Swiss-Prot:P3756; SEQ ID NO:45)

that is encoded by a 219 (222 including the stop codon) base pair polynucleotide (EMBL Primary Accession Number Z99113; SEQ ID NO:46).

Thus, in some embodiments, the modified *Bacillus* sp. cell of the invention further comprises a heterologous polynucleotide sequence that encodes ymaH. In one embodiment, the ymaH protein is encoded by the naturally-occurring polynucleotide sequence found in the genome of the wild-type *Bacillus subtilis* strain 168 (SEQ ID NO:45). In some embodiments, the modified *Bacillus* sp. cell of the invention comprises a heterologous polynucleotide sequence that encodes variants of the naturally occurring ymaH. Variant YamH proteins include proteins derived from the wild-type protein by deletion (i.e., truncation), addition, or substitution of one or more amino acids at one or more sites in the native protein. Methods for such deletions, additions and substitutions are generally known in the art. For example, amino acid sequence variants of the polypeptide can be prepared by mutations in the cloned DNA sequence encoding the native protein of interest. Methods for mutagenesis and nucleotide sequence alterations are well known in the art (See e.g., Kunkel (1985) Proc. Natl. Acad. Sci. USA 82:488 492; Kunkel et al. (1987) Methods Enzymol. 154:367 382; U.S. Pat. No. 4,873,192; and the references cited therein; herein incorporated by reference. In constructing variants of the proteins of interest, modifications to the nucleotide sequences encoding the variants will be made such that variants continue to possess the desired activity. As will be understood by the skilled artisan, due to the degeneracy of the genetic code, a variety of modified polynucleotides encode a YmaH protein. In some other embodiments of the present invention, the *Bacillus* sp. cell comprises a polynucleotide encoding a YmaH protein comprising a nucleotide sequence having at least about 70% sequence identity, at least about 75% sequence identity, at least about 80% sequence identity, at least about 85% sequence identity, at least about 90% sequence identity, at least about 92% sequence identity, at least about 95% sequence identity, at least about 97% sequence identity, at least about 98% sequence identity, or at least about 99% sequence identity to the polynucleotide sequence of SEQ ID NO:46.

In other embodiments, the modified *Bacillus* sp. cell comprises polynucleotide constructs that comprise ymaH coding sequences that are analogous to the ymaH coding sequence of *Bacillus subtilis* strain 168. The genome of this strain, which is contained in one 4215 kb genome, has been well-characterized (See, Kunst et al., Nature 390:249-256 [1997]; and Henner et al., Microbiol. Rev., 44:57-82 [1980]). In some embodiments, the YmaH-encoding polynucleotide constructs encode a YmaH protein that shares at least about 65% amino acid sequence identity, at least about 70% amino acid sequence identity, at least about 75% amino acid sequence identity, at least about 80% amino acid sequence identity, at least about 85% amino acid sequence identity, at least about 90% amino acid sequence identity, at least about 92% amino acid sequence identity, at least about 95% amino acid sequence identity, at least about 97% amino acid sequence identity, at least about 98% amino acid sequence identity, and at least about 99% amino acid sequence identity with the amino acid sequence of the wild-type form of the YmaH protein and that has comparable or improved ability to enhance the production of a protein of interest in a host cell when compared to the wild-type polypeptide (SEQ ID NO:45), and that retains the ability to enhance the expression of a protein of interest in a *Bacillus* sp. (e.g., *Bacillus subtilis*) host cell. In yet other embodiments, the modified *Bacillus* sp. cell comprises YmaH-encoding polynucleotide constructs comprising polynucleotide sequences that are homologous, orthologous or paralogous to genes of the wild-type *Bacillus* sequence of SEQ ID NO:46 and that retain the ability to enhance the production of a protein of interest.

In other embodiments, the modified *Bacillus* sp. cell of the invention also encompasses polynucleotide constructs that comprise coding sequences encoding YmaH proteins that are related by being structurally and/or functionally similar. In some embodiments, these proteins are derived from a different genus and/or species, including differences between classes of organisms (e.g., a bacterial protein and a fungal protein). In some embodiments, these proteins are derived from a different genus and/or species. In additional embodiments, related proteins are provided from the same species. Indeed, it is not intended that the present invention be limited to related proteins from any particular source(s). In addition, the term "related proteins" encompasses tertiary structural homologs and primary sequence homologs (e.g., the YmaH of the present invention). For example, the present invention encompasses such homologues including but not limited to such YmaH proteins as the YmaH of *E. coli*, (HFQ_ECOLI), *Shighella flexneri* (HFQ_SHIFL), *Salmonella typhimurium* (HFQ_SALTY), *Yersinia enterocolitica* (HFQ_YEREN), *Yersinia pestis* (HFQ_YERPE), *Erwinia carotovora* (HFQ_ERWCA), *Haemophilus influenzae* (HFQ_HAEIN), *Pasteurella multocida* (HFQ_PASMU), *Vibrio cholerae* (HFQ_VIBCH), *Pseudomonas aeruginosa* (HFQ_PSEAE), *Xanthomonas axonopodis* (HFQ_XANAC), *Xanthomonas campestris* (HFQ_XANCP), *Xylella fastidiosa* (GSQ_XYLFA), *Neisseria meningitidis* (HFQ_NEIMA), *Ralstonia solanacearum* (HFQ_RALSO), *Agrobacterium tumefaciens* (HFQ_AGRTS), *Brucella melitensis* (HFQ_BRUME), *Rhizobium loti* (HFQ_RHILO), *Azorhizobium caulinodans* (HFQ_AZOCA), *Caulobacter crescentus* (HFQ_CAUCR), *Aquifex melitensis* (HFQ_AQUAE), *Thermotoga maritime* (HFQ_THEMA), *Clostridium acetobutylicum* (HFQ_CLOAB), *Clostridium perfringens* (HFQ_CLOPE), *Bacillus halodurans* (HFQ_BACHD), *Bacillus subtilis* (HFQ_BACSU), *Thermoanaerobacter tengcongensis* (HFQ_THETN), *S. aureaus* (Q99UG9), and *M. jannasci* (Q58830) (Sauter et al., Nucleic Acids Res. 31:4091-4098 [2003]).

Related (and derivative) proteins comprise variant YmaH proteins. In some preferred embodiments, variant proteins differ from a parent protein and one another by a small number of amino acid residues. The number of differing amino acid residues may be one or more, preferably about 1, 2, 3, 4, 5, 10, 15, 20, 30, 40, 50, or more amino acid residues. In some preferred embodiments, the number of different amino acids between variants is between about 1 and about 10. In some particularly preferred embodiments, related proteins and particularly variant proteins comprise at least about 70%, about 75%, about 80%, about 85%, about 90%, about 95%, about 97%, about 98%, or about 99% amino acid sequence identity. Several methods are known in the art that are suitable for generating variants of the YmaH proteins of the present invention, including but not limited to site-saturation mutagenesis, scanning mutagenesis, insertional mutagenesis, random mutagenesis, site-directed mutagenesis, and directed-evolution, as well as various other recombinatorial approaches.

Characterization of wild-type and mutant proteins is accomplished via any means suitable and is preferably based on the assessment of properties of interest. For example, it is contemplated that YmaH proteins that are capable of further enhancing the production of a protein of interest by a modified *Bacillus* sp. cell will find use.

Overexpression of ymaH in the modified *Bacillus* sp. cell of the invention can be achieved by various means including enhancing the transcription and/or translation of the YmaH encoding polynucleotide. For example, at the transcriptional level, overexpression of ymaH can be achieved by increasing the number of polynucleotide sequences that encode ymaH in a host cell, and/or by increasing the binding strength of a ymaH promoter to enhance the activity of the cognate RNA polymerase. At the translational level, overexpression of ymaH can be achieved by enhancing the translational activity by mutating the ribosome binding site (RBS) to increase the affinity of ribosomes for the RBS. One skilled in the art will recognize that overexpression of ymaH can be effected by increasing the number of copies of the ymaH gene alone or in combination with other possible modifications made to the ymaH gene to achieve the overexpression of YmaH.

In one embodiment, the modified *Bacillus* sp. cells of the invention comprise a polynucleotide construct that comprises a polynucleotide sequence encoding ymaH operably linked to a ymaH promoter. The transcription of ymaH may be naturally driven by two promoters: a SigA promoter that is present upstream of miaA coding region, and the SigH promoter that is immediately upstream of the ymaH coding region in the miaA operon of *B. subtilis*. A ymaH promoter can be any promoter that drives the expression of yamH (e.g., a SigA and/or a SigH promoter), and may be any nucleic acid sequence which shows transcriptional activity in the host cell of choice and includes mutant, truncated and hybrid promoters, and may be obtained from genes encoding extracellular or intracellular polypeptides either homologous or heterologous to the host cell. The promoter sequence may be native or foreign to the host cell.

In one embodiment, the modified *Bacillus* sp. cells of the invention comprise a polynucleotide construct that comprises a polynucleotide sequence that encodes YmaH operably linked to a SigH promoter (e.g., SEQ ID NO:23, as shown below). SEQ ID NO:23 also exemplifies a polynucleotide construct that comprises a YmaH coding sequence that is naturally contiguous with a SigH promoter:

```
                                        (SEQ ID NO: 23)
ggcaccgaattcgacgtggtttcgcaacaaaatgcaggtcacatggtt cgatatgacaccgcctgttgatatggagctgaaaaaaaaggaaatttt cacacatatagcaggaaaactcgaactttaatcgaaactgtatgatat agagaatcaaggaggacgaaacatgaaaccgattaatattcaggatca gtttttgaatcaaatccggaaagaaaatacgtatgtcactgttttttt gctgaacggctttcagttgcggggccaggtgaaaggctttgataactt taccgtattgttggaatcggaaggtaagcagcagcttatatataaaca tgcgatctcaacgtttgcgccgcaaaaaaacgtccagcttgaactcga atagatcaaaaaatgccatgtcaagacatgaggaaaggctgtcgggggg ttcccggcggccatttttaacatgaatccacttttgctccaagctttt tgtgtaagctgaccatgccaaggcacggtctttttttatgagggatcc ggagcc.
```

In another embodiment, the modified *Bacillus* sp. cells of the invention comprise a polynucleotide construct that comprises a polynucleotide sequence that encodes YmaH operably linked to a SigA promoter (e.g., SEQ ID NO:26 (SigA1) and SEQ ID NO:31 (SigA2 construct)). SEQ ID NOs:26 and 31 exemplify embodiments wherein the ymaH coding sequence is contiguous with a SigA promoter sequence to provide a chimeric polynucleotide construct. In some preferred embodiments, chimeric polynucleotide constructs thus comprise a promoter sequence that in nature is not contiguous with the ymaH coding sequence. For example, SEQ ID NOS: 26 and 31 exemplify chimeric constructs that comprise a SigA promoter that is operably linked to a polynucleotide sequence encoding YmaH, as shown below:

```
                                        (SEQ ID NO: 26)
gcgccgaattctcatacctgaaaggaaagacaagggaaattgtcggc aatgagccgctcggcaggtagaaggatgtttaccgatgcaaaaaaagg gcaaaatggataggtggttgtccatgttgaatgctataatgggggaga tttataaaagagagtgatacatattgaataatacgaagcagcccaca catatagcaggaaaactcgaactttaatcgaaactgtatgatatagag aatcaaggaggacgaaacatgaaaccgattaatattcaggatcagttt
```

-continued
ttgaatcaaatccggaaagaaaatacgtatgtcactgttttttgctg aacggctttcagttgcgggccaggtgaaaggctttgataactttacc gtattgttggaatcggaaggtaagcagcagcttatatataaacatgcg atctcaacgtttgcgccgcaaaaaaacgtccagcttgaactcgaatag atcaaaaaatgccatgtcaagacatgaggaaaggctgtcggggttcc cggcggccattttaacatgaatccacttttgctccaagcttttgtg taagctgaccatgccaaggcacggtctttttttatgagggatccggtg cc (SEQ ID NO: 31)
gcgccgaattctcatacccgaaaggaaagacaagggaaattgtcggc aatgagccgctcggcaggtagaaggatgtttaccgatgcaaaaaagg gcaaatggataggtggttgtccatgttgaatgctataatgggggaga tttataaaagagagtgctcgaactttaatcgaaactgtatgatataga gaatcaaggaggacgaaacatgaaaccgattaatattcaggatcagtt tttgaatcaaatccggaaagaaaatacgtatgtcactgttttttgct gaacggctttcagttgcgggccaggtgaaaggctttgataactttac cgtattgttggaatcggaaggtaagcagcagcttatatataaacatgc gatctcaacgtttgcgccgcaaaaaaacgtccagcttgaactcgaata gatcaaaaaatgccatgtcaagacatgaggaaaggctgtcggggttc ccggcggccattttaacatgaatccacttttgctccaagcttttgt gtaagctgaccatgccaaggcacggtctttttttatgagggatccggt gcc In yet another embodiment, the *Bacillus* sp. cells of invention comprise a polynucleotide construct that comprise a polynucleotide sequence that encodes YmaH and a SigA and a SigH promoter (e.g., SEQ ID NO: 22, as shown below).

(SEQ ID NO: 22)
tcatacccgaaaggaaagacaagggaaattgtcggcaatgagccgct cggcaggtagaaggatgtttaccgatgcaaaaaagggcaaatggat aggtggttgtccatgttgaatgctataatgggggagatttataaaaga gagtgatacatattgaataatacgaagcagcccgttgtcattttagtc ggaccgacggcagtggggaaaaccaatttaagtattcagctagccaaa tccttaaacgcggaaattatcagcggagattcgatgcagatttataaa gggatggatattggaacagctaaaattaccgaacaggagatggaggga gtgcccatcatctgattgacattttagatccccaagactctttctct actgccgattatcaaagcttagtaagaaataaaatcagcgagattgca aatagaggaaagcttccgatgattgacggcggtacagggctttatata caatctgagctttacgattatacatttacggaagaggcaaatgatccc gtgtttcgagagagcatgcaaatggctgctgagcgggaaggcgctgac tttcttcatgccaaacttgctgcagcagatcccgaggcagcagctgcg attcatccgaataatacaagaagagtcattcgcgcactggaaattta catacgtccggaaaaacgatgtcccagcatttgaaggaacaaaaacga -continued
gaacttctgtacaatgcagtgttaattggcctgacaatggatagagac acgctttacgaaagaattaatcagcgggtcgatttgatgatgcagtca ggccttcttccggaagtgaaacgcttatacgacaagaacgtgagagac tgtcaatcaatacaggcgataggctataaagagctgtatgcatatttt gacggttttgtgacactttccgatgctgtcgaacagctaaagcagaac tcgaggcggtatgcgaaacgccagctgacgtggtttcgcaacaaaatg caggtcacatggttcgatatgacaccgcctgttgatatggagctgaaa aaaaaggaaattttcacacatatagcaggaaaactcgaactttaatcg aaactgtatgatatagagaatcaaggaggacgaaacatgaaaccgatt aatattcaggatcagttttgaatcaaatccggaaagaaaatacgtat gtcactgttttttgctgaacggctttcagttgcgggccaggtgaaa ggctttgataactttaccgtattgttggaatcggaaggtaagcagcag cttatatataaacatgcgatctcaacgtttgcgccgcaaaaaaacgtc cagcttgaactcgaatagatcaaaaaatgccatgtcaagacatgagga aaggctgtcggggttcccggcggccattttaacatgaatccactt tgctccaagcttttgtgtaagctgaccatgccaaggcacggtctttt tttatgag Examples of suitable promoters for directing the expression of the ymaH gene in are the SigA and the SigH promoters from the *B. subtilis* operon that encompasses the gene encoding miaA. For example, in one embodiment, the invention provides a polynucleotide sequence defining a SigA promoter (SEQ ID NO:47, as shown below).

(SEQ ID NO: 47)
tcatacccgaaaggaaagacaagggaaattgtcggcaatgagccgct cggcaggtagaaggatgtttaccgatgcaaaaaagggcaaatggat aggtggttgtccatgttgaatgctataatgggggagatttataaaaga gagtgatacata In another embodiment, the invention provides a polynucleotide sequence defining a SigH promoter (SEQ ID NO:48, as shown below).

(SEQ ID NO: 48)
aaaggaaattttcacacatatagcaggaaaactcgaactttaatcgaa actgtatgatatagagaatcaaggaggacgaaac Other examples of promoters that can be used for expressing the ymaH gene include Sigma A promoters that are recognized by $\sigma^A$ factor including the promoter of the *Streptomyces coelicolor* agarase gene (dagA), the promoter of the *Bacillus lentus* alkaline protease gene (aprH), the promoter of the *Bacillus licheniformis* alkaline protease gene (subtilisin Carlsberg gene), the promoter of the *Bacillus subtilis* levansucrase gene (sacB), the promoter of the *Bacillus subtilis* alpha-amylase gene (amyE), the promoter of the *Bacillus licheniformis* alpha-amylase gene (amyL), the promoter of the *Bacillus stearothermophilus* maltogenic amylase gene (amyM), and the promoter of the *Bacillus amtyloliquefacietis* alpha-amylase gene (amyQ). Examples of promoters that can be used for expressing the ymaH gene include Sigma H promoters that are recognized by $\sigma^H$ factors including spo0A, spo0F, spoVG and citG (See, Helmann, J. D. and C. P. Moran. 2002. RNA polymerase and sigma factors, pp 289-312 In A. L. Sonenshein, J. A. Hoch and R. Losick (ed), *Bacillus subtilis* and its closest relatives: from genes to cells. American Society for Microbiology, Washington, D.C.).

In some embodiments, a consensus SigA and/or SigH promoter finds use in the present invention. The construction of a consensus promoter may be accomplished by site-directed mutagenesis to create a promoter which conforms more perfectly to the established consensus sequences for the "−10" and "−35" regions of the "sigma A-type" promoters for *Bacillus subtilis* (Voskuil et al., Mol Microbiol 17: 271 279 [1995]). In other embodiments, a consensus promoter is created by site-directed mutagenesis to create a promoter which conforms more perfectly to the established consensus sequences for the "−10" and "−35" regions of the vegetative "sigma H-type" promoters for *Bacillus subtilis* (See, Helman and Moran in *Bacillus subtilis* and its closest relatives, Ch. 21, pg 289-312; Sonenshein et al (2002 ASM Press, Washington, D.C.) The consensus sequence for the "−35" region for the sigma A-type promoter is TTGaca and for the "−10" region is tgnTATaat, and the consensus sequence for the "−35" region for the sigma H-type promoter is RnAGGAwWW and for the "−10" region is RnnGAAT. Capital letters indicate highly conserved positions; lower case letters indicate less conserved positions; abbreviation R can be A or G, and W can be A or T. The consensus promoter may be obtained from any promoter which can function in a *Bacillus* host cell.

In some embodiments, the SigA promoter, which encompasses SEQ ID NO:47 is defined by a polynucleotide sequence that is naturally present upstream of the miaA coding sequence (NP_389615; SEQ ID NO:49, shown below), while the SigH promoter, which encompasses SEQ ID NO: 48, is defined by the polynucleotide sequence that is naturally present upstream of the yamH coding region (SEQ ID NO:46, shown below).

```
                                    (SEQ ID NO: 49)
ttgaataatacgaagcagcccgttgtcattttagtcggaccgacggca gtggggaaaaccaatttaagtattcagctagccaaatccttaaacgcg gaaattatcagcggagattcgatgcagatttataaagggatggatatt ggaacagctaaaattaccgaacaggagatggagggagtgccccatcat ctgattgacattttagatccccaagactctttctctactgccgattat caaagcttagtaagaaataaaatcagcgagattgcaaatagaggaaag cttccgatgattgacggcggtacagggctttatatacaatctgagctt tacgattatacatttacggaagaggcaaatgatcccgtgtttcgagag agcatgcaaatggctgctgagcgggaaggcgctgactttcttcatgcc aaacttgctgcagcagatcccgaggcagcagctgcgattcatccgaat aatacaagaagagtcattcgcgcactggaaattttacatacgtccgga aaaacgatgtcccagcatttgaaggaacaaaaacgagaacttctgtac aatgcagtgttaattggcctgacaatggatagagacacgctttacgaa agaattaatcagcgggtcgatttgatgatgcagtcaggccttcttccg gaagtgaaacgcttatacgacaagaacgtgagagactgtcaatcaata caggcgataggctataaagagctgtatgcatattttgacggttttgtg acactttccgatgctgtcgaacagctaaagcagaactcgaggcggtat
```

-continued
```
gcgaaacgccagctgacgtggtttcgcaacaaaatgcaggtcacatgg ttcgatatgacaccgcctgttgatatggagctgaaaaaaaaggaaatt ttcacacatatagcaggaaaactcgaactttaa
```

```
                            (NP_389616; SEQ ID NO: 46)
atgaaaccgattaatattcaggatcagttttttgaatcaaatccggaaa gaaaatacgtatgtcactgttttttttgctgaacggctttcagttgcgg ggccaggtgaaaggctttgataaactttaccgtattgttggaatcggaa ggtaagcagcagcttatatataaacatgcgatctcaacgtttgcgccg caaaaaaacgtccagcttgaactcgaatag
```

In some embodiments, the SigA/SigH constructs encompass promoter sequences that have been mutated to increase the activity of the promoter when compared to the activity of the corresponding wild-type promoter resulting in the overexpression of the YmaH protein. Thus, it is understood that variants of the sequences that define the SigA and SigH promoters find use in the YmaH-expression constructs. Methods for creating promoter variants in *Bacillus* sp. are well known in the art (See e.g., Helmann et al., 2002. RNA polymerase and sigma factors, pp 289-312 In A. L. Sonenshein, J. A. Hoch and R. Losick (ed), *Bacillus subtilis* and its closest relatives: from genes to cells. American Society for Microbiology, Washington, D.C.) It is not intended that the present invention be limited to any particular promoter, as any suitable promoter known to those skilled in the art finds use with the present invention. Nonetheless, in some embodiments, the promoter is the *B. subtilis* sigH promoter, while in other embodiments the promoter is the *B. subtilis* sigA promoter. In further embodiments, the sigH and the sigA promoters serve to effect the overexpression of YmaH protein.

In some embodiments, the SigA/SigH polynucleotide constructs of the invention also comprise the requisite ribosome binding site to ensure optimal translation of the ymaH RNA transcript. In some embodiments, the polynucleotide construct comprises the ribosome bind site (RBS) sequence of the miaA gene (aagagag; SEQ ID NO:50), while in other embodiments, polynucleotide construct comprises the RBS sequence of the ymaH gene (ggagg; SEQ ID NO:51). In yet other embodiments, the polynucleotide construct comprises the ribosome binding site sequences of the miaA and the ymaH genes. In some embodiments, the invention provides constructs having the promoter and ribosome binding site sequences upstream of the ymaH coding sequence. The invention is not limited to the ribosome binding site sequences disclosed herein, as it also encompasses any suitable ribosome binding site sequences that have been mutated to increase the level of expression of the ymaH gene. Methods for obtaining mutated ribosome binding sequences that increase the expression of a gene in *Bacillus* are known in the art. For example, Band and Henner successfully increased the level of expression of Interferon in *B. subtilis* by modifying the RBS to obtain a tighter base-pairing to the 16S rRNA (Band, L. and D. J. Henner, DNA 3:17-21 [1984]).

Production of a Protein of Interest in a Modified Cell

In some embodiments, the invention provides methods for producing a protein of interest in a modified *Bacillus* sp. host cell, which comprises at least one inactivated phr gene (e.g., an inactivated phrA and/or a phrE gene), or an inactivated phr and/or rap gene by culturing a modified cell that is capable of producing a protein of interest and growing the cell under suitable growth conditions for expressing the protein of interest. The methods provide for the production of any one protein of interest described above. In some embodiments, the protein of interest produced by the method of the invention is a protease (e.g., a subtilisin).

In one embodiment, the method of the invention comprises inactivating at least one phr gene by introducing an inactivating DNA construct into a *Bacillus* sp. host cell to generate a modified *Bacillus* sp. host cell, and growing the modified cell under suitable conditions to produce a protein of interest at a level that is greater than that produced by the unmodified or precursor *Bacillus* host cell. Precursor host cells include precursor host cells of *Bacillus* sp. strains as described above, including *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* strains. In some embodiments, the precursor host cell is a *Bacillus subtilis* host cell. Preferably, the precursor host cells are recombinant cells comprising a recombinant polynucleotide that encodes a polypeptide of interest, as described above. In some embodiments, the polypeptide of interest is an enzyme (e.g., a protease, such as a subtilisin). The method of inactivating at least one phr gene (e.g. phrA and/or phrE) in a precursor *Bacillus* sp. host cell, generates a modified *Bacillus* sp. cell that produces a polypeptide of interest at a level that is greater than that achieved by the corresponding unmodified precursor host cell.

In one embodiment, the method comprises inactivating a phrA gene by introducing into the precursor *Bacillus* sp. host cell an inactivating DNA construct that deletes the indigenous phrA gene. For example the inactivating DNA construct of SEQ ID NO:17 is introduced to delete the indigenous phrA gene by homologous recombination. In another embodiment, the method comprises inactivating a phrE gene by introducing into the precursor *Bacillus* sp. host cell an inactivating DNA construct that deletes the indigenous phrE gene. For example the inactivating DNA construct of SEQ ID NO:18 is introduced to delete the indigenous phrE gene by homologous recombination. In yet another embodiment, both the phrA and phrE genes are inactivated using the inactivating constructs of SEQ ID NOs:17 and 18. The method of the invention is similarly used to inactivate other phr genes including phrC, phrF, phrG, phrH, phrI, and phrK and/or the rap genes including rap B, rapC, rapD, rapE, rapF, rapG, rapH, rapt, rapJ and rapK.

According to one embodiment, inactivation of the phrA gene is by insertion of a selectable marker that interrupts the phrA gene. Alternatively, inactivation of the phrA gene results from the inactivation of the rapA gene by introducing a selectable marker comprising a terminator sequence in the rapA gene thereby preventing the functional expression of the rapA and phrA protein According to one embodiment, inactivation of the rapA gene is by insertion of a selectable marker that interrupts the rapA gene.

Methods for inactivating phr and/or rap genes are exemplified in the experimental section below.

Production of a protein of interest (e.g., a protease), by a modified *Bacillus* sp. cell comprising at least one inactivated phr gene and/or rap gene as described above, is greater than that obtained from a corresponding unmodified precursor cell.

In some embodiments, the production of a protein of interest by a modified *Bacillus* sp. cell is further enhanced from the expression of one or more copies of a YmaH-encoding polynucleotide comprised in an expression construct that is present on a multicopy/replicating plasmid that has been introduced into the modified cell. Any one of the YmaH-encoding polynucleotide constructs described above (e.g., SigA; SigA1, SigA2, SigA3) or SigH constructs, are used to transform the modified *Bacillus* sp. cells. In some embodiments, the YmaH-encoding polynucleotide that is present on a replicating plasmid is introduced into a precursor host cell prior to the precursor host cell being modified to contain a deletion in at least one phr and/or rap gene. Thus, in some embodiments, the invention provides for modified *Bacillus* sp. cell comprising a vector comprising an expression construct comprising a YmaH-encoding polynucleotide operably linked to a YmaH promoter that is incorporated into the vector. In some embodiments, overexpression of YmaH is achieved by introducing a SigH expression construct that comprises a YmaH-encoding polynucleotide operably linked to a SigH promoter (e.g., the expression construct of SEQ ID NO:23). In embodiments, overexpression of YmaH is achieved by introducing a SigA expression construct that comprises a YmaH-encoding polynucleotide operably linked to a SigA promoter. Examples of SigA constructs include the SigA1 expression construct of SEQ ID NO:26, the SigA2 expression construct of SEQ ID NO:31, and the SigA3 construct of SEQ ID NO:22.

In some embodiments, the vector is a multicopy/replicating plasmid vector which forms an extrachromosomal self-replicating genetic element that overexpresses YmaH in the modified cell. Typically, the vector is a plasmid vector, which carries a selectable marker gene that allows for ease of selecting the host cells that contain the plasmid. Vectors that replicate autonomously in a host cell include vectors that comprise an origin of replication, which enables the vector to replicate autonomously in the *Bacillus* cell. Examples of bacterial origins of replication are the origins of replication of plasmids pBR322, pUC19, pACYC177, and pACYC184 permitting replication in *E. coli*, and pUB110, pC194, pE194, pTA1060, and pAMβ1 permitting replication in *Bacillus*. The origin of replication may be one having a mutation to make its function temperature-sensitive in the *Bacillus* cell (See e.g., Ehrlich, Proceedings of the National Academy of Sciences USA 75:1433 [1978]).

As indicated above, in some embodiments of the present invention, a polynucleotide encoding the YmaH protein is introduced into a modified cell via an expression vector capable of replicating within the host cell. Suitable replicating and integrating plasmids for *Bacillus* known in the art (See e.g., Harwood and Cutting (eds), *Molecular Biological Methods for Bacillus*, John Wiley & Sons, [1990], in particular, chapter 3; suitable replicating plasmids for *B. subtilis* include those listed on page 92).

In some embodiments, the overexpression of a YmaH polypeptide results from the expression of at least one copy of a YmaH-encoding polynucleotide that is integrated into the genome of the host cell. Thus, in some embodiments, when the vector is introduced into the host cell, it is integrated into the genome and replicated together with the genome into which it has integrated. Multiple copies of the YmaH gene can be integrated at several positions in the genome of the host cell. Alternatively, an amplifiable expression cassette carrying a sequence encoding YmaH and a selectable marker (e.g., an antimicrobial resistance marker, such as a gene coding chloramphenicol acetyl transferase) can be integrated in the genome via a single cross-over event and then amplified by challenging the transformed host cell with increasing concentrations of the appropriate antimicrobial (e.g., chloramphenicol).

In other embodiments, the invention provides a polynucleotide construct that is incorporated into an integrating vector. In some embodiments, the polynucleotide constructs of the invention that are incorporated into an integrating vector are targeted to chromosomal sequences of the *Bacillus* sp. host cell to create modified host cells that comprise stable tandem integrations of multiple vector copies. The polynucleotide construct that is incorporated into the integration vector typically comprises a selectable marker gene that provides the cell with resistance to an antimicrobial agent and allows for the amplification of the integrated ymaH construct. Tandem integration into a single site as well as single-copy and two-site integration may occur. Whether the polynucleotide construct is incorporated into a vector or used without the presence of plasmid DNA, it is used to transform modified cells using any suitable method known in the art.

Culturing Methods

The invention provides methods for producing a protein of interest in a modified *Bacillus* cell by culturing the modified cell that is capable of producing a protein of interest and growing the cell under suitable growth conditions for expressing the protein of interest. In some embodiments, the host cells and modified host cells of the present invention are cultured in conventional nutrient media. The suitable specific culture conditions, such as temperature, pH and the like are known to those skilled in the art. Additional preferred culture conditions are well known to those of skill in the art and are described in various reference publications.

In some embodiments, the protein of interest produced by the modified host cell is confined to the intracellular milieu of the host cell, while in other embodiments the protein of interest produced by the host cell is secreted into the extracellular space (i.e., the culture medium). Thus, in some embodiments, the protein of interest can be recovered from the intracellular milieu of the cell in which it is expressed by lysing the host cell and recovering the protein of interest by methods known in the art. In other embodiments, modified host cells are cultured under conditions suitable for the expression and recovery of the protein of interest from the cell culture. The protein of interest produced by a modified host cell overexpressing ymaH according to the present invention is secreted into the culture media. In some embodiments, the protein of interest (e.g., a protease), produced by the cells is recovered from the culture medium by conventional procedures, including, but not limited to separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Thus, any method suitable for recovering the protease(s) of the present invention finds use in the present invention. Indeed, it is not intended that the present invention be limited to any particular purification method.

In some embodiments, other recombinant constructions join the heterologous or homologous polynucleotide sequences encoding the proteins of interest to nucleotide sequence encoding a polypeptide domain which facilitates purification of soluble proteins (Kroll D J et al., DNA Cell Biol 12:441-53 [1993]). Such purification facilitating domains include, but are not limited to, metal chelating peptides such as histidine-tryptophan modules that allow purification on immobilized metals (Porath, Protein Expr Purif 3:263-281 [1992]), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein also find use to facilitate purification.

In some embodiments, the transformed host cells of the present invention are cultured in a suitable nutrient medium under conditions permitting the expression of a protein of interest (e.g., a protease), after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (e.g., in catalogues of the American Type Culture Collection). In some embodiments, the host cells are cultured under batch, fed-batch or continuous fermentation conditions. Classical batch fermentation methods use a closed system, wherein the culture medium is made prior to the beginning of the fermentation run, the medium is inoculated with the desired organism(s), and fermentation occurs without the subsequent addition of any components to the medium. In certain cases, the pH and oxygen content, but not the carbon source content, of the growth medium are altered during batch methods. The metabolites and cell biomass of the batch system change constantly up to the time the fermentation is stopped. In a batch system, cells usually progress through a static lag phase to a high growth log phase and finally to a stationary phase where growth rate is diminished or halted. If untreated, cells in the stationary phase eventually die. In general terms, the cells in log phase produce most protein.

A variation on the standard batch system is the "fed-batch fermentation" system. In this system, nutrients (e.g., a carbon source, nitrogen source, $O_2$, and typically, other nutrients) are only added when their concentration in culture falls below a threshold. Fed-batch systems are useful when catabolite repression is apt to inhibit the metabolism of the cells and where it is desirable to have limited amounts of nutrients in the medium. Measurement of the actual nutrient concentration in fed-batch systems is estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined culture medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in some embodiments, a limiting nutrient such as the carbon source or nitrogen source is maintained at a fixed rate and all other parameters are allowed to moderate. In other systems, a number of factors affecting growth are altered continuously while the cell concentration, measured by media turbidity, is kept constant. Continuous systems strive to maintain steady state growth conditions. Thus, cell loss due to medium being drawn off may be balanced against the cell growth rate in the fermentation. Methods of modulating nutrients and growth factors for continuous fermentation processes as well as techniques for maximizing the rate of product formation are known to those of skill in the art and find use in the production of a protein of interest (e.g., a protease) according to the methods of the invention.

As indicated above, the modified *Bacillus* sp. of the invention produce proteins of interest at a level that is greater than that obtained from the corresponding unmodified precursor *Bacillus* sp. cells. The enhanced level of protein production by the modified cells is further increased by overexpressing YmaH. In some embodiments of the present invention, overexpression of YmaH in a *Bacillus* host cell results in an increase in the production of a protein of interest above the level obtained in the corresponding modified precursor *Bacillus* sp. cell that does not overexpress YmaH. In some embodiments, the invention provides modified *Bacillus* host cells that overexpress YmaH. In some embodiments the recombinant *Bacillus* host cell is a cell that was altered to produce greater levels of a protease than the unaltered parent/precursor *Bacillus* cell when grown under the same conditions.

The present invention also encompasses methods for producing a protein of interest in a modified cell that overexpresses YmaH in less time than that required by the precursor host cell. For example, the modified host cells of the invention are capable of producing a protein of interest at a greater level and at an earlier time than the corresponding unmodified precursor host cell. Thus, in some embodiments, the invention provides for methods of producing a protein of interest (e.g., a protease), at a level that is greater than that produced by the parent host cell and in about $\frac{1}{6}^{th}$ of the time it takes the precursor host cell to attain its maximum level of expression. In other embodiments, the modified host produces a protein of interest in about $\frac{1}{5}^{th}$, about $\frac{1}{4}^{th}$, about $\frac{1}{3}^{rd}$, or about $\frac{1}{2}$ of the time it takes the precursor host cell to attain its maximum level of expression.

Measurement of Production/Activity

Experimental

The following examples provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the experimental disclosure which follows, the following abbreviations apply: ° C. (degrees Centigrade); rpm (revolutions per minute); $H_2O$ (water); aa (amino acid); by (base pair); kb (kilobase pair); kD (kilodaltons); gm (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); h(s) and hr(s) (hour/hours); $OD_{280}$ (optical density at 280 nm); $OD_{405}$ (optical density at 405 nm); $OD_{600}$ (optical density at 600 nm); PAGE (polyacrylamide gel electrophoresis); LAS (lauryl sodium sulfonate); SDS (sodium dodecyl sulfate); and Tris (tris(hydroxymethyl)aminomethane).

Example 1 phr Gene Deletions

Figure 2:
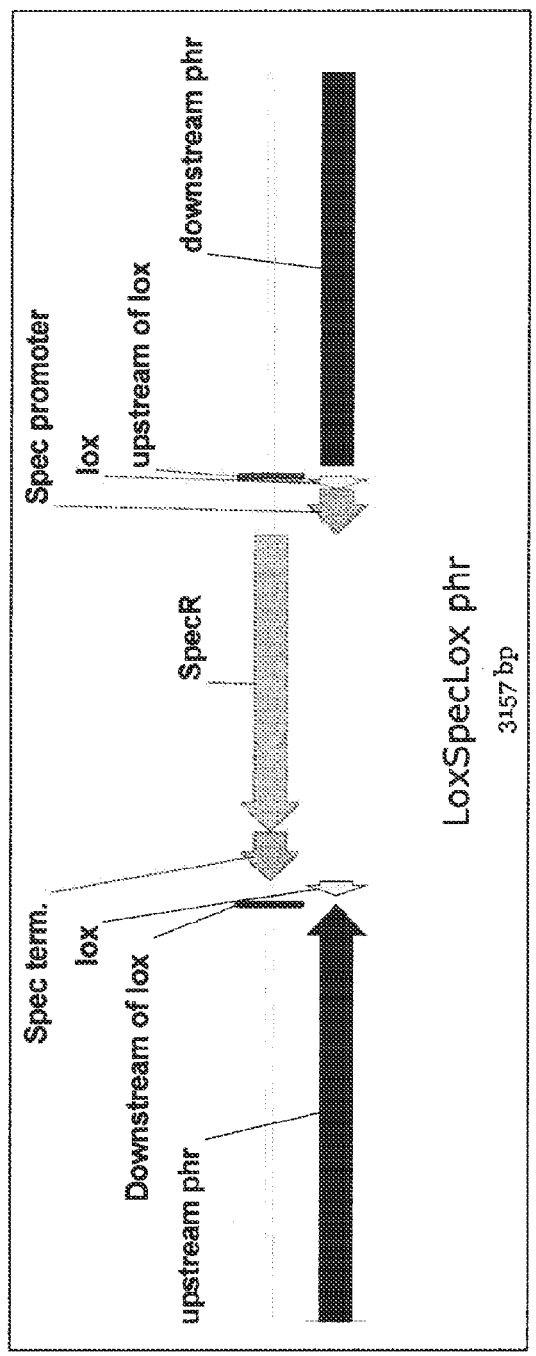
FIG. 2 schematically illustrates features common to the inactivation cassettes used to delete phr genes in *Bacillus subtilis*.

The phr genes: phrA, phrE, phrC, phrF, phrG, phrH, phrI and phrK were deleted in the *Bacillus subtilis* strain BG2942 (ΔnprE, degU(Hy)32, amyE::[PxyIRA-comK eryR]), and AprE protease expression in the resulting modified *Bacillus subtilis* strains was determined using an AAPF assay. Deletion of phr genes was performed by inserting a spectinomycin selectable marker flanked by the lox site in the phr locus of the *Bacillus* chromosome, while leaving the upstream rap gene and the downstream genes intact. The inactivation cassette used to delete the phr genes is illustrated in FIG. 2. The deletion of phrA and phrE genes was also performed in the *Bacillus subtilis* strain BG3594 (degU(Hy)32, oppA, ΔspoIIE, ΔaprE, ΔnprE), which carries the amplifiable expression construct PaprE-FNA (nucleotide sequence of aprE promoter-FNA: SEQ ID NO:19) for expressing FNA.

(SEQ ID NO: 19)
gaattcctccattttcttctgctatcaaaataacagactcgtgatttt ccaaacgagctttcaaaaaagcctctgcccctttgcaaatcggatgcct gtctataaaattcccgatattggcttaaacagcggcgcaatggcggcc gcatctgatgtctttgcttggcgaatgttcatcttatttcttcctccc tctcaataattttttcattctatccttttctgtaaagtttattttc agaatacttttatcatcatgctttgaaaaaatatcacgataatatcca ttgttctcacggaagcacacgcaggtcatttgaacgaattttttcgac aggaatttgccgggactcaggagcatttaacctaaaaaagcatgacat ttcagcataatgaacatttactcatgtctattttcgttcttttctgta tgaaaatagttatttcgagtctctacggaaatagcgagagatgatata cctaaatagagataaaatcatctcaaaaaaatgggtctactaaaatat tattccatctattacaataaattcacagaatagtcttttaagtaagtc tactctgaattttttaaaggagagggtaaagagtgagaagcaaaaa attgtggatcagtttgctgtttgctttagcgttaatctttacgatggc gttcggcagcacatcctctgcccaggcggcagggaaatcaaacgggga aaagaaatatattgtcgggtttaaacagacaatgagcacgatgagcgc cgctaagaagaaagatgtcatttctgaaaaaggcgggaaagtgcaaaa gcaattcaaatatgtagacgcagcttcagctacattaaacgaaaaagc tgtaaaagaattgaaaaaagacccgagcgtcgcttacgttgaagaaga tcacgtagcacatgcgtacgcgcagtccgtgccttacggcgtatcaca aattaaagcccctgctctgcactctcaaggctacactggatcaaatgt taaagtagcggttatcgacagcggtatcgattcttctcatcctgattt aaaggtagcaggcggagccagcatggttccttctgaaacaaatcctt ccaagacaacaactctcacggaactcacgttgccggcacagttgcggc tcttaataactcaatcggtgtattaggcgttgcgccaagcgcatcact ttacgctgtaaaagttctcggtgctgacggttccggccaatacagctg gatcattaacggaatcgagtgggcgatcgcaaacaatatggacgttat taacatgagcctcggcggaccttctggttctgctgctttaaaagcggc agttgataaagccgttgcatccggcgtcgtagtcgttgcggcagccgg taacgaaggcacttccggcagctcaagcacagtgggctaccctggtaa atacccttctgtcattgcagtaggcgctgttgacagcagcaaccaaag agcatcttctcaagcgtaggacctgagcttgatgtcatggcacctgg cgtatctatccaaagcacgcttcctggaaacaaatacggcgcgttgaa -continued
cggtacatcaatggcatctccgcacgttgccggagcggctgctttgat tctttctaagcacccgaactggacaaacactcaagtccgcagcagttt agaaaacaccactacaaaacttggtgattctttctactatggaaaagg gctgatcaacgtacaggcggcagctcagtaa.

The PaprE-FNA expression construct comprises a polynucleotide sequence encoding the FNA protease operably linked to the aprE promoter of *Bacillus subtilis*. FNA (PURAFECT
PRIME [Genencor]) is subtilisin BPN' from *B. amyloliquefaciens* that has the Y217N substitution (SEQ ID NO:20)

(SEQ ID NO: 20)
VRSKKLWISLLFALALIFTMAFGSTSSAQAAGKSNGEKKYIVGFKQTM

STMSAAKKKDVISEKGGKVQKQFKYVDAASATLNEKAVKELKKDPSVA

YVEEDHVAHAYAQSVPYGVSQIKAPALHSQGYTGSNVKVAVIDSGIDS

SHPDLKVAGGASMVPSETNPFQDNNSHGTHVAGTVAALNNSIGVLGVA

PSASLYAVKVLGADGSGQYSWIINGIEWAIANNMDVINMSLGGPSGSA

ALKAAVDKAVASGVVVVAAAGNEGTSGSSSTVGYPGKYPSVIAVGAVD

SSNQRASFSSVGPELDVMAPGVSIQSTLPGNKYGALNGTSMASPHVAG

AAALILSKHPNWTNTQVRSSLENTTTKLGDSFYYGKGLINVQAAAQ.

A more detailed description of the construction of these strains is set forth below. The sequences of the primers used for creating the constructs used to delete the phr genes are provided in Table 1.

For the phrA deletion cassette the upstream region of the phrA gene containing the rapA sequence was amplified with the primers CB2 008-007 (SEQ ID NO:1) and CB2 008-009 (SEQ ID NO:3) and fused to the spectinomycin cassette, flanked by the loxP sequence, and amplified with the oligos CB2 008-009R (SEQ ID NO:4) and CB2 008-010R (SEQ ID NO:6). The downstream region of the phrA gene was amplified with the oligos CB2 008-010 (SEQ ID NO:5) and CB2008-008 (SEQ ID NO:2) and fused to the PCR product containing the rapA sequences and the spectinomycin cassette.

To create the phrC deletion cassette, the upstream region of the phrC gene containing the rapC sequence was amplified with the primers CB2 008-015 and CB2 008-016 and fused to the spectinomycin cassette, flanked by the loxP sequence, and amplified with the oligos CB2 008-016R and CB2 008-017R. The downstream region of the phrC gene was amplified with the oligos CB2 008-017 and CB2008-018 and fused to the PCR product containing the rapC sequences and the spectinomycin cassette.

To create the phrE deletion cassette, the upstream region of the phrE gene containing the rapE sequence was amplified with the primers CB2008-019A (SEQ ID NO:7) and CB2008-019B (SEQ ID NO:9) and fused to the spectinomycin cassette amplified with the oligos CB2008-019R (SEQ ID NO:10) and CB2008-020R (SEQ ID NO:12). The downstream region of the phrE gene was amplified with the oligos CB2008-020 (SEQ ID NO:11). and CB2008-021 (SEQ ID NO:8). and fused to the purified PCR product containing the partial rapE sequence and the spectinomycin cassette.

To create the phrF deletion cassette, the upstream region of the phrF gene containing the rapF sequence was amplified with the primers CB2008-022 and CB2008-023 and fused to the spectinomycin cassette amplified with the oligos CB2008-023R and CB2008-024R. The downstream region of the phrF gene was amplified with the oligos CB2008-024 and CB2008-025 and fused to the purified PCR product containing the rapF sequence and the spectinomycin cassette.

To create the phrG deletion cassette, the upstream region of the phrG gene containing the rapG sequence was amplified with the primers CB2008-026 and CB2008-027R and fused to the spectinomycin cassette amplified with the oligos CB2008-027 and CB2008-028R. The downstream region of the phrG gene was amplified with the oligos CB2008-028 and CB2008-029 and fused to the purified PCR product containing the rapG sequence and the spectinomycin cassette.

To create the phrH deletion cassette, the upstream region of the phrH gene containing the rapH sequence was amplified with the primers CB2008-011 and CB2008-012 and fused to the spectinomycin cassette amplified with the oligos CB2008-012R and CB2008-013R. The downstream region of the phrH gene was amplified with the oligos CB2008-013 and CB2008-014 and fused to the purified PCR product containing the rapH sequence and the spectinomycin cassette.

To create the phrI deletion cassette, the upstream region of the phrI gene containing the rap/sequence was amplified with the primers CB2008-030 and CB2008-031 and fused to the spectinomycin cassette amplified with the oligos CB2008-031R and CB2008-032R. The downstream region of the phrI gene was amplified with the oligos CB2008-032 and CB2008-033 and fused to the purified PCR product containing the rapI sequence and the spectinomycin cassette.

To create the phrK deletion cassette, the upstream region of the phrK gene containing the rapK sequence was amplified with the primers CB2008-034 and CB2008-035 and fused to the spectinomycin cassette amplified with the oligos CB2008-035R and CB2008-036R. The downstream region of the phrK gene was amplified with the oligos CB2008-036 and CB2008-037 and fused to the purified PCR product containing the rapK sequence and the spectinomycin cassette.

Two loxP sites were introduced on both sides of the spectinomycin selectable marker to facilitate the removal of the antibiotic resistance. The final PCR products were purified and transformed into *Bacillus subtilis* BG2942 (ΔnprE, degU (Hy)32, amyE::[PxyIRA-comK-eryR]).

Once the DNA constructs were stably integrated, via double cross-over, into the chromosome of a competent *Bacillus subtilis* BG2942 strain, the deletions were confirmed by PCR analysis. The phrA region was amplified with the primers CB2008-041 (SEQ ID NO:13) and CB2008-042 (SEQ ID NO:14) and the phrE region was amplified with the primers CB2008-051 (SEQ ID NO:15) and CB2008-052 (SEQ ID NO:16). The resulting PCR products were sequenced to confirm the absence of PCR errors and the insertion of the antibiotic marker in the target phr gene.

The transformation of *Bacillus subtilis* BG2942, which carries an inducible ComK construct in the amyE site, was performed as described in the patent application published as US2002182734.

The BG2942 derived strains carrying the phrA or phrE deletion were then transformed with a plasmid expressing the Cre recombinase. This was a necessary step to eliminate the spectynomycin antibiotic marker by site-specific recombination.

The sequences and the descriptions of the primers used in the above experimental procedure are set are in Table 1.

TABLE 1

| | | |
|---|---|---|
| CB2008-007: | gag gat atg gaa gaa gac caa gat ttg ctg (SEQ ID NO: 1) | upstream phrA |
| CB2008-008: | ggc aat ccc tga cag tgt gtc acc (SEQ ID NO: 2) | downstream phrA |
| CB2008-009: | gcg gcc gcc ata tgc atc cta ggc ccc gac ccg caa cga gca aca aac c (SEQ ID NO: 3) | linker up phrA down-lox |
| CB2008-009-R: | ggt ttg ttg ctc gtt gcg gtc ggg gcc tag gat gca tat ggc ggc cgc (SEQ ID NO: 4) | linker up phrA down-lox |
| CB2008-010: | gga tcc agc tta tcg ata ccg tcg atg cat aaa aaa aga ccc tta ggg g (SEQ ID NO: 5) | linker down phrA up-lox |
| CB2008-010R: | ccc cta agg gtc ttt ttt tat gca tcg acg gta tcg ata agc tgg atc c (SEQ ID NO: 6) | linker down phrA up-lox |
| CB2008-011: | gga ggg aag ccg ttg agt caa gcc (SEQ ID NO: 59) | upstream phrH |
| CB2008-012: | gcg gcc gcc ata tgc atc cta ggc tca tca act ttt ttt ctt aat agg c (SEQ ID NO: 60) | linker up phrH down lox |
| CB2008-012R: | gcc tat taa gaa aaa aag tga tga gcc tag gat gca tat ggc ggc cgc (SEQ ID NO: 61) | linker up phrH down lox |
| CB2008-013: | gga tcc agc tta tcg ata ccg tcg agg ctt ttt ctt gct tta cgg aag acg g (SEQ ID NO: 62) | linker down phrH up lox |
| CB2008-013R: | ccg tct tcc gta aag caa gaa aaa gcc tcg acg gta tcg ata agc tgg atc c (SEQ ID NO: 63) | linker down phrH up lox |
| CB2008-014: | gcc atc att ttc atg gtg cat gct cgg (SEQ ID NO: 64) | downstream phrH |
| CB2008-015: | tca cta atg gaa ttc ggc acc agc ttt atg (SEQ ID NO: 65) | upstream phrC |
| CB2008-016: | gcg gcc gcc ata tgc atc cta ggc cat cgc ggc tgc ggc caa aca aat aac (SEQ ID NO: 66) | linker up phrC down lox |
| CB2008-016R: | gtt att tgt ttg gcc gca gcc gcg atg gcc tag gat gca tat ggc ggc cgc (SEQ ID NO: 67) | linker up phrC down lox |
| CB2008-017: | gga tcc agc tta tcg ata ccg tcg aga aca agc ccc ttc tca tta gcg aga agg g (SEQ ID NO: 68) | linker down phrC up lox |
| CB2008-017R: | ccc ttc tcg cta atg aga agg ggc ttg ttc tcg acg gta tcg ata agc tgg atc c (SEQ ID NO: 69) | linker down phrC up lox |
| CB2008-018: | gca gca ttt ata tca gca agt atc tca tga ac (SEQ ID NO: 70) | downstream phrC |
| CB2008-019A: | cta atg gcc ttt cgc cat aaa att atg ttg g (SEQ ID NO: 7) | upstream phrE |
| CB2008-019B: | gcg gcc gcc ata tgc atc cta ggc cgc aag tcc aat taa aac ggc gg (SEQ ID NO: 9) | linker up phrE down lox |
| CB2008-019R: | ccg ccg ttt aat tgg act tgc ggc cta gga tgc atg atg gcg gcc gc (SEQ ID NO: 10) | linker up phrE down lox |
| CB2008-020: | gga tcc agc tta tcg ata ccg tcg att cga taa aca aca tta gtt ctg att ccc (SEQ ID NO: 11) | linker down phrE up lox |
| CB2008-020R: | ggg aat cag aac taa tgt tgt tta tcg aat cga cgg tat cga taa gct gga tcc (SEQ ID NO: 12) | linker down phrE up lox |
| CB2008-021: | tgt agg cgt tag caa gct cat gcg c (SEQ ID NO: 8) | downstream phrE |
| CB2008-022: | agt ttc ggc aca acc taa tgc ttg agt acc (SEQ ID NO: 71) | upstream phrF |

TABLE 1-continued

| | | |
|---|---|---|
| CB2008-023: | gcg gcc gcc ata tgc atc cta ggc cag taa tag ttt aga ctt caa ttt cat ac (SEQ ID NO: 72) | linker up phrF down lox |
| CB2008-023R: | gta tga aat tga agt cta aac tat tac tgg cct agg atg cat atg gcg gcc gc (SEQ ID NO: 73) | linker up phrF down lox |
| CB2008-024: | gga tcc agc tta tcg ata ccg tcg acc gcc gtc cat cgg cgg ttt ttt cgt ccc c (SEQ ID NO: 74) | linker down phrF up lox |
| CB2008-024R: | ggg gac gaa aaa acc gcc gat gga cgg cgg tcg acg gta tcg ata agc tgg atc c (SEQ ID NO: 75) | linker down phrF up lox |
| CB2008-025: | tcg gac cgc aca atg tgt att cat tcg g (SEQ ID NO: 76) | downstream phrF |
| CB2008-026: | Aga gga tca gga ggt gct tgc cta c (SEQ ID NO: 77) | upstream phrG |
| CB2008-027: | cga acg gag gtt ata taa atg aaa agt cga cgg tat cga taa gct gga tcc (SEQ ID NO: 78) | linker up phrG and up lox |
| CB2008-027R: | gga tcc agc tta tcg ata ccg tcg act ttt cat tta tat aac ctc cgt tcg (SEQ ID NO: 79) | linker up phrG and up lox |
| CB2008-028: | gcg gcc gcc ata tgc atc cta ggc cat gaa aaa ccc cgc gga tg (SEQ ID NO: 80) | linker down phrG and down lox |
| CB2008-028R: | cat ccc gcg ggg gtt ttt cat ggc cta gga tgc ata tgg cgg ccg c (SEQ ID NO: 81) | linker down phrG and down lox |
| CB2008-029: | tct cgg tga cat tcc gat caa tcg cg (SEQ ID NO: 82) | downstream phrG |
| CB2008-030: | gaa ttg tta aac atg aaa gaa aat caa gat gcc ctg (SEQ ID NO: 83) | upstream phrI |
| CB2008-031: | gcg gcc gcc ata tgc atc cta ggc caa tac act act taa aat cac tgc tgc c (SEQ ID NO: 84) | linker up phrI down lox |
| CB2008-031R: | ggc agc agt gat ttt aag tag tgt att ggc cta gga tgc ata tgg cgg ccg c (SEQ ID NO: 85) | linker up phrI down lox |
| CB2008-032: | gga tcc agc tta tcg ata ccg tcg act ag ata att gga aaa gag gaa aaa agc tta atc (SEQ ID NO: 86) | linker down phrI up lox |
| CB2008-032R: | gat taa gct ttt ttc ctc ttt tcc aat tat cta gt cga cgg tat cga taa gct gga tcc (SEQ ID NO: 87) | linker down phrI up lox |
| CB2008-033: | ctg tcc cta tta gtt tat ctg ctt ttt tat ctc cat cag g (SEQ ID NO: 88) | downstream phrI |
| CB2008-034: | gat gaa atg gaa gaa gat caa gaa gtt ctt gcg (SEQ ID NO: 89) | upstream phrK |
| CB2008-035: | gga tcc agc tta tcg ata ccg tcg att aaa atc aca gct aaa ata gat acg c (SEQ ID NO: 90) | linker up phrK and lox |
| CB2008-035R: | gcg tat cta ttt tag ctg tga ttt taa tcg acg gta tcg ata agc tgg atc c (SEQ ID NO: 91) | linker up phrK and lox |
| CB2008-036: | gcg gcc gcc ata tgc atc cta ggc caa agg gtt gat aat taa tta ggg ccc (SEQ ID NO: 92) | linker down phrK and lox |
| CB2008-036R: | ggg cta att aat taa tc aac ctt tgg cct ag gat gca tat ggc ggc cgc (SEQ ID NO: 93) | linker down phrK and lox |
| CB2008-037: | atc gag act att tga gat acc tga aga tcc (SEQ ID NO: 94) | downstream phrK |
| CB2008-041: | actcatatccggcagttccacgtcgc (seq id no: 13) | 5' rapA |
| CB2008-042: | agatgccgtctgaggcagtttgatcacc (seq id no: 14) | 3' xlyB |

TABLE 1-continued

| | | | |
|---|---|---|---|
| CB2008-051: | agctgtacatgcacactcagcccctc (seq id no: 15) | 5' | rapE |
| CB2008-052: | agaggcgcttttgccttttgctgtcgc (seq id no: 16) | 3' | yqcG |

The nucleotide sequence of the phrA deletion construct is:

(SEQ ID NO: 17)

```
attcgttattgcaggtaattatgatgatatgcagtatccagaaagagcattgccccacttagaactggctttagatcttgcaaagaaaga
aggcaatccccgcctgatcagttctgccctatataatctcggaaactgctatgagaaatgggtgaactgcaaaaggcagccgaata
ctttgggaaatctgtttctatttgcaagtcggaaaagttcgataatcttccgcattctatctactcttttaacacaagttctgtataaacaaaaa
aatgacgccgaagcgcaaaaaaagtatcgtgaaggattggaaatcgcccgtcaatacagtgatgaattatttgtggagcttttttcaattt
ttacatgcgttatacggaaaaaacattgacacagaatcagtctcacacacctttcaatttcttgaagaacatatgctgtatccttatattga
agagctggcgcatgatgctgcccaattctatatagaaaacggacagcccgaaaaagcactttcattttatgagaaaatggtgcacgc
acaaaaacaaatccagagaggagattgtttatatgaaatctaaatggatgtcaggtttgttgctcgttgcggtcgggggcctaggatgc
atatggcggccgcataacttcgtatagcatacattatacgaagttatctagacatatgcaagggtttattgttttctaaaatctgattaccaa
ttagaatgaatatttcccaaatattaaataataaaacaaaaaaattgaaaaaagtgtttccaccattttttcaattttttataattttttttaatct
gttatttaaatagtttatagttaaatttacattttcattagtccattcaatattctctccaagataactacgaactgctaacaaaattctctcccta
tgttctaatggagaagattcagccactgcatttcccgcaatatcttttggtatgattttacccgtgtccatagttaaaatcatacggcataaa
gttaatatagagttggtttcatcatcctgataattatctattaattcctctgacgaatccataatggctcttctcacatcagaaatggaatat
caggtagtaattcctctaagtcataatttccgtatattcttttatttttttcgttttgcttggtaaagcattatggttaaatctgaatttaattccttctga
ggaatgtatccttgttcataaagctcttgtaaccattctccataaataaattcttgtttgggaggatgattccacggtaccatttcttgctgaat
aataattgttaattcaatatatcgtaagttgcttttatctcctatttttttttgaaataggtctaattttttgtataagtatttctttactttgatctgtc
aatggttcagatacgacgactaaaaagtcaagatcactatttggttttagtccactctcaactcctgatccaaacatgtaagtaccaataagg
ttatttttttaaatgtttccgaagtatttttttcactttattaatttgttcgtatgtattcaaatatatcctcctcactattttgattagtacctatttt
atatccatagttgttaattaaataaacttaatttagtttatttatagatttcattggcttctaaatttttatctagataacttcgtatagcatacattat
acgaagttatggatccagcttatcgataccgtcgctcggatccactagtatgcataaaaaaagacccttaggggtctttttattctcagcttcc
attctttatcgtcagctcagaagatccacttgccaccagcggatccgcatggccgatttccgctgcctcttccagtgaatctgcttcgatg
acatacgctccgcctgtggcgtcgctgaatggcccaaacatttttaaacgtttttctgcctgtaaacgatccagaaattcatagtgcccag
ccacatgctcctgattaaatttctccgttctcattgtcagcattaaatatggtatacatattcagacccctccgtgaacttcagtttaacacattt
atccatattacggtgatagatgatatgagcttttcgtcctacgaatgccacctatttatgaaaaaagaaaaggagagatgataggtgag
cattccagtaaagaaaatttggtttctgaggcgaaatacgcgttgaagtgtcctaatgcaatgtccgctgaatacattaccattcacaa
cacggcaaacgatgcatcagcggccaatgaaatcagctatatgatcgggaacacaagctcgacaagctttcattttgcggtcgatga
tcaagaggtgattcaaggtctgccgcttaaccgaaacgcttggcacactggtgacggcacaaacggtccgggaaaccgcaaatca
atcggtgttgagatttgctacagcaaatcggaggcccgaagtatgaggcagctgaagccttggcgatttcatttgttgcacagctgttg
aaggagcgcggctggggcatcgatcgggtgagaaagcatcaggactggagcggaaagtattgcccgcaccgcatttttatcagag
gggcgctgggatcaagtgaaggcggcgattgaaaaggaattaaacggggcgtatcagcgaaaaagctgcagtctcttcttcgg
cgtctgaatatcatgtaaaaaaggtgacacactgtcagggattgccgcatcacacgggggcc.
```

The nucleotide sequence of the phrC deletion construct is:

(SEQ ID NO: 95)

```
tcactaatggaattccggcaccagcttatgctggattatcttgagccgttagagaaattaaatatcgaagaccagcc
aagcctgtctgaattatcaagaaacattgacagcaaccaggcagatctcaaagggctgctcgactattacgtgaattttttttcgc
```

-continued

```
gggatgtatgaatttgataagcgggaatttatttctgccattacatactataaacaggcggagaaaaagctctcctttgtcgcag accatattgaacgggctgaattctatttaaaatcgcggaagcttattattatatgaagcaaacgtattttcattgattaatataaa aaacgcctatgaaatttacgtggagcaggaaacctataatgtgagaatcattcagtgccatttcgtcttcggggtcaacctgat ggatgaaagaaatttcgaacaagccgcacgccatttcaaattggcgctcaacatggcccaagcagaacaaaaagcccag ctggttggaagagcatactacaatctcgggttatgctattacaatcaagaccttctagaccctgccattgattactttgaaaaagc ggtctccacatttgaaagcagcaggatcgtcaattctctcccgcaagcctatttttaatcaccctgatttattataaacagggaa aacatgataaagcttcggaatatcacaagcggggctatgaatatgctaaagaaacagacgatgcagactatgccgtaaaat tcgagttttgcaatccctatatctggatcagcccaatgaagaaggaatcgaacgatgtttccagtacttaaaaaataaaaatat gtacgctgatatagaggatttagccctagaagtagcaaaatattactatgaacagaaatggtttaaactgtctgcttcctactttct acaagttgaagaggcaagaaaacaaatacaaaggagtgaaggtttgtatgaaattgaaatctaagttgtttgttatttgtttggc cgcagccgcgatggcctaggatgcatatggcggccgcataacttcgtatagcatacattatacgaagttatctagacatatgc aagggtttattgttttctaaaatctgattaccaattagaatgaatatttcccaaatattaaataataaaacaaaaaaattgaaaaa agtgtttccaccattttttcaattttttttataatttttttaatctgttatttaaatagtttatagttaaatttacattttcattagtccattcaatatt ctctccaagataactacgaactgctaacaaaattctctccctatgttctaatggagaagattcagccactgcatttcccgcaatat cttttggtatgattttacccgtgtccatagttaaaatcatacggcataaagttaatatagagttggtttcatcatcctgataattatctat taattcctctgacgaatccataatggctcttctcacatcagaaaatggaatatcaggtagtaattcctctaagtcataatttccgtat attcttttattttttcgttttgcttggtaaagcattatggttaaatctgaatttaattccttctgaggaatgtatccttgttcataaagctcttgt aaccattctccataaataaattcttgtttgggaggatgattccacggtaccatttcttgctgaataataattgttaattcaatatatcgt aagttgcttttatctcctattttttttgaaataggtctaattttttgtataagtatttctttactttgatctgtcaatggttcagatacgacgact aaaaagtcaagatcactatttggttttagtccactctcaactcctgatccaaacatgtaagtaccaataaggttattttttaaatgttt ccgaagtattttttttcactttattaatttgttcgtatgtattcaaatatatcctcctcactattttgattagtacctattttatatccatagttgtt aattaaataaacttaatttagtttatttatagatttcattggcttctaaatttttttatctagataacttcgtatagcatacattatacgaagt tatggatccagcttatcgataccgtcgagaacaagcccctt ctcattagcgagaagggg ttttcttttcaaaaaaacaccgca agacatagtcttgcggtgccgccttcatggagattacgtttatttagtagcctcctacaaatgcagttcccacaatgatcaagag gataaataacacaacaatcaaagcgaaagaagttccgtaacctgacattttgtgcacctccttgcgagattgcttcagcaaat gctgcaaaactgtggcggacagggtcccgcagagacggtcagcagcttagaagccgccaacaaacgcagtccctacgat aattaatagaataaacaatacaacgattaaagcgaaagaactgatgccgccgtaaccgccgccgttagagtatcctgacat aaggtttcacctccctatgaaggatactataagatatgctgaaccgatccatttggcagggataatagtggacaagagaaaa aatgaagaattcggctatatgaaggtgatataaaaaaatagcgggcgctgccgcccgctatttatgtacgattaagagatcag cacgcccgcgaaaaattcctggtataacgcttgaacggcttttcttt cttcggcttcttttacgccaaacatcatgctcacttcaga agaccctgattgatcatttcgatattcacctgtgcctctgataatgctttggcggctcttgccgttgtaccgacattgtggcgcatc gcttcccctacaaccataatcagggcgagatgatgctcgacgatgacttcatcggcatgcaaatcctcttcgatccgtttgatga cgctgcgttcagtggcggcatccatttgcccctgccgtaaaatgattgtcatgtcatcgattcccgatggaacatgctcatacgtc aaaccatgctcctccaggatttgaagggctctgcggccaaaaccgatttctctgttcatgagatacttgctgatataaatgctgc
```

The nucleotide sequence of the phrE deletion construct is:

(SEQ ID NO: 18)
```
tttttttctgttcagacataatggattttgatttggtgtaggcgttagcaagctcatgcgctaaaaaggtttcttctatgtaggcatctgataagtt ggcatcttctaaaaaaccaggaatactcgttaagaaagaaattttcatctcaattaaatcaatccattggtcagcaatgccagcttgatct tcataaaatgatttaatgttattagcgcctttgcctgaaaactcgctatcatctaaatctgcaacagctttgaacgctttctttaatttgaccatt ttacttttaaatctttgtattcctgtgctcgcttttcagcctcggtgagcaaggttttggcttcaaatactttcatgatcatatcctttcatttaatcg
```

-continued

```
tcataacaaaatattaccatggaagaatgatgaaactaactgttatgtggatcaaatggtggaaatgaatcattcgatctgtgtcatttta
cctatttgttaatcctttcaatgaaagggactttccaattgtaacatcgccatcatgaaaaaattcgataacgtagccagattcactaaa
cataaaagtatccgatccaacggcagttacatcatcaattacgtttaatgcatgctcaagactggttttaatgctggctgttctccgtaac
cccaaagaataataatgttcctatctttaaaatggtgtttagctagccaatcgtaaatctcttcctcgtaatctatagattgatgacaacaa
acttcttcccacttgattcgtccccaagatgtaagggaaaactgtttgaaagcagttcataatattttgccgttaattcttctgataagatttctt
tgtttttccctagagcttctaagcattcatcaaataagtccaaaatgttcacctcaaaagctttaagtatgatagatttttttcagtattagaaat
aagaaaaagccgttatgaaacggctaaagggaatcagaactaatgttgtttatcgaatcgacggtatatcgaaaggggaatgcatgt
atgaaatctaaattgtttatcagtttatccgccgttttaattggacttgcgaaaggcgaattccagcacactggcggccgttactagtgg at
ccgagctcggatccataacttcgtataatgtatgctatacgaagttatctagataaaaaatttagaagccaatgaaatctataaataaac
taaattaagtttatttaattaacaactatggatataaaataggtactaatcaaaatagtgaggaggatatatttgaatacatacgaacaa
attaataaagtgaaaaaaatacttcggaaacatttaaaaaataaccttattggtacttacatgtttggatcaggagttgagagtggacta
aaaccaaatagtgatcttgactttttagtcgtcgtatctgaaccattgacagatcaaagtaaagaaatacttatacaaaaaattagacct
atttcaaaaaaataggagataaaagcaacttacgatatattgaattaacaattattattcagcaagaaatggtaccgtggaatcatcc
tcccaaacaagaatttatttatggagaatggttacaagagctttatgaacaaggatacattcctcagaaggaattaaattcagatttaac
cataatgctttaccaagcaaaacgaaaaataaaagaatatacgaaaattatgacttagaggaattactacctgatattccattttctga
tgtgagaagagccattatggattcgtcagaggaattaatagataattatcaggatgatgaaaccaactctatattaactttatgccgtatg
attttaactatggacacgggtaaaatcataccaaaagatattgcgggaaatgcagtggctgaatcttctccattagaacataggaga
gaattttgttagcagttcgtagttatcttggagagaatattgaatggactaatgaaaatgtaaatttaactataaactatttaaataacagat
taaaaaaattataaaaaaattgaaaaaatggtggaaacacttttttcaattttttttgttttattatttaatatttgggaaatattcattctaattggt
aatcagatttagaaaacaataaaaccttgcatatgtctagataacttcgtataatgtatgctatacgaagttatgcggccgccatatgca
tcctaggccgcaagtccaattaaaacggcggataaactgataaacaatttagatttcatacatgcattccccttcgatatttgcttttgag
catataccatcttcttgaaacagatgatactatcctctattttcccattataatcgaaaaggttgcctcctaacaatgccagctcttccagat
aagggtatcctttgccgttctctaaacgagaaaaatgttgagaagtttaggtgtatcgccatttcttatataaagaacgtctaatgcttca
aataagttcataaatagttcgtctttaaaatctacagcacttctgattcctttgcggaagcaatccattgcttgtccttttttgccttgtttaaaat
aaatcaacgctaggtcatgataagcttgcggaagtacgtcagagttaatttttctgtattgaaccaaggcttgttcgatgtaacgagcag
ccttatttaagttgtccattttgtgatagcaattgccgagattgaaaaacgcagtggcatagatatgagtatttttacttttaagcagctcggc
accttttaaagcttcttgaaggtgggggagagcttttcatgattttcaaggtcatcgtagttaccggcaatgacaaaatggcactgaata
cgacgaacagagtaaagctcgtgtttcttataaatgttgtatgaaagctcagcgtaatgcatcgaaatgtgtgtcattttcatatgataata
gacttcagacagtttaaaataaaactcagcttttcaatcttgtcggagattgtaggaattttgcgttcagcttttttgtaatatgtaatggctctt
gtgtattcaccgtttctaaactcatacatcccgcggaagaagttataataatatgcccgcatattgtctaattttttcttatggccctcaatttta
tttaaatattctgaaagttccattcggttttcatcagatggcagcgtgtattccaacataatttttatggcgaaaggccattagttgataataaa
taagcaagtcttgatcttcttccataacctc.
```

The nucleotide sequence of the phrF deletion construct is:

(SEQ ID NO: 96)
```
agtttcggcacaacctaatgcttgagtaccttgaaccgttagaaaaaatgaggattgaggaacagccgagactgt
ctgatctgctgcttgagattgataaaaaacaggctcgtttaactggtctgcttgagtactattttaacttcttcagaggcatgtacga
gctggaccagcgggaatatctgtcggctattaaattttcaaaaaggccgaaagcaagctgatattcgttaaggatcggatag
agaaagctgagttttttctttaagatgtctgaatcttattactatatgaaacaaacgtattttttcaatggactatgcacggcaagcata
tgaaatatacaaagaacatgaagcttataatataagattgctgcagtgtcattcttatttgccaccaatttttttagatttaaaacag
tatgaggatgccatctcacattttcaaaaagcttattctatggcagaagctgaaaagcagccccaattaatggggagaactttg
```

-continued

```
tacaatatcgggctttgtaaaaacagccaaagccaatatgaggatgccataccttatttcaaaagagcaatagctgttttgaa
gaatcaaatattcttccttccttacctcaagcgtatttttttaattacacagatccattataaattaggaaaaatagataaagctcatg
aatatcatagtaagggaatggcttattcacaaaaggccggagatgtaatatatttatcagagtttgaattttttgaaatctttatactt
atcaggcccggatgaagaagcaattcaaggattttttttgattttctcgaaagtaaaatgttgtatgctgatcttgaagatttcgctatt
gatgtggcaaaatattatcatgaacgtaaaaattttcaaaaagcttctgcttattttttgaaggtggaacaagtaaggcaacttatt
caaggaggagtgagtttgtatgaaattgaagtctaaactattactggcctaggatgcatatggcggccgcataacttcgtatag
catacattatacgaagttatctagacatatgcaagggtttattgtttctaaaatctgattaccaattagaatgaatatttcccaaata
ttaaataataaaacaaaaaaattgaaaaaagtgtttccaccattttttcaattttttttataatttttttaatctgttatttaaatagtttata
gttaaatttacattttcattagtccattcaatattctctccaagataactacgaactgctaacaaaattctctccctatgttctaatgga
gaagattcagccactgcatttcccgcaatatcttttggtatgattttacccgtgtccatagttaaaatcatacggcataaagttaata
tagagttggtttcatcatcctgataattatctattaattcctctgacgaatccataatggctcttctcacatcagaaatggaatatca
ggtagtaattcctctaagtcataatttccgtatattctttttatttttttcgttttgcttggtaaagcattatggttaaatctgaatttaattccttc
tgaggaatgtatccttgttcataaagctcttgtaaccattctccataaataaattcttgtttgggaggatgattccacggtaccatttc
ttgctgaataataattgttaattcaatatatcgtaagttgcttttatctcctatttttttttgaaataggtctaattttttgtataagtatttcttta
ctttgatctgtcaatggttcagatacgacgactaaaaagtcaagatcactatttggttttagtccactctcaactcctgatccaaac
atgtaagtaccaataaggttattttttaaatgtttccgaagtatttttttcactttattaatttgttcgtatgtattcaaatatatcctcctcac
tattttgattagtacctatttatatccatagttgttaattaaataaacttaatttagtttatttatagatttcattggcttctaaatttttttatcta
gataacttcgtatagcatacattatacgaagttatggatccagcttatcgataccgtcgaccgccgtccatcggcggttttttcgtc
ccctctttaccaaagtctcccaatccatgctatgatcttttcaataatcttgaagagagtggaaatgcagcatgtctctaaaaagt
gtgagaacccactttactcaatggaatcgagaaaatgatgtgacggagttcgaaacgtcgagtgcgacagttgaacaggca
gctgagacaatcggcgtaagcctgtctagaatcgccaagtccctgtccttcagagggaaggagatcaggtgattctgattgt
ggcagccggcgatgccaagatcgacaacaaaaagtccaggcaaacatttggctttaaagcaagaatgctctctcctaatga
ggtgctggagcagacaggccatgaaattggaggagtttgcccatttggattggctcatgatcctgaggtttatcttgatgtatcgc
tgaaacggtttcagactgttttccccgcatgcggcagcagaaactccgctattgaattaacaccgaaagaattatccgaattttc
tttctcaaaagtgtggattgatgtttgtaaagactgggaataaaaaaacatccagacatcgtctggatgtttacttatttcacaaac
ccaagcagcatttcacggatgattttgctggctgtgtttgccgtttgctctgagtggtcgtataccggcgcgacttccactaaatca
gcgccctttacgtttacctctgaacgcgcaatttcatggaccgatgcaagcagttctttagacgtgatgccgccggcgtcaacc
gttcctgtacccggtgcgtgtgcagggtctaatacgtcaatgtcaattgtgacataaaccggacggcccgccagcttcggaag
caccctcttttcagcggttcaagcacttcaaattttgagatgtgcatgccgttttccttcgcccattcaaactcttctttcatgccggaac
ggattccgaatgaatacacattgtgcggtccga
```

The nucleotide sequence of the phrG deletion construct is:

(SEQ ID NO: 97)
```
agaggatcaggaggtgcttgcctacttctccttattggaactgcgccacaaggttttgcttcacgaggcgagaggac
agggctttcagcatgaggagccttctcatatgaatgctacgtctgacatgctgaaatattactttttttctgtttgaaggcatgtatga
ggcctataaaaataattatgacattgccattgggctgtataaagatgcagagcagtatctcgacaacattcccgatccgattga
aaaagccgaatttcacctgaaggtcggtaagctctattataagctgggacaaaatattgtgtccctcaatcatacacggcaag
cagtcaaaacattcagagaagagacagattataaaaagaagctggcttcagccctgattaccatgtcaggcaattttacaga
gatgagccagtttgaagaagctgaggcttatttggacgaagcaattcggatcacgagtgaattagaggatcattttttttgaagc
ccagcttttgcataacttcggccttctacatgcgcaaagcggcaaatcagaagaagcggtttcgaaattagaggaggctctac
agaacgatgagtatgcccgctccgcctattattatcattctgcctacttgctgatacgagagctgtttaagatcaaaaagaaaga
```

```
acaggccttatcttattaccaagacgtgaaggaaaaattgactgctgagccgaatagaatatgtgaggcaaaaatagacattt
tatatgccatttatgcagaaggggtcatgcggaaacgtttcacttatgcaaacaacatatggatgacttgttgtccgagaaag
agtatgacagtgtaagagaactttccattttggctggcgaacggtatagggaacttgagctttacaaagaagctgcccactttttt
tatgaagcattacagattgaagaactgattaaacgaacggaggttatataaatgaaaagatggcctaggatgcatatggcgg
ccgcataacttcgtatagcatacattatacgaagttatctagacatatgcaagggtttattgttttctaaaatctgattaccaattag
aatgaatatttcccaaatattaaataataaaacaaaaaaattgaaaaaagtgtttccaccattttttcaattttttttataatttttttaat
ctgttatttaaatagtttatagttaaatttacattttcattagtccattcaatattctctccaagataactacgaactgctaacaaaattc
tctccctatgttctaatggagaagattcagccactgcatttcccgcaatatcttttggtatgattttacccgtgtccatagttaaaatc
atacggcataaagttaatatagagttggtttcatcatcctgataattatctattaattcctctgacgaatccataatggctcttctcac
atcagaaaatggaatatcaggtagtaattcctctaagtcataatttccgtatattcttttatttttttcgttttgcttggtaaagcattatgg
ttaaatctgaatttaattccttctgaggaatgtatccttgttcataaagctcttgtaaccattctccataaataaattcttgtttgggagg
atgattccacggtaccatttcttgctgaataataattgttaattcaatatatcgtaagttgcttttatctcctattttttttgaaataggtcta
atttttttgtataagtatttctttactttgatctgtcaatggttcagatacgacgactaaaaagtcaagatcactatttggttttagtccact
ctcaactcctgatccaaacatgtaagtaccaataaggttattttttaaatgtttccgaagtattttttcactttattaatttgttcgtatgt
attcaaatatatcctcctcactattttgattagtacctattttatatccatagttgttaattaaataaacttaatttagtttatttatagatttc
attggcttctaaattttttatctagataacttcgtatagcatacattatacgaagttatggatccagcttatcgataccgtcgaatgaa
aaaccccgcgggatgcggggggttcaatttaacgaaagaatcctaaaacggtttgtagttttaggattcttcatcttttcagcgt
gattgaaaacccttgaagtctaggaagaacgagcattggagcgcagcgaatgtttggaattcgtgagcaccgaagcgcag
gcctgacaacgaatgcgagggtttgtcgacacgctgaaaacccgcgggtgcgggggttttcttattacagcagcttcttcccta
acagggattctacgagctctactgctgttttgcccgttttgttttttgtgatcaaggatcgggttaacctcaacgaattcggctgaggt
aatgatgcctgcgtcatacagcatttccatagccaaatggctctcccggtagctgatgccgccgacgacaggggttccgaca
cccggtgcgtcgttcggatcaagtccgtccagatcaaggctcagatggacgccatcacatgctgataaataatcaagggtttc
ttcaatgacctttgtcatgccaagacgatcgatttcgtgcattgtgtacaccttcatgccgcttttccttaatgtacttgcgctcccttc
atcaagtgaccgggcgccaatgatgacgacgttttccggtttgatttaggcgcgtagccttcaaggttaaccagtgactcgtgg
ccaatgcctaggctgaccgcgagcggcatgccgtgaatattgcccgatggtgaagtttcaagtgtattcaaatcgccgtgcgc
gtcataccagatgacgccgagattatcgtaatgcttcgctgtgcctgcaagcgtgccgatcgcaatactgtggtcaccgccca
ggacaagcgggaatttttctcttcaatgactttgttgaccttttgcgcgagttttcatttcccgccaaaacggaattcaggttttca
gttcctcgtcattttgattttttcgcgattgatcggaatgtcaccgaga
```

The nucleotide sequence of the phrH deletion construct is:

(SEQ ID NO: 98)
```
ggagggaagccgttgagtcaagccataccgtcttcgcgtgttggtgttaagattaatgaatggtataaaatgattcgc
cagttcagtgttccggatgctgag attctgaaagcggaggttgagcaggacattcagcagatggaagaagatcaggatttact
gatctattattctctgatgtgttttcggcaccagctgatgcttgattatttggagccgggaaaaacatacgggaatcgccctacagt
gacagagcttcttgaaacgatcgagacccctcagaaaaaactcacaggtcttttgaaatactactctttgttttccgcggcatgt
atgaatttgaccaaaaagaatatgtggaagcgatcggatattatcgcgaggcggagaaagaactgccgtttgtgtcagatga
tattgagaaagcggaattccatttaaagtggcagaagcgtattatcacatgaagcaaacccatgtgtcgatgtatcatattcttc
aagccttggacatttatcaaaaccatcctctatacagcattagaacgatacaaagcttgtttgtgatcgccggcaactatgatga
tttcaaacattatgataaagcgctcccgcatttagaggcggcgctggaattggcaatggacattcaaaatgacaggtttatcgc
catttctctattgaacattgcaaacagctatgacagatcaggagacgatcagatggctgtagaacatttccaaaaagcggcg
aaagtaagcagagagaaagtgcctgatctgcttccgaaagtcttgtttggattaagctggacattatgtaaagcgggccaaac
```

-continued

```
acagaaggcgtttcagttcatagaggaaggattagaccatatcacagcacgttctcacaaatttttataaagaattgtttctgttctt
gcaggccgtgtacaaggagactgttgatgaacgaaaaattcatgatcttttaagctatttcgaaaaaaagaacctgcacgctt
acattgaagcatgtgcccggagtgctgccgctgttttttgaaagcagctgtcactttgaacaagcagctgcgttttatcggaaagt
gctgaaagcccaagaagatattctaaaagggagagtgtttatatgcctattaagaaaaaaagtgatgaggcctaggatgcat
atggcggccgcataacttcgtatagcatacattatacgaagttatctagacatatgcaagggtttattgttttctaaaatctgattac
caattagaatgaatattttcccaaatattaaataataaaacaaaaaaattgaaaaaagtgtttccaccatttttttcaattttttttataat
ttttttaatctgttatttaaatagtttatagttaaattttacattttcattagtccattcaatattctctccaagataactacgaactgctaac
aaaattctctccctatgttctaatggagaagattcagccactgcatttcccgcaatatcttttggtatgattttacccgtgtccatagtt
aaaatcatacggcataaagttaatatagagttggtttcatcatcctgataattatctattaattcctctgacgaatccataatggctc
ttctcacatcagaaaatggaatatcaggtagtaattcctctaagtcataatttccgtatattctttttatttttttcgttttgcttggtaaagc
attatggttaaatctgaatttaattccttctgaggaatgtatccttgttcataaagctcttgtaaccattctccataaataaattcttgttt
gggaggatgattccacggtaccatttcttgctgaataataattgttaattcaatatatcgtaagttgcttttatctcctattttttttgaaat
aggtctaatttttgtataagtatttctttactttgatctgtcaatggttcagatacgacgactaaaaagtcaagatcactatttggtttt
agtccactctcaactcctgatccaaacatgtaagtaccaataaggttatttttttaaatgtttccgaagtatttttttcactttattaatttg
ttcgtatgtattcaaatatatcctcctcactattttgattagtacctattttatatccatagttgttaatttaaataaacttaatttagtttatta
tagatttcattggcttctaaattttttatctagataacttcgtatagcatacattatacgaagttatggatccagcttatcgataccgtc
gaggcttttttcttgcttacggaagacggttccattttccacatcgcggcattccttctatttctaacgcaagacactcgaaacaac
caaaccatttgaggtataatggataaagtgaataacagtatttagattgatatatatgaaagagagtggaacatcatgggccgt
aagtggaacaatattaaagagaagaaggcgtctaaggacgcaaatacgagtcggatttatgcgaagtttggccgtgagattt
atgtggcggcgaaacagggcgagcctgatccggaatccaaccaggcgctgaaggttgtgcttgaacgtgcgaagacttac
agcgtgccgaaaaacatcattgaacgtgcgatcgagaaggcgaagggcggagcggaagagaattacgatgagcttcgtt
atgagggcttcgggccgaacggatcaatgattatcgttgatgcgctgacgaataatgtaaaccgtacggcgccggaagtgc
gtgcggcgttcgggaaaaacggcggaaacatgggtgtgagcggatctgttgcttacatgtttgacgcgacggctgtaatcgtg
gtggaaggcaaaacggctgacgaagcgcttgaaatcctgatggaagcggatgttgatgtacgtgacattttagaagaggat
gacagcgcgatcgtgtatgccgagcctgatcaattccatgccggtgcaagaggcgtttaaaaacgcgggtgtcgaggaattta
cagtagcggagctgcaaatgcttgcgcaaagtgaagtaacgcttccggatgatgcaaaggaacagtttgaaaaattgattga
tgcattagaagatttggaagatgttcagcaggtatatcataacgttgatttaggtgagtaaggagtgagcaggctgttatggcct
gcttttttttgtcccggaaattgttttagctgtatgtaggcggccgcctatacgatctataagatattctcatactctggactgtaaccta
tgtgaaggagagagtaaatatgactgatacaagacatatgtatggcggacctggttttggtcattatcagggctttggtattggc
caccgggctatggcatgcaaagcacaggctatccgggctatggcatgtatggaggccacccgggctatggcatgcaagg
ctacccagatcacggcatacatggaggagtcggcggctatccgggatatggtgggtacggcggttacccaagcggcggct
atggaggctctccgggaactggaagctatccgagcatgcaccatgaaaatgatggc
```

The nucleotide sequence of the phrI deletion construct is:

(SEQ ID NO: 99)
```
gaattgttaaacatggaagaaaatcaagatgccctgttatattatcaactattagaatttagacatgagataatgctg
agttatatgaaatctaaggaaatagaagatctcaataatgcttatgagactataaaagaaattgagaagcaagggcaattaa
ctggcatgttggaatactattttactntttaagggtatgtacgagtttaggcgtaaagaattaatttcagcgataagtgcttatcga
atagctgaatcaaagttgtcagaagttgaggatgaaatagagaaagcagagttttttttcaaagtgtcctatgtatattattatatg
aaacaaacatacttctccatgaattatgcaaatcgtgcactcaaaatatttagagagtatgaagaatatgctgtccagactgtg
cgttgtcaatttattgtagcaggaaacttgatcgattcattggaatatgaaagagccttggaacaatttttgaagtctttggaaattt
```

-continued

```
ccaaggaaagtaacatagagcatttaattgcaatgtcacatatgaatattgggatttgttatgatgaattgaaagaatataaga
aggcttcacaacatttaattttagcgttagaaattttgaaaaatcaaaacatagtttcttaacaaagactttattcactctaacctat
gtagaagcaaaacaacaaaattataatgttgctttgatatactttaggaaagggcgatttattgccgataaagtgatgataag
gaatactcagcgaaattcaaaatattagagggattattttttctgatggtgagactcaattaataaagaatgcattttcatatctgg
cttcgagaaaatgtttgctgatgttgaaattttttcgattgaagtcgctgattattttcatgaacaaggaaatttaatgctctctaat
gaatattatcgtatgagtattgaagcaagacgaaaaattaaaaaaggggagattattgatgaaaatcagccggattctattgg
cagcagtgattttaagtagtgtattggcctaggatgcatatggcggccgcataacttcgtatagcatacattatacgaagttatct
agacatatgcaagggtttattgttttctaaaatctgattaccaattagaatgaatatttcccaaatattaaataataaaacaaaaa
aattgaaaaagtgtttccaccatttttcaatttttttataatttttttaatctgttatttaaatagtttatagttaaatttacattttcattagtc
cattcaatattctctccaagataactacgaactgctaacaaaattctctccctatgttctaatggagaagattcagccactgcattt
cccgcaatatcttttggtatgattttacccgtgtccatagttaaaatcatacggcataaagttaatatagagttggtttcatcatcctg
ataattatctattaattcctctgacgaatccataatggctcttctcacatcagaaaatggaatatcaggtagtaattcctctaagtca
taatttccgtatattcttttattttttcgtttgcttggtaaagcattatggttaaatctgaatttaattccttctgaggaatgtatccttgttcat
aaagctcttgtaaccattctccataaataaattcttgtttggggaggatgattccacggtaccatttcttgctgaataataattgttaatt
caatatcgtaagttgcttttatctcctattttttttgaaataggtctaatttttttgtataagtatttctttacttttgatctgtcaatggttcag
atacgacgactaaaaagtcaagatcactatttggttttagtccactctcaactcctgatccaaacatgtaagtaccaataaggtt
attttttaaatgtttccgaagtatttttttcactttattaatttgttcgtatgtattcaaatatatcctcctcactattttgattagtacctattttat
atccatagttgttaattaaataaacttaatttagtttatttatagatttcattggcttctaaatttttatctagataacttcgtatagcatac
attatacgaagttatggatccagcttatcgataccgtcgacttagataattggaaagaggaaaaagcttaatcttttttcgaa
ggttaagcttttctttttatttataaaaagtgaactaactatcagaaagaaattatattaaatttattttttgtttaaaaagtagattata
taaaggcaagctaggtgggggaaaatatgtttaaaaaagaaaaagtcacagaatacatttggactatactaataccaacaa
tcatcacttttatcattagttgggttgggtcttattacaatggtacttcgacagttagtattggacaacctacaaaagtttccggtcag
tatatcacgccaataaatataagtccctatcatgatattaaggaattaagaataacttttccgcaaaaactagatgtaaaacaa
attagttcaaatgagcctataaatgtaaaatcagataagaacaatataggagttgaaagtaattccacttttgagattgcgaaa
atcgttgaaaataatagcgttcagttgctaattacaacacaaaaaagttaaacgataaggaaattagaattgataaaaatgg
aaataacatttctgtaaattatgaatctcagattgttaatcctgcaaaaaaacaattaatcaatcttataattacgtcatctatttatttt
ataatgcttaatatactagcattgattatgaacaaaagatgggataagtattatgcaaaatgaaaaatgaaatcaaagaattt
gaggataatgcaaagatcttgataaaaaatcaaagaagaaaagcgaggaattatcggagctgcgaaagaccttgaacc
aagcgtttgaggaaactgataggataaaatatcatgagaagaaaaaacaaatcctcctcttagctaagttaaacgattataa
aaaagaactaaccttttggagaaatacaataagaaaagttctttatgaacttcctgatggagataaaaaagcagataaacta
atagggacag
```

The nucleotide sequence of the phrK deletion construct is:

(SEQ ID NO: 100)
```
gatgaaatggaagaagatcaagaagttcttgcgtattatagtctattagaagaaagacataaaatgttgctgcattct
tcacgaggagagcctttacaaaagcacacctattttactgaagacaatcaaaacttcataacaaaaacaaatgataaattag
aatacaacttttatttatttgaagcaatgtacgaggcatacaacaaaaactatgatcgagcaattaacctatatggattagctga
gaaaaagcttgcagaaattccagatgaaattgaagcagctgaattttactctaaagtctcttacttatatactcttgttaaacaaa
gcattgtggcacaacattatataaaaaatgcaatttcaatatataagcgacaccctgattataaatgcaaactagctacatcaa
caatgattgcagctgcaaactatgctgatatgaaacgatttgaggaagcagaacaatattacttagaagcaattgatattgca
aaagaaacaaaagatgaattttttaaaagctcaattatttcacaatcttagtatcgtttattctgattggaacaaacctgataaatg
```

-continued

```
cattgaatctcttgaaaaagcaataggaaatgaatcttggttacattcgatttattatataaattctttattcatgatgattaaagaac tctttaaaattgacgaaaaaatgaaagccattaattttacaataaagcacaggaaagactcatattaatggagaataaagtat acg aagccaaaatcagcatcctgtataacctttattgtggggaattaaaaaataatttcaataattgtattagtaatattgagttttt aaaacagcaaaatgaacttgaaagtgtagatgaattgtcctacatagctgcaaaaaggtttgaatcaataggtgcttttgaag aagcaacgagctttttcaatgcgaaaatttgggctgaacagaaaatgaatcaggtggagggaatcttatgaaaaaacttgtg ctttgcgtatctattttagctgtgattttaatcgacggtatcgataagctggatccataacttcgtataatgtatgctatacgaagttat ctagataaaaaatttagaagccaatgaaatctataaataaactaaattaagtttatttaattaacaactatggatataaaatagg tactaatcaaaatagtgaggaggatatatttgaatacatacgaacaaattaataaagtgaaaaaaatacttcggaaacattta aaaaataaccttattggtacttacatgtttggatcaggagttgagagtggactaaaaccaaatagtgatcttgacttttagtcgtc gtatctgaaccattgacagatcaaagtaaagaaatacttatacaaaaaattagacctatttcaaaaaaaataggagataaaa gcaacttacgatatattgaattaacaattattattcagcaagaaatggtaccgtgaatcatcctcccaaacaagaatttatttat ggagaatggttacaagagctttatgaacaaggatacattcctcagaaggaattaaattcagatttaaccataatgctttaccaa gcaaaacgaaaaaataaaagaatatacggaaattatgacttagaggaattactacctgatattccatttctgatgtgagaag agccattatggattcgtcagaggaattaatagataattatcaggatgatgaaaccaactctatattaactttatgccgtatgatttt aactatggacacgggtaaaatcataccaaaagatattgcgggaaatgcagtggctgaatcttctccattagaacataggag agaattttgttagcagttcgtagttatcttggagagaatattgaatggactaatgaaaatgtaaatttaactataaactatttaaata acagattaaaaaaattataaaaaaattgaaaaaatggtgaaacactttttcaattttttgttttattatttaatatttgggaaatatt cattctaattggtaatcagattttagaaaacaataaaccttgcatatgtctagataacttcgtataatgtatgctatacgaagttat gcggccgccatatgcatcctaggccaaaaggttgattaattaatttagccctactcaaacatttgagtgggcttttattttatgattt atgtccaccggtcagccctgctctgtggagcgcagtacctgcaaacgtaactgagatacttctcactgttttttgcccgagtaaa acttattaaagaacatcaagcaacacttataaatatccatcgtgatatttgtgggaaaatcaattgtttggatcgatgaaaacca ccgccaagctcatcttactgtatccaattcctagacttattgttcgaccaactttattatatgtacgtgcccttcttgcgacttcctcac aaatctccaagagcacagctttaatctcttctctctttgtataatccctaaacaaaatctgactcttaccaaaactaatctgcccct gcatcaatggagctcctatttcagataaatcaattccgtgagcatgatagtacaactggtttcccattattccgaacttcttttcaag cagctctaaaggaaatttagctaactgacctacagttgatatacccattcgattcagatttctttccatcctccctcctatcccccac attttagacaaaggtcgaactttccagagtctatttggcacatcttcatatctcaacgtgcaataccactctttgttttcttactctcc aggtcaagtgcaagcttactaagcaacatattgtcaccaattccaactgtgcacatcaaaccaaattctctccacatgctgcttt ggattgctttggccatttcttcaggattctcttttcctgcatctaaaaaagattaatcaattgaatacgtgtggacacatttttcagga acaaatctgtaaaacagctttgtaatctcagttgaaactctgatgaaaagcttcatttgtggatttacaatgtatattcttggatcttc aggtatctcaaatagtctcgat
```

Example 2

Protease Expression in *Bacillus* sp. Cells

BG2942 precursor host cells (ΔnprE, degU(Hy)32, amyE::[PxyIRA-comK eryR] and the derived modified strains BG2942phrA::spc (CB2-1), BG2942phrE::spc (CB2-2), BG2942 phrC:spc (CB2-3), BG2942 phrF:spc (CB2-4), BG2942 phrG:spc (CB2-5), BG2942 phrI:spc (CB207) and BG2942 phrK:spc (CB2-8) were streaked onto Luria-Bertani medium-1.6% skim milk plates for overnight growth at 37° C. For each strain, single colonies were then inoculated into 10 ml of Luria-Bertani medium and grown over-night at 30° C. The pre-cultures were used to inoculate 25 ml of freshly prepared 2× SNB medium in a 250-ml flask. This medium contained the following (per liter): 16 g of Difco nutrient broth, 50 ml of 10% maltrin M150, and 40 ml of 25× SNB salts (25× salts contain [per liter] 3.7 g of $CaCl_2.2H_2O$, 9.6 mg of $FeSO_4.7H_2O$, 6 mg of $MnCl_2.4H_2O$, 25.0 g of KCl, and 3.26 g of $MgSO_4.7H_2O$). The strains were grown for nine hours and samples were taken at hourly intervals. The supernatants were tested for AprE expression and activity.

Each of the *Bacillus subtilis* cultures was assayed for the production of the native subtlisin AprE (Swiss-Prot:P37562): MRSKKLWISLLFALTLIFTMAFSNMSVQAAGKSSTE-KKYIVGFKQTMSAMSSAKKKDVISEKGGKVQKQF-KYVNAAAATLDEKAVKELKKDPSVAYVEEDHIAHE-YAQSVPYGISQIKAPALHSQGYTGSNVKVAVIDSGID-SSHPDLNVRGGASFVPSETNPYQDGSSHGTHVAGTI-AALNNSIGVLGVSPSASLYAVKVLDSTGSGQYSWIIN-GIEWAISNNMDVINMSLGGPTGSTALKTVVDKAVSS-GIVVAAAAGNEGSSGSTSTVGYPAKYPSTIAVGAVNS-SNQRASFSSAGSELDVMAPGVSIQSTLPGGTYGAYN-GTSMATPHVAGAAALILSKHPTWTNAQVRDRLESTA- TYLGNSFYYGKGLINVQAAA (SEQ ID NO:21) The enzyme produced was assayed for activity against the substrate, succinyl-L-Ala-L-Ala-L-Pro-L-Phe-p-nitroanalide (AAPF). The assay measured the production of protease as the increase in absorbance at 405 nm/min resulting from the hydrolysis and release of p-nitroanaline (Estell et al., J Biol Chem., 260:6518-6521 (1985)). The measurements were made using the Sofmax Pro software, and the specified conditions were set as: Type: Kinetic; Reduction: Vmax Points (Read best 15/28 points); Lm1: 405 nm; Time: 5 minutes; and Interval: 11 Seconds. Twenty microliters of each of the *B. subtilis* supernatants were diluted in 100 ul of Tris Buffer, containing 10 mM Tris+0.005% TWEEN®-80, pH 8.6; and 25 ul of 100 mg/ml AAPF. Assays were done in microtiter plates and the Softmax Pro Software was used.

Figure 3:
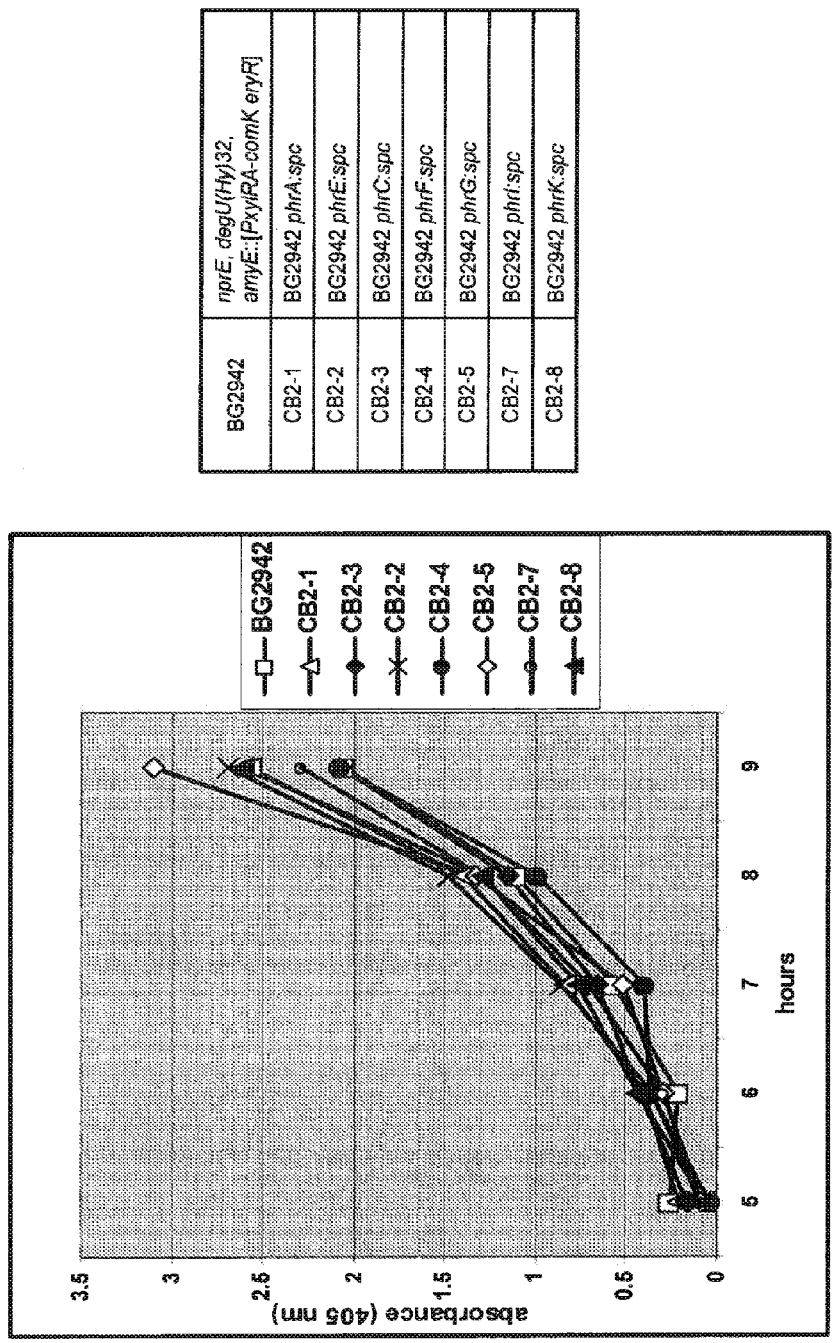
FIG. 3 shows the production of the AprE protease in the modified *Bacillus subtilis* strains that comprise a deletion of the phrA, phrE, phrC, phrF, phrG, phrI, and phrK.

The relative amounts and the activities of the AprE protease produced by the unmodified precursor strain BG2942 and from each of the modified strains CB2-1, 2-2, 2-3, 2-4, 2-5, 2-7, and 2-8 were determined and graphed as a function of absorbance (A405 nm) as shown in FIG. 3. The results for the BG2942 derived strains (CB2-1 and CB2-2) carrying the deletion of the phrA and phrE genes, respectively, are also shown in FIG. 4.

Figure 4:
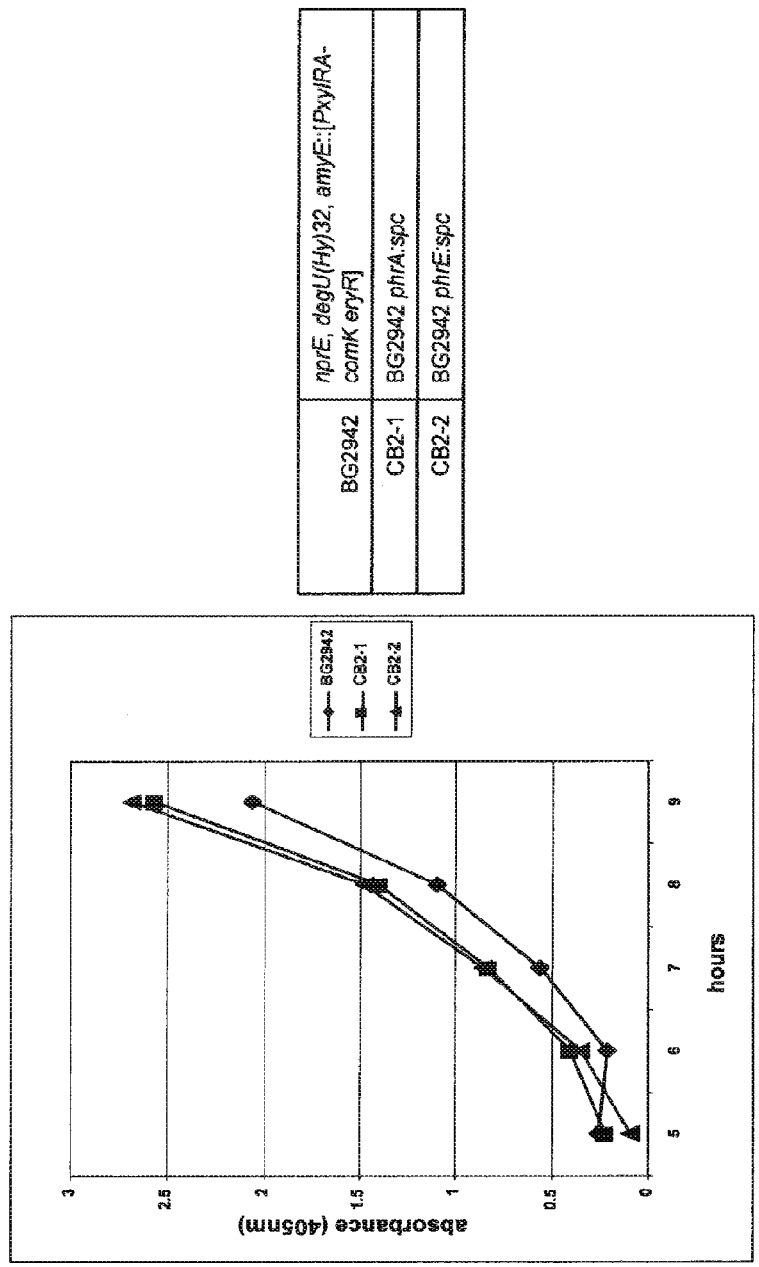
FIG. 4 is a graph showing the production of AprE in the control *Bacillus subtilis* parent strain BG2942 (diamonds) and in the modified *Bacillus subtilis* strains CB2-1 (squares) and CB2-2 (triangles), which respectively contain the deletion of the phrA and the phrE gene.

The data shown in FIGS. 3 and 4 show that that the deletion of phrA, phrE, phrC, phrG, phr I and phrK increases AprE expression in the modified CB2-1, CB2-2, CB2-3, CB2-5, CB2-7 and CB2-8 *Bacillus* sp. cells when compared to the production in the unmodified parent strain BG2942 (diamonds).

Example 3

Protease Expression in *Bacillus* sp. Cells Containing a Deletion of the phrA or the phrE Gene The inactivation constructs cassettes of phrA and phrE (SEQ ID NOS:17 and 18, respectively) were introduced into the *Bacillus subtilis* strain CF471. The CF471 strain is the BG3594 strain described above (degU(Hy)32, oppA, ΔspoIIE, ΔaprE, ΔnprE) and that further comprises the PaprE-FNA expression construct (SEQ ID NO:19), which encodes for the protease FNA (SEQ ID NO:20). The resulting modified strains CB3-47 (BG3594 phrA::spcR, aprE:[PaprE-FNA, cat]), and CB3-48 (BG3594 phrE::spcR, aprE:[PaprE-FNA, cat]) were grown in autoclaved suitable growth medium for 50 hours. Samples of the cell culture were centrifuged, and the production of protease was quantified as a function of the activity of the secreted FNA protease present in the supernatants according to the AAPF assay described above.

Figure 5:
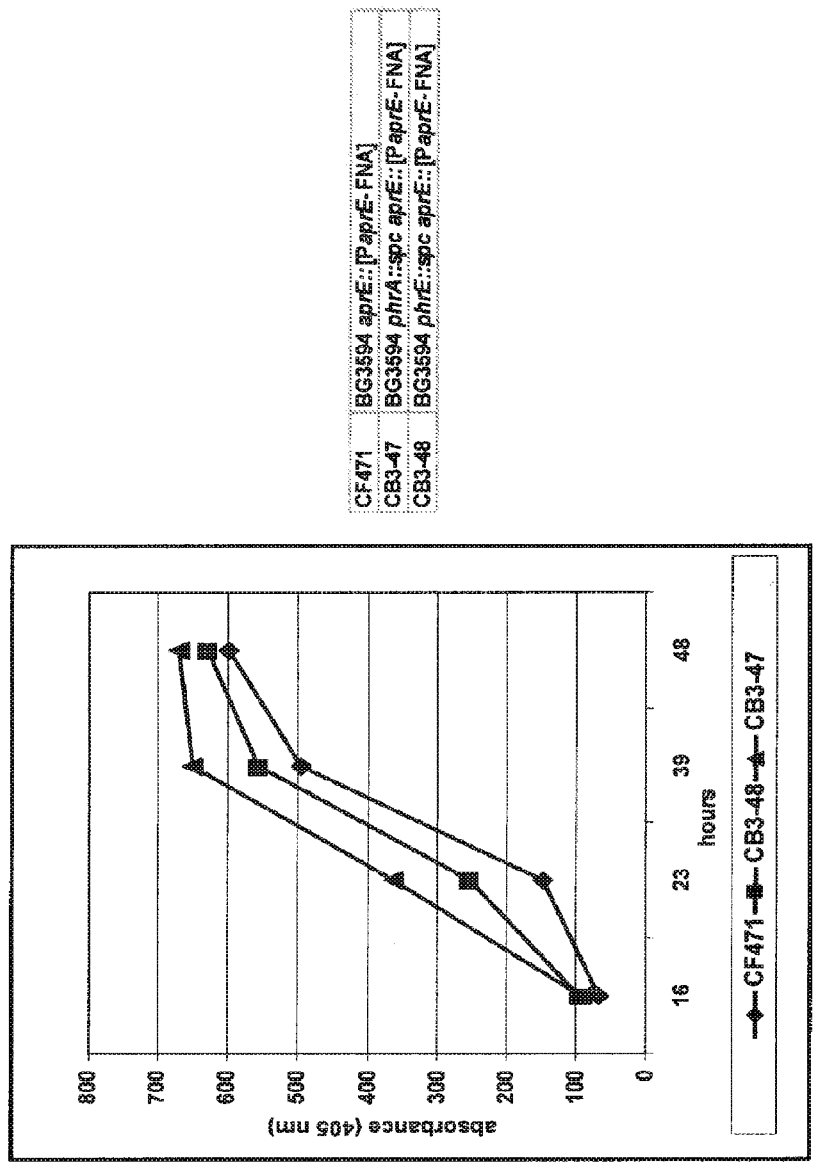
FIG. 5 is a graph showing the production of the protease FNA in the parent *B. subtilis* strain CF471 (diamonds), and in the modified *Bacillus subtilis* strains CB3-48 (squares) and CB3-47 (triangles), which respectively contain the deletion of the phrE and the phrA gene.

The results are graphed in FIG. 5, and they show that the modified cells carrying deletions of the phrA (triangles) and the phrE (squares) genes produce PaprE dependent FNA protease expression at a greater level than that produced by the unmodified parent strain CF471 (BG3594, aprE::[PaprE-FNA]; diamonds), which does not contain a deletion of either phrA and/or phrE.

Therefore, deleting phrA and phrE in a *Bacillus* sp. cell (e.g., a *Bacillus subtilis* cell), enhances the level of production of the protease FNA.

Example 4

Figure 6:
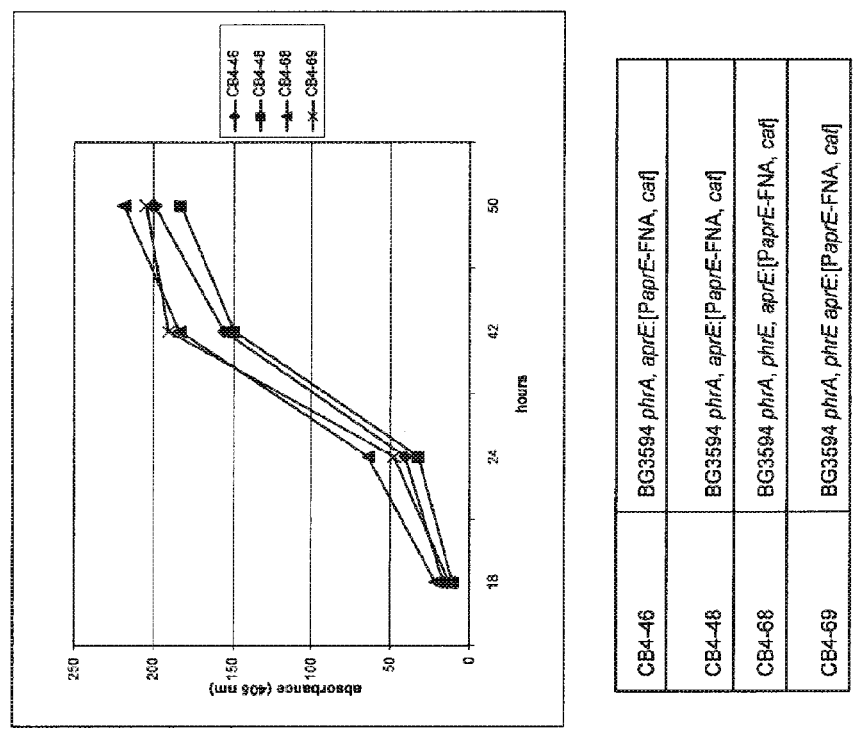
FIG. 6 is a graph showing a combined effect of deleting phrA and phrE gene on protease production in *Bacillus subtilis*.

Protease Expression in *Bacillus* sp. Cells Containing Deletions of phrA and phrE Genes The spectinomycin cassette associated with the deletion of phrA was removed through the lox recombination system in strain CF471 (BG3594, aprE::[PaprE-FNA]). The resulting strain was transformed with the construct carrying the deletion of the phrE gene. After the antibiotic resistance cassette was removed the strain was tested for PaprE dependent protease expression. FIG. 6 shows a graph of protease expression in the double phr deleted strains (CB4-68: BG3594 phrA, phrE, aprE:[PaprE-FNA, cat]; triangles, CB4-69: BG3594 phrA, phrE aprE:[PaprE-FNA, cat]; crosses) compared to the phrA deleted strains (CB4-46: BG3594 phrA, aprE:[PaprE-FNA, cat]; diamonds, CB4-48: BG3594 phrE, aprE:[PaprE-FNA, cat]; squares). The BG3594 derived strains carrying the deletion of the two phrA and phrE genes were grown in suitable growth medium for 50 hours and the supernatants were tested in an AAPF assay.

The strains carrying both deletions of the phrA and phrE genes (i.e., strains CB4-68 and CB4-69 showed an increase in FNA production when compared to the production by the strains CB4-46 and CB4-48, which both carried the deletion of only the phrA gene).

Therefore, deleting the phrA and the phrE genes from a *Bacillus* sp. cell (e.g., *Bacillus subtilis*) enhances the level of production of FNA when compared to the level of production by the *Bacillus subtilis* cells that were modified to contain the deletion of only the phrA gene.

Example 5

Overexpression of YmaH

Generation of SigA and SigH Polynucleotide Constructs

Polynucleotide constructs SigH, SigA1, SigA2, and SigA3 were generated to overexpress YmaH in host cells of *Bacillus subtilis*.

Figure 7:
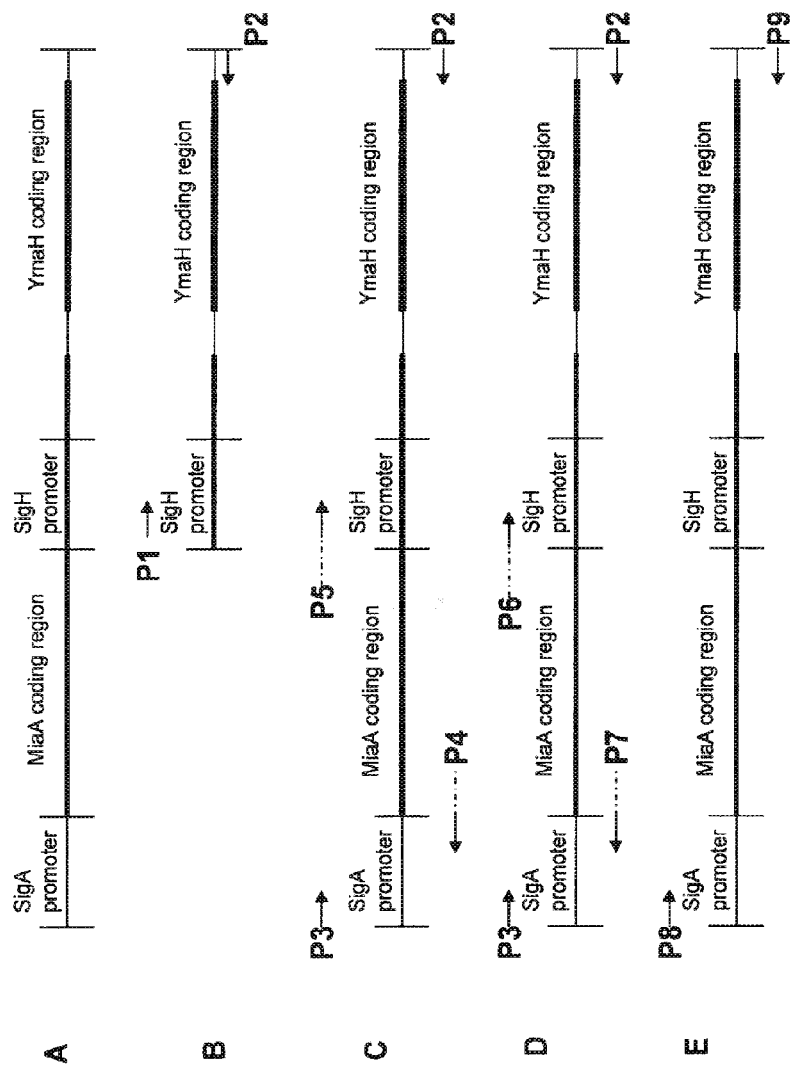
FIG. 7 illustrates the location of primers used for generating polynucleotide constructs used to overexpress YmaH in *Bacillus subtilis*. Panels B-E show the position of the primers used to generate construct SigH (panel B), and SigA constructs SigA1 (panel C), SigA2 (panel D) and SigA3 (panel E) relative to the *Bacillus* chromosomal sequence of the miaA operon of *Bacillus subtilis* (base pairs 1865428-1867019 of the *Bacillus subtilis* strain 168; NCBI accession number NC000964), which is illustrated in Panel A. Primer pairs P4-P5 and P6-P7 are fusion primers, which comprise a "tail" of base pairs at their 5' end that are homologous to the sequence being directly amplified, and are complementary to each other. The complementary tails of the fusion primers allow fusion of the amplified Sigma A promoter DNA to the amplified YmaH-encoding DNA to obtain chimeric polynucleotides containing the Sigma A promoter sequence adjacent to the YmaH-encoding sequence while deleting most, or all, of the miaA coding sequence.

PCR primers were designed to be homologous to the *Bacillus subtilis* genome (FIG. 7A) and to contain a 6 base pair restriction enzyme site located 6 base pairs from the 5' end of the primer. Primers were designed to engineer unique restriction sites at the upstream and downstream ends of the construct. The primary source of genome sequence (Kunst et al., Nature 390:249-256 [1997]), gene localization, and start and stop codon information was obtained from the NCBI Database: Completed *Bacillus subtilis* subsp. *subtilis* str. 168, or from the SubtiList World Wide Web Server known to those in the art (Moser, I. 1998. FEBS Lett. 430(1-2):28-36). The sequence considered is reported as SEQ ID NO:22 with coordinates 1865428-1867019 in the NCBI database, ACC No NC000964 is shown in FIG. 7A.

(SEQ ID NO: 22)

```
tcatacccctgaaaggaaagacaagggaaattgtcggcaatgagccgctcggcaggtagaaggatgtttaccgat gcaaaaaagggcaaaatggataggtggttgtccatgttgaatgctataatgggggagatttataaaagagagtgatacata ttgaataatacgaagcagcccgttgtcatttttagtcggaccgacggcagtggggaaaaccaatttaagtattcagctagccaa
```

-continued

```
atccttaaacgcggaaattatcagcggagattcgatgcagatttataaagggatggatattggaacagctaaaattaccgaac aggagatggagggagtgccccatcatctgattgacattttagatccccaagactctttctctactgccgattatcaaagcttagta agaaataaaatcagcgagattgcaaatagaggaaagcttccgatgattgacggcggtacagggctttatatacaatctgagc tttacgattatacattttacggaagaggcaaatgatcccgtgtttcgagagagcatgcaaatggctgctgagcgggaaggcgct gactttcttcatgccaaacttgctgcagcagatcccgaggcagcagctgcgattcatccgaataatacaagaagagtcattcg cgcactggaaattttacatacgtccggaaaaacgatgtcccagcattttgaaggaacaaaaacgagaacttctgtacaatgca gtgttaattggcctgacaatggatagagacacgctttacgaaagaattaatcagcgggtcgatttgatgatgcagtcaggcctt cttccggaagtgaaacgcttatacgacaagaacgtgagagactgtcaatcaatacaggcgataggctataaagagctgtat gcatattttgacggttttgtgacactttccgatgctgtcgaacagctaaagcagaactcgaggcggtatgcgaaacgccagctg acgtggtttcgcaacaaaatgcaggtcacatggttcgatatgacaccgcctgttgatatggagctgaaaaaaaaggaaatttt cacacatatagcaggaaaactcgaactttaatcgaaactgtatgatatagagaatcaaggaggacgaaacatgaaaccga ttaatattcaggatcagttttgaatcaaatccggaaagaaaatacgtatgtcactgttttttgctgaacggctttcagttgcgggg ccaggtgaaaggctttgataactttaccgtattgttggaatcggaaggtaagcagcagcttatatataaacatgcgatctcaac gtttgcgccgcaaaaaacgtccagcttgaactcgaatagatcaaaaaatgccatgtcaagacatgaggaaaggctgtcg ggggttcccggcggccattttaacatgaatccacttttgctccaagcttttgtgtaagctgaccatgccaaggcacggtctttttt atgag.
```

The SigH construct (FIG. 5B; SEQ ID NO:23) ggcaccgaattcgacgtggtttcgcaacaaaatgcaggtcacatggttcgatatgacaccgcctgtgatatggagctgaaaaaaaggaaattttcacacatatagcaggaaaactcgaactttaatcgaaactgtatgatatagagaatcaaggaggacgaaacatgaaaccgattaatattcaggatcagttttgaatcaaatccggaaagaaaatacgtatgtcactgttttttgctgaacggctttcagttgcggggccaggtgaaaggctttgataactttaccgtattgttggaatcggaaggtaagcagcagcttatatataaacatgcgatctcaacgtttgcgccgcaaaaaacgtccagcttgaactcgaatagatcaaaaaatgccatgtcaagacatgaggaaaggctgtcgggggttcccggcggccattttaacatgaatccacttttgctccaagcttttgtgtaagctgaccatgccaaggcacggtctttttttatgagggatccgagcc (SEQ ID NO:23) was generated to comprise the polynucleotide sequence encompassing the Sigma H promoter aaaggaaattttcacacatatagcaggaaaactcgaactttaatcgaaactgtatgatatagagaatcaaggaggacgaaac; SEQ ID NO:48, and the adjacent sequence atgaaaccgattaatattcaggatcagttttgaatcaaatccggaaagaaaatacgtatgtcactgttttttgctgaacggctttcagttgcgggggccaggtgaaaggctttgataactttaccgtattgttggaatcggaaggtaagcagcagcttatatataaacatgcgatctcaacgtttgcgccgcaaaaaacgtccagcttgaactcgaatag; SEQ ID NO:46 (NP_389616), encoding the YmaH protein MKPINIQDQFLNQIRKENTYVTVFLLNGFQLRGQVKGFDNFTVLLESEGKQQLIYKHAISTFAPQKNVQLELE; SEQ ID NO:45 (Swiss-Prot:P3756). The Sigma H promoter is naturally located within the polynucleotide sequence encoding the miaA gene, close to the 3' end of the gene, and immediately upstream of the ymaH gene. The entire Sigma H promoter and adjacent ymaH coding sequence was amplified by PCR using the forward primer P1: ggcaccgaattcgacgtggtttcgcaacaaaatgcag (SEQ ID NO:24; position 987 to 1011 of SEQ ID N0:22), with an EcoRI restriction site added at the 5' end, and a reverse primer P2: ggcaccggatccctcataaaaaaagaccgtgccttgg (SEQ ID NO:25, at position 1472 to 1496 of SEQ ID NO:22), with and added BamHI restriction site (FIG. 7B).

The SigA1 and SigA2 constructs were generated in a three step process by 1) amplifying individual fragments of *Bacillus subtilis* chromosomal DNA, 2) purifying and assembling the fragments; and 3) amplifying the assembled product by PCR.

The SigA1 construct (FIG. 7C; SEQ ID NO:26) gcgccgaattctcataccctgaaaggaaagacaagggaaattgtcggcaatgagccgctcggcaggtagaaggatgtttaccgatgcaaaaaaagggcaaaatggataggtggttgtccatgttgaatgctataatgggggagatttataaagagagtgatacatattgaataatacgaagcagccccacacatatagcaggaaaactcgaactttaatcgaaactgtatgatatagagaatcaaggaggacgaaacatgaaaccgattaatattcaggatcagttttgaatcaaatccggaaagaaaatacgtatgtcactgttttttgctgaacggctttcagttgcggggccaggtgaaaggctttgataactttaccgtattgttggaatcggaaggtaagcagcagcttatatataaacatgcgatctcaacgtttgcgccgcaaaaaacgtccagcttgaactcgaatagatcaaaaaatgccatgtcaagacatgaggaaaggctgtcgggggttcccggcggccattttaacatgaatccacttttgctccaagcttttgtgtaagctgaccatgccaaggcacggtctttttttatgagggatccggtgcc (SEQ ID NO:26) was generated using two sets of primers. A first set of primers: forward primer P3: gcgccgaattctcatacccctgaaaggaaagacaagg (SEQ ID NO:27) located at the 5' end of SEQ ID NO:22; and reverse primer P4: ttcgagttttcctgctatatgtgtggggctgcttcgtattattcaatatg (SEQ ID NO:28) located from by 153 to by 177 on the SEQ ID NO:22, was used to amplify a first fragment containing the SigA promoter, Ribosome Binding Site, start codon and the first few codons of the miaA gene ttgaataatacgaagcagcccgttgtcatttagtcggaccgacggcagtggggaaaaccaatttaagtattcagctagccaaatccttaaacgcggaaattatcagcggagattcgatgcagatttataaagggatggatattggaacagctaaaattaccgaacaggagatggagggagtgccccatcatctgattgacattttagatccccaagactctttctctactgccgattatcaaagcttagtaagaaataaaatcagcgagattgcaaatagaggaaagcttccgatgattgacggcggtacagggctttatatacaatctgagctttacgattatacattttacggaagaggcaaatgatcccgtgtttcgagagagcatgcaaatggctgctgagcgggaaggcgctgactttcttcatgccaaacttgctgcagcagatcccgaggcagcagctgcgattcatccgaataatacaagaagagtcattcgcgcactggaaattttacatacgtccggaaaaacgatgtcccagcattttgaaggaacaaaaacgagaacttctgtacaatgcagtgttaattggcctgacaatggatagagacacgctttacgaaagaattaatcagcgggtcgatttgatgatgcagtcaggccttcttccggaagtgaaacgcttatacgacaagaacgtgagagactgtcaatcaatacaggcgataggctataaagagctgtatgcatattttgacggttttgtgacactttccgatgctgtcgaacagctaaagcagaactcgaggcggtatgcgaaacgccagctgacgtggtttcgcaacaaaatgcaggtcacatggttcgatatgacaccgcctgttgatatgagctgaaaaaaaggaaattttcacacatatagcaggaaaactcgaactttaa; SEQ ID NO:49. A second set of primers, forward primer P5:

catattgaataatacgaagcagccccacacatatagcaggaaaactcgaa (SEQ ID NO:29) located from by 1071 to by 1095 on the SEQ ID NO:22 and reverse primer P2 (SEQ ID NO:25), were used to amplify a second fragment containing the DNA sequence encoding the YmaH protein. Reverse primer P4 and forward primer P5 are fusion primers that were designed to contain tails that are complementary to each other but that are not homologous to the sequence that is being amplified to eliminate the intervening miaA coding sequence. The two fragments were annealed, and the resulting SigA1 construct contained the SigA promoter (SEQ ID NO:47) tcatacctgaaaggaaagacaagggaaattgtcggcaatgagccgctcggcaggtagaaggatgtt-taccgatgcaaaaaagggcaaaatggataggtggttgtccatgttgaatgctataatggggagatttataaaagagagtgatacata; (SEQ ID NO:47), the ribosome binding site aagagag; SEQ ID NO:50, and the transcription start site of the miaA gene. The SigA1 construct was amplified using forward primer P3 (SEQ ID NO:27) and reverse primer P2 (SEQ ID NO:25), which respectively contain an EcoRI and a BamHI restriction site, and ligated into the polylinker of replicating plasmid pBS19. The polynucleotide sequence of pBS19 is shown below (SEQ ID NO:30). The pBS19 plasmid can replicate in *E. coli* and *Bacillus subtilis*, and carries the chloamphenicol resistance selection marker gene.

(SEQ ID NO: 30)

```
gaattcgagctcggtacccggggatcctctagagtcgacctgcaggcatgcaagcttggcgatcctgcctcgcgcgtttcggtgatga
cggtgaaaacctctgacacatgcagctcccggagacggtcacagcttgtctgtaagcggatgccgggagcagacaagcccgtcag
ggcgcgtcagcgggtgttggcgggtgtcggggcgcagccatgacccagtcacgtagcgatagcggagtgtatactggcttaactatg
cggcatcagagcagattgtactgagagtgcaccatatgcggtgtgaaataccgcacagatgcgtaaggagaaaataccgcatcag
gcgctcttccgcttcctcgctcactgactcgctgcgctcggtcgttcggctgcggcgagcggtatcagctcactcaaaggcggtaatac
ggttatccacagaatcaggggataacgcaggaaagaacatgtgagcaaaaggccagcaaaaggccaggaaccgtaaaaagg
ccgcgttgctggcgttttttccataggctccgcccccctgacgagcatcacaaaaatcgacgctcaagtcagaggtggcgaaacccga
caggactataaagataccaggcgtttccccctggaagctccctcgtgcgctctcctgttccgaccctgccgcttaccggatacctgtccg
cctttctcccttcgggaagcgtggcgctttctcatagctcacgctgtaggtatctcagttcggtgtaggtcgttcgctccaagctgggctgtg
tgcacgaaccccccgttcagcccgaccgctgcgccttatccggtaactatcgtcttgagtccaacccggtaagacacgacttatcgcc
actggcagcagccactggtaacaggattagcagagcgaggtatgtaggcggtgctacagagttcttgaagtggtggcctaactacg
gctacactagaaggacagtatttggtatctgcgctctgctgaagccagttaccttcggaaaaagagttggtagctcttgatccggcaaa
caaaccaccgctggtagcggtggtttttttgtttgcaagcagcagattacgcgcagaaaaaaaggatctcaagaagatcctttgatcttt
tctacggggtctgacgctcagtggaacgaaaactcacgttaagggattttggtcatgagattatcaaaaaggatctggagctgtaatat
aaaaaccttcttcaactaacggggcaggttagtgacattagaaaaccgactgtaaaaagtacagtcggcattatctcatattataaaa
gccagtcattaggcctatctgacaattcctgaatagagttcataaacaatcctgcatgataaccatcacaaacagaatgatgtacctgt
aaagatagcggtaaatatattgaattacctttattaatgaattttcctgctgtaataatgggtagaaggtaattactattattattgatatttaa
gttaaacccagtaaatgaagtccatggaataatagaaagagaaaaagcattttcaggtataggtgttttgggaaacaatttccccgaa
ccattatatttctctacatcagaaaggtataaatcataaaactctttgaagtcattctttacaggagtccaaataccagagaatgttttagat
acaccatcaaaaattgtataaagtggctctaacttatcccaataacctaactctccgtcgctattgtaaccagttctaaaagctgtatttga
gtttatcacccttgtcactaagaaaataaatgcagggtaaaatttatatccttcttgtttttatgtttcggtataaaacactaatatcaatttctgt
ggttatactaaaagtcgtttgttggttcaaataatgattaaatatctcttttctcttccaattgtctaaatcaattttattaaagttcatttgatatgc
ctcctaaattttttatctaaagtgaatttaggaggcttacttgtctgctttcttcattagaatcaatcctttttaaagtcaatattactgtaacata
aatatatattttaaaaatatcccactttatccaattttcgtttgttgaactaatgggtgctttagttgaagaataaaagaccacattaaaaaat
gtggtcttttgtgttttttaaaggatttgagcgtagcgaaaatcctttctttcttatcttgataataagggtaactattgccggttgtccattcat
ggctgaactctgcttcctctgttgacatgacacacatcatctcaatatccgaatagggccatcagtctgacgaccaagagagccata
aacaccaatagccttaacatcatccccatatttatccaatattcgttccttaatttcatgaacaatcttcattctttcttctctagtcattattattg
gtccattcactattctcattccttttcagataattttagatttgcttttctaaataagaatatttggagagcaccgttcttattcagctattaataa
ctcgtcttcctaagcatccttcaatccttttaataacaattatagcatctaatcttcaacaaactggcccgtttgttgaactactctttaataaa
ataattttccgttcccaattccacattgcaataatagaaaatccatcttcatcggctttttcgtcatcatctgtatgaatcaaatcgccttcttct
gtgtcatcaaggtttaattttttatgtatttcttttaacaaaccaccataggagattaaccttttacggtgtaaaccttcctccaaatcagacaa
acgtttcaaattcttttcttcatcatcggtcataaaatccgtatccttttacaggatattttgcagtttcgtcaattgccgattgtatatccgatttat
```

-continued
```
atttattttt cggtcgaatc atttgaactttt acatttggat catagtctaatt tcattgcctttttc caaaattgaatc cattgttttt gattcacgtag ttttctgtatt cttaaaataagt tggttccacacat accaatacatg catgtgctgatt ataagaattat ctttt att attt attgtcactt ccgttgc acgcataaaaccaacaagattttt att aatttttttt atattgcat catt cggcgaaat ccttgagccatat ctgacaaact cttatttaatt cttc gccatcataaacattttt aactgtt aatgtgagaaac aaccaacgaact gttggctttt gttt aataactt cagcaacaaccttttgt gactg aatgccatgttt cattgctctcctccagttgcacatt ggacaaagcctggatttacaaaaccacactcgatacaactttctttcgcctgtttc acgattttgttt atactctaatatttcagcacaatcttttactctttcagcctttttaaattcaagaatatgcagaagttcaaagtaatcaacatt agcgattttcttttctctccatggtctcacttttccactttttgtcttgtccactaaaaccctt gattttt catctgaataaatgctactattaggaca cataatattaaaagaaaccccc atctatttagttatttgtttagtcacttataactttaacagatgggttttt ctgtgcaaccaatttt aagggt tttcaatactttaaaacacat acat accaacacttcaacgcacctttcagcaactaaaat aaaaat gacgtt atttctatatgtatcaagat aagaaagaacaagttcaaaaccatcaaaaaaagacacctttt caggtgcttttttt atttt ataaactcatt ccctgatctcgacttcgttctt tttttacctctcggttatgagttagttcaaatt cgttctttt aggttctaaat cgtgttttt cttggaattgtgctgttttatcctttaccttgtctacaaa cccctt aaaaacgttttt aaaggcttttaagccgtctgtacgttccttaag
```

The SigA2 construct (FIG. 7C; SEQ ID NO:31)

(SEQ ID NO: 31)
```
gcgccgaattctcatacc ctgaaaggaaagacaagggaaattgtcggcaatgagccgctcggcaggtagaaggatgtttaccgat gcaaaaaagggcaaaatggataggtggttgtccatgttgaatgctataatgggggagatttataaaagagagtgctcgaactttaat cgaaactgtatgatatagagaatcaaggaggacgaaacatgaaaccgattaatattcaggatcagttttttgaatcaaatccggaaag aaaatacgtatgtcactgttttttgctgaacggctttcagttgcggggccaggtgaaaggctttgataactttaccgtattgttggaatcgg aaggtaagcagcagcttatatataaacatgcgatctcaacgtttgcgccgcaaaaaaacgtccagcttgaactcgaatagatcaaaa aatgccatgtcaagacatgaggaaaggctgtcggggggttcccggcggccatttttaacatgaatccacttttgctccaagcttttttgtgta agctgaccatgccaaggcacggtcttttttt atgagggatccggtgcc
``` was generated according to the method described for the construction of the SigA1 construct using the following primers (FIG. 7D). The first fragment containing the SigA promoter was amplified using forward primer P3 (SEQ ID NO:27) and reverse fusion primer P7:

catacagtttcgattaaagttcgagcactctcttttataaatctcccca (SEQ ID NO:33)

located from by 125 to by 149 on the SEQ ID NO:22. The second fragment containing the DNA sequence encoding the YmaH protein was amplified using the forward fusion primer P6:

tggggggagatttataaaagagagtgctcgaactttaatcgaaactgtatg (SEQ ID NO:32) located from by 1090 to by 1114 on the SEQ ID NO:22 and the reverse primer P2 (SEQ ID NO:25). The two fragments were annealed, and the resulting SigA2 construct contained the SigA promoter, the ribosome binding site GGAGG; SEQ ID NO:51) and the transcription start site of the ymaH gene.

The invention also encompasses a fourth SigA construct (SigA3; SEQ ID NO:22; FIG. 7E), which is generated by amplifying the miaA ymaH region of the *Bacillus* chromosomal DNA that includes a SigA promoter, the region encoding the MiaA protein, the a YmaH promoter and the region encoding the YmaH protein.

The SigA3 construct was generated using forward primer P8 gcgcgcgaattcagggaaattgtcggcaatgagccgctcggc (SEQ ID NO:34) and reverse primer P9 gcgcgccatggctgattcgtctcagttctgcttcactttca (SEQ ID NO:35). SEQ ID NO:34 places an EcoRI restriction site at the 5' end of the fragment, while SEQ ID NO:35 places a NcoI site at the 3' end. This allows to clone the fragment in the pBN3 vector reported as SEQ ID NO:36, shown below:

(SEQ ID NO: 36)
```
gacgtctaagaaaccattattatcatgacattaacctataaaaataggcgtatcacgaggcccttcgtcttcaagaattaattctcatgttt gacagcttatcatcgataagcttgcatgcctgcaggtcgactctagaggatccccgggtaccgagctcgaattccttaaggaacgtac agacggcttaaaagcctttaaaaacgttttt aaggggtttgtagacaaggtaaaggataaaacagcacaattccaagaaaaacacg atttagaacctaaaagaacgaatttgaactaactcataaccgagaggtaaaaaaagaacgaagtcgagatcagggaatgagttt ataaaataaaaaagcacctgaaaaggtgtcttttttgatggttttgaacttgttctttcttatcttgatacatatagaaataacgtcattttat tttagttgctgaaaggtgcgttgaagtgttggtatgtatgtgttttaaagtattgaaaacccttaaaattggttgcacagaaaaaccccatct gttaaagttataagtgactaaacaaataactaaatagatgggggtttcttttaatattatgtgtcctaatagtagcatttattcagatgaaaa
```

-continued

```
atcaagggttttagtggacaagacaaaaagtggaaaagtgagaccatggagagaaaagaaaatcgctaatgttgattactttgaact tctgcatattcttgaatttaaaaaggctgaaagagtaaaagattgtgctgaaatattagagtataaacaaaatcgtgaaacaggcgaa agaaagttgtatcgagtgtggttttgtaaatccaggctttgtccaatgtgcaactggaggagagcaatgaaacatggcattcagtcaca aaaggttgttgctgaagttattaaacaaaagccaacagttcgttggttgtttctcacattaacagttaaaaatgtttatgatggcgaagaat taaataagagtttgtcagatatggctcaaggatttcgccgaatgatgcaatataaaaaaattaataaaaatcttgttggttttatgcgtgca acggaagtgacaataaataataaagataattcttataatcagcacatgcatgtattggtatgtgtggaaccaacttattttaagaataca gaaaactacgtgaatcaaaaacaatggattcaattttggaaaaaggcaatgaaattagactatgatccaaatgtaaaagttcaaatg attcgaccgaaaaataaatataaatcggatatacaatcggcaattgacgaaactgcaaaatatcctgtaaaggatacggattttatga ccgatgatgaagaaaagaatttgaaacgtttgtctgatttggaggaaggtttacaccgtaaaaggttaatctcctatggtggtttgttaaa agaaatacataaaaaattaaaccttgatgacacagaagaaggcgatttgattcatacagatgatgacgaaaaagccgatgaagat ggattttctattattgcaatgtggaattgggaacggaaaaattattttattaaagagtagttcaacaaacgggccagtttgttgaagattag atgctataattgttattaaaaggattgaaggatgcttaggaagacgagttattaatagctgaataagaacggtgctctccaaatattcttat ttagaaaagcaaatctaaaattatctgaaaagggaatgagaatagtgaatggaccaataataatgactagagaagaaagaatgaa gattgttcatgaaattaaggaacgaatattggataaatatggggatgatgttaaggctattggtgtttatggctctcttggtcgtcagactga tgggccctattcggatattgagatgatgtgtgtcatgtcaacagaggaagcagagttcagccatgaatggacaaccggtgagtggaa ggtggaagtgaattttgatagcgaagagattctactagattatgcatctcaggtggaatcagattggccgcttacacatggtcaatttttct ctattttgccgatttatgattcaggtggatacttagagaaagtgtatcaaactgctaaatcggtagaagcccaaacgttccacgatgcga tttgtgcccttatcgtagaagagctgtttgaatatgcaggcaaatggcgtaatattcgtgtgcaaggaccgacaacatttctaccatccttg actgtacaggtagcaatggcaggtgccatgttgattggtctgcatcatcgcatctgttatacgacgagcgcttcggtcttaactgaagca gttaagcaatcagatcttccttcaggttatgaccatctgtgccagttcgtaatgtctggtcaacttttccgactctgagaaacttctggaatcg ctagagaatttctggaatgggattcaggagtggacagaacgacacggatatatagtggatgtgtcaaaacgcataccattttgaacg atgacctctaataattgttaatcatgttggttacctgcctcgcgcgtttcggtgatgacggtgaaaacctctgacacatgcagctcccgga gacggtcacagcttgtctgtaagcggatgccgggagcagacaagcccgtcagggcgcgtcagcgggtgttggcgggtgtcggggc gcagccatgacccagtcacgtagcgatagcggagtgtatactggcttaactatgcggcatcagagcagattgtactgagagtgcacc atatgcggtgtgaaataccgcacagatgcgtaaggagaaaataccgcatcaggcgctcttccgcttcctcgctcactgactcgctgcg ctcggtcgttcggctgcggcgagcggtatcagctcactcaaaggcggtaatacggttatccacagaatcaggggataacgcaggaa agaacatgtgagcaaaaggccagcaaaaggccaggaaccgtaaaaaggccgcgttgctggcgtttttccataggctccgccccc tgacgagcatcacaaaaatcgacgctcaagtcagaggtggcgaaacccgacaggactataaagataccaggcgtttccccctgg aagctccctcgtgcgctctcctgttccgaccctgccgcttaccggatacctgtccgcctttctcccttcgggaagcgtggcgctttctcata gctcacgctgtaggtatctcagttcggtgtaggtcgttcgctccaagctgggctgtgtgcacgaaccccccgttcagcccgaccgctgc gccttatccggtaactatcgtcttgagtccaacccggtaagacacgacttatcgccactggcagcagccactggtaacaggattagca gagcgaggtatgtaggcggtgctacagagttcttgaagtggtggcctaactacggctacactagaaggacagtatttggtatctgcgct ctgctgaagccagttaccttcggaaaaagagttggtagctcttgatccggcaaacaaaccaccgctggtagcggtggtttttttgtttgca agcagcagattacgcgcagaaaaaaaggatctcaagaagatcctttgatcttttctacggggtctgacgctcagtggaacgaaaact cacgttaagggattttggtcatgagattatcaaaaaggatcttcacctagatccttttaaattaaaaatgaagttttaaatcaatctaaagt atatatgagtaaacttggtctgacagttaccaatgcttaatcagtgaggcacctatctcagcgatctgtctatttcgttcatccatagttgcct gactccccgtcgtgtagataactacgatacgggagggcttaccatctggccccagtgctgcaatgataccgcgagacccacgctcac cggctccagatttatcagcaataaaccagccagccggaagggccgagcgcagaagtggtcctgcaactttatccgcctccatccag tctattaattgttgccgggaagctagagtaagtagttcgccagttaatagtttgcgcaacgttgttgccattgctacaggcatcgtggtgtc acgctcgtcgtttggtatggcttcattcagctccggttcccaacgatcaaggcgagttacatgatcccccatgttgtgcaaaaaagcggtt agctccttcggtcctccgatcgttgtcagaagtaagttggccgcagtgttatcactcatggttatggcagcactgcataattctcttactgtc
```

-continued

```
atgccatccgtaagatgcttttctgtgactggtgagtactcaaccaagtcattctgagaatagtgtatgcggcgaccgagttgctcttgcc cggcgtcaatacgggataataccgcgccacatagcagaactttaaaagtgctcatcattggaaaacgttcttcggggcgaaaactct caaggatcttaccgctgttgagatccagttcgatgtaacccactcgtgcacccaactgatcttcagcatcttttactttcaccagcgtttctg ggtgagcaaaaacaggaaggcaaaatgccgcaaaaaagggaataagggcgacacggaaatgttgaatactcatactcttcctttt caatattattgaagcatttatcagggttattgtctcatgagcggatacatatttgaatgtatttagaaaaataaacaaatagggggttccgcg cacatttccccgaaaagtgccacct
```

All PCR reactions were performed in 50 ul volume containing 1-2 ul DNA or from a colony resuspension, 5 ul of 10× Pfu Ultra buffer (Stratagene), 1 uL of 10 mM dNTP blend (Roche), 0.5 uL of 0.2 uM primers, 1 ul Pfu Ultra High Fidelity Polymerase, and the volume adjusted with water to have a total volume of 50 ul. The PCR conditions were: 95° C. for 2 min, 30 cycles of 95° C. for 30 sec, 62° C. for 30 sec, 72° C. for 1 min, followed by 1 cycle of 72° C. for 10 min.

The obtained PCR fragments were gel purified using Qiagen Gel Purification Kit according to the manufacturers instructions.

Fusion constructs were obtained by annealing 0.25 ul aliquots of purified PCR fragments that were mixed together and added into fresh PCR mix following the above recipe using primers P3 and P2. The total volume of the PCR mixture was 50 µl. The PCR conditions were the same as above adjusting the annealing temperature according to the Tm of the primers.

The desired SigH, SigA1, and SigA2 constructs were ligated into pBS19 plasmids that had been digested with EcoRI and BamHI to generate SigA and SigH expression vectors that were used to transform host cells as described in Example 4.

The transformation mixture was plated on LB+1.6% skim milk+5 ug/ml cmp plates. The next day, halo-forming colonies were picked and plated for single colonies. The colony purification was performed twice. Five individual clones were analyzed by sequencing of aprE promoter region. All of them had consensus sequence at −35 region of aprE promoter.

Example 6

Host Cell Transformation and Expression of AprE Protease

Five microliters of the ligation mixture containing either the SigA1 or SigH constructs were used to transform *E. coli* Top10 cells (Invitrogen) by electroporation. The transformed cells were plated onto LB agar plates containing 5 ppm/ml chloramphenicol (Cm), and colonies were allowed to grow overnight at 37 C. Individual colonies were picked and transferred to tubes containing 5 ml of LB+5 ppm/ml Cm. Cultures were grown overnight at 37° C. while shaking at 250 rpm. Plasmid DNA was prepared from the *E. coli* cultures, and a portion of the plasmid DNA preparation was sequenced (Sequetech). Automated sequence analysis was performed using Phrep, Phrap, Consed, Custal W software.

The plasmid bearing the right construct from each of the expression vectors was used to transform *Bacillus subtilis* host cells. The expression vectors containing the SigH (SEQ ID NO:23) and SigA1 (SEQ ID NO:26) and SigA2 (SEQ ID NO:31) constructs were named pBS19 ymaH-H and pBS19 ymaH-A1 and pBS19 ymaH-A2 were transformed into *B. subtilis* strains BG2941 and BG2942 as follows. Two microliters of the plasmid DNA carrying the appropriate constructs were used to transform 100 µl of *B. subtilis* cells BG 2941 (ΔnprE, amyE::PxyIRA-comK-phleoR) and BG2942 (ΔnprE, degU(Hy)32, amyE::PxyIRA-comK-eryR). The BG2941 and BG2942 transformants carrying the SigH constructs were named 41 SigH and 42SigH, respectively; and the BG2941 and BG2942 transformants carrying the SigA1 constructs were named 41 SigA1 and 42SigA1, respectively. Some BG2941 and BG2942 host cells were also transformed with a control (empty) pBS19 plasmid, and were named 41pBS19 and 42pBS19. Both BG2941 and BG2942 host cells carry the deletion of the nprE gene, which abolishes most of the non-aprE background proteolytic activity, thus facilitating the measurement of the alkaline protease (AprE) produced. The BG2941 and BG2942 host cells also carry the cassette amyE::PxyIRA-comK-phleoR, which allows to make competent cells by inducing a growing culture with xylose (Hahn et al., Mol Microbiol. 18:755-67 [1995]). The BG2942 host cells also carry a mutation in the degU gene (degU(Hy)32 mutation), which alone increases the level of subtilisin secreted by the host cells by several fold relative to that secreted by host cells that do not carry the degU(Hy) mutation (Msadek et al. J Bacteriol, 172:824-834 [1990]).

The effect of overexpressing YmaH in *Bacillus* host cells was determined qualitatively and quantitatively in assays described in Example 7.

Example 7

Effect of Overexpressing YmaH on the Production of Protease

Casein assay:—The effect of overexpressing YmaH on the production of endogenous AprE subtilisin protease by *Bacillus* host cells was determined first by a qualitative assay that compares the size of the halos produced by the colonies grown on agar plates containing casein in the form of skim milk. As protease enzyme is secreted by the *Bacillus* cells, it digests the casein in the skim milk, and forms regions of clearing, or halos around the growing colony. Host cells which have an inactive protease will exhibit little or no halo around the colonies. Thus, the size of the halo provides a qualitative assessment of the amount of protease that is produced by the secreting colony (Wells, T. A. et al. Nucleic Acids Res., 11, 7911-7925: [1983]).

BG2941 and BG2942 *Bacillus subtilis* host cells transformed with SigH or SigA1 expression vectors were plated onto LB agar plates containing 1.6% skim milk and 5 ppm Cm, and incubated overnight in at 37° C. The following day, colonies from some of the transformants were single colony isolated on LB agar plates with 5 ppm Cm, and the plates were incubated overnight at 37 C. Single colony isolates were picked and patched on the same type of plates and incubated again at 37° C. overnight.

The largest halos were produced by the 42SigH host cells. The 42SigH cells are BG2942 *Bacillus subtilis* host cells that carry the degU(Hy)32 mutation and the SigH construct that enables the overexpression of YmaH protein. In particular, the size of the halos of the 42SigH cells evidences that overexpressing ymaH further enhances the production of subtilisin in host cells that already produce levels of the enzyme that are greater than those produced by wild-type cells. For example, 42SigH cells produce halos that are bigger than those produced by the 42pBS19 cells, which carry the degU (Hy) mutation but do not carry a construct that enables overexpression of ymaH, but which in turn produce halos that are bigger than the halos produced by the 41pBS19 cells, which are BG2941 *Bacillus subtilis* host cells that do not carry the degU(Hy)32 mutation and do not carry a construct that enables overexpression of ymaH. The halos produced by the 42SigH cells were also greater than the halos produced by the 41 SigH cells, which do not carry the degU(Hy) mutation but carry the SigH construct to enable overexpression of YmaH.

AAPF assay—The production of subtilisin by transformed *Bacillus* host cells 42SigH, 42SigA1, 41 SigA2, which overexpress ymaH, and their respective controls 42pBS19, and 41pBS19 was quantified as a function of the activity of the secreted AprE protease. The proteolytic activity of the secreted protease was determined as the rate of hydrolysis of the substrate succinyl-L-Ala-L-Ala-L-Pro-L-Phe-p-nitroanalide (AAPF from Sigma Chemical Co). The assay measured the level of production of protease as the absorbance at 405 nm/min resulting from the hydrolysis and release of p-nitroanaline (Estell et al., J Biol Chem., 260:6518-6521 [1985]). The measurements were made using the Sofmax Pro software, and the specified conditions were set as: Type: Kinetic; Reduction: Vmax Points (Read best 15/28 points); Lm1: 405 nm; Time: 5 minutes; and Interval: 11 Seconds.

Liquid cultures of *B. subtilis* control host cells 41pBS19 and 42pBS19, and host cells overexpressing YmaH were obtained by inoculating 5 ml of LB containing 5 pmm of chloramphenicol (Cm) with single colonies of transformed cells 41SigH and 42SigA1 and 42SigH, and allowing the cells to grow while shaking at 37 C until growth reached mid-logarithmic phase. Each of the cultures was diluted 1:100 with fresh complex medium containing 5 ppm Cm, and allowed to grow at 37° C. while shaking at 250 rpm. Samples of the cultures were taken at the times indicated in the figures. The samples were centrifuged and the supernatants were tested for production of subtilisin.

Ten microliters of each of the *B. subtilis* cultures supernatants were diluted 100 ul of Tris Buffer, containing 10 mM Tris+0.005% TWEEN®-80, pH 8.6; and 25 ul of 100 mg/ml AAPF. The activity of each of the protease was calculated, and the effect of overexpressing YmaH on the production of the protease is shown in FIGS. 10A-B and FIG. 11.

Figure 10A:
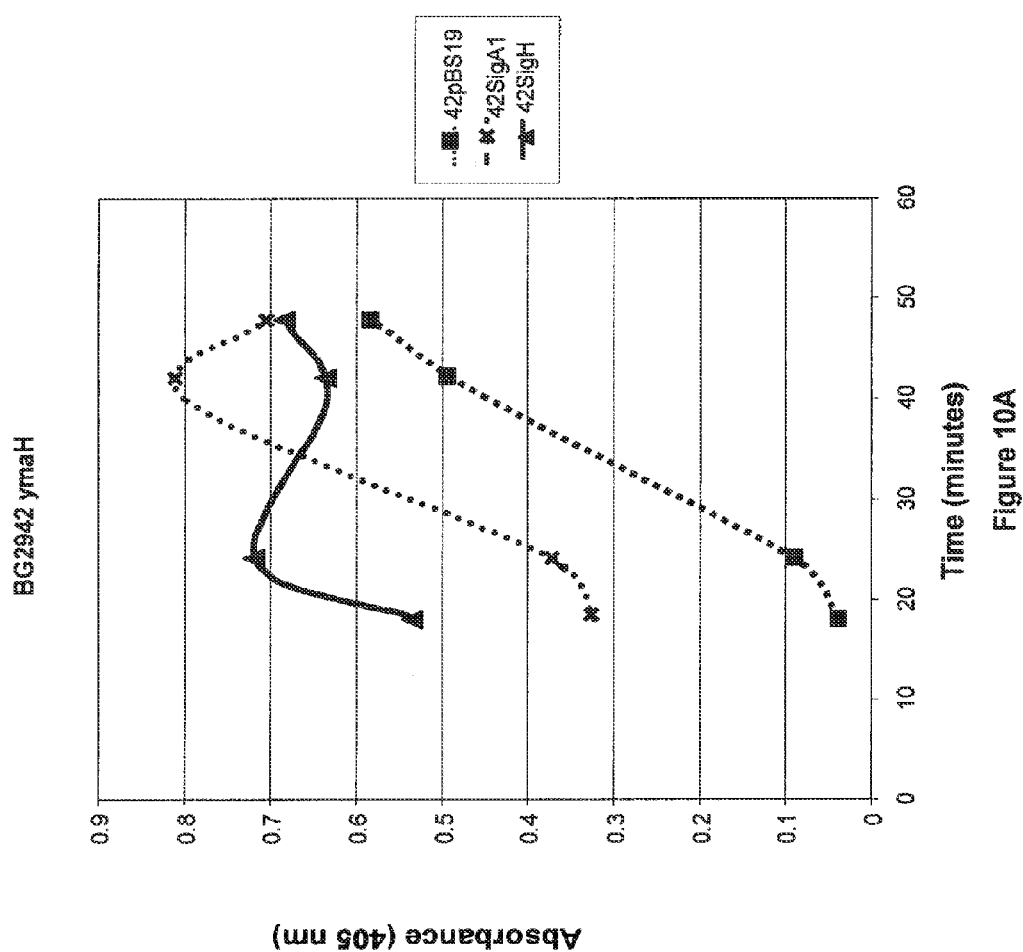
FIG. 10 (A-B) Panel A shows a graph of the proteolytic activity of subtilisin produced by *Bacillus* control host cells (42pBS) and by *Bacillus subtilis* host cells that overexpress ymaH (42SigA1 and 42SigH). Panel B shows the subtilisin activity produced by *Bacillus* control host cells (41 pBS) and by *Bacillus subtilis* host cells that overexpress ymaH (41 SigH). The proteolytic activity was measured as the increase in absorbance at 405 nm due to the hydrolysis and release of p-nitroanaline. The level of enzymatic activity is indicative of the effect of overexpressing ymaH on the production of subtilisin by *Bacillus* host cells.

FIGS. 10A and 10B show that overexpressing YmaH in *Bacillus* host cells, whether in presence (42SigA and 42SigH; FIG. 10A) or absence (41SigH; FIG. 10B) of the degU(Hy) mutation, enhances the production of the AprE subtilisin by several fold when compared to the level produces by the respective control cells 41pBS19 and 42pBS19. In addition, cells that overexpress YmaH produce elevated levels of the AprE subtilisin earlier than cells that do not overexpress YmaH. For example, FIG. 10A shows that 42sigH cells produce almost as much subtilisin at 20 hours of growth as the parent control cells produce at 48 hours. Similarly, FIG. 10B shows that 41 SigH cells produce more subtilisin at 25 hours than the 41 pBS control cells produce at 48 hours. The graph shown in FIG. 11 shows that cells that the expression of YmaH when driven by the SigH promoter (42SigH) results in the production of subtilisin that is greater than that produced by cells in which YmaH expression is driven by the Sigma A promoter (42SigA). FIG. 11 also shows that overexpression of YmaH whether driven by the SigH or SigA promoter results in enhanced production of AprE subtilisin as early as after only one hour of cell growth.

Example 8

Effect of YmaH Overexpression on Protease Expression in Modified *Bacillus* sp. Host Cells Containing an Inactivated phrA or phrE Gene The effect of overexpressing YmaH protein on the enhanced ability of *Bacillus* cells that lack phrA or phrE to produce protease was tested.

The expression construct SigH, which comprises the ymaH gene operably linked to its native promoter (SigH promoter), was amplified by PCR using the primers ymaH 1F EcoRI (P1; SEQ ID NO:24) and ymaH 3'R BamHI (P2; SEQ ID NO:25) and cloned in the multicopy plasmid pBS19 using EcoRI and BamHI restriction sites to generate plasmid pBS19 ymaH sigH (SEQ ID NO:37).

The sequence of the primers used for the amplification is set forth below:

| Primer | Sequence | Description |
|---|---|---|
| ymaH 1F EcoRI (P1) | ggcaccgaattcgacgtggttt cgcaacaaaatgcag (SEQ ID NO: 24) | 5' ymaH |
| ymaH 3'R BamHI (P2) | ggcaccggatcctcataaaaaa agaccgtgccttgg (SEQ ID NO: 25 | 3' ymaH |

Figure 9:
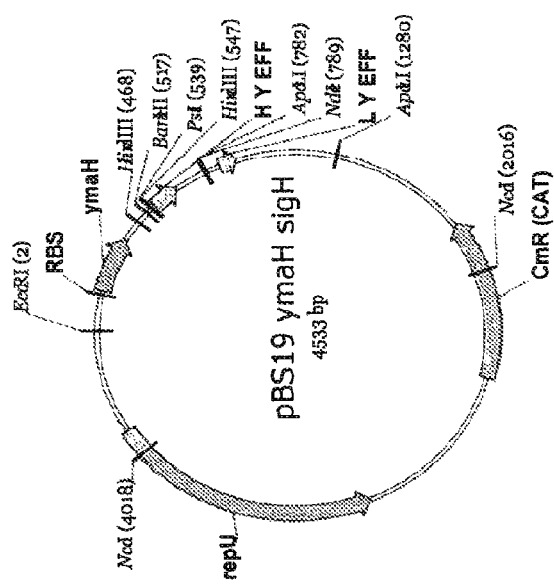
FIG. 9 shows a map of the plasmid pBS19-ymaH sigH.

The map of the plasmid pBS19 ymaH sigH is set forth in FIG. 9, and the sequence of the plasmid pBS19 ymaH sigH is set forth below:

(SEQ ID NO: 37)

```
gaattcgacgtggtttcgcaacaaaatgcaggtcacatggttcgatatgacaccgcctgttgatatggagctgaaaaaaaaggaaatt ttcacacatatagcaggaaaactcgaactttaatcgaaactgtatgatatagagaatcaaggaggacgaaacatgaaaccgattaat attcaggatcagttttttgaatcaaatccggaaagaaaatacgtatgtcactgttttttttgctgaacggctttcagttgcggggccaggtgaa aggctttgataactttaccgtattgttggaatcggaaggtaagcagcagcttatatataaacatgcgatctcaacgtttgcgccgcaaaa aaacgtccagcttgaactcgaatagatcaaaaaatgccatgtcaagacatgaggaaaggctgtcgggggttcccggcggccatttttt aacatgaatccacttttgctccaagcttttttgtgtaagctgaccatgccaaggcacggtcttttttttatgaggatcctctagagtcgacctgc aggcatgcaagcttggcgatcctgcctcgcgcgtttcggtgatgacggtgaaaacctctgacacatgcagctcccggagacggtcac
```

```
agcttgtctgtaagcggatgccgggagcagacaagcccgtcagggcgcgtcagcgggtgttggcgggtgtcggggcgcagccatg
acccagtcacgtagcgatagcggagtgtatactggcttaactatgcggcatcagagcagattgtactgagagtgcaccatatgcggtg
tgaaataccgcacagatgcgtaaggagaaaataccgcatcaggcgctcttccgcttcctcgctcactgactcgctgcgctcggtcgttc
ggctgcggcgagcggtatcagctcactcaaaggcggtaatacggttatccacagaatcagggggataacgcaggaaagaacatgt
gagcaaaaggccagcaaaaggccaggaaccgtaaaaaggccgcgttgctggcgtttttccataggctccgcccccctgacgagc
atcacaaaaatcgacgctcaagtcagaggtggcgaaacccgacaggactataaagataccaggcgtttccccctggaagctccct
cgtgcgctctcctgttccgaccctgccgcttaccggatacctgtccgcctttctcccttcgggaagcgtggcgctttctcatagctcacgct
gtaggtatctcagttcggtgtaggtcgttcgctccaagctgggctgtgtgcacgaaccccccgttcagcccgaccgctgcgccttatccg
gtaactatcgtcttgagtccaacccggtaagacacgacttatcgccactggcagcagccactggtaacaggattagcagagcgagg
tatgtaggcggtgctacagagttcttgaagtggtggcctaactacggctacactagaaggacagtatttggtatctgcgctctgctgaag
ccagttaccttcggaaaaagagttggtagctcttgatccggcaaacaaaccaccgctggtagcggtggtttttttgtttgcaagcagcag
attacgcgcagaaaaaaaggatctcaagaagatcctttgatcttttctacggggtctgacgctcagtggaacgaaaactcacgttaag
ggattttggtcatgagattatcaaaaaggatctgagctgtaatataaaaaccttcttcaactaacggggcaggttagtgacattagaa
aaccgactgtaaaaagtacagtcggcattatctcatattataaaagccagtcattaggcctatctgacaattcctgaatagagttcataa
acaatcctgcatgataaccatcacaaacagaatgatgtacctgtaaagatagcggtaaatatattgaattacctttattaatgaattttcct
gctgtaataatgggtagaaggtaattactattattattgatatttaagttaaacccagtaaatgaagtccatggaataatagaaagagaa
aaagcattttcaggtataggtgttttgggaaacaatttccccgaaccattatatttctctacatcagaaaggtataaatcataaaactctttg
aagtcattctttacaggagtccaaataccagagaatgttttagatacaccatcaaaaattgtataaagtggctctaacttatcccaataa
cctaactctccgtcgctattgtaaccagttctaaaagctgtatttgagtttatcacccttgtcactaagaaaataaatgcagggtaaaattta
tatccttcttgttttatgtttcggtataaaacactaatatcaatttctgtggttatactaaaagtcgtttgttggttcaaataatgattaaatatctct
tttctcttccaattgtctaaatcaattttattaaagttcatttgatatgcctcctaaattttttatctaaagtgaatttaggaggcttacttgtctgctt
cttcattagaatcaatcctttttaaaagtcaatattactgtaacataaatatatttttaaaaatatcccacttatccaattttcgtttgttgaac
taatgggtgctttagttgaagaataaaagaccacattaaaaaatgtggtcttttgtgttttttaaaggatttgagcgtagcgaaaaatccttt
tctttcttatcttgataataagggtaactattgccggttgtccattcatggctgaactctgcttcctctgttgacatgacacacatcatctcaat
atccgaatagggcccatcagtctgacgaccaagagagccataaacaccaatagccttaacatcatcccatatttatccaatattcgtt
ccttaatttcatgaacaatcttcattctttcttctctagtcattattattggtccattcactattctcattcccttttcagataatttttagatttgcttttct
aaataagaatatttggagagcaccgttcttattcagctattaataactcgtcttcctaagcatccttcaatccttttaataacaattatagcat
ctaatcttcaacaaactggcccgtttgttgaactactcttttaataaaataatttttccgttcccaattccacattgcaataatagaaaatccat
cttcatcggcttttcgtcatcatctgtatgaatcaaatcgccttcttctgtgtcatcaaggtttaatttttttatgtatttcttttaacaaaccaccat
aggagattaaccttttacggtgtaaaccttcctccaaatcagacaaacgtttcaaattcttttcttcatcatcggtcataaaatccgtatcctt
tacaggatattttgcagtttcgtcaattgccgattgtatatccgatttatatttattttcggtcgaatcatttgaacttttacatttggatcatagtct
aatttcattgccttttttccaaaattgaatccattgttttttgattcacgtagttttctgtattcttaaaataagttggttccacacataccaatacatg
catgtgctgattataagaattatctttatttattgtcacttccgttgcacgcataaaaccaacaagattttattaattttttttatattgcatcatt
cggcgaaatccttgagccatatctgacaaactcttatttaattcttcgccatcataaacatttttaactgttaatgtgagaaacaaccaacg
aactgttggcttttgtttaataacttcagcaacaaccttllgtgactgaatgccatgtttcattgctctcctccagttgcacattggacaaagc
ctggatttacaaaaccacactcgatacaactttctttcgcctgtttcacgattttgtttatactctaatatttcagcacaatcttttactctttcagc
cttttaaattcaagaatatgcagaagttcaaagtaatcaacattagcgattttctttctctccatggtctcacttttccacttttttgtcttgtcca
ctaaaacccttgattttcatctgaataaatgctactattaggacacataatatattaaaagaaaccccatctatttagttatttgtttagtcact
tataactttaacagatggggttttctgtgcaaccaatttttaagggttttcaatactttaaaacacatacataccaacacttcaacgcacctttt
cagcaactaaaataaaaatgacgttatttctatatgtatcaagataagaaagaacaagttcaaaaccatcaaaaaaagacacctttc
```

-continued

```
aggtgcttttttttattttataaactcattccctgatctcgacttcgttcttttttacctctcggttatgagttagttcaaattcgttcttttaggttctaa atcgtgtttttcttggaattgtgctgttttatcctttaccttgtctacaaacccttaaaaacgtttttaaaggcttttaagccgtctgtacgttcctt aag.
```

The strain BG2942 deleted for the phrA (CB2-1) and the strain BG2942 deleted for the phrE gene (CB 2-2) were each transformed with the multicopy plasmid pBS19 ymaH sigH (SEQ ID NO:37) to generate strains CB2-11 (BG2942 phrA: spc, pBS19 ymaH sigH) and CB2-12 (BG2942 phrE:spc, pBS19 ymaH sigH), respectively, and tested for the expression of aprE. BG2942 cells that do not carry a deletion of either the phrA or the phrE gene were transformed with the pBS19 ymaH sigH plasmid to generate the control strain 42SigH (BG2942 pBS19 ymaH sigH). All BG2942 derived strains (42SigH, CB2-11 and CB2-12) were grown for nine hours in 2× SNB media and the supernatants were utilized for assaying the activity of AprE using the AAPF assay.

Figure 12:
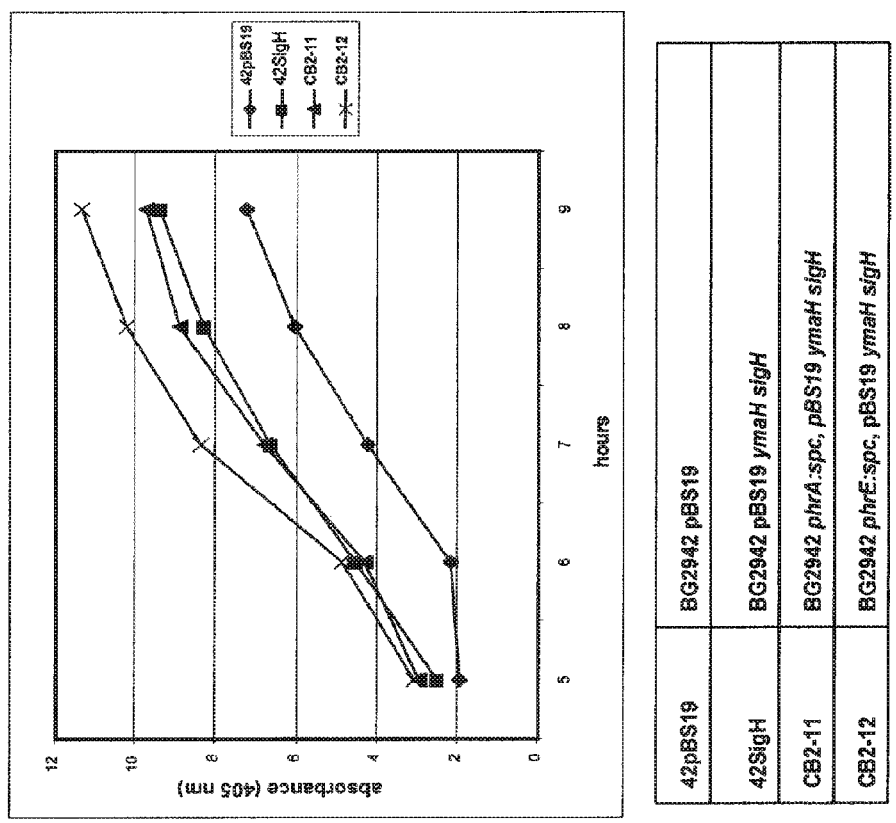
FIG. 12 is a graph showing a synergistic effect of phr deletion and YamH over-expression (using multicopy plasmid pBS19-ymaH sigH) on AprE expression. The effect of overexpression of YmaH is shown in the *Bacillus subtilis* strain named YmaH (squares), and in the modified strains CB2-11 (triangles) and CB2-12 (crosses), which respectively contain a deletion of the phrA and phrE gene, and is compared to the production of AprE in the control strain 42pBS19.

FIG. 12 shows the effect of overexpressing YmaH on the production of protease by strains carrying the deletion of either the phrA or phrE gene. The strains carrying the multicopy plasmid pBS19 ymaH sigH 42SigH), CB2-11 and CB2-12, showed a higher protease expression when compared to the BG2942 strain that was transformed only with a control pBS19 plasmid (42pBS19). In particular, the results show that overexpression of YmaH in the 42SigH strain (BG2942 pBS19 ymaH sigH) (squares) enhances the production of the AprE protease obtained in the control BG2942 pBS19 (diamonds). In addition, the results also show that deletion of phrE in combination with overexpression of ymaH (CB2-12; crosses) further enhances the production of protease by the BG2942 pBS19 ymaH sigH strain (42SigH; squares) when compared to the production by the modified *Bacillus subtilis* strain CB2-2 (BG2942 phrE:spc) or to the 42SigH (BG2942 ymaH sigH) strain.

Thus, while overexpression of YmaH enhances the production of a protein of interest (e.g., a subtilisin), combining the overexpression of YmaH with the deletion of a phr gene, in particular, the phrE gene, further enhances the production of a protein of interest.

Example 9

Protease Expression in *Bacillus* sp. Cells Containing a Deletion of the rapA/phrA Genes Transcription of the rapA/phrA operon was abolished in *Bacillus subtilis* strain BG3594 (degU(Hy)32, oppA, ΔspoIIE, ΔaprE, ΔnprE) that carries the PaprE-FNA expression construct to generate strain JS1121 according to the following.

Figure 13:
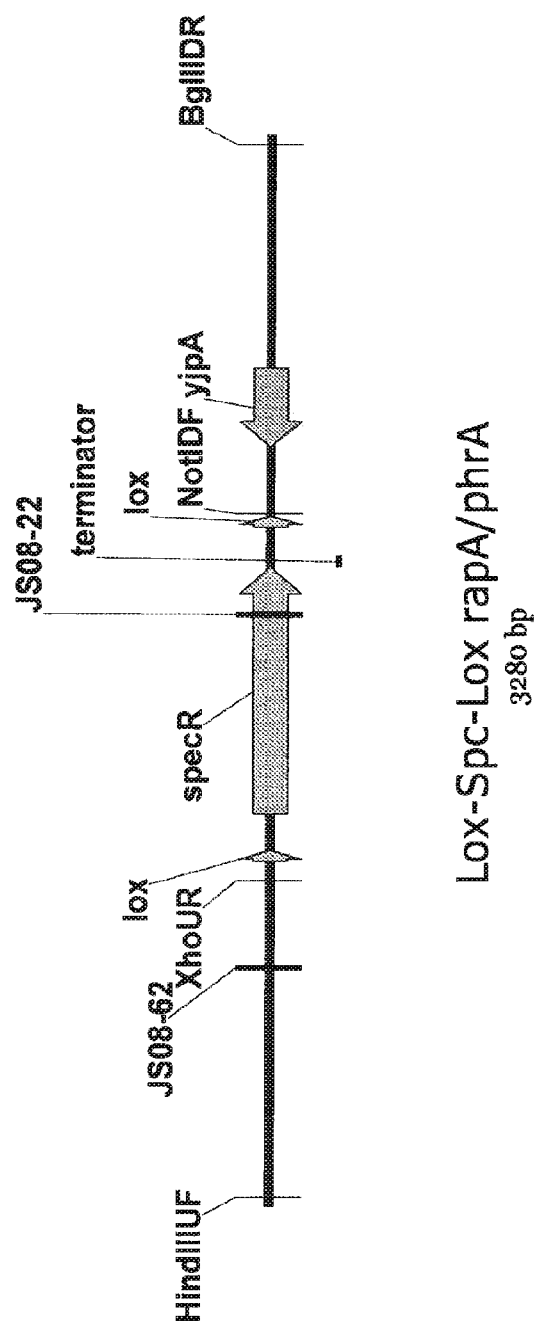
FIG. 13 schematically illustrates the DNA construct used to delete the rapA gene.

The deletion cassette of the rapA/phrA operon is diagramed in FIG. 13, and the polynucleotide sequence is: tggagggagtcagaccgcgtcttgggaaaaaagcaagcggaaagtgaccgtgt- ttacggatggagatggagggacttcaagagagcaggaagccattgtcagagagg- ttcagcggagtcaagtcatcatgaatccgctattgaaaaaagagatatacagatcaa- ttgatcagttttttcatagtgataaatcgtttatcaaacatatgacatcccttacaagcg- cggcattctgttatatggacctcctggaaacggaaagacgacgttagtgaagtcga- tcgcaggcagtatcgatgcacctgttgcttattggcaaattactgaatttacgtcgag- cgagacaatagaagaagtcttcaggcagcgagacgcctcgctcctgcagttctg- gtcatcgaggatatagattcgatgccggaagatgtgcggtccttttttctcaatacgc- tggacggcgcgacatcaaagaggggctatttctcatcggtacgacaaactatcc- cgaagagatcgatccaggtttgatgaatcgtcaggacgattgaccgtgcctatg- aaatcgggcttccggatgaagagctgcggctggaatatatgaaatgagaggctt- tggcatcttttgagtgaaggagaaataaaaaacgccgcaaaacttacagaaggct- tttcctttgcacagctgggagaattatatgtatcttcagcccttcaatggcaccaagaa- gggaatcaccatattgaaaccatggtgaaagacatgacaggagagcaaagaaaa- agccagcggggaagctggatggaaagaaacaaagtcggttttcactaaaagaaa- gcacgggtgtttgaaaaaacccgtgcttttttgttgcggttagccgaaattcgacaatt- gcggttattttgcgttcttcttttttcttgtaaatatgataaaatatgacatatctcgggtaa- ttcaaaagggggggattaattgaggatgaagcagacgctcgaggtcgacggtatc- gataagctggatccataacttcgtataatgtatgctatacgaagttatctagataaaaa- atttagaagccaatgaaatctataaataaactaaattaagtttatttaattaacaactat- ggatataaaataggtactaatcaaaatagtgaggaggatatatttgaatacatacga- acaaattaataaagtgaaaaaaatacttcggaaacatttaaaaaataaccttattggt- acttacatgtttggatcaggagttgagagtggactaaaaccaaatagtgatcttgact- ttttagtcgtcgtatctgaaccattgacagatcaaagtaaagaaatacttatacaaaa- aattagacctatttcaaaaaaaataggagataaaagcaacttacgatatattgaatta- acaattattattcagcaagaaatggtaccgtggaatcatcctcccaaacaagaattta- tttatggagaatggttacaagagctttatgaacaaggatacattcctcagaaggaatt- aaattcagatttaaccataatgcttaccaagcaaaacgaaaaaataaaagaatata- cggaaattatgacttagaggaattactacctgatattccatttttctgatgtgagaagag- ccattatggattcgtcagaggaattaatagataattatcaggatgatgaaaccaact- ctatattaacttttatgccgtatgatttttaactatggacacgggtaaaatcataccaaaa- gatattgcgggaaatgcagtggctgaatcttctccattagaacataggggagagaatt- ttgttagcagttcgtagttatcttggagagaatattgaatggactaatgaaaatgtaaa- tttaactataaactatttaaataacagattaaaaaaattataaaaaaattgaaaaaatg- gtggaaacacttttttcaatttttttgttttattatttaatatttgggaaatattcattctaatt- ggtaatcagattttagaaaacaataaaccttgcatatgtctagataacttcgtataat- gtatgctatacgaagttatgcggccgccacgcacaaaaacaaatccagagagga- gattgttatatgaaatctaaatggatgtcaggtttgttgctcgttgcggtcgggttca- gctttactcaggtgatggttcatgcaggtgaaacagcaaacacagaagggaaaac- atttcatattgcggcacgcaatcaaacatgatgcataaaaaaagacccttaggggt- cttttttatttcttcagcttccattctttttatcgtcagctcagaagatccacttgccacca- gcggatccgcatggccgatttccgctgcctcttccagtgaatctgcttcgatgacat- acgctccgcctgtggcgtcgctgaatggcccaaacatttttaaacgttttctgcctg- taaacgatccagaaattcatagtgcccagccacatgctcctgattaaatttctccgtt- ctcattgtcagcattaaatatggtatacatattcagaccctccgtgaacttcagtttaac- acatttatccatattacggtgatagatgatatgagcttttcgtcctacgaatgccacct- atttatgaaaaagaaaaggagagatgataggtgagcattccagtaaagaaaaatt- tggtttctgaggcgaaatacgcgttgaagtgtcctaatgcaatgtccgctgaatacat- taccattcacaacacggcaaacgatgcatcagcggccaatgaaatcagctatatg- atcgggaacacaagctcgacaagcttttcatttttgcggtcgatgatcaagaggtgat- tcaaggtctgccgcttaaccgaaacgcttggcacactggtgacggcacaaacggt- ccggggaaaccgcaaatcaatcggtgttgagatttgctacagcaaatcgggaggcc- cgaagtatgaggcagctgaagccttggcgatttcatttgttgcacagctgttgaagg- agcgcggctggggcatcgatcgggtgagaaagcatcaggactggagcggaaa- gtattgcccgcaccgcatttatcagaggggcgctgggatcaagtgaaggcggcg- attgaaaaggaattaaacggggcgtatcagcgaaaaaagctgcagtctcttcttc- ggcgtctgaatatcatgtaaaaaaaggtgacacactgtcagggattgccgcatca; SEQ ID NO:52, was made by PCR amplification of the two partial yjo nucleotide sequences and ligation of the amplified fragments to the lox-Spectinomycin-lox cassette. The partial yjoB gene sequence located upstream the rapA sequence was amplified using the oligos HindIIIUF gcgtgcaagcttggagggagtcagaccgcgtctttgg; SEQ ID NO:56, and XhoUR agaggactcgagcgtctgcttcatcctcaattaatc; SEQ ID NO:55, and the sequence located downstream the rapA gene containing the phrA and yjpA gene sequences was amplified using oligos NotIDF ttatgagagcggccgccacgcacaaaaacaaatccagagag; SEQ ID NO:57, and BglIIIDR ccccgtagatctcggcaatccctga- cagtgtgtcacc; SEQ ID NO:58.

Since the phrA gene is transcribed by the rapA promoter (McQuade et al. J. Bacteriology 2001 August; 183(16):4905-9) both the rapA (NP_389125) and the phrA (NP_389126) sequences are not transcribed in this construct.

*Bacillus* sp. strains CF471, CB3-47, JS1121, which contain the PaprE-FNA expression cassette, were grown in a suitable growth medium for 50 hours in shake flasks, and the supernatants were sampled at 18, 24, 42, 48 hours and tested in an AAPF assay as described above.

Figure 14:
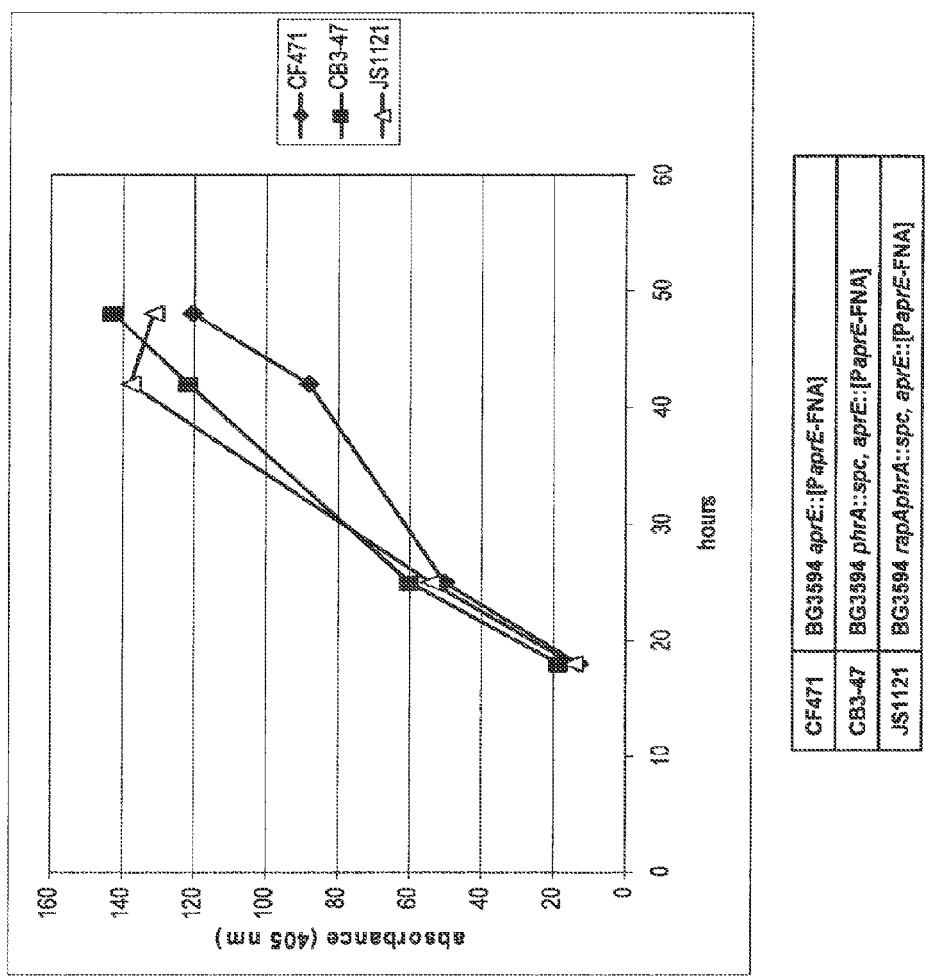
FIG. 14 shows the level of production of subtilisin FNA by *Bacillus subtilis* control host cells CF471 (filled diamond), the modified *Bacillus subtilis* cells CB3-47 (filled square) comprising an inactivated phrA gene, and the modified *Bacillus subtilis* cells JS1121 (open triangle) comprising an inactivated rapA gene and an inactivated phrA gene.
Figure 15:
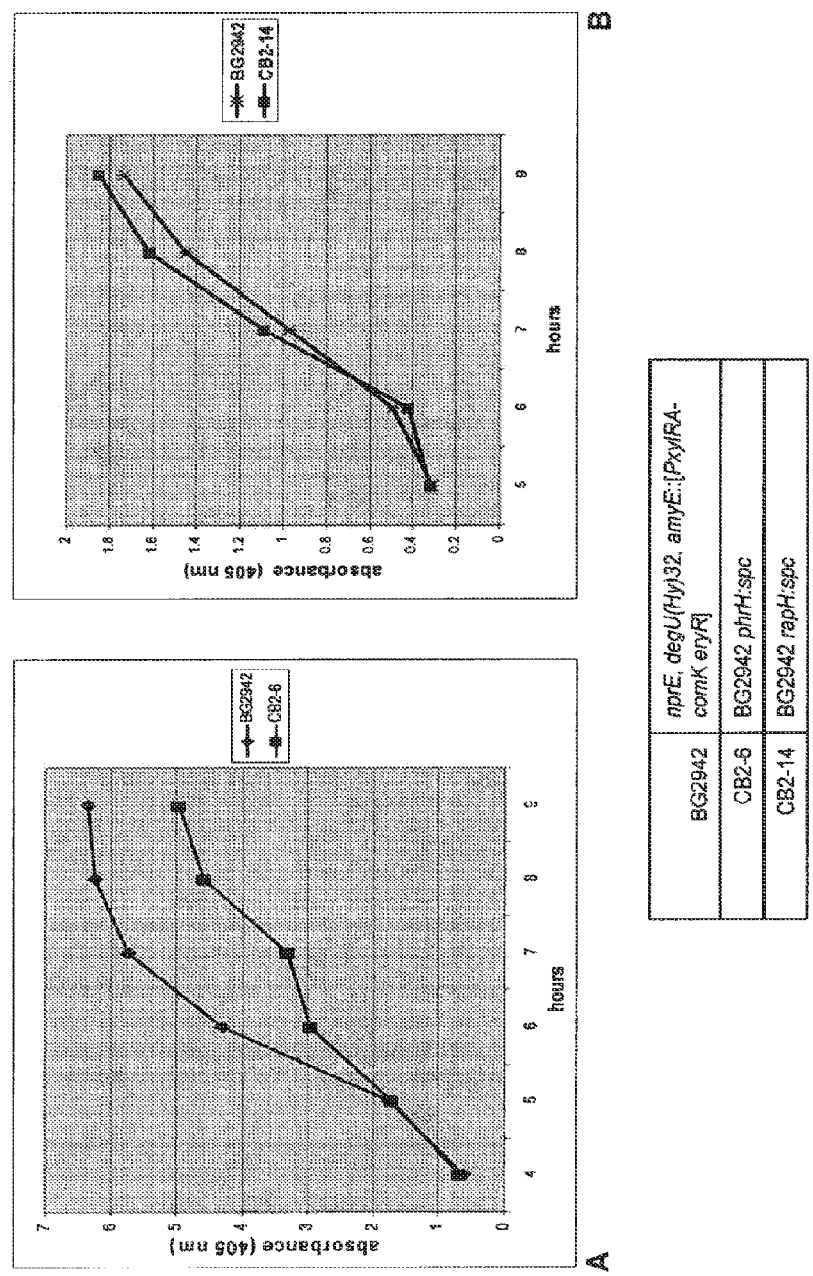
FIG. 15 (A-B) shows the effect of deleting the phrH gene (filled square, panel A) or the rapH gene (filled square, panel B) genes on the production of AprE by *Bacillus subtilis*.

The results (FIG. 14) showed that the strain carrying the deletion of phrA (CB3-47; closed squares), and the strain carrying the deletion of rapA and phrA genes (JS1121; open triangles) exhibit increased FNA expression when compared to the control strain CF471 (closed diamonds).

Therefore, inactivation of the phrA and/or the rapA genes increases the production of the heterologous subtilisin FNA when compared to the production of the same enzyme by the unmodified precursor host cell.

While particular embodiments of the present invention have been illustrated and described, it will be apparent to those skilled in the art that various other changes and modifications can be made without departing from the spirit and scope of the invention. It is therefore intended to cover in the appended claims all such changes and modifications that are within the scope of this invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. A host cell comprising a rap operon comprising at least one inactivated rap gene, wherein said host cell further overexpresses YmaH.

2. The host cell of claim 1, wherein said host cell further comprises a recombinant nucleic acid.

3. The host cell of claim 2, wherein said recombinant nucleic acid further comprises a polynucleotide sequence encoding a protein of interest.

4. The host cell of claim 3, wherein said recombinant nucleic acid further comprises a promoter that is operably linked to said polynucleotide sequence encoding said protein of interest.

5. The host cell of claim 4, wherein said promoter is the wild-type or a mutant aprE promoter.

6. The host cell of claim 3, wherein said host cell produces said protein of interest at a level that is greater than that produced by a host cell that does not comprise at least one inactivated rap gene and does not overexpress YmaH.

7. The host cell of claim 6, wherein said protein of interest is an enzyme.

8. The host cell of claim 7, wherein said enzyme is a protease.

9. The host cell of claim 1, wherein said at least one inactivated rap gene is the rapA gene.

10. The host cell of claim 1, comprising an inactivated rapA gene and a recombinant nucleic acid encoding a protein of interest.

11. The host cell of any of claim 1, wherein said host cell is a *Bacillus* sp. host cell.

12. The host cell of claim 11, wherein said *Bacillus* sp. host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus,*

*Bacillus licheniformis, Bacillus megaterium, Bacillus pumilus, Bacillus stearothermophilus, Bacillus subtilis,* or *Bacillus thuringiensis* cell.

13. The host cell of claim 11, wherein said *Bacillus* sp. host cell is a *Bacillus subtilis* host cell.

14. A method for producing at least one protein of interest comprising providing a host cell comprising a rap operon comprising at least one inactivated rap gene, wherein said host cell further overexpresses YmaH; and growing said host cell under suitable conditions for producing said at least one protein of interest.

15. The method of claim 14, wherein said protein of interest is encoded by a recombinant nucleic acid present in said host cell.

16. The method of claim 15, wherein said recombinant nucleic acid comprises a promoter that is operably linked to the polynucleotide sequence encoding said protein of interest.

17. The method of claim 14, wherein production of said protein of interest by said host cell is greater than the production of said protein of interest by a host cell that does not comprise at least one inactivated rap gene and does not overexpress YmaH.

18. The method of claim 14, wherein the protein of interest is an enzyme.

19. The method of claim 18, wherein said enzyme is a protease.

20. The method of claim 14, wherein said host cell further comprises a mutation in at least one gene chosen from degU, degQ, degS, sco4, spoIIE, degQ and degR.

21. The method of claim 20, wherein said host cell comprises a deg(Hy)32 mutation.

22. The method of claim 14, wherein said inactivated rap gene is rapA.

23. The method of claim 14, wherein said overexpression of YmaH is achieved by introducing a SigH construct into said host cell.

24. The method of claim 23, wherein said SigH construct comprises SEQ ID NO:23, comprising a SigH promoter operably linked to a polynucleotide encoding YmaH protein.

25. The method of claim 14, wherein said overexpression of YmaH is achieved by introducing a SigA construct into said precursor or said modified host cell.

26. The method of claim 25, wherein said SigA construct comprises SEQ ID NO:26 and/or 31, comprising a SigA promoter operably linked to a polynucleotide encoding YmaH.

27. The method of claim 14, wherein said host cell is a *Bacillus* sp. host cell.

28. The method of claim 27, wherein said *Bacillus* sp. host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* cell.

29. The method of claim 27, wherein said *Bacillus* sp. host cell is a *Bacillus subtilis* cell.

30. The method of claim 14, wherein said host cell comprises an inactivated rapA gene and a recombinant nucleic acid encoding said protein of interest.

* * * * *

UNITED STATES PATENT AND TRADEMARK OFFICE
CERTIFICATE OF CORRECTION

Page 1 of 1

PATENT NO. : 8,476,042 B2
APPLICATION NO. : 13/622968
DATED : July 2, 2013
INVENTOR(S) : Cristina Bongiorni et al.

It is certified that error appears in the above-identified patent and that said Letters Patent is hereby corrected as shown below:

In the Claims

Claim 11, column 166, line 61, delete "any of"

Claim 12, column 167, line 1, replace "lichenifonnis" with "licheniformis"

Signed and Sealed this
Fourteenth Day of October, 2014

Michelle K. Lee
*Deputy Director of the United States Patent and Trademark Office*

SEQUENCE LISTING

<160> NUMBER OF SEQ ID NOS: 101

<210> SEQ ID NO 1
<211> LENGTH: 30
<212> TYPE: DNA
<213> ORGANISM: Artificial Sequence
<220> FEATURE:
<223> OTHER INFORMATION: Synthetic primer CB2008-007: upstream phrA

<400> SEQUENCE: 1
gaggatatgg aagaagacca agatttgctg                                    30

<210> SEQ ID NO 2
<211> LENGTH: 24
<212> TYPE: DNA
<213> ORGANISM: Artificial Sequence
<220> FEATURE:
<223> OTHER INFORMATION: Synthetic primer CB2008-008: downstream phrA

<400> SEQUENCE: 2
ggcaatccct gacagtgtgt cacc                                          24

<210> SEQ ID NO 3
<211> LENGTH: 49
<212> TYPE: DNA
<213> ORGANISM: Artificial Sequence
<220> FEATURE:
<223> OTHER INFORMATION: Synthetic primer CB2008-009: linker up phrA
      down-lox

<400> SEQUENCE: 3
gcggccgcca tatgcatcct aggcccccga ccgcaacgag caacaaacc            49

<210> SEQ ID NO 4
<211> LENGTH: 49
<212> TYPE: DNA
<213> ORGANISM: Artificial Sequence
<220> FEATURE:
<223> OTHER INFORMATION: Synthetic primer CB2008-009-R:  linker up phrA
      down-lox

<400> SEQUENCE: 4
ggtttgttgc tcgttgcggt cgggggccta ggatgcatat ggcggccgc            49

<210> SEQ ID NO 5
<211> LENGTH: 49
<212> TYPE: DNA
<213> ORGANISM: Artificial Sequence
<220> FEATURE:
<223> OTHER INFORMATION: Synthetic primer CB2008-010:  linker down phrA
      up-lox

<400> SEQUENCE: 5
ggatccagct tatcgatacc gtcgatgcat aaaaaaagac ccttaggggg            49

<210> SEQ ID NO 6
<211> LENGTH: 49
<212> TYPE: DNA
<213> ORGANISM: Artificial Sequence
<220> FEATURE:
<223> OTHER INFORMATION: Synthetic primer CB2008-010R:  linker down phrA
      up-lox

<400> SEQUENCE: 6
cccctaaggg tcttttttta tgcatcgacg gtatcgataa gctggatcc            49

<210> SEQ ID NO 7
<211> LENGTH: 31
<212> TYPE: DNA
<213> ORGANISM: Artificial Sequence
<220> FEATURE:
<223> OTHER INFORMATION: Synthetic primer CB2008-019A:  upstream phrE

<400> SEQUENCE: 7
ctaatggcct ttcgccataa aattatgttg g                              31

<210> SEQ ID NO 8
<211> LENGTH: 25
<212> TYPE: DNA
<213> ORGANISM: Artificial Sequence
<220> FEATURE:
<223> OTHER INFORMATION: Synthetic primer CB2008-021:  downstream phrE

<400> SEQUENCE: 8
tgtaggcgtt agcaagctca tgcgc                                      25

<210> SEQ ID NO 9
<211> LENGTH: 47
<212> TYPE: DNA
<213> ORGANISM: Artificial Sequence
<220> FEATURE:
<223> OTHER INFORMATION: Synthetic primer CB2008-019B:  linker up phrE
      down lox

<400> SEQUENCE: 9
gcggccgcca tatgcatcct aggccgcaag tccaattaaa acggcgg              47

```
<210> SEQ ID NO 10
<211> LENGTH: 47
<212> TYPE: DNA
<213> ORGANISM: Artificial Sequence
<220> FEATURE:
<223> OTHER INFORMATION: Synthetic primer CB2008-019R:  linker up phrE
      down lox

<400> SEQUENCE: 10
ccgccgtttt aattggactt gcggcctagg atgcatatgg cggccgc                47

<210> SEQ ID NO 11
<211> LENGTH: 54
<212> TYPE: DNA
<213> ORGANISM: Artificial Sequence
<220> FEATURE:
<223> OTHER INFORMATION: Synthetic primer CB2008-020:  linker down phrE
      up lox

<400> SEQUENCE: 11
ggatccagct tatcgatacc gtcgattcga taaacaacat tagttctgat tccc       54

<210> SEQ ID NO 12
<211> LENGTH: 54
<212> TYPE: DNA
<213> ORGANISM: Artificial Sequence
<220> FEATURE:
<223> OTHER INFORMATION: Synthetic primer CB2008-020R:  linker down phrE
      up lox

<400> SEQUENCE: 12
gggaatcaga actaatgttg tttatcgaat cgacggtatc gataagctgg atcc       54

<210> SEQ ID NO 13
<211> LENGTH: 26
<212> TYPE: DNA
<213> ORGANISM: Artificial Sequence
<220> FEATURE:
<223> OTHER INFORMATION: Synthetic primer CB2008-041:  5' rapA

<400> SEQUENCE: 13
actcatatcc ggcagttcca cgtcgc                                       26

<210> SEQ ID NO 14
<211> LENGTH: 28
<212> TYPE: DNA
<213> ORGANISM: Artificial Sequence
<220> FEATURE:
<223> OTHER INFORMATION: Synthetic primer CB2008-042:  3' xlyB

<400> SEQUENCE: 14
agatgccgtc tgaggcagtt tgatcacc                                     28

<210> SEQ ID NO 15
<211> LENGTH: 26
<212> TYPE: DNA
<213> ORGANISM: Artificial Sequence
<220> FEATURE:
<223> OTHER INFORMATION: Synthetic primer CB2008-051:  5' rapE

<400> SEQUENCE: 15
agctgtacat gcacactcag cccctc                                       26

<210> SEQ ID NO 16
<211> LENGTH: 27
<212> TYPE: DNA
<213> ORGANISM: Artificial Sequence
```

<220> FEATURE:
<223> OTHER INFORMATION: Synthetic primer CB2008-052: 3' yqcG

<400> SEQUENCE: 16
agaggcgctt tgcctttg ctgtcgc                                          27

<210> SEQ ID NO 17
<211> LENGTH: 2739
<212> TYPE: DNA
<213> ORGANISM: Artificial Sequence
<220> FEATURE:
<223> OTHER INFORMATION: Synthetic construct: nucleotide sequence of the
      phrA deletion construct

<400> SEQUENCE: 17

```
attcgttatt gcaggtaatt atgatgatat gcagtatcca gaaagagcat tgccccactt      60
agaactggct ttagatcttg caaagaaaga aggcaatccc cgcctgatca gttctgccct     120
atataatctc ggaaactgct atgagaaaat gggtgaactg caaaaggcag ccgaatactt     180
tgggaaatct gtttctattt gcaagtcgga aaagttcgat aatcttccgc attctatcta     240
ctcttaaca caagttctgt ataaacaaaa aaatgacgcc gaagcgcaaa aaagtatcg      300
tgaaggattg gaaatcgccc gtcaatacag tgatgaatta tttgtggagc ttttcaatt     360
tttacatgcg ttatacggaa aaaacattga cacagaatca gtctcacaca cctttcaatt     420
tcttgaagaa catatgctgt atccttatat tgaagagctg gcgcatgatg ctgcccaatt     480
ctatatagaa aacggacagc ccgaaaaagc actttcattt tatgagaaaa tggtgcacgc     540
acaaaaacaa atccagagag gagattgttt atatgaaatc taaatggatg tcaggtttgt     600
tgctcgttgc ggtcggggc ctaggatgca tatggcggcc gcataacttc gtatagcata     660
cattatacga agttatctag acatatgcaa gggtttattg ttttctaaaa tctgattacc     720
aattagaatg aatatttccc aaatattaaa taataaaaca aaaaaattga aaaagtgtt     780
tccaccattt tttcaatttt tttataattt ttttaatctg ttatttaaat agtttatagt     840
taaatttaca ttttcattag tccattcaat attctctcca agataactac gaactgctaa     900
caaaattctc tccctatgtt ctaatggaga agattcagcc actgcattc ccgcaatatc     960
ttttggtatg attttaccccg tgtccatagt taaaatcata cggcataaag ttaatataga    1020
gttggtttca tcatcctgat aattatctat taattcctct gacgaatcca taatggctct    1080
tctcacatca gaaaatggaa tatcaggtag taattcctct aagtcataat ttccgtatat    1140
tcttttattt tttcgttttg cttggtaaag cattatggtt aaatctgaat ttaattcctt    1200
ctgaggaatg tatccttgtt cataaagctc ttgtaaccat tctccataaa taaattcttg    1260
tttgggagga tgattccacg gtaccatttc ttgctgaata ataattgtta attcaatata    1320
tcgtaagttg cttttatctc ctattttttt tgaaataggt ctaatttttt gtataagtat    1380
ttctttactt tgatctgtca atggttcaga tacgacgact aaaaagtcaa gatcactatt    1440
tggttttagt ccactctcaa ctcctgatcc aaacatgtaa gtaccaataa ggttattttt    1500
taaatgtttc cgaagtattt ttttcacttt attaatttgt tcgtatgtat tcaaatatat    1560
cctcctcact attttgatta gtacctattt tatatccata gttgttaatt aaataaactt    1620
aattagttt atttatagat ttcattggct tctaaatttt ttatctagat aacttcgtat    1680
agcatacatt atacgaagtt atggatccag cttatcgata ccgtcgctcg gatccactag    1740
tatgcataaa aaagaccct agggtctt ttttatttct tcagcttcca ttctttatc     1800
gtcagctcag aagatccact tgccaccagc ggatccgcat ggccgatttc cgctgcctct    1860
```

```
tccagtgaat ctgcttcgat gacatacgct ccgcctgtgg cgtcgctgaa tggcccaaac    1920 attttaaac gttttctgc ctgtaaacga tccagaaatt catagtgccc agccacatgc      1980
tcctgattaa atttctccgt tctcattgtc agcattaaat atggtataca tattcagacc    2040
ctccgtgaac ttcagtttaa cacatttatc catattacgg tgatagatga tatgagcttt    2100
tcgtcctacg aatgccacct atttatgaaa aagaaaagg agagatgata ggtgagcatt     2160
ccagtaaaga aaaatttggt ttctgaggcg aaatacgcgt tgaagtgtcc taatgcaatg    2220
tccgctgaat acattaccat tcacaacacg gcaaacgatg catcagcggc caatgaaatc    2280
agctatatga tcgggaacac aagctcgaca agctttcatt ttgcggtcga tgatcaagag    2340
gtgattcaag gtctgccgct taaccgaaac gcttggcaca ctggtgacgg cacaaacggt    2400
ccgggaaacc gcaaatcaat cggtgttgag atttgctaca gcaaatcggg aggcccgaag    2460
tatgaggcag ctgaagcctt ggcgatttca tttgttgcac agctgttgaa ggagcgcggc    2520
tggggcatcg atcgggtgag aaagcatcag gactggagcg gaaagtattg cccgcaccgc    2580
attttatcag aggggcgctg ggatcaagtg aaggcggcga ttgaaaagga attaaacggg    2640
ggcgtatcag cgaaaaaagc tgcagtctct tcttcggcgt ctgaatatca tgtaaaaaaa    2700
ggtgacacac tgtcagggat tgccgcatca cacggggcc                           2739
```

<210> SEQ ID NO 18
<211> LENGTH: 3268
<212> TYPE: DNA
<213> ORGANISM: Artificial Sequence
<220> FEATURE:
<223> OTHER INFORMATION: Synthetic construct: nucleotide sequence of the phrE deletion construct

<400> SEQUENCE: 18

```
tttttctgt tcagacataa tggattttga tttggtgtag gcgttagcaa gctcatgcgc     60 taaaaggtt tcttctatgt aggcatctga taagttggca tcttctaaaa aaccaggaat    120
actcgttaag aaagaaattt tcatctcaat taaatcaatc cattggtcag caatgccagc   180
ttgatcttca taaatgatt taatgttatt agcgcctttg cctgaaaact cgctatcatc    240
taaatctgca acagctttga acgctttctt taatttgacc attttacttt ttaaatcttt   300
gtattcctgt gctcgctttt cagcctcggt gagcaaggtt ttggcttcaa atactttcat   360
gatcatatcc tttcatttaa tcgtcataac aaaatattac catggaagaa tgatgaaact   420
aactgttatg tggatcaaat ggtggaaatg aatcattcga tctgtgtcat tttacctatt   480
tgttaatcct ttcaatgaaa ggggacttc caattgtaac atcgccatca tgaaaaaatt    540
cgataacgta gccagattca ctaaacataa agtatccga tccaacggca gttacatcat     600
caattacgtt taatgcatgc tcaagactgg tttttaatgc tggctgttct ccgtaaccc     660 aaagaataat aatgttccta tctttaaaat ggtgtttagc tagccaatcg taaatctctt   720
cctcgtaatc tatagattga tgacaacaaa cttcttccca cttgattcgt ccccaagatg   780
taagggaaaa ctgttgaaa gcagttcata atattttgcc gttaattctt ctgataagat    840
ttctttgttt ttccctagag cttctaagca ttcatcaaat aagtccaaaa tgttcacctc   900
aaaagcttta agtatgatag attttttcag tattagaaat aagaaaaagc cgttatgaaa   960
cggctaaagg gaatcagaac taatgttgtt tatcgaatcg acggtatatc gaagggaa    1020 tgcatgtatg aaatctaaat tgtttatcag tttatccgcc gttttaattg gacttgcgaa   1080
aggcgaattc cagcacactg gcggccgtta ctagtggatc cgagctcgga tccataactt   1140
cgtataatgt atgctatacg aagttatcta gataaaaaat ttagaagcca atgaaatcta   1200
```

```
taaataaact aaattaagtt tatttaatta acaactatgg atataaaata ggtactaatc    1260
aaaatagtga ggaggatata tttgaataca tacgaacaaa ttaataaagt gaaaaaaata    1320
cttcggaaac atttaaaaaa taaccttatt ggtacttaca tgtttggatc aggagttgag    1380
agtggactaa aaccaaatag tgatcttgac ttttagtcg tcgtatctga accattgaca     1440
gatcaaagta agaaatact tatacaaaaa attagaccta tttcaaaaaa ataggagat     1500 aaaagcaact tacgatatat tgaattaaca attattattc agcaagaaat ggtaccgtgg    1560
aatcatcctc ccaaacaaga atttatttat ggagaatggt tacaagagct ttatgaacaa    1620
ggatacattc ctcagaagga attaaattca gatttaacca taatgcttta ccaagcaaaa    1680
cgaaaaaata aagaatata cggaaattat gacttagagg aattactacc tgatattcca     1740
ttttctgatg tgagaagagc cattatggat tcgtcagagg aattaataga taattatcag    1800
gatgatgaaa ccaactctat attaacttta tgccgtatga ttttaactat ggacacgggt    1860
aaaatcatac caaagatat tgcgggaaat gcagtggctg aatcttctcc attagaacat     1920
agggagagaa ttttgttagc agttcgtagt tatcttggag agaatattga atggactaat    1980
gaaaatgtaa atttaactat aaactattta aataacagat taaaaaatt ataaaaaaat     2040 tgaaaaaatg gtggaaacac tttttcaat ttttttgttt tattatttaa tatttgggaa     2100
atattcattc taattggtaa tcagatttta gaaaacaata aacccttgca tatgtctaga    2160
taacttcgta taatgtatgc tatacgaagt tatgcggccg ccatatgcat cctaggccgc    2220
aagtccaatt aaaacggcgg ataaactgat aaacaattta gatttcatac atgcattccc    2280
ctttcgatat ttgcttttga gcatatacca tcttcttgaa acagatgata ctatcctcta    2340
ttttcccatt ataatcgaaa aggttgcctc ctaacaatgc cagctcttcc agataagggt    2400
atcctttgcc gttctctaaa cgagaaaaaa tgttgagaag tttaggtgta tcgccatttc    2460
ttatataaag aacgtctaat gcttcaaata agttcataaa tagttcgtct ttaaaatcta    2520
cagcacttct gattcctttg cggaagcaat ccattgcttg tcctttttg ccttgtttaa     2580 aataaatcaa cgctaggtca tgataagctt gcggaagtac gtcagagtta atttttctgt    2640
attgaaccaa ggcttgttcg atgtaacgag cagccttatt taagttgtcc attttgtgat    2700
agcaattgcc gagattgaaa aacgcagtgg catagatatg agtattttta cttttaagca    2760
gctcggcacc tttaaagct tcttgaaggt ggggagagc ttttcatga ttttcaaggt       2820 catcgtagtt accggcaatg acaaaatggc actgaatacg acgaacagag taaagctcgt    2880
gtttcttata aatgttgtat gaaagctcag cgtaatgcat cgaaatgtgt gtcattttca    2940
tatgataata gacttcagac agtttaaaat aaaactcagc ttttcaatc ttgtcggaga     3000 ttgtaggaat tttgcgttca gcttttttgt aatatgtaat ggctcttgtg tattcaccgt    3060
ttctaaactc atacatcccg cggaagaagt tataataata tgcccgcata ttgtctaatt    3120 tttcttatg gccctcaatt ttatttaaat attctgaaag ttccattcgg ttttcatcag     3180
atggcagcgt gtattccaac ataattttat ggcgaaaggc cattagttga taataaataa    3240
gcaagtcttg atcttcttcc ataacctc                                       3268
```

<210> SEQ ID NO 19
<211> LENGTH: 1759
<212> TYPE: DNA
<213> ORGANISM: Artificial Sequence
<220> FEATURE:
<223> OTHER INFORMATION: Synthetic construct: nucleotide sequence of aprE promoter-FNA

<400> SEQUENCE: 19

```
gaattcctcc attttcttct gctatcaaaa taacagactc gtgatttttcc aaacgagctt      60
tcaaaaaagc ctctgcccct tgcaaatcgg atgcctgtct ataaaattcc cgatattggc     120
ttaaacagcg gcgcaatggc ggccgcatct gatgtctttg cttggcgaat gttcatctta     180
tttcttcctc cctctcaata atttttttcat tctatcccctt ttctgtaaag tttatttttc    240
agaatacttt tatcatcatg ctttgaaaaa atatcacgat aatatccatt gttctcacgg     300
aagcacacgc aggtcatttg aacgaatttt tcgacagga atttgccggg actcaggagc     360
atttaaccta aaaagcatg acatttcagc ataatgaaca tttactcatg tctattttcg     420
ttcttttctg tatgaaaata gttatttcga gtctctacgg aaatagcgag agatgatata     480
cctaaataga gataaaatca tctcaaaaaa atgggtctac taaaatatta ttccatctat     540
tacaataaat tcacagaata gtcttttaag taagtctact ctgaattttt ttaaaaggag     600
agggtaaaga gtgagaagca aaaaattgtg gatcagtttg ctgtttgctt tagcgttaat     660
ctttacgatg gcgttcggca gcacatcctc tgcccaggcg gcagggaaat caaacgggga     720
aaagaaatat attgtcgggt ttaaacagac aatgagcacg atgagcgccg ctaagaagaa     780
agatgtcatt tctgaaaaag gcgggaaagt gcaaaagcaa ttcaaatatg tagacgcagc     840
ttcagctaca ttaaacgaaa aagctgtaaa agaattgaaa aaagacccga gcgtcgctta     900
cgttgaagaa gatcacgtag cacatgcgta cgcgcagtcc gtgccttacg gcgtatcaca     960
aattaaagcc cctgctctgc actctcaagg ctacactgga tcaaatgtta agtagcggt    1020
tatcgacagc ggtatcgatt cttctcatcc tgatttaaag gtagcaggcg gagccagcat    1080
ggttccttct gaaacaaatc ctttccaaga caacaactct cacggaactc acgttgccgg    1140
cacagttgcg gctcttaata actcaatcgg tgtattaggc gttgcgccaa gcgcatcact    1200
ttacgctgta aaagttctcg gtgctgacgg ttccggccaa tacagctgga tcattaacgg    1260
aatcgagtgg gcgatcgcaa acaatatgga cgttattaac atgagcctcg gcggaccttc    1320
tggttctgct gctttaaaag cggcagttga taaagccgtt gcatccggcg tcgtagtcgt    1380
tgcggcagcc ggtaacgaag gcacttccgg cagctcaagc acagtgggct accctggtaa    1440
ataccttct gtcattgcag taggcgctgt tgacagcagc aaccaaagag catctttctc    1500
aagcgtagga cctgagcttg atgtcatggc acctggcgta tctatccaaa gcacgcttcc    1560
tggaaacaaa tacggcgcgt tgaacggtac atcaatggca tctccgcacg ttgccggagc    1620
ggctgctttg attcttttcta agcacccgaa ctggacaaac actcaagtcc gcagcagttt    1680
agaaaacacc actacaaaac ttggtgattc tttctactat ggaaaagggc tgatcaacgt    1740
acaggcggca gctcagtaa                                                 1759
```

<210> SEQ ID NO 20
<211> LENGTH: 382
<212> TYPE: PRT
<213> ORGANISM: B. amyloliquefaciens

<400> SEQUENCE: 20

```
Val Arg Ser Lys Lys Leu Trp Ile Ser Leu Leu Phe Ala Leu Ala Leu
 1               5                   10                  15

Ile Phe Thr Met Ala Phe Gly Ser Thr Ser Ser Ala Gln Ala Ala Gly
                20                  25                  30

Lys Ser Asn Gly Glu Lys Lys Tyr Ile Val Gly Phe Lys Gln Thr Met
            35                  40                  45
```

Ser Thr Met Ser Ala Ala Lys Lys Lys Asp Val Ile Ser Glu Lys Gly
          50                  55                  60

Gly Lys Val Gln Lys Gln Phe Lys Tyr Val Asp Ala Ser Ala Thr
 65                  70                  75                  80

Leu Asn Glu Lys Ala Val Lys Glu Leu Lys Lys Asp Pro Ser Val Ala
                  85                  90                  95

Tyr Val Glu Glu Asp His Val Ala His Ala Tyr Ala Gln Ser Val Pro
                 100                 105                 110

Tyr Gly Val Ser Gln Ile Lys Ala Pro Ala Leu His Ser Gln Gly Tyr
                 115                 120                 125

Thr Gly Ser Asn Val Lys Val Ala Val Ile Asp Ser Gly Ile Asp Ser
                 130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                 165                 170                 175

Gly Thr Val Ala Ala Leu Asn Asn Ser Ile Gly Val Leu Gly Val Ala
                 180                 185                 190

Pro Ser Ala Ser Leu Tyr Ala Val Lys Val Leu Gly Ala Asp Gly Ser
                 195                 200                 205

Gly Gln Tyr Ser Trp Ile Ile Asn Gly Ile Glu Trp Ala Ile Ala Asn
                 210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                 245                 250                 255

Val Ala Ala Ala Gly Asn Glu Gly Thr Ser Gly Ser Ser Ser Thr Val
                 260                 265                 270

Gly Tyr Pro Gly Lys Tyr Pro Ser Val Ile Ala Val Gly Ala Val Asp
                 275                 280                 285

Ser Ser Asn Gln Arg Ala Ser Phe Ser Ser Val Gly Pro Glu Leu Asp
                 290                 295                 300

Val Met Ala Pro Gly Val Ser Ile Gln Ser Thr Leu Pro Gly Asn Lys
305                 310                 315                 320

Tyr Gly Ala Leu Asn Gly Thr Ser Met Ala Ser Pro His Val Ala Gly
                 325                 330                 335

Ala Ala Ala Leu Ile Leu Ser Lys His Pro Asn Trp Thr Asn Thr Gln
                 340                 345                 350

Val Arg Ser Ser Leu Glu Asn Thr Thr Thr Lys Leu Gly Asp Ser Phe
                 355                 360                 365

Tyr Tyr Gly Lys Gly Leu Ile Asn Val Gln Ala Ala Gln
                 370                 375                 380

<210> SEQ ID NO 21
<211> LENGTH: 381
<212> TYPE: PRT
<213> ORGANISM: Bacillus subtilis

<400> SEQUENCE: 21

Met Arg Ser Lys Lys Leu Trp Ile Ser Leu Leu Phe Ala Leu Thr Leu
 1                5                  10                  15

Ile Phe Thr Met Ala Phe Ser Asn Met Ser Val Gln Ala Ala Gly Lys
                 20                  25                  30

Ser Ser Thr Glu Lys Lys Tyr Ile Val Gly Phe Lys Gln Thr Met Ser
                 35                  40                  45

```
Ala Met Ser Ser Ala Lys Lys Lys Asp Val Ile Ser Glu Lys Gly Gly
            50                  55                  60

Lys Val Gln Lys Gln Phe Lys Tyr Val Asn Ala Ala Ala Thr Leu
 65              70                  75                  80

Asp Glu Lys Ala Val Lys Glu Leu Lys Lys Asp Pro Ser Val Ala Tyr
                85                  90                  95

Val Glu Glu Asp His Ile Ala His Gly Tyr Ala Gln Ser Val Pro Tyr
                100                 105                 110

Gly Ile Ser Gln Ile Lys Ala Pro Ala Leu His Ser Gln Gly Tyr Thr
            115                 120                 125

Gly Ser Asn Val Lys Val Ala Val Ile Asp Ser Gly Ile Asp Ser Ser
            130                 135                 140

His Pro Asp Leu Asn Val Arg Gly Gly Ala Ser Phe Val Pro Ser Glu
145                 150                 155                 160

Thr Asn Pro Tyr Gln Asp Gly Ser Ser His Gly Thr His Val Ala Gly
                165                 170                 175

Thr Ile Ala Ala Leu Asn Asn Ser Ile Gly Val Leu Gly Val Ser Pro
            180                 185                 190

Ser Ala Ser Leu Tyr Ala Val Lys Val Leu Asp Ser Thr Gly Ser Gly
            195                 200                 205

Gln Tyr Ser Trp Ile Ile Asn Gly Ile Glu Trp Ala Ile Ser Asn Asn
            210                 215                 220

Met Asp Val Ile Asn Met Ser Leu Gly Gly Pro Thr Gly Ser Thr Ala
225                 230                 235                 240

Leu Lys Thr Val Val Asp Lys Ala Val Ser Ser Gly Ile Val Val Ala
                245                 250                 255

Ala Ala Ala Gly Asn Glu Gly Ser Ser Gly Ser Thr Ser Thr Val Gly
            260                 265                 270

Tyr Pro Ala Lys Tyr Pro Ser Thr Ile Ala Val Gly Ala Val Asn Ser
            275                 280                 285

Ser Asn Gln Arg Ala Ser Phe Ser Ser Ala Gly Ser Glu Leu Asp Val
            290                 295                 300

Met Ala Pro Gly Val Ser Ile Gln Ser Thr Leu Pro Gly Gly Thr Tyr
305                 310                 315                 320

Gly Ala Tyr Asn Gly Thr Ser Met Ala Thr Pro His Val Ala Gly Ala
                325                 330                 335

Ala Ala Leu Ile Leu Ser Lys His Pro Thr Trp Thr Asn Ala Gln Val
            340                 345                 350

Arg Asp Arg Leu Glu Ser Thr Ala Thr Tyr Leu Gly Asn Ser Phe Tyr
            355                 360                 365

Tyr Gly Lys Gly Leu Ile Asn Val Gln Ala Ala Gln
            370                 375                 380

<210> SEQ ID NO 22
<211> LENGTH: 1496
<212> TYPE: DNA
<213> ORGANISM: Artificial Sequence
<220> FEATURE:
<223> OTHER INFORMATION: Synthetic polynucleotide construct that
      comprise a polynucleotide sequence that encodes YmaH and a SigA
      and a SigH promoter

<400> SEQUENCE: 22
tcataccctg aaaggaaaga caagggaaat tgtcggcaat gagccgctcg gcaggtagaa      60
ggatgtttac cgatgcaaaa aaagggcaaa atgataggt ggttgtccat gttgaatgct     120
ataatggggg agatttataa agagagtga tacatattga ataatacgaa gcagcccgtt     180
```

```
gtcattttag tcggaccgac ggcagtgggg aaaaccaatt taagtattca gctagccaaa      240
tccttaaacg cggaaattat cagcggagat tcgatgcaga tttataaagg gatggatatt     300
ggaacagcta aaattaccga acaggagatg gagggagtgc cccatcatct gattgacatt      360
ttagatcccc aagactcttt ctctactgcc gattatcaaa gcttagtaag aaataaaatc     420
agcgagattg caaatagagg aaagcttccg atgattgacg gcggtacagg gctttatata      480
caatctgagc tttacgatta tacatttacg gaagaggcaa atgatcccgt gtttcgagag      540
agcatgcaaa tggctgctga gcgggaaggc gctgactttc ttcatgccaa acttgctgca      600
gcagatcccg aggcagcagc tgcgattcat ccgaataata caagaagagt cattcgcgca      660
ctggaaattt tacatacgtc cggaaaaacg atgtcccagc atttgaagga acaaaaacga      720
gaacttctgt acaatgcagt gttaattggc ctgacaatgg atagagacac gctttacgaa      780
agaattaatc agcgggtcga tttgatgatg cagtcaggcc ttcttccgga agtgaaacgc      840
ttatacgaca agaacgtgag agactgtcaa tcaatacagg cgataggcta taaagagctg      900
tatgcatatt ttgacggttt tgtgacactt tccgatgctg tcgaacagct aaagcagaac      960
tcgaggcggt atgcgaaacg ccagctgacg tggtttcgca acaaaatgca ggtcacatgg     1020
ttcgatatga caccgcctgt tgatatggag ctgaaaaaaa aggaaatttt cacacatata     1080
gcaggaaaac tcgaacttta atcgaaactg tatgatatag agaatcaagg aggacgaaac     1140
atgaaaccga ttaatattca ggatcagttt ttgaatcaaa tccggaaaga aaatacgtat     1200
gtcactgttt ttttgctgaa cggctttcag ttgcggggcc aggtgaaagg ctttgataac     1260
tttaccgtat tgttggaatc ggaaggtaag cagcagctta tatataaaca tgcgatctca     1320
acgtttgcgc cgcaaaaaaa cgtccagctt gaactcgaat agatcaaaaa atgccatgtc     1380
aagacatgag gaaaggctgt cggggggttcc cggcggccat tttttaacatg aatccacttt    1440 tgctccaagc ttttttgtgta agctgaccat gccaaggcac ggtctttttt tatgag        1496
```

<210> SEQ ID NO 23
<211> LENGTH: 534
<212> TYPE: DNA
<213> ORGANISM: Artificial Sequence
<220> FEATURE:
<223> OTHER INFORMATION: Synthetic SigH construct

<400> SEQUENCE: 23

```
ggcaccgaat tcgacgtggt ttcgcaacaa atgcaggtc acatggttcg atatgacacc       60
gcctgttgat atggagctga aaaaaaagga aatttcaca catatagcag gaaaactcga      120
actttaatcg aaactgtatg atatagagaa tcaaggagga cgaaacatga aaccgattaa     180
tattcaggat cagttttga atcaaatccg gaaagaaaat acgtatgtca ctgttttttt    240
gctgaacggc tttcagttgc ggggccaggt gaaaggcttt gataacttta ccgtattgtt     300
ggaatcggaa ggtaagcagc agcttatata aaacatgcg atctcaacgt ttgcgccgca      360 aaaaacgtc cagcttgaac tcgaatagat caaaaatgc catgtcaaga catgaggaaa      420
ggctgtcggg ggttcccggc ggccattttt aacatgaatc cacttttgct ccaagctttt      480
tgtgtaagct gaccatgcca aggcacggtc ttttttatg agggatccgg agcc            534
```

<210> SEQ ID NO 24
<211> LENGTH: 37
<212> TYPE: DNA
<213> ORGANISM: Artificial Sequence
<220> FEATURE:
<223> OTHER INFORMATION: Synthetic primer: ymaH 1F EcoRI (P1)

```
<400> SEQUENCE: 24
ggcaccgaat tcgacgtggt ttcgcaacaa aatgcag                          37

<210> SEQ ID NO 25
<211> LENGTH: 37
<212> TYPE: DNA
<213> ORGANISM: Artificial Sequence
<220> FEATURE:
<223> OTHER INFORMATION: Synthetic primer: reverse primer P2

<400> SEQUENCE: 25
ggcaccggat ccctcataaa aaaagaccgt gccttgg                          37

<210> SEQ ID NO 26
<211> LENGTH: 626
<212> TYPE: DNA
<213> ORGANISM: Artificial Sequence
<220> FEATURE:
<223> OTHER INFORMATION: Synthetic SigA1 construct

<400> SEQUENCE: 26
gcgccgaatt ctcataccct gaaaggaaag acaagggaaa ttgtcggcaa tgagccgctc    60
ggcaggtaga aggatgttta ccgatgcaaa aaaagggcaa aatggatagg tggttgtcca   120
tgttgaatgc tataatgggg gagatttata aagagagtg atacatattg aataatacga   180
agcagcccca cacatatagc aggaaaactc gaactttaat cgaaactgta tgatatagag   240
aatcaaggag gacgaaacat gaaaccgatt aatattcagg atcagttttt gaatcaaatc   300
cggaaagaaa atacgtatgt cactgttttt ttgctgaacg gctttcagtt gcggggccag   360
gtgaaaggct ttgataactt taccgtattg ttggaatcgg aaggtaagca gcagcttata   420
tataaacatg cgatctcaac gtttgcgccg caaaaaaacg tccagcttga actcgaatag   480
atcaaaaaat gccatgtcaa gacatgagga aaggctgtcg gggggttcccg gcggccattt   540 ttaacatgaa tccacttttg ctccaagctt tttgtgtaag ctgaccatgc caaggcacgg   600 tctttttttta tgagggatcc ggtgcc                                      626

<210> SEQ ID NO 27
<211> LENGTH: 36
<212> TYPE: DNA
<213> ORGANISM: Artificial Sequence
<220> FEATURE:
<223> OTHER INFORMATION: Synthetic forward primer P3

<400> SEQUENCE: 27
gcgccgaatt ctcataccct gaaaggaaag acaagg                          36

<210> SEQ ID NO 28
<211> LENGTH: 50
<212> TYPE: DNA
<213> ORGANISM: Artificial Sequence
<220> FEATURE:
<223> OTHER INFORMATION: Synthetic reverse primer P4

<400> SEQUENCE: 28
ttcgagtttt cctgctatat gtgtggggct gcttcgtatt attcaatatg             50

<210> SEQ ID NO 29
<211> LENGTH: 50
<212> TYPE: DNA
<213> ORGANISM: Artificial Sequence
<220> FEATURE:
<223> OTHER INFORMATION: Synthetic forward primer P5
```

-continued

<400> SEQUENCE: 29
catattgaat aatacgaagc agccccacac atatagcagg aaaactcgaa    50

<210> SEQ ID NO 30
<211> LENGTH: 4039
<212> TYPE: DNA
<213> ORGANISM: Artificial Sequence
<220> FEATURE:
<223> OTHER INFORMATION: Synthetic polynucleotide sequence of pBS19

<400> SEQUENCE: 30

| | | | | |
|---|---|---|---|---|
| gaattcgagc | tcggtacccg | ggatcctct | agagtcgacc | tgcaggcatg caagcttggc | 60 |
| gatcctgcct | cgcgcgtttc | ggtgatgacg | gtgaaaacct | ctgacacatg cagctcccgg | 120 |
| agacggtcac | agcttgtctg | taagcggatg | ccggagcag | acaagcccgt cagggcgcgt | 180 |
| cagcgggtgt | tggcgggtgt | cggggcgcag | ccatgaccca | gtcacgtagc gatagcggag | 240 |
| tgtatactgg | cttaactatg | cggcatcaga | gcagattgta | ctgagagtgc accatatgcg | 300 |
| gtgtgaaata | ccgcacagat | gcgtaaggag | aaaataccgc | atcaggcgct cttccgcttc | 360 |
| ctcgctcact | gactcgctgc | gctcggtcgt | tcggctgcgg | cgagcggtat cagctcactc | 420 |
| aaaggcggta | atacggttat | ccacagaatc | aggggataac | gcaggaaaga acatgtgagc | 480 |
| aaaaggccag | caaaaggcca | ggaaccgtaa | aaaggccgcg | ttgctggcgt ttttccatag | 540 |
| gctccgcccc | cctgacgagc | atcacaaaaa | tcgacgctca | agtcagaggt ggcgaaaccc | 600 |
| gacaggacta | taaagatacc | aggcgtttcc | ccctggaagc | tccctcgtgc gctctcctgt | 660 |
| tccgaccctg | ccgcttaccg | gatacctgtc | cgcctttctc | ccttcgggaa gcgtggcgct | 720 |
| ttctcatagc | tcacgctgta | ggtatctcag | ttcggtgtag | tcgttcgct ccaagctggg | 780 |
| ctgtgtgcac | gaaccccccg | ttcagcccga | ccgctgcgcc | ttatccggta actatcgtct | 840 |
| tgagtccaac | ccggtaagac | acgacttatc | gccactggca | gcagccactg gtaacaggat | 900 |
| tagcagagcg | aggtatgtag | gcggtgctac | agagttcttg | aagtggtggc ctaactacgg | 960 |
| ctacactaga | aggacagtat | ttggtatctg | cgctctgctg | aagccagtta ccttcggaaa | 1020 |
| aagagttggt | agctcttgat | ccggcaaaca | aaccaccgct | ggtagcggtg ttttttttgt | 1080 |
| ttgcaagcag | cagattacgc | gcagaaaaaa | aggatctcaa | gaagatcctt tgatcttttc | 1140 |
| tacgggtct | gacgctcagt | ggaacgaaaa | ctcacgttaa | gggattttgg tcatgagatt | 1200 |
| atcaaaaagg | atctggagct | gtaatataaa | aaccttcttc | aactaacggg gcaggttagt | 1260 |
| gacattagaa | aaccgactgt | aaaaagtaca | gtcggcatta | tctcatatta taaaagccag | 1320 |
| tcattaggcc | tatctgacaa | ttcctgaata | gagttcataa | acaatcctgc atgataacca | 1380 |
| tcacaaacag | aatgatgtac | ctgtaaagat | agcggtaaat | atattgaatt acctttatta | 1440 |
| atgaattttc | ctgctgtaat | aatgggtaga | aggtaattac | tattattatt gatatttaag | 1500 |
| ttaaacccag | taaatgaagt | ccatggaata | atagaaagag | aaaaagcatt ttcaggtata | 1560 |
| ggtgttttgg | gaaacaattt | ccccgaacca | ttatatttct | ctacatcaga aaggtataaa | 1620 |
| tcataaaact | cttgaagtc | attctttaca | ggagtccaaa | taccagagaa tgttttagat | 1680 |
| acaccatcaa | aaattgtata | aagtggctct | aacttatccc | aataacctaa ctctccgtcg | 1740 |
| ctattgtaac | cagttctaaa | agctgtattt | gagtttatca | cccttgtcac taagaaaata | 1800 |
| aatgcagggt | aaaatttata | tccttcttgt | tttatgtttc | ggtataaaac actaatatca | 1860 |
| atttctgtgg | ttatactaaa | agtcgttgt | tggttcaaat | aatgattaaa tatctctttt | 1920 |
| ctcttccaat | tgtctaaatc | aatttattta | agttcatttt | gatatgcctc ctaaattttt | 1980 |

```
atctaaagtg aatttaggag gcttacttgt ctgctttctt cattagaatc aatccttttt    2040
taaaagtcaa tattactgta acataaatat atattttaaa aatatcccac tttatccaat    2100
tttcgtttgt tgaactaatg ggtgctttag ttgaagaata aagaccaca ttaaaaaatg     2160 tggtcttttg tgttttttta aaggatttga gcgtagcgaa aaatccttt ctttcttatc    2220 ttgataataa gggtaactat tgccggttgt ccattcatgg ctgaactctg cttcctctgt    2280
tgacatgaca cacatcatct caatatccga atagggccca tcagtctgac gaccaagaga    2340
gccataaaca ccaatagcct taacatcatc cccatattta tccaatattc gttccttaat    2400
ttcatgaaca atcttcattc tttcttctct agtcattatt attggtccat tcactattct    2460
cattcccttt tcagataatt ttagatttgc ttttctaaat aagaatattt ggagagcacc    2520
gttcttattc agctattaat aactcgtctt cctaagcatc cttcaatcct tttaataaca    2580
attatagcat ctaatcttca acaaactggc ccgtttgttg aactactctt taataaaata    2640 attttccgt tcccaattcc acattgcaat aatagaaaat ccatcttcat cggcttttc    2700 gtcatcatct gtatgaatca aatcgccttc ttctgtgtca tcaaggttta attttttatg    2760
tatttctttt aacaaaccac cataggagat taacctttta cggtgtaaac cttcctccaa    2820
atcagacaaa cgtttcaaat tcttttcttc atcatcggtc ataaaatccg tatcctttac    2880
aggatatttt gcagtttcgt caattgccga ttgtatatcc gatttatatt tattttcgg    2940 tcgaatcatt tgaactttta catttggatc atagtctaat ttcattgcct tttccaaaa    3000 ttgaatccat tgtttttgat tcacgtagtt ttctgtattc ttaaaataag ttggttccac    3060
acataccaat acatgcatgt gctgattata agaattatct ttattattta ttgtcacttc    3120
cgttgcacgc ataaaaccaa caagattttt attaattttt ttatattgca tcattcggcg    3180
aaatccttga gccatatctg acaaactctt atttaattct tcgccatcat aaacattttt    3240
aactgttaat gtgagaaaca accaacgaac tgttggcttt tgtttaataa cttcagcaac    3300
aaccttttgt gactgaatgc catgtttcat tgctctcctc cagttgcaca ttggacaaag    3360
cctggattta caaaccaca ctcgatacaa cttctttcg cctgtttcac gattttgttt    3420
atactctaat atttcagcac aatcttttac tctttcagcc tttttaaatt caagaatatg    3480
cagaagttca agtaatcaa cattagcgat tttctttct ctccatggtc tcacttttcc     3540 acttttgtc ttgtccacta aaaccttga ttttcatct gaataaatgc tactattagg     3600
acacataata ttaaaagaaa cccccatcta tttagttatt tgtttagtca cttataactt    3660
taacagatgg ggttttctg tgcaaccaat tttaagggtt ttcaatactt taaaacacat    3720
acataccaac acttcaacgc accttcagc aactaaaata aaaatgacgt tatttctata    3780
tgtatcaaga taagaaagaa caagttcaaa accatcaaaa aaagacacct tttcaggtgc    3840
tttttttatt ttataaactc attccctgat ctcgacttcg ttcttttttt acctctcggt    3900
tatgagttag ttcaaattcg ttcttttag gttctaaatc gtgttttct tggaattgtg     3960 ctgttttatc ctttaccttg tctacaaacc ccttaaaaac gtttttaaag gcttttaagc    4020
cgtctgtacg ttccttaag                                                 4039
```

<210> SEQ ID NO 31
<211> LENGTH: 579
<212> TYPE: DNA
<213> ORGANISM: Artificial Sequence
<220> FEATURE:
<223> OTHER INFORMATION: Synthetic SigA2 construct -continued

```
<400> SEQUENCE: 31
gcgccgaatt ctcatacctt gaaaggaaag acaagggaaa ttgtcggcaa tgagccgctc    60
ggcaggtaga aggatgttta ccgatgcaaa aaaagggcaa aatggatagg tggttgtcca   120
tgttgaatgc tataatgggg gagatttata aagagagtg ctcgaacttt aatcgaaact    180
gtatgatata gagaatcaag gaggacgaaa catgaaaccg attaatattc aggatcagtt   240
tttgaatcaa atccggaaag aaaatacgta tgtcactgtt ttttgctga acggctttca    300 gttgcgggc caggtgaaag ctttgataa ctttaccgta ttgttggaat cggaaggtaa     360
gcagcagctt atatataaac atgcgatctc aacgtttgcg ccgcaaaaaa acgtccagct   420
tgaactcgaa tagatcaaaa aatgccatgt caagacatga ggaaaggctg tcgggggttc   480
ccggcggcca ttttaacat gaatccactt ttgctccaag cttttgtgt aagctgacca     540 tgccaaggca cggtcttttt ttatgaggga tccggtgcc                          579

<210> SEQ ID NO 32
<211> LENGTH: 50
<212> TYPE: DNA
<213> ORGANISM: Artificial Sequence
<220> FEATURE:
<223> OTHER INFORMATION: Synthetic forward fusion primer P6

<400> SEQUENCE: 32
tgggggagat ttataaaaga gagtgctcga actttaatcg aaactgtatg              50

<210> SEQ ID NO 33
<211> LENGTH: 50
<212> TYPE: DNA
<213> ORGANISM: Artificial Sequence
<220> FEATURE:
<223> OTHER INFORMATION: Synthetic reverse fusion primer P7

<400> SEQUENCE: 33
catacagttt cgattaaagt tcgagcactc tcttttataa atctccccca              50

<210> SEQ ID NO 34
<211> LENGTH: 42
<212> TYPE: DNA
<213> ORGANISM: Artificial Sequence
<220> FEATURE:
<223> OTHER INFORMATION: Synthetic forward primer P8

<400> SEQUENCE: 34
gcgcgcgaat tcagggaaat tgtcggcaat gagccgctcg gc                      42

<210> SEQ ID NO 35
<211> LENGTH: 41
<212> TYPE: DNA
<213> ORGANISM: Artificial Sequence
<220> FEATURE:
<223> OTHER INFORMATION: Synthetic reverse primer P9

<400> SEQUENCE: 35
gcgcgccatg gctgattcgt ctcagttctg cttcactttc a                       41

<210> SEQ ID NO 36
<211> LENGTH: 4768
<212> TYPE: DNA
<213> ORGANISM: Artificial Sequence
<220> FEATURE:
<223> OTHER INFORMATION: Synthetic pBN3 vector
```

```
<400> SEQUENCE: 36
gacgtctaag aaaccattat tatcatgaca ttaacctata aaataggcg tatcacgagg      60 cccttcgtc ttcaagaatt aattctcatg tttgacagct tatcatcgat aagcttgcat    120
gcctgcaggt cgactctaga ggatccccgg gtaccgagct cgaattcctt aaggaacgta   180
cagacggctt aaaagccttt aaaaacgttt taaggggtt tgtagacaag gtaaaggata    240
aaacagcaca attccaagaa aaacacgatt tagaacctaa aaagaacgaa tttgaactaa   300
ctcataaccg agaggtaaaa aaagaacgaa gtcgagatca gggaatgagt ttataaaata   360
aaaaaagcac ctgaaaaggt gtctttttt gatggttttg aacttgttct ttcttatctt    420
gatacatata gaaataacgt cattttatt ttagttgctg aaaggtgcgt tgaagtgttg    480
gtatgtatgt gttttaaagt attgaaaacc cttaaaattg gttgcacaga aaaccccat    540 ctgttaaagt tataagtgac taaacaaata actaaataga tgggggttc tttaatatt    600 atgtgtccta atagtagcat ttattcagat gaaaaatcaa gggttttagt ggacaagaca   660
aaaagtggaa aagtgagacc atggagagaa aagaaaatcg ctaatgttga ttactttgaa   720
cttctgcata ttcttgaatt taaaaaggct gaaagagtaa aagattgtgc tgaaatatta   780
gagtataaac aaaatcgtga aacaggcgaa agaaagttgt atcgagtgtg gttttgtaaa   840
tccaggcttt gtccaatgtg caactggagg agagcaatga acatggcat tcagtcacaa    900 aaggttgttg ctgaagttat taaacaaaag ccaacagttc gttggttgtt tctcacatta   960
acagttaaaa atgtttatga tggcgaagaa ttaaataaga gtttgtcaga tatggctcaa  1020
ggatttcgcc gaatgatgca atataaaaaa attaataaaa atcttgttgg ttttatgcgt  1080
gcaacggaag tgacaataaa taataaagat aattcttata atcagcacat gcatgtattg  1140
gtatgtgtgg aaccaactta ttttaagaat acagaaaact acgtgaatca aaaacaatgg  1200 attcaattt ggaaaaaggc aatgaaatta gactatgatc caaatgtaaa agttcaaatg   1260
attcgaccga aaaataaata taaatcggat atacaatcgg caattgacga aactgcaaaa  1320
tatcctgtaa aggatacgga ttttatgacc gatgatgaag aaaagaattt gaaacgtttg  1380
tctgatttgg aggaaggttt acaccgtaaa aggttaatct cctatggtgg tttgttaaaa  1440
gaaatacata aaaaattaaa ccttgatgac acagaagaag gcgatttgat tcatacagat  1500
gatgacgaaa agccgatga agatggattt tctattattg caatgtggaa ttgggaacgg  1560
aaaaattatt ttattaaaga gtagttcaac aaacgggcca gtttgttgaa gattagatgc  1620
tataattgtt attaaaagga ttgaaggatg cttaggaaga cgagttatta atagctgaat  1680
aagaacggtg ctctccaaat attcttattt agaaaagcaa atctaaaatt atctgaaaag  1740
ggaatgagaa tagtgaatgg accaataata atgactagaa agaaagaat gaagattgtt  1800 catgaaatta aggaacgaat attggataaa tatggggatg atgttaaggc tattggtgtt  1860
tatggctctc ttggtcgtca gactgatggg ccctattcgg atattgagat gatgtgtgtc  1920
atgtcaacag aggaagcaga gttcagccat gaatggacaa ccggtgagtg gaaggtggaa  1980
gtgaattttg atagcgaaga gattctacta gattatgcat ctcaggtgga atcagattgg  2040
ccgcttacac atggtcaatt tttctctatt ttgccgattt atgattcagg tggatactta  2100
gagaaagtgt atcaaactgc taaatcggta gaagcccaaa cgttccacga tgcgatttgt  2160
gcccttatcg tagaagagct gttttgaatat gcaggcaaat ggcgtaatat tcgtgtgcaa  2220
ggaccgacaa catttctacc atccttgact gtacaggtag caatggcagg tgccatgttg  2280
attggtctgc atcatcgcat ctgttatacg acgagcgctt cggtcttaac tgaagcagtt  2340
```

```
aagcaatcag atcttccttc aggttatgac catctgtgcc agttcgtaat gtctggtcaa    2400
ctttccgact ctgagaaact tctggaatcg ctagagaatt tctggaatgg gattcaggag    2460
tggacagaac gacacggata tatagtggat gtgtcaaaac gcataccatt ttgaacgatg    2520
acctctaata attgttaatc atgttggtta cctgcctcgc gcgtttcggt gatgacggtg    2580
aaaacctctg acacatgcag ctcccggaga cggtcacagc ttgtctgtaa gcggatgccg    2640
ggagcagaca gcccgtcag ggcgcgtcag cgggtgttgg cgggtgtcgg ggcgcagcca    2700
tgacccagtc acgtagcgat agcggagtgt atactggctt aactatgcgg catcagagca    2760
gattgtactg agagtgcacc atatgcggtg tgaaataccg cacagatgcg taaggagaaa    2820
ataccgcatc aggcgctctt ccgcttcctc gctcactgac tcgctgcgct cggtcgttcg    2880
gctgcggcga gcggtatcag ctcactcaaa ggcggtaata cggttatcca cagaatcagg    2940
ggataacgca ggaaagaaca tgtgagcaaa aggccagcaa aaggccagga accgtaaaaa    3000
ggccgcgttg ctggcgtttt tccataggct ccgcccccct gacgagcatc acaaaaatcg    3060
acgctcaagt cagaggtggc gaaacccgac aggactataa agataccagg cgtttccccc    3120
tggaagctcc ctcgtgcgct ctcctgttcc gaccctgccg cttaccggat acctgtccgc    3180
ctttctccct tcgggaagcg tggcgctttc tcatagctca cgctgtaggt atctcagttc    3240
ggtgtaggtc gttcgctcca agctgggctg tgtgcacgaa ccccccgttc agcccgaccg    3300
ctgcgcctta tccggtaact atcgtcttga gtccaacccg gtaagacacg acttatcgcc    3360
actggcagca gccactggta acaggattag cagagcgagg tatgtaggcg gtgctacaga    3420
gttcttgaag tggtggccta actacggcta cactagaagg acagtatttg gtatctgcgc    3480
tctgctgaag ccagttacct tcggaaaaag agttggtagc tcttgatccg gcaaacaaac    3540
caccgctggt agcggtggtt ttttgtttg caagcagcag attacgcgca gaaaaaaagg    3600
atctcaagaa gatcctttga tcttttctac ggggtctgac gctcagtgga acgaaaactc    3660
acgttaaggg attttggtca tgagattatc aaaaaggatc ttcacctaga tccttttaaa    3720
ttaaaaatga agttttaaat caatctaaag tatatatgag taaacttggt ctgacagtta    3780
ccaatgctta atcagtgagg cacctatctc agcgatctgt ctatttcgtt catccatagt    3840
tgcctgactc cccgtcgtgt agataactac gatacgggag ggcttaccat ctggccccag    3900
tgctgcaatg ataccgcgag acccacgctc accggctcca gatttatcag caataaacca    3960
gccagccgga agggccgagc gcagaagtgg tcctgcaact ttatccgcct ccatccagtc    4020
tattaattgt tgccgggaag ctagagtaag tagttcgcca gttaatagtt tgcgcaacgt    4080
tgttgccatt gctacaggca tcgtggtgtc acgctcgtcg tttggtatgg cttcattcag    4140
ctccggttcc caacgatcaa ggcgagttac atgatccccc atgttgtgca aaaaagcggt    4200
tagctccttc ggtcctccga tcgttgtcag aagtaagttg gccgcagtgt tatcactcat    4260
ggttatggca gcactgcata attctcttac tgtcatgcca tccgtaagat gcttttctgt    4320
gactggtgag tactcaacca agtcattctg agaatagtgt atgcggcgac cgagttgctc    4380
ttgcccggcg tcaatacggg ataataccgc gccacatagc agaactttaa aagtgctcat    4440
cattggaaaa cgttcttcgg ggcgaaaact ctcaaggatc ttaccgctgt tgagatccag    4500
ttcgatgtaa cccactcgtg cacccaactg atcttcagca tcttttactt tcaccagcgt    4560
ttctgggtga gcaaaaacag gaaggcaaaa tgccgcaaaa aagggaataa gggcgacacg    4620
gaaatgttga atactcatac tcttcctttt tcaatattat tgaagcattt atcagggtta    4680
```

```
ttgtctcatg agcggataca tatttgaatg tatttagaaa aataaacaaa tagggggttcc    4740 gcgcacattt ccccgaaaag tgccacct                                        4768

<210> SEQ ID NO 37
<211> LENGTH: 4533
<212> TYPE: DNA
<213> ORGANISM: Artificial Sequence
<220> FEATURE:
<223> OTHER INFORMATION: Synthetic sequence of the plasmid pBS19 ymaH
      sigH

<400> SEQUENCE: 37
gaattcgacg tggtttcgca acaaaatgca ggtcacatgg ttcgatatga caccgcctgt      60
tgatatggag ctgaaaaaaa aggaaatttt cacacatata gcaggaaaac tcgaacttta     120
atcgaaactg tatgatatag agaatcaagg aggacgaaac atgaaaccga ttaatattca     180
ggatcagttt ttgaatcaaa tccggaaaga aaatacgtat gtcactgttt ttttgctgaa     240
cggctttcag ttgcggggcc aggtgaaagg ctttgataac tttaccgtat tgttggaatc     300
ggaaggtaag cagcagctta tatataaaca tgcgatctca acgtttgcgc gcaaaaaaa     360 cgtccagctt gaactcgaat agatcaaaaa atgccatgtc aagacatgag gaaaggctgt     420
cgggggttcc cggcggccat ttttaacatg aatccacttt tgctccaagc ttttttgtgta    480 agctgaccat gccaaggcac ggtcttttt tatgaggatc ctctagagtc gacctgcagg     540
catgcaagct tggcgatcct gcctcgcgcg tttcggtgat gacggtgaaa acctctgaca     600
catgcagctc ccgagacggg tcacagcttg tctgtaagcg gatgccggga gcagacaagc     660
ccgtcagggc gcgtcagcgg gtgttggcgg gtgtcggggc gcagccatga cccagtcacg     720
tagcgatagc ggagtgtata ctggcttaac tatgcggcat cagagcagat tgtactgaga     780
gtgcaccata tgcggtgtga ataccgcac agatgcgtaa ggagaaaata ccgcatcagg     840
cgctcttccg cttcctcgct cactgactcg ctgcgctcgg tcgttcggct gcggcgagcg     900
gtatcagctc actcaaaggc ggtaatacgg ttatccacag aatcagggga taacgcagga     960
aagaacatgt gagcaaaagg ccagcaaaag gccaggaacc gtaaaaaggc cgcgttgctg    1020
gcgtttttcc ataggctccg ccccctgac gagcatcaca aaaatcgacg ctcaagtcag    1080
aggtggcgaa acccgacagg actataaaga taccaggcgt ttccccctgg aagctccctc    1140
gtgcgctctc ctgttccgac cctgccgctt accggatacc tgtccgcctt tctcccttcg    1200
ggaagcgtgg cgctttctca tagctcacgc tgtaggtatc tcagttcggt gtaggtcgtt    1260
cgctccaagc tgggctgtgt gcacgaaccc cccgttcagc ccgaccgctg cgccttatcc    1320
ggtaactatc gtcttgagtc aacccggta agacacgact tatcgccact ggcagcagcc    1380
actggtaaca ggattagcag agcgaggtat gtaggcggtg ctacagagtt cttgaagtgg    1440
tggcctaact acggctacac tagaaggaca gtatttggta tctgcgctct gctgaagcca    1500
gttaccttcg gaaaaagagt tggtagctct tgatccggca acaaaccac cgctggtagc    1560 ggtggttttt tgtttgcaa gcagcagatt acgcgcagaa aaaaaggatc tcaagaagat    1620
cctttgatct tttctacggg gtctgacgct cagtggaacg aaaactcacg ttaagggatt    1680
ttggtcatga gattatcaaa aaggatctgg agctgtaata aaaaacctt cttcaactaa    1740 cggggcaggt tagtgacatt agaaaaccga ctgtaaaaag tacagtcggc attatctcat    1800
attataaaag ccagtcatta ggcctatctg acaattcctg aatagagttc ataaacaatc    1860
ctgcatgata accatcacaa acagaatgat gtacctgtaa agatagcggt aaatatattg    1920
aattaccttt attaatgaat ttcctgctg taataatggg tagaaggtaa ttactattat    1980
```

```
tattgatatt taagttaaac ccagtaaatg aagtccatgg aataatagaa agagaaaaag   2040 catttttcagg tataggtgtt ttgggaaaca atttccccga accattatat ttctctacat   2100
cagaaaggta taaatcataa aactctttga agtcattctt tacaggagtc caaataccag   2160
agaatgtttt agatacacca tcaaaaattg tataaagtgg ctctaactta tcccaataac   2220
ctaactctcc gtcgctattg taaccagttc taaaagctgt atttgagttt atcacccttg   2280
tcactaagaa aataaatgca gggtaaaatt tatatccttc ttgttttatg tttcggtata   2340
aaacactaat atcaatttct gtggttatac taaaagtcgt tgttggttc aaataatgat    2400 taaatatctc ttttctcttc caattgtcta aatcaatttt attaaagttc atttgatatg   2460
cctcctaaat ttttatctaa agtgaattta ggaggcttac ttgtctgctt tcttcattag   2520
aatcaatcct ttttttaaaag tcaatattac tgtaacataa atatatattt taaaaatatc  2580
ccactttatc caattttcgt tgttgaact aatgggtgct ttagttgaag aataaaagac    2640
cacattaaaa aatgtggtct tttgtgtttt tttaaaggat ttgagcgtag cgaaaaatcc   2700
ttttctttct tatcttgata ataagggtaa ctattgccgg ttgtccattc atggctgaac   2760
tctgcttcct ctgttgacat gacacacatc atctcaatat ccgaataggg cccatcagtc   2820
tgacgaccaa gagagccata aacaccaata gccttaacat catccccata tttatccaat   2880
attcgttcct taatttcatg aacaatcttc attctttctt ctctagtcat tattattggt    2940
ccattcacta ttctcattcc cttttcagat aattttagat ttgcttttct aaataagaat   3000
atttggagag caccgttctt attcagctat taataactcg tcttcctaag catccttcaa   3060 tcctttttaat aacaattata gcatctaatc ttcaacaaac tggcccgttt gttgaactac  3120
tctttaataa aataattttt ccgttcccaa ttccacattg caataataga aaatccatct   3180
tcatcggctt tttcgtcatc atctgtatga atcaaatcgc cttcttctgt gtcatcaagg   3240
tttaattttt tatgtatttc ttttaacaaa ccaccatagg agattaacct tttacggtgt   3300
aaaccttcct ccaaatcaga caaacgtttc aaattctttt cttcatcatc ggtcataaaa   3360
tccgtatcct ttacaggata ttttgcagtt tcgtcaattg ccgattgtat atccgattta   3420
tatttatttt tcggtcgaat catttgaact tttacatttg gatcatagtc taatttcatt   3480 gccttttttcc aaaattgaat ccattgtttt tgattcacgt agtttctgt attcttaaaa   3540 taagttggtt ccacacatac caatacatgc atgtgctgat tataagaatt atctttatta   3600
tttattgtca cttccgttgc acgcataaaa ccaacaagat ttttattaat tttttttatat 3660 tgcatcattc ggcgaaatcc ttgagccata tctgacaaac tcttatttaa ttcttcgcca   3720
tcataaacat ttttaactgt taatgtgaga acaaccaac gaactgttgg cttttgttta    3780
ataacttcag caacaacctt ttgtgactga atgccatgtt tcattgctct cctccagttg   3840
cacattggac aaagcctgga tttacaaaac cacactcgat acaactttct ttcgcctgtt   3900 tcacgattt gtttatactc taatatttca gcacaatctt ttactctttc agcctttta    3960 aattcaagaa tatgcagaag ttcaaagtaa tcaacattag cgatttcttt ttctctccat   4020
ggtctcactt ttccactttt tgtcttgtcc actaaaaccc ttgatttttc atctgaataa   4080
atgctactat taggacacat aatattaaaa gaaacccccca tctatttagt tatttgttta  4140
gtcacttata actttaacag atggggtttt tctgtgcaac caatttttaag ggttttcaat   4200 actttaaaac acatacatac caacacttca acgcaccttt cagcaactaa aataaaaatg   4260
acgttatttc tatatgtatc aagataagaa agaacaagtt caaaaccatc aaaaaaagac   4320
accttttcag gtgctttttt tatttttataa actcattccc tgatctcgac ttcgttcttt   4380
```

```
ttttacctct cggttatgag ttagttcaaa ttcgttcttt ttaggttcta aatcgtgttt       4440
ttcttggaat tgtgctgttt tatcctttac cttgtctaca aaccccttaa aaacgtttttt      4500 aaaggctttt aagccgtctg tacgttcctt aag                                   4533

<210> SEQ ID NO 38
<211> LENGTH: 46
<212> TYPE: DNA
<213> ORGANISM: Bacillus subtilis

<400> SEQUENCE: 38
tgggtcttga caaatattat tccatctatt acaataaatt cacaga                     46

<210> SEQ ID NO 39
<211> LENGTH: 46
<212> TYPE: DNA
<213> ORGANISM: Bacillus subtilis

<400> SEQUENCE: 39
tgggtctact aaaatattat tccatctatt acaataaatt cacaga                     46

<210> SEQ ID NO 40
<211> LENGTH: 46
<212> TYPE: DNA
<213> ORGANISM: Bacillus subtilis

<400> SEQUENCE: 40
tgggtcttga caaatattat tccatctatt acaataaatt cacaga                     46

<210> SEQ ID NO 41
<211> LENGTH: 132
<212> TYPE: DNA
<213> ORGANISM: Bacillus subtilis

<400> SEQUENCE: 41
atgaaatcta aatggatgtc aggtttgttg ctcgttgcgg tcgggttcag ctttactcag      60
gtgatggttc atgcaggtga acagcaaac acagaaggga aaacatttca tattgcggca      120
cgcaatcaaa ca                                                          132

<210> SEQ ID NO 42
<211> LENGTH: 44
<212> TYPE: PRT
<213> ORGANISM: Bacillus subtilis

<400> SEQUENCE: 42

Met Lys Ser Lys Trp Met Ser Gly Leu Leu Leu Val Ala Val Gly Phe
1               5                   10                  15

Ser Phe Thr Gln Val Met Val His Ala Gly Glu Thr Ala Asn Thr Glu
            20                  25                  30

Gly Lys Thr Phe His Ile Ala Ala Arg Asn Gln Thr
        35                  40

<210> SEQ ID NO 43
<211> LENGTH: 132
<212> TYPE: DNA
<213> ORGANISM: Bacillus subtilis

<400> SEQUENCE: 43
atgaaatcta aattgtttat cagtttatcc gccgttttaa ttggacttgc cttttttcgga    60 tctatgtata atggcgaaat gaaggaagca tcccggaatg taactctcgc acctactcat    120
gaattccttg tt                                                          132
```

```
<210> SEQ ID NO 44
<211> LENGTH: 44
<212> TYPE: PRT
<213> ORGANISM: Bacillus subtilis

<400> SEQUENCE: 44

Met Lys Ser Lys Leu Phe Ile Ser Leu Ser Ala Val Leu Ile Gly Leu
1               5                   10                  15

Ala Phe Phe Gly Ser Met Tyr Asn Gly Glu Met Lys Glu Ala Ser Arg
            20                  25                  30

Asn Val Thr Leu Ala Pro Thr His Glu Phe Leu Val
        35                  40

<210> SEQ ID NO 45
<211> LENGTH: 73
<212> TYPE: PRT
<213> ORGANISM: Bacillus subtilis

<400> SEQUENCE: 45

Met Lys Pro Ile Asn Ile Gln Asp Gln Phe Leu Asn Gln Ile Arg Lys
1               5                   10                  15

Glu Asn Thr Tyr Val Thr Val Phe Leu Leu Asn Gly Phe Gln Leu Arg
            20                  25                  30

Gly Gln Val Lys Gly Phe Asp Asn Phe Thr Val Leu Leu Glu Ser Glu
        35                  40                  45

Gly Lys Gln Gln Leu Ile Tyr Lys His Ala Ile Ser Thr Phe Ala Pro
    50                  55                  60

Gln Lys Asn Val Gln Leu Glu Leu Glu
65                  70

<210> SEQ ID NO 46
<211> LENGTH: 222
<212> TYPE: DNA
<213> ORGANISM: Bacillus subtilis

<400> SEQUENCE: 46
atgaaaccga ttaatattca ggatcagttt ttgaatcaaa tccggaaaga aaatacgtat      60
gtcactgttt ttttgctgaa cggctttcag ttgcggggcc aggtgaaagg ctttgataac     120
tttaccgtat tgttggaatc ggaaggtaag cagcagctta tatataaaca tgcgatctca     180
acgtttgcgc cgcaaaaaaa cgtccagctt gaactcgaat ag                        222

<210> SEQ ID NO 47
<211> LENGTH: 156
<212> TYPE: DNA
<213> ORGANISM: Artificial Sequence
<220> FEATURE:
<223> OTHER INFORMATION: Synthetic SigA1construct containing the SigA
      promoter

<400> SEQUENCE: 47 tcatacccctg aaaggaaaga caagggaaat tgtcggcaat gagccgctcg gcaggtagaa     60
ggatgtttac cgatgcaaaa aaagggcaaa atggataggt ggttgtccat gttgaatgct    120
ataatggggg agatttataa aagagagtga tacata                              156

<210> SEQ ID NO 48
<211> LENGTH: 82
<212> TYPE: DNA
<213> ORGANISM: Bacillus subtilis
```

-continued

<400> SEQUENCE: 48

```
aaaggaaatt ttcacacata tagcaggaaa actcgaactt taatcgaaac tgtatgatat    60
agagaatcaa ggaggacgaa ac                                              82
```

<210> SEQ ID NO 49
<211> LENGTH: 945
<212> TYPE: DNA
<213> ORGANISM: Bacillus subtilis

<400> SEQUENCE: 49

```
ttgaataata cgaagcagcc cgttgtcatt ttagtcggac cgacggcagt ggggaaaacc    60
aatttaagta ttcagctagc caaatcctta aacgcggaaa ttatcagcgg agattcgatg   120
cagatttata aagggatgga tattggaaca gctaaaatta ccgaacagga gatggaggga   180
gtgccccatc atctgattga catttagat ccccaagact ctttctctac tgccgattat    240
caaagcttag taagaaataa aatcagcgag attgcaaata gaggaaagct tccgatgatt   300
gacggcggta cagggcttta tatacaatct gagctttacg attatacatt tacggaagag   360
gcaaatgatc ccgtgtttcg agagagcatg caaatggctg ctgagcggga aggcgctgac   420
tttcttcatg ccaaacttgc tgcagcagat cccgaggcag cagctgcgat tcatccgaat   480
aatacaagaa gagtcattcg cgcactggaa attttacata cgtccggaaa aacgatgtcc   540
cagcatttga aggaacaaaa acgagaactt ctgtacaatg cagtgttaat tggcctgaca   600
atggatagag acacgcttta cgaaagaatt aatcagcggg tcgatttgat gatgcagtca   660
ggccttcttc cggaagtgaa acgcttatac gacaagaacg tgagagactg tcaatcaata   720
caggcgatag gctataaaga gctgtatgca tattttgacg gttttgtgac actttccgat   780
gctgtcgaac agctaaagca gaactcgagg cggtatgcga aacgccagct gacgtggttt   840
cgcaacaaaa tgcaggtcac atggttcgat atgacaccgc ctgttgatat ggagctgaaa   900
aaaaaggaaa ttttcacaca tatagcagga aaactcgaac tttaa                   945
```

<210> SEQ ID NO 50
<211> LENGTH: 7
<212> TYPE: DNA
<213> ORGANISM: Bacillus subtilis

<400> SEQUENCE: 50

```
aagagag                                                              7
```

<210> SEQ ID NO 51
<211> LENGTH: 5
<212> TYPE: DNA
<213> ORGANISM: Bacillus subtilis

<400> SEQUENCE: 51

```
ggagg                                                                5
```

<210> SEQ ID NO 52
<211> LENGTH: 3258
<212> TYPE: DNA
<213> ORGANISM: Artificial Sequence
<220> FEATURE:
<223> OTHER INFORMATION: Chemically synthesized deletion cassette of the
      rapA/phrA operon

<400> SEQUENCE: 52

```
tggagggagt cagaccgcgt ctttgggaaa aaagcaagcg aaagtgacc gtgtttacgg     60
atggagatgg agggacttca agagagcagg aagccattgt cagagaggtt cagcggagtc   120
```

-continued

| | |
|---|---:|
| aagtcatcat gaatccgcta ttgaaaaaag agatatacag atcaattgat cagtttttc | 180 |
| atagtgataa atcgttttat caaacatatg acatcccta caagcgcggc attctgttat | 240 |
| atggacctcc tggaaacgga aagacgacgt tagtgaagtc gatcgcaggc agtatcgatg | 300 |
| cacctgttgc ttattggcaa attactgaat ttacgtcgag cgagacaata gaagaagtct | 360 |
| ttcaggcagc gagacgcctc gctcctgcag ttctggtcat cgaggatata gattcgatgc | 420 |
| cggaagatgt gcggtccttt tttctcaata cgctggacgg cgcgacatca aaagaggggc | 480 |
| tatttctcat cggtacgaca aactatcccg aagagatcga tccaggtttg atgaatcgtg | 540 |
| caggacgatt tgaccgtgcc tatgaaatcg ggcttccgga tgaagagctg cggctggaat | 600 |
| atatgaaaat gagaggcttt ggcatctttt tgagtgaagg agaaataaaa aacgccgcaa | 660 |
| aacttacaga aggcttttcc tttgcacagc tgggagaatt atatgtatct tcagcccttc | 720 |
| aatggcacca agaagggaat caccatattg aaaccatggt gaaagacatg acaggagagc | 780 |
| aaagaaaaag ccagcgggga agctggatgg aaagaaacaa agtcggtttt cactaaaaga | 840 |
| aagcacgggt gtttgaaaaa cccgtgcttt tttgttgcgg ttagccgaaa ttcgacaatt | 900 |
| gcggttattt tgcgttcttc tttttcttgt aaatatgata aaatatgaca tatctcgggt | 960 |
| aattcaaaag gggggattaa ttgaggatga agcagacgct cgaggtcgac ggtatcgata | 1020 |
| agctggatcc ataacttcgt ataatgtatg ctatacgaag ttatctagat aaaaaattta | 1080 |
| gaagccaatg aaatctataa ataaactaaa ttaagtttat ttaattaaca actatggata | 1140 |
| taaaataggt actaatcaaa atagtgagga ggatatattt gaatacatac gaacaaatta | 1200 |
| ataaagtgaa aaaatactt cggaaacatt taaaaaataa ccttattggt acttacatgt | 1260 |
| ttggatcagg agttgagagt ggactaaaac caaatagtga tcttgactt ttagtcgtcg | 1320 |
| tatctgaacc attgacagat caaagtaaag aaatacttat acaaaaaatt agacctattt | 1380 |
| caaaaaaaat aggagataaa agcaacttac gatatattga attaacaatt attattcagc | 1440 |
| aagaaatggt accgtggaat catcctccca acaagaatt tatttatgga gaatggttac | 1500 |
| aagagcttta tgaacaagga tacattcctc agaaggaatt aaattcagat ttaaccataa | 1560 |
| tgctttacca agcaaaacga aaaaataaaa gaatatacgg aaattatgac ttagaggaat | 1620 |
| tactacctga tattccattt tctgatgtga gaagagccat tatggattcg tcagaggaat | 1680 |
| taatagataa ttatcaggat gatgaaacca actctatatt aacttatgc cgtatgattt | 1740 |
| taactatgga cacgggtaaa atcataccaa aagatattgc gggaaatgca gtggctgaat | 1800 |
| cttctccatt agaacatagg gagagaattt tgttagcagt tcgtagttat cttgagaga | 1860 |
| atattgaatg gactaatgaa aatgtaaatt taactataaa ctatttaaat aacagattaa | 1920 |
| aaaaattata aaaaaattga aaaaatggtg gaaacacttt tttcaatttt tttgtttat | 1980 |
| tatttaatat ttgggaaata ttcattctaa ttggtaatca gattttagaa aacaataaac | 2040 |
| ccttgcatat gtctagataa cttcgtataa tgtatgctat acgaagttat gcggccgcca | 2100 |
| cgcacaaaaa caaatccaga gaggagattg tttatatgaa atctaaatgg atgtcaggtt | 2160 |
| tgttgctcgt tgcggtcggg ttcagcttta ctcaggtgat ggttcatgca ggtgaaacag | 2220 |
| caaacacaga agggaaaaca tttcatattg cggcacgcaa tcaaacatga tgcataaaaa | 2280 |
| aagaccctta ggggtctttt ttatttcttc agcttccatt cttttatcgt cagctcagaa | 2340 |
| gatccacttg ccaccagcgg atccgcatgg ccgatttccg ctgcctcttc cagtgaatct | 2400 |
| gcttcgatga catacgctcc gcctgtggcg tcgctgaatg gcccaaacat ttttaaacgt | 2460 |
| ttttctgcct gtaaacgatc cagaaattca tagtgcccag ccacatgctc ctgattaaat | 2520 |

-continued

```
ttctccgttc tcattgtcag cattaaatat ggtatacata ttcagaccct ccgtgaactt     2580
cagtttaaca catttatcca tattacggtg atagatgata tgagcttttc gtcctacgaa     2640
tgccacctat ttatgaaaaa agaaaaggag agatgatagg tgagcattcc agtaaagaaa     2700
aatttggttt ctgaggcgaa atacgcgttg aagtgtccta atgcaatgtc cgctgaatac     2760
attaccattc acaacacggc aaacgatgca tcagcggcca atgaaatcag ctatatgatc     2820
gggaacacaa gctcgacaag ctttcatttt gcggtcgatg atcaagaggt gattcaaggt     2880
ctgccgctta accgaaacgc ttggcacact ggtgacggca caaacggtcc gggaaaccgc     2940
aaatcaatcg gtgttgagat ttgctacagc aaatcgggag cccgaagta tgaggcagct      3000 gaagccttgg cgatttcatt tgttgcacag ctgttgaagg agcgcggctg gggcatcgat     3060
cgggtgagaa agcatcagga ctggagcgga aagtattgcc cgcaccgcat tttatcagag     3120
gggcgctggg atcaagtgaa ggcggcgatt gaaaaggaat aaacggggg cgtatcagcg       3180 aaaaaagctg cagtctcttc ttcggcgtct gaatatcatg taaaaaaagg tgacacactg     3240
tcagggattg ccgcatca                                                   3258
```

<210> SEQ ID NO 53
<211> LENGTH: 1134
<212> TYPE: DNA
<213> ORGANISM: Bacillus subtilis

<400> SEQUENCE: 53

```
ttgaggatga agcagacgat tccgtcctct tatgtcgggc ttaaaattaa tgaatggtat       60
actcatatcc ggcagttcca cgtcgctgaa gccgaacggg tcaagctcga agtagaaaga      120
gaaattgagg atatggaaga agaccaagat ttgctgctgt attattcttt aatggagttc      180
aggcaccgtg tcatgctgga ttacattaag ccttttggag aggacacgtc gcagctagag      240
ttttcagaat tgttagaaga catcgaaggg aatcagtaca agctgacagg gcttctcgaa      300
tattacttta attttttcg aggaatgtat gaatttaagc agaagatgtt tgtcagtgcc       360
atgatgtatt ataaacgggc agaaaagaat cttgccctcg tctcggatga tattgagaaa      420
gcagagtttg cttttaaaat ggctgagatt ttttacaatt taaacaaac ctatgtttcg        480 atgagctacg ccgttcaggc attagaaaca taccaaatgt atgaaacgta caccgtccgc      540
agaatccaat gtgaattcgt tattgcaggt aattatgatg atatgcagta tccagaaaga      600
gcattgcccc acttagaact ggctttagat cttgcaaaga aagaaggcaa tccccgcctg      660
atcagttctg ccctatataa tctcggaaac tgctatgaga aatgggtga actgcaaaag       720 gcagccgaat actttgggaa atctgtttct atttgcaagt cggaaaagtt cgataatctt      780
ccgcattcta tctactcttt aacacaagtt ctgtataaac aaaaaaatga cgccgaagcg     840
caaaaaaagt atcgtgaagg attggaaatc gcccgtcaat acagtgatga attatttgtg     900 gagcttttc aattttttaca tgcgttatac ggaaaaaaca ttgacacaga atcagtctca     960
cacacctttc aatttcttga agaacatatg ctgtatcctt atattgaaga gctggcgcat    1020
gatgctgccc aattctatat agaaaacgga cagcccgaaa aagcactttc attttatgag    1080
aaaatggtgc acgcacaaaa acaaatccag agaggagatt gtttatatga aatc          1134
```

<210> SEQ ID NO 54
<211> LENGTH: 378
<212> TYPE: PRT
<213> ORGANISM: Bacillus subtilis

<400> SEQUENCE: 54

```
Met Arg Met Lys Gln Thr Ile Pro Ser Ser Tyr Val Gly Leu Lys Ile
1               5                   10                  15
Asn Glu Trp Tyr Thr His Ile Arg Gln Phe His Val Ala Glu Ala Glu
            20                  25                  30
Arg Val Lys Leu Glu Val Glu Arg Ile Glu Asp Met Glu Glu Asp
        35                  40                  45
Gln Asp Leu Leu Leu Tyr Tyr Ser Leu Met Glu Phe Arg His Arg Val
    50                  55                  60
Met Leu Asp Tyr Ile Lys Pro Phe Gly Glu Asp Thr Ser Gln Leu Glu
65                  70                  75                  80
Phe Ser Glu Leu Leu Glu Asp Ile Gly Asn Gln Tyr Lys Leu Thr
                85                  90                  95
Gly Leu Leu Glu Tyr Tyr Phe Asn Phe Arg Gly Met Tyr Glu Phe
            100                 105                 110
Lys Gln Lys Met Phe Val Ser Ala Met Met Tyr Lys Arg Ala Glu
        115                 120                 125
Lys Asn Leu Ala Leu Val Ser Asp Ile Glu Lys Ala Glu Phe Ala
    130                 135                 140
Phe Lys Met Ala Glu Ile Phe Tyr Asn Leu Lys Gln Thr Tyr Val Ser
145                 150                 155                 160
Met Ser Tyr Ala Val Gln Ala Leu Glu Thr Gln Met Tyr Glu Thr
                165                 170                 175
Tyr Thr Val Arg Arg Ile Gln Cys Glu Phe Val Ile Ala Gly Asn Tyr
            180                 185                 190
Asp Asp Met Gln Tyr Pro Glu Arg Ala Leu Pro His Leu Glu Leu Ala
        195                 200                 205
Leu Asp Leu Ala Lys Lys Glu Gly Asn Pro Arg Leu Ile Ser Ser Ala
    210                 215                 220
Leu Tyr Asn Leu Gly Asn Cys Tyr Glu Lys Met Gly Glu Leu Gln Lys
225                 230                 235                 240
Ala Ala Glu Tyr Phe Gly Lys Ser Val Ser Ile Cys Lys Ser Glu Lys
                245                 250                 255
Phe Asp Asn Leu Pro His Ser Ile Tyr Ser Leu Thr Gln Val Leu Tyr
            260                 265                 270
Lys Gln Lys Asn Asp Ala Glu Ala Gln Lys Lys Tyr Arg Glu Gly Leu
        275                 280                 285
Glu Ile Ala Arg Gln Tyr Ser Asp Glu Leu Phe Val Glu Leu Phe Gln
    290                 295                 300
Phe Leu His Ala Leu Tyr Gly Lys Asn Ile Asp Thr Glu Ser Val Ser
305                 310                 315                 320
His Thr Phe Gln Phe Leu Glu Glu His Met Leu Tyr Pro Tyr Ile Glu
                325                 330                 335
Glu Leu Ala His Asp Ala Ala Gln Phe Tyr Ile Glu Asn Gly Gln Pro
            340                 345                 350
Glu Lys Ala Leu Ser Phe Tyr Glu Lys Met Val His Ala Gln Lys Gln
        355                 360                 365
Ile Gln Arg Gly Asp Cys Leu Tyr Glu Ile
    370                 375
```

<210> SEQ ID NO 55
<211> LENGTH: 36
<212> TYPE: DNA
<213> ORGANISM: Artificial Sequence

```
<220> FEATURE:
<223> OTHER INFORMATION: Synthetic oligonucleotide: XhoUR

<400> SEQUENCE: 55
agaggactcg agcgtctgct tcatcctcaa ttaatc                                36

<210> SEQ ID NO 56
<211> LENGTH: 37
<212> TYPE: DNA
<213> ORGANISM: Artificial Sequence
<220> FEATURE:
<223> OTHER INFORMATION: Synthetic oligonucleotide: HindIIIUF

<400> SEQUENCE: 56
gcgtgcaagc ttggagggag tcagaccgcg tctttgg                               37

<210> SEQ ID NO 57
<211> LENGTH: 41
<212> TYPE: DNA
<213> ORGANISM: Artificial Sequence
<220> FEATURE:
<223> OTHER INFORMATION: Synthetic oligonucleotide: NotIDF

<400> SEQUENCE: 57
ttatgagagc ggccgccacg cacaaaaaca aatccagaga g                          41

<210> SEQ ID NO 58
<211> LENGTH: 37
<212> TYPE: DNA
<213> ORGANISM: Artificial Sequence
<220> FEATURE:
<223> OTHER INFORMATION: Synthetic oligonucleotide: BglIIDR

<400> SEQUENCE: 58
ccccgtagat ctcggcaatc cctgacagtg tgtcacc                               37

<210> SEQ ID NO 59
<211> LENGTH: 24
<212> TYPE: DNA
<213> ORGANISM: Artificial Sequence
<220> FEATURE:
<223> OTHER INFORMATION: Synthetic primer CB2008-011:  upstream phrH

<400> SEQUENCE: 59
ggagggaagc cgttgagtca agcc                                             24

<210> SEQ ID NO 60
<211> LENGTH: 49
<212> TYPE: DNA
<213> ORGANISM: Artificial Sequence
<220> FEATURE:
<223> OTHER INFORMATION: Synthetic primer CB2008-012:  linker up phrH
      down lox

<400> SEQUENCE: 60
gcggccgcca tatgcatcct aggcctcatc actttttttc ttaataggc                  49

<210> SEQ ID NO 61
<211> LENGTH: 49
<212> TYPE: DNA
<213> ORGANISM: Artificial Sequence
<220> FEATURE:
<223> OTHER INFORMATION: Synthetic primer CB2008-012R:  linker up phrH
      down lox

<400> SEQUENCE: 61
gcctattaag aaaaaaagtg atgaggccta ggatgcatat ggcggccgc                  49
```

<210> SEQ ID NO 62
<211> LENGTH: 52
<212> TYPE: DNA
<213> ORGANISM: Artificial Sequence
<220> FEATURE:
<223> OTHER INFORMATION: Synthetic primer CB2008-013: linker down phrH up lox

<400> SEQUENCE: 62
ggatccagct tatcgatacc gtcgaggctt tttcttgctt tacggaagac gg    52

<210> SEQ ID NO 63
<211> LENGTH: 52
<212> TYPE: DNA
<213> ORGANISM: Artificial Sequence
<220> FEATURE:
<223> OTHER INFORMATION: Synthetic primer CB2008-013R: linker down phrH up lox

<400> SEQUENCE: 63
ccgtcttccg taaagcaaga aaaagcctcg acggtatcga taagctggat cc    52

<210> SEQ ID NO 64
<211> LENGTH: 27
<212> TYPE: DNA
<213> ORGANISM: Artificial Sequence
<220> FEATURE:
<223> OTHER INFORMATION: Synthetic primer CB2008-014: downstream phrH

<400> SEQUENCE: 64
gccatcattt tcatggtgca tgctcgg    27

<210> SEQ ID NO 65
<211> LENGTH: 30
<212> TYPE: DNA
<213> ORGANISM: Artificial Sequence
<220> FEATURE:
<223> OTHER INFORMATION: Synthetic primer CB2008-015: upstream phrC

<400> SEQUENCE: 65
tcactaatgg aattccggca ccagcttatg    30

<210> SEQ ID NO 66
<211> LENGTH: 51
<212> TYPE: DNA
<213> ORGANISM: Artificial Sequence
<220> FEATURE:
<223> OTHER INFORMATION: Synthetic primer CB2008-016: linker up phrC down lox

<400> SEQUENCE: 66
gcggccgcca tatgcatcct aggccatcgc ggctgcggcc aaacaaataa c    51

<210> SEQ ID NO 67
<211> LENGTH: 51
<212> TYPE: DNA
<213> ORGANISM: Artificial Sequence
<220> FEATURE:
<223> OTHER INFORMATION: Synthetic primer CB2008-016R: linker up phrC down lox

<400> SEQUENCE: 67
gttatttgtt tggccgcagc cgcgatggcc taggatgcat atggcggccg c    51

<210> SEQ ID NO 68
<211> LENGTH: 55
<212> TYPE: DNA
<213> ORGANISM: Artificial Sequence

```
<220> FEATURE:
<223> OTHER INFORMATION: Synthetic primer CB2008-017: linker down phrC
      up lox

<400> SEQUENCE: 68
ggatccagct tatcgatacc gtcgagaaca agccccttct cattagcgag aaggg    55

<210> SEQ ID NO 69
<211> LENGTH: 55
<212> TYPE: DNA
<213> ORGANISM: Artificial Sequence
<220> FEATURE:
<223> OTHER INFORMATION: Synthetic primer CB2008-017R: linker down phrC
      up lox

<400> SEQUENCE: 69
cccttctcgc taatgagaag gggcttgttc tcgacggtat cgataagctg gatcc    55

<210> SEQ ID NO 70
<211> LENGTH: 32
<212> TYPE: DNA
<213> ORGANISM: Artificial Sequence
<220> FEATURE:
<223> OTHER INFORMATION: Synthetic primer CB2008-018: downstream phrC

<400> SEQUENCE: 70
gcagcattta tatcagcaag tatctcatga ac                              32

<210> SEQ ID NO 71
<211> LENGTH: 30
<212> TYPE: DNA
<213> ORGANISM: Artificial Sequence
<220> FEATURE:
<223> OTHER INFORMATION: Synthetic primer CB2008-022: upstream phrF

<400> SEQUENCE: 71
agtttcggca caacctaatg cttgagtacc                                 30

<210> SEQ ID NO 72
<211> LENGTH: 53
<212> TYPE: DNA
<213> ORGANISM: Artificial Sequence
<220> FEATURE:
<223> OTHER INFORMATION: Synthetic primer CB2008-023: linker up phrF
      down lox

<400> SEQUENCE: 72
gcggccgcca tatgcatcct aggccagtaa tagtttagac ttcaatttca tac        53

<210> SEQ ID NO 73
<211> LENGTH: 53
<212> TYPE: DNA
<213> ORGANISM: Artificial Sequence
<220> FEATURE:
<223> OTHER INFORMATION: Synthetic primer CB2008-023R: linker up phrF
      down lox

<400> SEQUENCE: 73
gtatgaaatt gaagtctaaa ctattactgg cctaggatgc atatggcggc cgc        53

<210> SEQ ID NO 74
<211> LENGTH: 55
<212> TYPE: DNA
<213> ORGANISM: Artificial Sequence
<220> FEATURE:
<223> OTHER INFORMATION: Synthetic primer CB2008-024: linker down phrF
      up lox
```

-continued

```
<400> SEQUENCE: 74
ggatccagct tatcgatacc gtcgaccgcc gtccatcggc ggttttttcg tcccc          55

<210> SEQ ID NO 75
<211> LENGTH: 55
<212> TYPE: DNA
<213> ORGANISM: Artificial Sequence
<220> FEATURE:
<223> OTHER INFORMATION: Synthetic primer CB2008-024R:  linker down phrF
      up lox

<400> SEQUENCE: 75
ggggacgaaa aaaccgccga tggacggcgg tcgacggtat cgataagctg gatcc          55

<210> SEQ ID NO 76
<211> LENGTH: 28
<212> TYPE: DNA
<213> ORGANISM: Artificial Sequence
<220> FEATURE:
<223> OTHER INFORMATION: Synthetic primer CB2008-025:  downstream phrF

<400> SEQUENCE: 76
tcggaccgca caatgtgtat tcattcgg                                        28

<210> SEQ ID NO 77
<211> LENGTH: 25
<212> TYPE: DNA
<213> ORGANISM: Artificial Sequence
<220> FEATURE:
<223> OTHER INFORMATION: Synthetic primer CB2008-026:  upstream phrG

<400> SEQUENCE: 77
agaggatcag gaggtgcttg cctac                                           25

<210> SEQ ID NO 78
<211> LENGTH: 51
<212> TYPE: DNA
<213> ORGANISM: Artificial Sequence
<220> FEATURE:
<223> OTHER INFORMATION: Synthetic primer CB2008-027:  linker up phrG
      and up lox

<400> SEQUENCE: 78
cgaacggagg ttatataaat gaaaagtcga cggtatcgat aagctggatc c              51

<210> SEQ ID NO 79
<211> LENGTH: 51
<212> TYPE: DNA
<213> ORGANISM: Artificial Sequence
<220> FEATURE:
<223> OTHER INFORMATION: Synthetic primer CB2008-027R:  linker up phrG
      and up lox

<400> SEQUENCE: 79
ggatccagct tatcgatacc gtcgactttt catttatata acctccgttc g              51

<210> SEQ ID NO 80
<211> LENGTH: 46
<212> TYPE: DNA
<213> ORGANISM: Artificial Sequence
<220> FEATURE:
<223> OTHER INFORMATION: Synthetic primer CB2008-028:  linker down phrG
      and down lox

<400> SEQUENCE: 80
gcggccgcca tatgcatcct aggccatgaa aaaccccgc gggatg                     46
```

```
<210> SEQ ID NO 81
<211> LENGTH: 46
<212> TYPE: DNA
<213> ORGANISM: Artificial Sequence
<220> FEATURE:
<223> OTHER INFORMATION: Synthetic primer CB2008-028R:  linker down phrG
      and down lox

<400> SEQUENCE: 81
catcccgcgg gggtttttca tggcctagga tgcatatggc ggccgc                  46

<210> SEQ ID NO 82
<211> LENGTH: 26
<212> TYPE: DNA
<213> ORGANISM: Artificial Sequence
<220> FEATURE:
<223> OTHER INFORMATION: Synthetic primer CB2008-029:  downstream phrG

<400> SEQUENCE: 82
tctcggtgac attccgatca atcgcg                                        26

<210> SEQ ID NO 83
<211> LENGTH: 36
<212> TYPE: DNA
<213> ORGANISM: Artificial Sequence
<220> FEATURE:
<223> OTHER INFORMATION: Synthetic primer CB2008-030:  upstream phrI

<400> SEQUENCE: 83
gaattgttaa acatggaaga aaatcaagat gccctg                             36

<210> SEQ ID NO 84
<211> LENGTH: 52
<212> TYPE: DNA
<213> ORGANISM: Artificial Sequence
<220> FEATURE:
<223> OTHER INFORMATION: Synthetic primer CB2008-031:  linker up phrI
      down lox

<400> SEQUENCE: 84
gcggccgcca tatgcatcct aggccaatac actacttaaa atcactgctg cc           52

<210> SEQ ID NO 85
<211> LENGTH: 52
<212> TYPE: DNA
<213> ORGANISM: Artificial Sequence
<220> FEATURE:
<223> OTHER INFORMATION: Synthetic primer CB2008-031R:  linker up phrI
      down lox

<400> SEQUENCE: 85
ggcagcagtg attttaagta gtgtattggc ctaggatgca tatggcggcc gc           52

<210> SEQ ID NO 86
<211> LENGTH: 60
<212> TYPE: DNA
<213> ORGANISM: Artificial Sequence
<220> FEATURE:
<223> OTHER INFORMATION: Synthetic primer CB2008-032:  linker down phrI
      up lox

<400> SEQUENCE: 86
ggatccagct tatcgatacc gtcgacttag ataattggaa agaggaaaaa aagcttaatc   60

<210> SEQ ID NO 87
<211> LENGTH: 60
<212> TYPE: DNA
<213> ORGANISM: Artificial Sequence
```

-continued

```
<220> FEATURE:
<223> OTHER INFORMATION: Synthetic primer CB2008-032R: linker down phrI
      up lox

<400> SEQUENCE: 87
gattaagctt ttttcctctt ttccaattat ctaagtcgac ggtatcgata agctggatcc    60

<210> SEQ ID NO 88
<211> LENGTH: 40
<212> TYPE: DNA
<213> ORGANISM: Artificial Sequence
<220> FEATURE:
<223> OTHER INFORMATION: Synthetic primer CB2008-033: downstream phrI

<400> SEQUENCE: 88
ctgtccctat tagtttatct gcttttttat ctccatcagg                          40

<210> SEQ ID NO 89
<211> LENGTH: 33
<212> TYPE: DNA
<213> ORGANISM: Artificial Sequence
<220> FEATURE:
<223> OTHER INFORMATION: Synthetic primer CB2008-034: upstream phrK

<400> SEQUENCE: 89
gatgaaatgg aagaagatca agaagttctt gcg                                 33

<210> SEQ ID NO 90
<211> LENGTH: 52
<212> TYPE: DNA
<213> ORGANISM: Artificial Sequence
<220> FEATURE:
<223> OTHER INFORMATION: Synthetic primer CB2008-035: linker up phrK
      and lox

<400> SEQUENCE: 90
ggatccagct tatcgatacc gtcgattaaa atcacagcta aaatagatac gc            52

<210> SEQ ID NO 91
<211> LENGTH: 52
<212> TYPE: DNA
<213> ORGANISM: Artificial Sequence
<220> FEATURE:
<223> OTHER INFORMATION: Synthetic primer CB2008-035R: linker up phrK
      and lox

<400> SEQUENCE: 91
gcgtatctat tttagctgtg attttaatcg acggtatcga taagctggat cc            52

<210> SEQ ID NO 92
<211> LENGTH: 51
<212> TYPE: DNA
<213> ORGANISM: Artificial Sequence
<220> FEATURE:
<223> OTHER INFORMATION: Synthetic primer CB2008-036: linker down phrK
      and lox

<400> SEQUENCE: 92
gcggccgcca tatgcatcct aggccaaaag gttgattaat taatttagcc c             51

<210> SEQ ID NO 93
<211> LENGTH: 51
<212> TYPE: DNA
<213> ORGANISM: Artificial Sequence
<220> FEATURE:
<223> OTHER INFORMATION: Synthetic primer CB2008-036R: linker down phrK
      and lox
```

-continued

```
<400> SEQUENCE: 93
gggctaaatt aattaatcaa cctttggcc taggatgcat atggcggccg c        51

<210> SEQ ID NO 94
<211> LENGTH: 30
<212> TYPE: DNA
<213> ORGANISM: Artificial Sequence
<220> FEATURE:
<223> OTHER INFORMATION: Synthetic primer CB2008-037:  downstream phrK

<400> SEQUENCE: 94
atcgagacta tttgagatac ctgaagatcc                               30

<210> SEQ ID NO 95
<211> LENGTH: 3110
<212> TYPE: DNA
<213> ORGANISM: Artificial Sequence
<220> FEATURE:
<223> OTHER INFORMATION: Synthetic construct: nucleotide sequence of the
      phrC deletion construct

<400> SEQUENCE: 95
tcactaatgg aattccggca ccagcttatg ctggattatc ttgagccgtt agagaaatta    60
aatatcgaag accagccaag cctgtctgaa ttatcaagaa acattgacag caaccaggca   120
gatctcaaag gctgctcga ctattacgtg aatttttttc gcgggatgta tgaatttgat    180
aagcgggaat ttatttctgc cattacatac tataaacagg cggagaaaaa gctctccttt   240
gtcgcagacc atattgaacg ggctgaattc tattttaaaa tcgcggaagc ttattattat   300
atgaagcaaa cgtatttttc attgattaat ataaaaacg cctatgaaat ttacgtggag    360
caggaaacct ataatgtgag aatcattcag tgccatttcg tcttcggggt caacctgatg   420
gatgaaagaa atttcgaaca gccgcacgc catttcaaat tggcgctcaa catggcccaa   480
gcagaacaaa aagcccagct ggttggaaga gcatactaca atctcgggtt atgctattac   540
aatcaagacc ttctagaccc tgccattgat tactttgaaa agcggtctc cacatttgaa    600 agcagcagga tcgtcaattc tctcccgcaa gcctattttt taatcaccct gatttattat   660
aaacagggaa aacatgataa agcttcggaa tatcacaagc ggggctatga atatgctaaa   720
gaaacagacg atgcagacta tgccgtaaaa ttcgagtttt tgcaatccct atatctggat   780
cagcccaatg aagaaggaat cgaacgatgt ttccagtact aaaaaataa aaatatgtac    840 gctgatatag aggatttagc cctagaagta gcaaatatt actatgaaca gaaatggttt    900
aaactgtctg cttcctactt tctacaagtt gaagaggcaa gaaaacaaat acaaaggagt   960
gaaggtttgt atgaaattga atctaagtt gtttgttatt tgtttggccg cagccgcgat   1020
ggcctaggat gcatatggcg gccgcataac ttcgtatagc atacattata cgaagttatc   1080
tagacatatg caagggttta ttgttttcta aaatctgatt accaattaga atgaatattt   1140
cccaaatatt aataataaa acaaaaaaat tgaaaaagt gtttccacca ttttttcaat    1200 tttttataa ttttttttaat ctgttatttta aatagtttat agttaaattt acattttcat   1260
tagtccattc aatattctct ccaagataac tacgaactgc taacaaaatt ctctccctat   1320
gttctaatgg agaagattca gccactgcat ttcccgcaat atcttttggt atgattttac   1380
ccgtgtccat agttaaaatc atacggcata agttaaatat agagttggtt tcatcatcct   1440
gataattatc tattaattcc tctgacgaat ccataatggc tcttctcaca tcagaaaatg   1500
gaatatcagg tagtaattcc tctaagtcat aatttccgta tattctttta tttttttcgtt   1560 ttgcttggta aagcattatg gttaaatctg aatttaattc cttctgagga atgtatcctt   1620
```

```
gttcataaag ctcttgtaac cattctccat aaataaattc ttgtttggga ggatgattcc    1680
acggtaccat ttcttgctga ataataattg ttaattcaat atatcgtaag ttgctttat    1740 ctcctatttt ttttgaaata ggtctaattt tttgtataag tatttcttta ctttgatctg    1800
tcaatggttc agatacgacg actaaaaagt caagatcact atttggtttt agtccactct    1860
caactcctga tccaaacatg taagtaccaa taaggttatt ttttaaatgt ttccgaagta    1920 ttttttcac tttattaatt tgttcgtatg tattcaaata tatcctcctc actattttga    1980
ttagtaccta ttttatatcc atagttgtta attaaataaa cttaatttag tttatttata    2040
gatttcattg gcttctaaat tttttatcta gataacttcg tatagcatac attatacgaa    2100
gttatggatc cagcttatcg ataccgtcga gaacaagccc cttctcatta gcgagaaggg    2160
gttttctttt tcaaaaaaac accgcaagac atagtcttgc ggtgccgcct tcatggagat    2220
tacgtttatt tagtagcctc ctacaaatgc agttcccaca atgatcaaga ggataaataa    2280
cacaacaatc aaagcgaaag aagttccgta acctgacatt ttgtgcacct ccttgcgaga    2340
ttgcttcagc aaatgctgca aaactgtggc ggacagggtc ccgcagagac ggtcagcagc    2400
ttagaagccg ccaacaaacg cagtccctac gataattaat agaataaaca atacaacgat    2460
taaagcgaaa gaactgatgc cgccgtaacc gccgccgtta gagtatcctg acataaggtt    2520
tcacctccct atgaaggata ctataagata tgctgaaccg atccatttgg cagggataat    2580
agtggacaag agaaaaaatg aagaattcgg ctatatgaag gtgatataaa aaaatagcgg    2640
gcgctgccgc ccgctattta tgtacgatta agagatcagc acgccgcgca aaaattcctg    2700
gtataacgct tgaacggctt ttcttcttc ggcttctttt acgccaaaca tcatgctcac    2760
ttcagaagac ccctgattga tcatttcgat attcacctgt gcctctgata atgctttggc    2820
ggctcttgcc gttgtaccga cattgtgcg catcgcttcc cctacaacca taatcagggc    2880
gagatgatgc tcgacgatga cttcatcggc atgcaaatcc tcttcgatcc gtttgatgac    2940
gctgcgttca gtggcggcat ccatttgccc ctgccgtaaa atgattgtca tgtcatcgat    3000
tcccgatgga acatgctcat acgtcaaacc atgctcctcc aggatttgaa gggctctgcg    3060
gccaaaaccg atttctctgt tcatgagata cttgctgata taaatgctgc               3110
```

<210> SEQ ID NO 96
<211> LENGTH: 3088
<212> TYPE: DNA
<213> ORGANISM: Artificial Sequence
<220> FEATURE:
<223> OTHER INFORMATION: Synthetic construct: nucleotide sequence of the phrF deletion construct

<400> SEQUENCE: 96

```
agtttcggca aacctaatg cttgagtacc ttgaaccgtt agaaaaatg aggattgagg     60 aacagccgag actgtctgat ctgctgcttg agattgataa aaaacaggct cgtttaactg    120
gtctgcttga gtactatttt aacttcttca gaggcatgta cgagctggac cagcgggaat    180
atctgtcggc tattaaattt ttcaaaaagg ccgaaagcaa gctgatattc gttaaggatc    240
ggatagagaa agctgagttt ttcttttaaga tgtctgaatc ttattactat atgaaacaaa    300
cgtatttttc aatggactat gcacggcaag catatgaaat atacaaagaa catgaagctt    360
ataatataag attgctgcag tgtcattctt tatttgccac caatttttta gatttaaaac    420
agtatgagga tgccatctca cattttcaaa aagcttattc tatggcagaa gctgaaaagc    480
agccccaatt aatggggaga actttgtaca atatcgggct ttgtaaaaac agccaaagcc    540
aatatgagga tgccataccct tatttcaaaa gagcaatagc tgttttttgaa gaatcaaata    600
```

```
ttcttccttc cttacctcaa gcgtattttt taattacaca gatccattat aaattaggaa    660
aaatagataa agctcatgaa tatcatagta agggaatggc ttattcacaa aaggccggag    720
atgtaatata tttatcagag tttgaatttt tgaaatcttt atacttatca ggcccggatg    780
aagaagcaat tcaaggattt tttgattttc tcgaaagtaa aatgttgtat gctgatcttg    840
aagatttcgc tattgatgtg gcaaaatatt atcatgaacg taaaaatttt caaaaagctt    900 ctgcttatt  tttgaaggtg gaacaagtaa ggcaacttat tcaaggagga gtgagtttgt    960
atgaaattga agtctaaact attactggcc taggatgcat atggcggccg cataacttcg   1020
tatagcatac attatacgaa gttatctaga catatgcaag ggtttattgt tttctaaaat   1080
ctgattacca attagaatga atatttccca aatattaaat aataaaacaa aaaaattgaa   1140
aaaagtgttt ccaccatttt ttcaattttt ttataatttt tttaatctgt tatttaaata   1200
gtttatagtt aaatttacat tttcattagt ccattcaata ttctctccaa gataactacg   1260
aactgctaac aaaattctct ccctatgttc taatggagaa gattcagcca ctgcatttcc   1320
cgcaatatct tttggtatga ttttacccgt gtccatagtt aaaatcatac ggcataaagt   1380
taatatagag ttggtttcat catcctgata attatctatt aattcctctg acgaatccat   1440
aatggctctt ctcacatcag aaaatggaat atcaggtagt aattcctcta agtcataatt   1500
tccgtatatt cttttatttt ttcgttttgc ttggtaaagc attatggtta aatctgaatt   1560
taattccttc tgaggaatgt atccttgttc ataaagctct tgtaaccatt tccataaat    1620 aaattcttgt ttgggaggat gattccacgg taccattcct tgctgaataa taattgttaa   1680
ttcaatatat cgtaagttgc ttttatctcc tatttttttt gaaataggtc taatttttg    1740 tataagtatt tctttacttt gatctgtcaa tggttcagat acgacgacta aaagtcaag    1800 atcactattt ggttttagtc cactctcaac tcctgatcca aacatgtaag taccaataag   1860 gttattttt  aaatgtttcc gaagtatttt tttcactta ttaatttgtt cgtatgtatt   1920
caaatatatc ctcctcacta ttttgattag tacctattt atatccatag ttgttaatta   1980
aataaactta atttagttta tttatagatt tcattggctt ctaaattttt tatctagata   2040
acttcgtata gcatacatta tacgaagtta tggatccagc ttatcgatac cgtcgaccgc   2100
cgtccatcgg cggttttttc gtcccctctt taccaaagtc tcccaatcca tgctatgatc   2160
ttttcaataa tcttgaagag agtggaaatg cagcatgtct ctaaaaagtg tgagaaccca   2220 cttactcaa  tggaatcgag aaaatgatgt gacggagttc gaaacgtcga gtgcgacagt   2280
tgaacaggca gctgagacaa tcggcgtaag cctgtctaga atcgccaagt ccctgtcctt   2340
cagaggggaa ggagatcagg tgattctgat tgtggcagcc ggcgatgcca agatcgacaa   2400
caaaaagtcc aggcaaacat ttggctttaa agcaagaatg ctctctccta atgaggtgct   2460
ggagcagaca ggccatgaaa ttggaggagt ttgcccattt ggattggctc atgatcctga   2520
ggtttatctt gatgtatcgc tgaaacggtt tcagactgtt ttccccgcat gcggcagcag   2580
aaactccgct attgaattaa caccgaaaga attatccgaa tttctttct  caaaagtgtg   2640 gattgatgtt tgtaaagact gggaataaaa aaacatccag acatcgtctg atgtttact    2700 tatttcacaa acccaagcag catttcacgg atgattttgc tggctgtgtt tgccgtttgc   2760
tctgagtggt cgtataccgg cgcgacttcc actaaatcag cgcctttac gtttacctct   2820 gaacgcgcaa tttcatggac cgatgcaagc agttctttag acgtgatgcc gccggcgtca   2880
accgttcctg tacccggtgc gtgtgcaggg tctaatacgt caatgtcaat tgtgacataa   2940
accggacggc ccgccagctt cggaagcacc tctttcagcg gttcaagcac ttcaaatttt   3000
```

-continued

| gagatgtgca tgccgttttc cttcgcccat tcaaactctt ctttcatgcc ggaacggatt | 3060 |
| ccgaatgaat acacattgtg cggtccga | 3088 |

<210> SEQ ID NO 97
<211> LENGTH: 3079
<212> TYPE: DNA
<213> ORGANISM: Artificial Sequence
<220> FEATURE:
<223> OTHER INFORMATION: Synthetic construct: nucleotide sequence of the phrG deletion construct

<400> SEQUENCE: 97

| agaggatcag gaggtgcttg cctacttctc cttattggaa ctgcgccaca aggttttgct | 60 |
| tcacgaggcg agaggacagg gctttcagca tgaggagcct tctcatatga atgctacgtc | 120 |
| tgacatgctg aaatattact tttttctgtt tgaaggcatg tatgaggcct ataaaaataa | 180 |
| ttatgacatt gccattgggc tgtataaaga tgcagagcag tatctcgaca acattcccga | 240 |
| tccgattgaa aaagccgaat ttcacctgaa ggtcggtaag ctctattata agctgggaca | 300 |
| aaatattgtg tccctcaatc atacacggca agcagtcaaa acattcagag aagagacaga | 360 |
| ttataaaaag aagctggctt cagccctgat taccatgtca ggcaatttta cagagatgag | 420 |
| ccagtttgaa gaagctgagg cttatttgga cgaagcaatt cggatcacga gtgaattaga | 480 |
| ggatcatttt tttgaagccc agcttttgca taacttcggc cttctacatg cgcaaagcgg | 540 |
| caaatcagaa gaagcggttt cgaaattaga ggaggctcta cagaacgatg agtatgcccg | 600 |
| ctccgcctat tattatcatt ctgcctactt gctgatacga gagctgttta agatcaaaaa | 660 |
| gaaagaacag gccttatctt attaccaaga cgtgaaggaa aaattgactg ctgagccgaa | 720 |
| tagaatatgt gaggcaaaaa tagacatttt atatgccatt tatgcagaag ggggtcatgc | 780 |
| ggaaacgttt cacttatgca aacaacatat ggatgacttg ttgtccgaga aagagtatga | 840 |
| cagtgtaaga gaacttttcca ttttggctgg cgaacggtat agggaacttg agctttacaa | 900 |
| agaagctgcc cacttttttt atgaagcatt acagattgaa gaactgatta aacgaacgga | 960 |
| ggttatataa atgaaaagat ggcctaggat gcatatggcg gccgcataac ttcgtatagc | 1020 |
| atacattata cgaagttatc tagacatatg caagggttta ttgttttcta aaatctgatt | 1080 |
| accaattaga atgaatattt cccaaatatt aaataataaa acaaaaaaat tgaaaaaagt | 1140 |
| gtttccacca ttttttcaat tttttttataa tttttttaat ctgttattta aatagtttat | 1200 |
| agttaaattt acattttcat tagtccattc aatattctct ccaagataac tacgaactgc | 1260 |
| taacaaaatt ctctccctat gttctaatgg agaagattca gccactgcat ttcccgcaat | 1320 |
| atctttggt atgattttac ccgtgtccat agttaaaatc atacggcata agttaatat | 1380 |
| agagttggtt tcatcatcct gataattatc tattaattcc tctgacgaat ccataatggc | 1440 |
| tcttctcaca tcagaaaatg gaatatcagg tagtaattcc tctaagtcat aatttccgta | 1500 |
| tattctttta tttttttcgtt ttgcttggta agcattatg gttaaatctg aatttaattc | 1560 |
| cttctgagga atgtatcctt gttcataaag ctcttgtaac cattctccat aaataaattc | 1620 |
| ttgtttggga ggatgattcc acggtaccat ttcttgctga ataataattg ttaattcaat | 1680 |
| atatcgtaag ttgcttttat ctcctatttt ttttgaaata ggtctaattt tttgtataag | 1740 |
| tatttctttta ctttgatctg tcaatggttc agatacgacg actaaaaagt caagatcact | 1800 |
| atttggttt agtccactct caactcctga tccaaacatg taagtaccaa taaggttatt | 1860 |
| ttttaaatgt ttccgaagta tttttttcac tttattaatt tgttcgtatg tattcaaata | 1920 |
| tatcctcctc actatttga ttagtaccta ttttatatcc atagttgtta attaaataaa | 1980 |

```
cttaatttag tttatttata gatttcattg gcttctaaat tttttatcta gataacttcg    2040
tatagcatac attatacgaa gttatggatc cagcttatcg ataccgtcga atgaaaaacc    2100
cccgcgggat gcgggggttc aatttaacga agaatccta aaacggtttg tagttttagg     2160
attctttcat cttttcagcg tgattgaaaa cccttgaagt ctaggaagaa cgagcattgg    2220
agcgcagcga atgtttggaa ttcgtgagca ccgaagcgca ggcctgacaa cgaatgcgag    2280
ggtttgtcga cacgctgaaa acccgcgggt gcggggtttt cttattaca gcagcttctt    2340 ccctaacagg gattctacga gctctactgc tgttttgccc gttttgtttt tgtgatcaag    2400
gatcgggtta acctcaacga attcggctga ggtaatgatg cctgcgtcat acagcatttc    2460
catagccaaa tggctctccc ggtagctgat gccgccgacg acaggggttc cgacacccgg    2520
tgcgtcgttc ggatcaagtc cgtccagatc aaggctcaga tggacgccat cacatgctga    2580
taaataatca agggtttctt caatgacctt tgtcatgcca agacgatcga tttcgtgcat    2640
tgtgtacacc ttcatgccgc tttccttaat gtacttgcgc tccccttcat caagtgaccg    2700
ggcgccaatg atgacgacgt tttccggttt gattttaggc gcgtagcctt caaggttaac    2760
cagtgactcg tggccaatgc ctaggctgac cgcgagcggc atgccgtgaa tattgcccga    2820
tggtgaagtt tcaagtgtat tcaaatcgcc gtgcgcgtca taccagatga cgccgagatt    2880
atcgtaatgc ttcgctgtgc ctgcaagcgt gccgatcgca atactgtggt caccgcccag    2940
gacaagcggg aattttttct cttcaatgac tttgttgacc ttttgcgcga gtttttcatt    3000
tcccgccaaa acggaattca ggttttcag ttcctcgtca ttttttgattt tttcgcgatt    3060 gatcggaatg tcaccgaga                                                 3079

<210> SEQ ID NO 98
<211> LENGTH: 3564
<212> TYPE: DNA
<213> ORGANISM: Artificial Sequence
<220> FEATURE:
<223> OTHER INFORMATION: Synthetic construct: nucleotide sequence of the
      phrH deletion construct

<400> SEQUENCE: 98
ggagggaagc cgttgagtca agccataccg tcttcgcgtg ttggtgttaa gattaatgaa      60
tggtataaaa tgattcgcca gttcagtgtt ccggatgctg agattctgaa agcggaggtt    120
gagcaggaca ttcagcagat ggaagaagat caggatttac tgatctatta ttctctgatg    180
tgttttcggc accagctgat gcttgattat tggagccgg gaaaaacata cgggaatcgc     240
cctacagtga cagagcttct tgaaacgatc gagacccctc agaaaaaact cacaggtctt    300
ttgaaatact actctttgtt tttccgcggc atgtatgaat ttgaccaaaa agaatatgtg    360
gaagcgatcg gatattatcg cgaggcggag aaagaactgc cgtttgtgtc agatgatatt    420
gagaaagcgg aattccattt taaagtggca gaagcgtatt atcacatgaa gcaaacccat    480
gtgtcgatgt atcatattct tcaagccttg gacatttatc aaaaccatcc tctatacagc    540
attagaacga tacaaagctt gtttgtgatc gccggcaact atgatgattt caaacattat    600
gataaagcgc tcccgcattt agaggcggcg ctggaattgg caatggacat tcaaaatgac    660
aggtttatcg ccatttctct attgaacatt gcaaacagct atgacagatc aggagacgat    720
cagatggctg tagaacattt ccaaaaagcg gcgaaagtaa gcagagagaa agtgcctgat    780
ctgcttccga aagtcttgtt tggattaagc tggacattat gtaaagcggg ccaaacacag    840
aaggcgtttc agttcataga ggaaggatta gaccatatca cagcacgttc tcacaaattt    900
tataaagaat tgtttctgtt cttgcaggcc gtgtacaagg agactgttga tgaacgaaaa    960
```

```
attcatgatc ttttaagcta tttcgaaaaa aagaacctgc acgcttacat tgaagcatgt    1020
gcccggagtg ctgccgctgt ttttgaaagc agctgtcact ttgaacaagc agctgcgttt    1080
tatcggaaag tgctgaaagc ccaagaagat attctaaaag ggagagtgtt tatatgccta    1140
ttaagaaaaa aagtgatgag gcctaggatg catatggcgg ccgcataact tcgtatagca    1200
tacattatac gaagttatct agacatatgc aagggtttat tgttttctaa atctgattac    1260
ccaattagaa tgaatatttc ccaaatatta ataataaaa caaaaaaatt gaaaaaagtg     1320
tttccaccat ttttttcaatt tttttataat tttttaatc tgttatttaa atagtttata    1380
gttaaattta cattttcatt agtccattca atattctctc caagataact acgaactgct    1440
aacaaaattc tctccctatg ttctaatgga gaagattcag ccactgcatt tcccgcaata    1500
tcttttggta tgattttacc cgtgtccata gttaaaatca tacggcataa agttaatata    1560
gagttggttt catcatcctg ataattatct attaattcct ctgacgaatc cataatggct    1620
cttctcacat cagaaaatgg aatatacagg agtaattcct ctaagtcata atttccgtat    1680
attcttttat tttttcgttt tgcttggtaa agcattatgg ttaaatctga atttaattcc    1740
ttctgaggaa tgtatccttg ttcataaagc tcttgtaacc attctccata aataaattct    1800
tgtttgggag gatgattcca cggtaccatt tcttgctgaa taataattgt taattcaata    1860
tatcgtaagt tgcttttatc tcctattttt tttgaaatag gtctaatttt ttgtataagt    1920
atttctttac tttgatctgt caatggttca gatacgacga ctaaaaagtc aagatcacta    1980
tttggtttta gtccactctc aactcctgat ccaaacatgt aagtaccaat aaggttattt    2040
tttaaatgtt tccgaagtat tttttttcact ttattaattt gttcgtatgt attcaaatat    2100
atcctcctca ctattttgat tagtacctat tttatatcca tagttgttaa ttaaataaac    2160
ttaatttagt ttatttatag atttcattgg cttctaaatt ttttatctag ataacttcgt    2220
atagcataca ttatacgaag ttatggatcc agcttatcga taccgtcgag gcttttctt    2280 gctttacgga agacggttcc attttccaca tcgcggcatt ccttctattt ctaacgcaag    2340
acactcgaaa caaccaaacc atttgaggta taatggataa agtgaataac agtatttaga    2400
ttgatatata tgaaagagag tggaacatca tgggccgtaa gtggaacaat attaaagaga    2460
agaaggcgtc taaggacgca aatacgagtc ggatttatgc gaagtttggc cgtgagattt    2520
atgtggcggc gaaacagggc gagcctgatc cggaatccaa ccaggcgctg aaggttgtgc    2580
ttgaacgtgc gaagacttac agcgtgccga aaaacatcat tgaacgtgcg atcgagaagg    2640
cgaagggcgg agcggaagag aattacgatg agcttcgtta tgagggcttc gggccgaacg    2700
gatcaatgat tatcgttgat gcgctgacga ataatgtaaa ccgtacggcg ccggaagtgc    2760
gtgcggcgtt cggaaaaaac ggcggaaaca tgggtgtgag cggatctgtt gcttacatgt    2820
ttgacgcgac ggctgtaatc gtggtggaag gcaaaacggc tgacgaagcg cttgaaatcc    2880
tgatggaagc ggatgttgat gtacgtgaca ttttagaaga ggatgacagc gcgatcgtgt    2940
atgccgagcc tgatcaattc catgcggtgc aagaggcgtt taaaaacgcg ggtgtcgagg    3000
aatttacagt agcggagctg caaatgcttg cgcaaagtga agtaacgctt ccggatgatg    3060
caaaggaaca gtttgaaaaa ttgattgatg cattagaaga tttggaagat gttcagcagg    3120
tatatcataa cgttgattta ggtgagtaag gagtgagcag gctgttatgg cctgcttttt    3180
ttgtcccgga aattgtttta gctgtatgta ggcggccgcc tatacgatct ataagatatt    3240
ctcatactct ggactgtaac ctatgtgaag gagagagtaa atatgactga tacaagacat    3300
atgtatggcg gacctggttt tggtcattat cagggctttg gtattggcca cccgggctat    3360
```

| | |
|---|---|
| ggcatgcaaa gcacaggcta tccgggctat ggcatgtatg gaggccaccc gggctatggc | 3420 |
| atgcaaggct acccagatca cggcatacat ggaggagtcg gcggctatcc gggatatggt | 3480 |
| gggtacggcg gttacccaag cggcggctat ggaggctctc cgggaactgg aagctatccg | 3540 |
| agcatgcacc atgaaaatga tggc | 3564 |

<210> SEQ ID NO 99
<211> LENGTH: 3147
<212> TYPE: DNA
<213> ORGANISM: Artificial Sequence
<220> FEATURE:
<223> OTHER INFORMATION: Synthetic construct: nucleotide sequence of the phrI deletion construct

<400> SEQUENCE: 99

| | |
|---|---|
| gaattgttaa acatggaaga aaatcaagat gccctgttat attatcaact attagaattt | 60 |
| agacatgaga taatgctgag ttatatgaaa tctaaggaaa tagaagatct caataatgct | 120 |
| tatgagacta taaaagaaat tgagaagcaa gggcaattaa ctggcatgtt ggaatactat | 180 |
| tttacttttt ttaagggtat gtacgagttt aggcgtaaag aattaatttc agcgataagt | 240 |
| gcttatcgaa tagctgaatc aaagttgtca gaagttgagg atgaaataga gaaagcagag | 300 |
| ttttttttca agtgtcccta tgtatattat tatatgaaac aaacatactt ctccatgaat | 360 |
| tatgcaaatc gtgcactcaa aatatttaga gagtatgaag aatatgctgt ccagactgtg | 420 |
| cgttgtcaat ttattgtagc aggaaacttg atcgattcat ggaatatga agagccttg | 480 |
| gaacaatttt tgaagtcttt ggaaatttcc aaggaaagta acatagagca tttaattgca | 540 |
| atgtcacata tgaatattgg gatttgttat gatgaattga agaatataa gaaggcttca | 600 |
| caacatttaa tttagcgtt agaaattttt gaaaaatcaa aacatagttt cttaacaaag | 660 |
| actttattca ctctaaccta tgtagaagca aaacaacaaa attataatgt tgctttgata | 720 |
| tactttagga aagggcgatt tattgccgat aaaagtgatg ataaggaata ctcagcgaaa | 780 |
| ttcaaaatat tagagggatt attttttttct gatggtgaga ctcaattaat aaagaatgca | 840 |
| ttttcatatc tggcttcgag aaaaatgttt gctgatgttg aaaattttc gattgaagtc | 900 |
| gctgattatt ttcatgaaca aggaaattta atgctctcta atgaatatta tcgtatgagt | 960 |
| attgaagcaa gacgaaaaat taaaaagggg gagattattg atgaaaatca gccggattct | 1020 |
| attggcagca gtgatttaa gtagtgtatt ggcctaggat gcatatggcg gccgcataac | 1080 |
| ttcgtatagc atacattata cgaagttatc tagacatatg caagggttta ttgttttcta | 1140 |
| aaatctgatt accaattaga atgaatattt cccaaatatt aataataaa acaaaaaat | 1200 |
| tgaaaaaagt gtttccacca tttttcaat tttttataa ttttttaat ctgttattta | 1260 |
| aatagtttat agttaaattt acattttcat tagtccattc aatattctct ccaagataac | 1320 |
| tacgaactgc taacaaaatt ctctccctat gttctaatgg agaagattca gccactgcat | 1380 |
| ttcccgcaat atcttttggt atgatttac ccgtgtccat agttaaaatc atacggcata | 1440 |
| aagttaatat agagttggtt tcatcatcct gataattatc tattaattcc tctgacgaat | 1500 |
| ccataatggc tcttctcaca tcagaaaatg gaatatcagg tagtaattcc tctaagtcat | 1560 |
| aatttccgta tattctttta ttttttcgtt ttgcttggta aagcattatg gttaaatctg | 1620 |
| aatttaattc cttctgagga atgtatcctt gttcataaag ctcttgtaac cattctccat | 1680 |
| aaataaattc ttgtttggga ggatgattcc acggtaccat tcttgctga ataataattg | 1740 |
| ttaattcaat atatcgtaag ttgctttat ctcctatttt tttgaaata ggtcaatttt | 1800 |
| tttgtataag tatttctta ctttgatctg tcaatggttc agatacgacg actaaaaagt | 1860 |

| | |
|---|---|
| caagatcact atttggtttt agtccactct caactcctga tccaaacatg taagtaccaa | 1920 |
| taaggttatt ttttaaatgt ttccgaagta ttttttttcac tttattaatt tgttcgtatg | 1980 |
| tattcaaata tatcctcctc actatttttga ttagtaccta ttttatatcc atagttgtta | 2040 |
| attaaataaa cttaatttag tttatttata gatttcattg gcttctaaat ttttttatcta | 2100 |
| gataacttcg tatagcatac attatacgaa gttatggatc cagcttatcg ataccgtcga | 2160 |
| cttagataat tggaaaagag gaaaaaagct taatcttttt tcgaaggtta agcttttttct | 2220 |
| tttatttata aaaagtgaac taactatcag aaagaaatta tattaaattt tatttttttg | 2280 |
| tttaaaaagt agattatata aaggcaagct aggtggggga aaatatgttt aaaaaagaaa | 2340 |
| aagtcacaga atacatttgg actatactaa taccaacaat catcactttt atcattagtt | 2400 |
| gggttgggtc ttattacaat ggtacttcga cagttagtat tggacaacct acaaaagttt | 2460 |
| ccggtcagta tatcacgcca ataaatataa gtccctatca tgatattaag gaattaagaa | 2520 |
| taacttttcc gcaaaaacta gatgtaaaac aaattagttc aaatgagcct ataaatgtaa | 2580 |
| aatcagataa gaacaatata ggagttgaaa gtaattccac ttttgagatt gcgaaaatcg | 2640 |
| ttgaaaataa tagcgttcag ttgctaatta caacacaaaa aaagttaaac gataaggaaa | 2700 |
| ttagaattga taaaaatgga aataacattt ctgtaaatta tgaatctcag attgttaatc | 2760 |
| ctgcaaaaaa acaattaatc aatcttataa ttacgtcatc tatttatttt ataatgctta | 2820 |
| atatactagc attgattatg aacaaaagat gggataagta ttatgcaaaa atgaaaaatg | 2880 |
| aaatcaaaga atttgaggat aatgcaaaag atcttgataa aaaatcaaag aagaaaagcg | 2940 |
| aggaattatc ggagctgcga aagaccttga accaagcgtt tgaggaaact gataggataa | 3000 |
| aatatcatga gaagaaaaaa caaatcctcc tcttagctaa gttaaacgat tataaaaaag | 3060 |
| aactaacctt ttggagaaat acaataagaa aagttcttta tgaacttcct gatggagata | 3120 |
| aaaaagcaga taaactaata gggacag | 3147 |

<210> SEQ ID NO 100
<211> LENGTH: 3114
<212> TYPE: DNA
<213> ORGANISM: Artificial Sequence
<220> FEATURE:
<223> OTHER INFORMATION: Synthetic construct: nucleotide sequence of the
      phrK deletion construct

<400> SEQUENCE: 100

| | |
|---|---|
| gatgaaatgg aagaagatca agaagttctt gcgtattata gtctattaga agaaagacat | 60 |
| aaaatgttgc tgcattcttc acgaggagag cctttacaaa agcacaccta ttttactgaa | 120 |
| gacaatcaaa acttcataac aaaaacaaat gataaattag aatacaactt ttatttattt | 180 |
| gaagcaatgt acgaggcata caacaaaaac tatgatcgag caattaaccct atatggatta | 240 |
| gctgagaaaa agcttgcaga aattccagat gaaattgaag cagctgaatt ttactctaaa | 300 |
| gtctcttact tatatactct tgttaaacaa agcattgtgg cacaacatta tataaaaaat | 360 |
| gcaatttcaa tatataagcg acaccctgat tataaatgca aactagctac atcaacaatg | 420 |
| attgcagctg caaactatgc tgatatgaaa cgatttgagg aagcagaaca atattactta | 480 |
| gaagcaattg atattgcaaa agaaacaaaa gatgaatttt taaagctca attatttcac | 540 |
| aatcttagta tcgtttattc tgattggaac aaacctgata aatgcattga atctcttgaa | 600 |
| aaagcaatag gaaatgaatc ttggttacat tcgatttatt atataaattc tttattcatg | 660 |
| atgattaaag aactctttaa aattgacgaa aaaatgaaag ccattaattt ttacaataaa | 720 |
| gcacaggaaa gactcatatt aatggagaat aaagtatacg aagccaaaat cagcatcctg | 780 |

```
tataaccttt attgtgggga attaaaaaat aatttcaata attgtattag taatattgag      840
tttttaaaac agcaaaatga acttgaaagt gtagatgaat tgtcctacat agctgcaaaa      900
aggtttgaat caataggtgc ttttgaagaa gcaacgagct ttttcaatgc gaaaatttgg      960
gctgaacaga aaatgaatca ggtggaggga atcttatgaa aaaacttgtg ctttgcgtat     1020
ctattttagc tgtgatttta atcgacggta tcgataagct ggatccataa cttcgtataa     1080
tgtatgctat acgaagttat ctagataaaa aatttagaag ccaatgaaat ctataaataa     1140
actaaattaa gtttatttaa ttaacaacta tggatataaa ataggtacta atcaaaatag     1200
tgaggaggat atatttgaat acatcgaac aaattaataa agtgaaaaaa atacttcgga      1260
aacatttaaa aaataacctt attggtactt acatgtttgg atcaggagtt gagagtggac     1320
taaaaccaaa tagtgatctt gactttttag tcgtcgtatc tgaaccattg acagatcaaa     1380
gtaaagaaat acttatacaa aaaattagac ctatttcaaa aaaaatagga gataaaagca     1440
acttacgata tattgaatta acaattatta ttcagcaaga aatggtaccg tggaatcatc     1500
ctcccaaaca agaatttatt tatggagaat ggttacaaga gctttatgaa caaggataca     1560
ttcctcagaa ggaattaaat tcagatttaa ccataatgct ttaccaagca aaacgaaaaa     1620
ataaaagaat atacggaaat tatgacttag aggaattact acctgatatt ccatttttctg    1680
atgtgagaag agccattatg gattcgtcag aggaattaat agataattat caggatgatg     1740
aaaccaactc tatattaact ttatgccgta tgatttaac tatggacacg ggtaaaatca      1800
taccaaaaga tattgcggga aatgcagtgg ctgaatcttc tccattagaa catagggaga     1860
gaattttgtt agcagttcgt agttatcttg gagagaatat tgaatggact aatgaaaatg     1920
taaatttaac tataaactat ttaaataaca gattaaaaaa attataaaaa aattgaaaaa     1980
atggtggaaa cactttttc aattttttg ttttattatt taatatttgg gaaatattca       2040
ttctaattgg taatcagatt ttagaaaaca ataaaccctt gcatatgtct agataacttc     2100
gtataatgta tgctatacga agttatgcgg ccgccatatg catcctaggc caaaaggttg     2160
attaattaat ttagccctac tcaaacattt gagtgggctt ttatttatg atttatgtcc      2220
accggtcagc cctgctctgt ggagcgcagt acctgcaaac gtaactgaga tacttctcac     2280
tgttttttgc ccgagtaaaa cttattaaag aacatcaagc aacacttata aatatccatc     2340
gtgatatttg tgggaaaatc aattgttttg gatcgatgaa aaccaccgcc aagctcatct     2400
ttactgtatc caattcctag acttattgtt cgaccaactt tattatatgt acgtgccctt     2460
cttgcgactt cctcacaaat ctccaagagc acagctttaa tctcttctct ctttgtataa     2520
tccctaaaca aaatctgact cttaccaaaa ctaatctgcc cctgcatcaa tggagctcct     2580
atttcagata aatcaattcc gtgagcatga tagtacaact ggtttcccat tattccgaac     2640
ttcttttcaa gcagctctaa aggaaattta gctaactgac ctacagttga tatcccatt     2700
cgattcagat ttctttccat cctccctcct atccccaca ttttagacaa aggtcgaact      2760
ttccagagtc tatttggcac atcttcatat ctccaacgtg caataccact ctttgttttc     2820
ttactctcca ggtcaagtgc aagcttacta agcaacatat tgtcaccaat tccaactgtg     2880
cacatcaaac caaattctct ccacatgctg ctttggattg ctttggccat tcttcagga     2940
ttctcttttc ctgcatctaa aaaagattaa tcaattgaat acgtgtggac acattttttca   3000
ggaacaaatc tgtaaaacag ctttgtaatc tcagttgaaa ctctgatgaa aagcttcatt     3060
tgtggattta caatgtatat tcttggatct tcaggtatct caaatagtct cgat           3114
```

```
<210> SEQ ID NO 101
<211> LENGTH: 1496
<212> TYPE: DNA
<213> ORGANISM: Bacillus subtilis

<400> SEQUENCE: 101
tcataccctg aaaggaaaga caagggaaat tgtcggcaat gagccgctcg gcaggtagaa      60
ggatgtttac cgatgcaaaa aaagggcaaa atggataggt ggttgtccat gttgaatgct     120
ataatggggg agatttataa aagagagtga tacatattga ataatacgaa gcagcccgtt     180
gtcattttag tcggaccgac ggcagtgggg aaaaccaatt taagtattca gctagccaaa     240
tccttaaacg cggaaattat cagcggagat tcgatgcaga tttataaagg gatggatatt     300
ggaacagcta aaattaccga acaggagatg gagggagtgc cccatcatct gattgacatt     360
ttagatcccc aagactcttt ctctactgcc gattatcaaa gcttagtaag aaataaaatc     420
agcgagattg caaatagagg aaagcttccg atgattgacg gcggtacagg gcttatata     480 caatctgagc tttacgatta tacatttacg gaagaggcaa atgatcccgt gtttcgagag     540
agcatgcaaa tggctgctga gcgggaaggc gctgactttc ttcatgccaa acttgctgca     600
gcagatcccg aggcagcagc tgcgattcat ccgaataata caagaagagt cattcgcgca     660
ctggaaattt tacatacgtc cggaaaaacg atgtcccagc atttgaagga acaaaaacga     720
gaacttctgt acaatgcagt gttaattggc ctgacaatgg atagagacac gctttacgaa     780
agaattaatc agcgggtcga tttgatgatg cagtcaggcc ttcttccgga agtgaaacgc     840
ttatacgaca agaacgtgag agactgtcaa tcaatacagg cgataggcta taaagagctg     900
tatgcatatt ttgacggttt tgtgacactt tccgatgctg tcgaacagct aaagcagaac     960
tcgaggcggt atgcgaaacg ccagctgacg tggtttcgca acaaaatgca ggtcacatgg    1020
ttcgatatga caccgcctgt tgatatggag ctgaaaaaaa aggaaatttt cacacatata    1080
gcaggaaaac tcgaacttta atcgaaactg tatgatatag agaatcaagg aggacgaaac    1140
atgaaaccga ttaatattca ggatcagttt ttgaatcaaa tccggaaaga aaatacgtat    1200
gtcactgttt ttttgctgaa cggctttcag ttgcggggcc aggtgaaagg ctttgataac    1260
tttaccgtat tgttggaatc ggaaggtaag cagcagctta tatataaaca tgcgatctca    1320
acgtttgcgc cgcaaaaaaa cgtccagctt gaactcgaat agatcaaaaa atgccatgtc    1380
aagacatgag gaaaggctgt cggggttcc cggcggccat ttttaacatg aatccacttt    1440
tgctccaagc ttttttgtgta agctgaccat gccaaggcac ggtcttttt tatgag        1496
```